US010435706B2

(12) United States Patent
Barry et al.

(10) Patent No.: US 10,435,706 B2
(45) Date of Patent: Oct. 8, 2019

(54) INSECTICIDAL PROTEINS AND METHODS FOR THEIR USE

(71) Applicants: PIONEER HI-BRED INTERNATIONAL, INC., Johnston, IA (US); E. I. DU PONT DE NEMOURS AND COMPANY, Wilmington, DE (US)

(72) Inventors: Jennifer Kara Barry, Ames, IA (US); Deborah W. Clark, Garnet Valley, PA (US); James J English, San Ramon, CA (US); Azalea Ong, Castro Valley, CA (US); Eric J Schepers, Port Deposit, IA (US); Julie Qi, Urbandale, IA (US); Janet A. Rice, Wilmington, DE (US)

(73) Assignees: PIONEER HI-BRED INTERNATIONAL, INC., IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/518,709

(22) PCT Filed: Oct. 14, 2015

(86) PCT No.: PCT/US2015/055502
§ 371 (c)(1),
(2) Date: Apr. 12, 2017

(87) PCT Pub. No.: WO2016/061206
PCT Pub. Date: Apr. 21, 2016

(65) Prior Publication Data
US 2017/0233440 A1 Aug. 17, 2017

Related U.S. Application Data

(60) Provisional application No. 62/064,810, filed on Oct. 16, 2014.

(51) Int. Cl.
| C12N 15/82 | (2006.01) |
| A01N 37/46 | (2006.01) |
| A01N 65/04 | (2009.01) |
| C07K 14/415 | (2006.01) |
| A01N 47/44 | (2006.01) |
| A01N 65/00 | (2009.01) |

(52) U.S. Cl.
CPC ......... *C12N 15/8286* (2013.01); *A01N 37/46* (2013.01); *A01N 47/44* (2013.01); *A01N 65/00* (2013.01); *A01N 65/04* (2013.01); *C07K 14/415* (2013.01); *C07K 2319/00* (2013.01); *Y02A 40/162* (2018.01)

(58) Field of Classification Search
CPC ... C12N 15/8286; C07K 14/415; A01N 65/04
See application file for complete search history.

(56) References Cited

U.S. PATENT DOCUMENTS

2017/0166921 A1  6/2017 Barry et al.

FOREIGN PATENT DOCUMENTS

WO    2015/120270 A1    8/2015

OTHER PUBLICATIONS

Evaluation of Fern and Moss Protein-Based Defenses Against Phytophagous Insects Kevin Markham, Tanya Chalk, and C. Neal Stewart Jr. International Journal of Plant Sciences 2006 167:1, 111-117 (Year: 2006).*
Guo et al (PNAS Jun. 22, 2004 vol. 101 No. 25 9205-9210) (Year: 2004).*
International Search Report and Written Opinion for International Application PCT/US15/55502 dated Jan. 15, 2016.
EBI accession No. UNIPROT:F2ZAL6 Database accession (2011).
EBI accession No. UNIPROT:Q5CZR5 Database accession (2007).
Tamura, Saki, et al.: "Purification, characterization and cDNA cloning of two natterin-like toxins from the skin secretion of oriental catfish Plotosus lineatus", Toxicon, 2011, vol. 58, pp. 430-438.

* cited by examiner

*Primary Examiner* — Lee A Visone

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

23 Claims, 24 Drawing Sheets
Specification includes a Sequence Listing.

Fig. 1A

```
                    1                                                  50
PtIP-96Aa    (1)    --------------------------------------------------
PtIP-96Ab    (1)    --------------------------------------------------
PtIP-96Ac    (1)    --------------------------------------------------
PtIP-96Ad    (1)    --------------------------------------------------
PtIP-96Ae    (1)    --------------------------------------------------
PtIP-96Af    (1)    --------------------------------------------------
PtIP-96Ag    (1)    --------------------------------------------------
PtIP-96Ah    (1)    --------------------------------------------------
PtIP-96Ca    (1)    --------------------------------------------------
PtIP-96Cb    (1)    --------------------------------------------------
PtIP-96Cc    (1)    --------------------------------------------------
PtIP-96Cd    (1)    --------------------------------------------------
PtIP-96Ce    (1)    --------------------------------------------------
PtIP-96Cf    (1)    --------------------------------------------------
PtIP-96Cg    (1)    --------------------------------------------------
PtIP-96Ch    (1)    --------------------------------------------------
PtIP-96Da    (1)    --------------------------------------------------
PtIP-96Db    (1)    --------------------------------------------------
PtIP-96Dc    (1)    --------------------------------------------------
PtIP-96Dd    (1)    --------------------------------------------------
PtIP-96De    (1)    --------------------------------------------------
PtIP-96Df    (1)    --------------------------------------------------
PtIP-96Ea    (1)    --------------------------------------------------
PtIP-96Eb    (1)    --------------------------------------------------
PtIP-96Ec    (1)    --------------------------------------------------
PtIP-96Ed    (1)    --------------------------------------------------
PtIP-96Ee    (1)    --------------------------------------------------
PtIP-96Ef    (1)    --------------------------------------------------
PtIP-96Eg    (1)    --------------------------------------------------
PtIP-96Eh    (1)    --------------------------------------------------
PtIP-96Ei    (1)    --------------------------------------------------
PtIP-96Ej    (1)    --------------------------------------------------
PtIP-96Ek    (1)    --------------------------------------------------
PtIP-96El    (1)    --------------------------------------------------
PtIP-96Em    (1)    --------------------------------------------------
PtIP-96En    (1)    --------------------------------------------------
PtIP-96Eo    (1)    --------------------------------------------------
PtIP-96Ep    (1)    --------------------------------------------------
PtIP-96Eq    (1)    --------------------------------------------------
PtIP-96Er    (1)    --------------------------------------------------
PtIP-96Es    (1)    --------------------------------------------------
PtIP-96Et    (1)    --------------------------------------------------
PtIP-96Eu    (1)    --------------------------------------------------
PtIP-96Ev    (1)    --------------------------------------------------
PtIP-96Ha    (1)    MQYGLANTEASPLIEKFQALMEGGIDESILATKLVGAEGDASHLPPPGET
PtIP-96Hd    (1)    MQYGLANTEASPLIEKFQALMEGGIDESILATKLVGAEGDASRVPPPGET
PtIP-96He    (1)    MQYGLANTEASPLIEKFQALMEGGIDESILATKLVGAEGDASHLPPPGET
PtIP-96Hf    (1)    MQYGLANTEASPLIEKFQALMEGGIDESILATKLVGAEGDASRVPPPGET
PtIP-96Hg    (1)    MQYGLANTEASPLIEKFQALMEGGIDESILATKLVGAEGDASRVPPPGET
PtIP-96Hh    (1)    MQYGLANMEASPLIEKFQSLMEGGIDESILATKLVGAEGDASHLPPPGET
PtIP-96Hi    (1)    MQYGLANMEASPLIEKFQSLMEGGIDESILATKLVGAEGDASHLPPPGET
PtIP-96Hj    (1)    MQYGLANTEASPLIEKFQALMEGGIDESILATKLVGAEGDASHLPPPGET
```

Fig. 1B

```
                    51                                              100
PtIP-96Aa   (1)  -------------------------------MSIHQTPVTLIGGRGGAAF
PtIP-96Ab   (1)  -------------------------------MSIHQTPVTLIGGRGGAAF
PtIP-96Ac   (1)  -------------------------------MSIHQTPVTLIGGRGGAAF
PtIP-96Ad   (1)  -------------------------------MSIHQTPVTLIGGRGGAAF
PtIP-96Ae   (1)  -------------------------------MSIHQTPVTLIGGRGGAAF
PtIP-96Af   (1)  -------------------------------MSIHQTPVTLIGGRGGAAF
PtIP-96Ag   (1)  -------------------------------MSIHQTPVTLIGGRGGAAF
PtIP-96Ah   (1)  -------------------------------MSIYQTPVTLIGGRGGAAF
PtIP-96Ca   (1)  ------------------------------MSTAIFQTPVHVIGGQGGSEF
PtIP-96Cb   (1)  ------------------------------MSTAIFQTPVHVIGGQGGSEF
PtIP-96Cc   (1)  ---------------------------------MSIHQTPVHVIGGQGGSEF
PtIP-96Cd   (1)  ------------------------------MSTAIFQTPVHVIGGQGGSEF
PtIP-96Ce   (1)  ---------------------------------MSIYQTPVHVIGGQGGSEF
PtIP-96Cf   (1)  ---------------------------------MSIYQTPVHVIGGQGGSEF
PtIP-96Cg   (1)  ---------------------------------MSIYQTPVHVIGGQGGSEF
PtIP-96Ch   (1)  ------------------------------MSTAIFQTPVHVIGGQGGSEF
PtIP-96Da   (1)  --------------------------------MSIVQSPIHVIGGSGGSAF
PtIP-96Db   (1)  ---------------------------------MSIFQTPVHVIGGQGGAF
PtIP-96Dc   (1)  ---------------------------------MSITPVHVIGGQGGAF
PtIP-96Dd   (1)  ---------------------------------MSIFQTTVHVIGGQGGAF
PtIP-96De   (1)  ---------------------------------MSIYQTPVSLIGGQGTAF
PtIP-96Df   (1)  ------------------------------MSTAIFQTPVSLIGGQGTAF
PtIP-96Ea   (1)  ---------------------------------MALYQTPVYVIGGQGGNSF
PtIP-96Eb   (1)  ---------------------------------MALYQTPVYVIGGQGGNSF
PtIP-96Ec   (1)  ---------------------------------MSLVQTPVYVIGGQGGNAF
PtIP-96Ed   (1)  ---------------------------------MSLYQTPVTIIGGQGGNSF
PtIP-96Ee   (1)  ---------------------------------MSLVQTPVYVIGGQGGNAF
PtIP-96Ef   (1)  ---------------------------------MSLVQTPVYVIGGQGGNAF
PtIP-96Eg   (1)  ---------------------------------MSLVQTPVYVIGGQGGNAF
PtIP-96Eh   (1)  ---------------------------------MSLVQTPVYVIGGQGGNAF
PtIP-96Ei   (1)  ---------------------------------MSLVQTPVYVIGGQGGNAF
PtIP-96Ej   (1)  ---------------------------------MSLVQTPVYVIGGQGGNAF
PtIP-96Ek   (1)  ---------------------------------MSLVQTPVYVIGGQGGNAF
PtIP-96El   (1)  ---------------------------------MSLVQTPVYVIGGQGGNAF
PtIP-96Em   (1)  ---------------------------------MSLVQTPVYVIGGQGGNAF
PtIP-96En   (1)  ---------------------------------MSLVQTPVYVIGGQGGNAF
PtIP-96Eo   (1)  ---------------------------------MSIYQTPVSVIGGTGGSAF
PtIP-96Ep   (1)  ---------------------------------MSIYQTPVSVIGGTGGSAF
PtIP-96Eq   (1)  ---------------------------------MSIYQTPISVIGGTGGSAF
PtIP-96Er   (1)  ---------------------------------MALYQTPVSIIGGQGCTSF
PtIP-96Es   (1)  ---------------------------------MALYQTPVSIIGGQGCTSF
PtIP-96Et   (1)  ---------------------------------MALYQTPVYVIGGQGGNSF
PtIP-96Eu   (1)  ---------------------------------MALYQTPVYVIGGQGGNAF
PtIP-96Ev   (1)  ---------------------------------MALYQTPVYVIGGQGGNSF
PtIP-96Ha  (51)  PSEDGAGKDPPNESLETEDVEEHADDSKARSAS-VTAPLRFIGGPGGSQR
PtIP-96Hd  (51)  PSEDGAGKDPPNESLETEDVEEHADDSKARSAS-VTAPLRFIGGTGGSQR
PtIP-96He  (51)  PSEDGAGKDPPNESLETEDVEEHADDSKARSASSVTAPLRFIGGTGGSQR
PtIP-96Hf  (51)  PGEDGAGKDPPNESLETEDVEEHADDSKARSAS-VTAPLRFIGGPGGSQR
PtIP-96Hg  (51)  PGEDGAGKDPPNESLETEDVEEHADDSKARSAS-VTAPLRFIGGPGGSQR
PtIP-96Hh  (51)  PSEDGAGKDPPNESLETEDVEEHADDSKARSAS-VTAPLRFIGGPGGSQR
PtIP-96Hi  (51)  PSEDGAGKDPPNESLETEDVEEHADDSKARSAS-VTAPLRFIGGPGGSQR
PtIP-96Hj  (51)  PSEDGAGKDPPNESLETEDVEEHADDSKARSASSVTAPLRFIGGTGGSQR
```

Fig. 1C

```
            101                                                150
PtIP-96Aa  (20) TYNAGASCRILRRIGVWAGGSQLRGIRVWWTGLDSPITYGTPNVGSYQEF
PtIP-96Ab  (20) TYNAGASCRILRRIGVWAGGSQLRGIRVWWTGLDSPITYGTPNVGSYQEF
PtIP-96Ac  (20) TYNAGASCRILRRIGVWAGGSQLRGIRVWWTGLDSPITYGTPNVGSYQEF
PtIP-96Ad  (20) TYNAGASCRILRRIGVWAGGSQLRGIRVWWTGLDSPITYGTPNVGSYQEF
PtIP-96Ae  (20) TYNAGASCRILRRIGVWAGGSQLRGIRVWWTGLDSPITYGTPNVGSYQEF
PtIP-96Af  (20) TYNAGASCRILRRIGVWAGGSQLRGIRVWWTGLDSPITYGTPNVGSYQEF
PtIP-96Ag  (20) TYNAGASCRILRRIGVWAGGSQLRGIRVWWTGLDSPITYGTPNVGSYQEF
PtIP-96Ah  (20) TYNAGASCRILRRIGVWAGGSQLRGIRVWWTGLDSPITYGTPNVGSYQEF
PtIP-96Ca  (22) FYNAGASCRILRRIGVWAGRSFLGGIRSWWTGLDSPITYGTPNSGSYREF
PtIP-96Cb  (22) FYNAGASCRILSRIGVWAGRSFLGGIRSWWTGLDSPITYGTPNSGSYREF
PtIP-96Cc  (20) FYNAGASCRILRRIGVWAGRSFLGGIRSWWTGLDSPITYGTPNSGSYREF
PtIP-96Cd  (22) FYNAGASCRILRRIGVWAGRSFLGGIRSWWTGLDSPITYGTPNSGSYREF
PtIP-96Ce  (20) FYNAGASCRILRRIGVWAGRSFLGGIRSWWTGLDSPITYGTPNSGSYREF
PtIP-96Cf  (20) FYNAGASCRILRRIGVWAGRSFLGGIRSWWTGLDSPITYGTPNSGSYREF
PtIP-96Cg  (20) FYNAGASCRILRRIGVWAGRSFLGGIRSWWTGLDSPITYGTPNSGSYREF
PtIP-96Ch  (22) FYNAGASCRILRRIGVWAGRSFLGGIRSWWTGLDSPITYGTPNSGSYREF
PtIP-96Da  (20) SYNAGTNCRILRRIGVWAGGWFLGGIRAWWTGLDNPVLFGTANVGSYKEF
PtIP-96Db  (20) SYNAGASCRVLRRIGVWAGGWYLGGIRLWWTGLDDSITYGTANSGSYREF
PtIP-96Dc  (20) SYNAGASCRVLRRIGVWAGGWYLGGIRLWWTGLDDSITYGTANSGSYREF
PtIP-96Dd  (20) SYNAGASCRVLRRIGVWAGGWYLGGIRLWWTGLDDSITYGTANSGSYREF
PtIP-96De  (20) TYNAGESCRVLRRIGVWAVDSALRGIRVWWTGLDSPLTYGTANSGFYKEF
PtIP-96Df  (22) TYNAGESCRVLRRIGVWAVDSALRGIRVWWTGLDSPLTYGTANSGFYKEF
PtIP-96Ea  (20) TYDQSRNCKVLTKIGVWAGEWQLRGIRVWMSGSDSPTTFGTA-SGSYSEY
PtIP-96Eb  (20) TYDQSRNCKVLTKIGVWAGEWQLRGIRVWMSGSDSPTTFGTA-SGSYSEY
PtIP-96Ec  (20) TYDQSRNCRILRRIGVWAGEWQLRGIRVWMTGTDTPATFGTA-TGSYSEY
PtIP-96Ed  (20) SYEQSRNCKILRKIGVWAGEWQLRGIRIWMSGSDSSVTYGTANVGSYKEY
PtIP-96Ee  (20) TYDQSRNCRILRRIGVWAGEWQLRGIRVWMTGTDTPATFGTA-TGSYSEY
PtIP-96Ef  (20) SYDQSRNCRILRRIGVWAGEWQLRGIRVWMTGTDTPATFGTA-TGSYSEY
PtIP-96Eg  (20) SYDQSRNCRILRRIGVWAGEWQLRGIRVWMTGTDTPATFGTA-TGSYSEY
PtIP-96Eh  (20) TYDQSRNCRILRRIGVWAGEWQLRGIRVWMTGTDTPATFGTA-TGSYSEY
PtIP-96Ei  (20) TYDQSRNCRILRRIGVWAGEWQLRGIRVWMTGTDTPATFGTA-TGSYSEY
PtIP-96Ej  (20) TYDQSRNCRILRRIGVWAGEWQLRGIRVWMTGTDTPATFGTA-TGSYSEY
PtIP-96Ek  (20) SYDQSRNCRILRRIGVWAGEWQLRGIRVWMTGTDTPATFGTA-TGSYSEY
PtIP-96El  (20) SYDQSRNCRILRRIGVWAGEWQLRGIRVWMTGTDTPATFGTA-TGSYSEY
PtIP-96Em  (20) SYDQSRNCRILRRIGVWAGEWQLRGIRVWMTGTDTPATFGTA-TGSYSEY
PtIP-96En  (20) TYDQSRNCRILRRIGVWAGEWQLRGIRVWMTGTDTPATFGTA-TGSYSEY
PtIP-96Eo  (20) SYNAGASCRILRKIGVWAGGWYLGGIRVWWTGLDTPSTFGTANVGSYKEY
PtIP-96Ep  (20) SYNAGASCRILRKIGVWAGGWYLGGIRVWWTGLDTPSTFGTANVGSYKEY
PtIP-96Eq  (20) SYNAGASCRILRKIGVWAGGWYLGGIRVWWTGLDTPSTFGTANVGSYKEY
PtIP-96Er  (20) TYDQSPNCKIMRKIGVWAGEWQLRGIRIWVSGSDDPTTFGTA-SGSYNEY
PtIP-96Es  (20) TYDQSPNCKIMRKIGVWAGEWQLRGIRIWVSGSDDPTTFGTA-SGSYNEY
PtIP-96Et  (20) TYDQSRNCKVLRKIGVWAGEWQLRGIRVWMSGSDSPATFGTA-SGSYNEY
PtIP-96Eu  (20) TYDQSRNCRILRRIGVWAGEWQLRGIRVWMTGTDTPATFGTA-TGSYSEY
PtIP-96Ev  (20) TYDQSRNCKVLRKIGVWAGEWQLRGIRVWMSGSDSPATFGTA-SGSYNEY
PtIP-96Ha (100) SVRGWTNCRVITRMRVYRARGTIKAYQIWLTDSA-PQTHCVPGNSDFAEY
PtIP-96Hd (100) SVRGWTNCRVITRMRVYRARGTIKAYRIWLTDSG-PETHCVPGNSDFAEY
PtIP-96He (101) SVRGWTNCRVITRMRVYRARGTIKAYRIWLTDSG-PETHCVPGNSDFAEY
PtIP-96Hf (100) SVRGWTNCRVITRMRVYRARGTIKAYQIWLTDSG-PETHCVPGNSDFAEY
PtIP-96Hg (100) SVRGWTNCRVITRMRVYRARGTIKAYQIWLTDSG-PETHCVPGNSDFAEY
PtIP-96Hh (100) SVRGWTNCRVITRMRVYRARGTIKAYQIWLTDSA-PQTHCVPGNSDFAEY
PtIP-96Hi (100) SVRGWTNCRVITRMRVYRARGTIKAYQIWLTDSG-PETHCVPGNSDFAEY
PtIP-96Hj (101) SVRGWTNCRVITRMRVYRARGTIKAYRIWLTDSG-PETHCVPGNSDFAEY
```

Fig. 1D

```
                    151                                                    200
PtIP-96Aa   (70)   TYQDGERITSLSLWGNGAGTRSGGIREYTTTGRRFFHHMTSWGLKQEYPV
PtIP-96Ab   (70)   TYQDGERITSLSLWGNGAGTRSGGIREYTTTGRRFFHHMTSWGLKQEYPV
PtIP-96Ac   (70)   TYQDGERITSLSLWGNGAGTRSGGIREYTTTGRRFFHHMTSWGLKQEYPV
PtIP-96Ad   (70)   TYQDGERITSLSLWGNGAGTRSGGIREYTTTGRRFFHHMTSWGLKQEYPV
PtIP-96Ae   (70)   TYQDGERITSLSLWGNGAGTRSCGIREYTTTGRRFFHHMTSWGLKQEYPV
PtIP-96Af   (70)   TYQDGERITSLSLWGNGAGTRSGGIREYTTTGRRFFHHMTSWGLKQEYPV
PtIP-96Ag   (70)   TYQDGERITSLSLWGNGAGTRSGGIREYTTTGRRFFHHMTSWGLKQEYPV
PtIP-96Ah   (70)   TYQDGERITSLSLWGNGAGTRSGGIREYTTTGRRFFHHMTSWGLKQEYPV
PtIP-96Ca   (72)   TYEDGERITSLSLWGNGIGTRSGGIRENTSTGRQFFHHMTSWSLQQEYAI
PtIP-96Cb   (72)   TYEDGERITSLSLWGNGIGTRSGGIRENTSTGRQFFHHMTSWSLQQEYAI
PtIP-96Cc   (70)   TYEDGERITSLSLWGNGIGTRSGGIRENTSTGRQFFHHMTSWSLQQEYAI
PtIP-96Cd   (72)   TYEDGERITSLSLWGNGIGTRSGGIRENTSTGRQFFHHMTSWSLQQEYAI
PtIP-96Ce   (70)   TYEDGERITSLSLWGNGIGTRSGGIRENTSTGRQFFHHMTSWSLQQEYAI
PtIP-96Cf   (70)   TYEDGERITSLSLWGNGIGTRSGGIRENTSTGRQFFHHMTSWSLQQEYAI
PtIP-96Cg   (70)   TYEDGERITSLSLWGNGIGTRSGGIRENTSTGRQFFHHMTSWSLQQEYAI
PtIP-96Ch   (72)   TYEDGERITSLSLWGNGIGTRSGGIRENTSTGRQFFHHMTSWSLQQEYAI
PtIP-96Da   (70)   TYEDGERITSLSLWGNGAGTRSGGIRERTTGREFHYMTSWGLQQEYPI
PtIP-96Db   (70)   TYEDGERITSLSLWGNGAGTRSGGIRERTTGREFHYMTSWGLQQEYPI
PtIP-96Dc   (70)   TYEDGERITSLSLWGNGAGTRSGGIRERTTGREFHYMTSWGLQQEYPI
PtIP-96Dd   (70)   TYEDGERITSLSLWGNGAGTRSGGIRERTTGREFHYMTSWGLQQEYPI
PtIP-96De   (70)   SYQVGERITSLSLWGNGAGTRSGAIRYISTGREFHYMTSWGLKQEYPI
PtIP-96Df   (72)   SYQVGERITSLSLWGNGAGTRSGAIRYISTGREFHYMTSWGLKQEYPI
PtIP-96Ea   (69)   TYAAGERITRLSLWGNGAGTRSGAIRYTTTGGSFPKMTSWDLKTEYPI
PtIP-96Eb   (69)   TYAAGERITRLSLWGNGAGTRSGAIRYTTTGGSFPKMTSWDLKTEYPI
PtIP-96Ec   (69)   TYADGERITRLSLWGNGAGTRSGGIRYTTTGGSFPKMTSWGLQTEYPI
PtIP-96Ed   (70)   EYKDGERITRLSLWGNGAGTRSGGIRYTTTGGQFFHYMTSWGLKQEYPI
PtIP-96Ee   (69)   TYADGERITRLSLWGNGAGTRSGGIRYTTTGGSFHKMTSWGLQTEYPI
PtIP-96Ef   (69)   TYTDGERITRLSLWGNGAGTRSGGIRYTTTGGSFHKMTSWGLQTEYPI
PtIP-96Eg   (69)   TYADGERITRLSLWGNGAGTRSGGIRYTTTGGSFHKMTSWGLQTEYPI
PtIP-96Eh   (69)   TYADGERITRLSLWGNGAGTRSGGIRYTTTGGSFHKMTSWGLQTEYPI
PtIP-96Ei   (69)   TYADGERITRLSLWGNGAGTRSGGIRYTTTGGSFHKMTSWGLQTEYPI
PtIP-96Ej   (69)   TYADGERITRLSLWGNGAGTRSGGIRYTTTGGSFHKMTSWGLQTEYPI
PtIP-96Ek   (69)   TYTDGERITRLSLWGNGAGTRSGGIRYTTTGGSFHKMTSWGLQTEYPI
PtIP-96El   (69)   TYTDGERITRLSLWGNGAGTRSGGIRYTTTGGSFHKMTSWGLQTEYPI
PtIP-96Em   (69)   TYTDGERITRLSLWGNGAGTRSGGIRYTTTGGSFHKMTSWGLQTEYPI
PtIP-96En   (69)   TYADGERITRLSLWGNGAGTRSGGIRYTTTGGSFHKMTSWGLQTEYPI
PtIP-96Eo   (70)   TYEDGERITSLSLWGNGAGTRSGGIRERTKGSEFHYMTSWGLKQEYPM
PtIP-96Ep   (70)   TYEDGERITSLSLWGNGAGTRSGGIRERTKGSEFHYMTSWGLKQEYPM
PtIP-96Eq   (70)   TYEDGERITSLSLWGNGAGTRSGGIRERTKGSEFHYMTSWGLKQEYPI
PtIP-96Er   (69)   TYADGETITSLSLWGNGAGTRSGAIRYISTGGSFPKMTSWGLKTEYPI
PtIP-96Es   (69)   TYADGETITSLSLWGNGAGTRSGAIRYISTGGSFPKMTSWDLKTEYPI
PtIP-96Et   (69)   TYADGERITRLSLWGNGAGTRSGGIRYTTTGGSFAKMTSWGLQTEYPI
PtIP-96Eu   (69)   TYADGERITRLSLWGNGAGTRSGGIRYTTTGGSFHKMTSWGLQTEYPI
PtIP-96Ev   (69)   TYADGERITRLSLWGNGAGTRSGGIRYTTTGGSFAKMTSWGLQTEYPI
PtIP-96Ha   (149)  TYRTGERLTRLTLWGNGMGTRAGWIEETSLGGRFSYGMSHWSLRTPYPV
PtIP-96Hd   (149)  TYRTGERLTRLTLWGNGIGTRAGWIEETSLGGRFSYGMSHWSLRTPYPV
PtIP-96He   (150)  TYRTGERLTRLTLWGNGIGTRAGWIEETSLGGRFSYGMSHWSLRTPYPV
PtIP-96Hf   (149)  TYRTGERLTRLTLWGNGIGTRAGWIEETSLGGRFSYGMSHWSLRTPYPV
PtIP-96Hg   (149)  TYRTGERLTRLTLWGNGIGTRAGWIEETSLGGRFSYGMSHWSLRTSYPV
PtIP-96Hh   (149)  TYRTGERLTRLTLWGNGMGTRAGWIEETSLGGRFSYGMSHWSLRTPYPV
PtIP-96Hi   (149)  TYRTGERLTRLTLWGNGIGTRAGWIEETSLGGRFSYGMSHWSLRTPYPV
PtIP-96Hj   (150)  TYRTGERLTRLTLWGNGIGTRAGWIEETSLGGRFSYGMSHWSLRTPYPV
```

Fig. 1E

```
                      201                                                250
PtIP-96Aa    (120)    DVVDGVCVGLTGRQGADIDALGFMFLRTMTSARMINVKYPTLGLETAGIV
PtIP-96Ab    (120)    DVVDGVCVGLTGRQGADIDALGFMFLRTMTSARMINVKYPTLGLETAGIV
PtIP-96Ac    (120)    DVVDGVCVGLTGRQGADIDALGFMCLRTMTSARMINVKYPTLGLETAGIV
PtIP-96Ad    (120)    DVVDGVCVGLTGRQGADIDALGFMCLRTMTSARMINVKYPTLGLETAGIV
PtIP-96Ae    (120)    DVVDGVCVGLTGRQGADIDALGFMCLRTMTSARMINVKYPTLGLETAGIV
PtIP-96Af    (120)    DVVDGVCVGLTGRQGADIDALGFMCLRTMTSARMINVKYPTLGLETAGIV
PtIP-96Ag    (120)    DVVDGVCVGLTGRQGADIDALGFMFLRTMTSARMINVKYPTLGLETAGIV
PtIP-96Ah    (120)    DVVDGVCVGLTGRQGADIDALGFMFLRTMTSARMINVKYPTLGLETAGIV
PtIP-96Ca    (122)    DVASGLCVGLWGRHGVEIDSLGFMFLRPIASARMINVRYPTLGLETAGIV
PtIP-96Cb    (122)    DVASGLCVGLWGRHGVEIDSLGFMFLRPIASARMINVRYPTLGLETAGIV
PtIP-96Cc    (120)    DVASGLCVGLWGRHGVEIDSLGFMFLRPIASARMINVRYPTLGLETAGIV
PtIP-96Cd    (122)    DVASGLCVGLWGRHGVEIDSLGFMFLRPIASARMINVRYPTLGLETAGIV
PtIP-96Ce    (120)    DVASGLCVGLWGRHGVEIDSLGFMFLRPIASARMINVRYPTLGLETAGIV
PtIP-96Cf    (120)    DVASVLCVGLWGRHGVEIDSLGFMFLRPIASARMINVRYPTLGLETAGIV
PtIP-96Cg    (120)    DVASGLCVGLWGRHGVEIDSLGFMFLRPIASARMINVRYPTLGLETAGIV
PtIP-96Ch    (122)    DVASGLCVGLWGRHGVEIDSLGFMFLRPIASARMINVRYPTLGLETAGIV
PtIP-96Da    (120)    DVASGLCVGLIGRHGEHIDSLGFMFLRSIASARMINVSYPTLGLETAGIV
PtIP-96Db    (120)    DVASGLCVGVIGRHGDHIDSLGFMFLRTIASARMINVSYPTLDLETAGIV
PtIP-96Dc    (120)    DVASGLCVGVIGRHGDHIDSLGFMFLRTIASARMINVSYPTLDLETAGIV
PtIP-96Dd    (120)    DVASGLCVGVIGRHGDHIDSLGFMFLRTIASARMINVSYPTLDLETAGIV
PtIP-96De    (120)    DVVDGLCVGVTGRHGTDIDALGFMFLRTMTSARMVDVTYPTLGFDTAGIA
PtIP-96Df    (122)    DVVDGLCVGVTGRHGTDIDALGFMFLRTMTSARMVDVTYPTLGFDTAGIA
PtIP-96Ea    (119)    DVASGLCVGIIGRASADIDSLGFMFLRTIASSRMINVSYPTLGLEQAGII
PtIP-96Eb    (119)    DVASGLCVGIIGRASADIDSLGFMFLRTIASSRMINVSYPTLGLEQAGII
PtIP-96Ec    (119)    DVASGLCVGIMGRANVDVDSLGVLFLRTIASARMINVSYPTLGLEQAGII
PtIP-96Ed    (120)    DVASGLCVGILGRANADIDALGFYFLKSIASARMINVSYPTLSLETAGII
PtIP-96Ee    (119)    DVASGLCVGIMGRANVDVDSLGVLFLRTIASARMINVSYPTLGLEQAGII
PtIP-96Ef    (119)    DVASGLCVGIMGRANVDVDSLGVLFLRTIASARMINVSYPTLGLEQAGII
PtIP-96Eg    (119)    DVASGLCVGIMGRANVDVDSLGVLFLRTIASARMINVSYPTLGLEQAGII
PtIP-96Eh    (119)    DVASGLCVGIMGRANVDVDSLGVLFLRTIASARMINVSYPTLGLEQAGII
PtIP-96Ei    (119)    DVASGLCVGIMGRANVDVDSLGVLFLRTIASARMINVSYPTLGLEQAGII
PtIP-96Ej    (119)    DVASGLCVGIMGRANVDVDSLGVLFLRTIASARMINVSYPTLGLEQAGII
PtIP-96Ek    (119)    DVASGLCVGIMGRANVDVDSLGVLFLRTIASARMINVSYPTLGLEQAGII
PtIP-96El    (119)    DVASGLCVGIMGRANVDVDSLGVLFLRTIASARMINVSYPTLGLEQAGII
PtIP-96Em    (119)    DVASGLCVGIMGRANVDVDSLGVLFLRTIASARMINVSYPTLGLEQAGII
PtIP-96En    (119)    DVASGLCVGIMGRANVDVDSLGVLFLRTIASARMINVSYPTLGLEQAGII
PtIP-96Eo    (120)    DVASGLCVGVIGRHGEHIDSLGFMFLRSIASARMINVSYPTLALETAGIV
PtIP-96Ep    (120)    DVASGLCVGVIGRHGEHIDSLGFMFLRSIASARMINVSYPTLALETAGIV
PtIP-96Eq    (120)    DVAAGLCVGVIGRHGEHIDSLGFMFLRSIASARMINVSYPTLALETAGIV
PtIP-96Er    (119)    DVASGLCVGIMGRAGDDIDALGFLFLRTITSARMINVTYPTLGLEEAAII
PtIP-96Es    (119)    DVASGLCVGIMGRAGDDIDALGFLFLRTITSARMINVTYPTLGLEEAAII
PtIP-96Et    (119)    DVASGLCVGILGRANVDIDSLGFMFLRTIASARMINVSYPTLGLEQAGIV
PtIP-96Eu    (119)    DVASGLCVGIMGRANVDVDSLGVLFLRTIASARMINVSYPTLGLEQAGII
PtIP-96Ev    (119)    DVASGLCVGILGRANVDIDSLGFMFLRTIASARMINVSYPTLGLEQAGIV
PtIP-96Ha    (199)    DVGSGILVGYIFNAGEDVDAHGFWFLNHIEQAELTNVRYPTLGFDTAGIV
PtIP-96Hd    (199)    DVGSGILVGYIFNAGEDVDAHGFWFLNHIQQAELTNVRYPTLGFDTAGIV
PtIP-96He    (200)    DVGSGILVGYIFNAGEEVDAHGFWFLNHIQQAELTNVRYPTLGFDTAGIV
PtIP-96Hf    (199)    DVGSGILVGYIFNAGEDVDAHGFWFLNHIEQAELTNVRYPTLGFDTAGIV
PtIP-96Hg    (199)    DVGSGILVGYIFNAGEDVDAHGFWFLNHIEQAELTNVRYPTLGFDTAGIV
PtIP-96Hh    (199)    DVGSGILVGYIFNAGEDVDAHGFWFLNHIEQAELTNVRYPTLGFDTAGIV
PtIP-96Hi    (199)    DVGSGILVGYIFNAGEDVDAHGFWFLNHIEQAELTNVRYPTFGFDTAGIV
PtIP-96Hj    (200)    DVGSGILVGYIFNAGEEVDAHGFWFLNHIQQAELTNVRYPTLGFDTAGIV
```

Fig. 1F

```
                  251                                                  300
PtIP-96Aa  (170)  PVTLDFMSDSNNASSISKTWSFQGSREVTVSSSWSTTTGIELHASITVSA
PtIP-96Ab  (170)  PVTLDFMSDSNNAGSISKTWSFQGSREVTVSSSWSTTTGIELHASITVSA
PtIP-96Ac  (170)  TVTLDFMSDSNNASSISKTWSFQGSREVTVSSSWSTTTGIELHASITVSA
PtIP-96Ad  (170)  PVTLDFMSDSNNASSISKTWSFQGSREVTVSSSWSTTTGIELHASITVSA
PtIP-96Ae  (170)  PVTLDFMSDSNNASSISKTWSFQGSREVTVSSSWSTTTGIELHASITVSA
PtIP-96Af  (170)  PVTLDFMSDSNNASSISKTWSFQGSREVTVSSSWSTTTGIELHASITVSA
PtIP-96Ag  (170)  PVTLDFMSDSNNASSISKTWSFQGSREVTVSSSWSTTTGIELHASITVSA
PtIP-96Ah  (170)  PVTLDFMSDSNNAGSISKTWSFQGSREVTVSSSWSTTTGIELHASITVSA
PtIP-96Ca  (172)  PVTLDSMSDSNNSASMPKNWSFQGSRDVTISSSWSITAGIELHASINVSA
PtIP-96Cb  (172)  PVTLDSMSDSNNSASMPKNWSFQGSRDVTISSSWSITAGIELHASINVSA
PtIP-96Cc  (170)  PVTLDSMSDSNNSASMPKNWSFQGSRDVTISSSWSITAGIELHASINVSA
PtIP-96Cd  (172)  PVTLDSMSDSNNSASMPKNWSFQGSRDVTISSSWSITAGIELHASINVSA
PtIP-96Ce  (170)  PVTLDSMSDSNNSASMPKNWSFQGSRDVTISSSWSITAGIELHASINVSA
PtIP-96Cf  (170)  PVTLDSMSDSNNSASMPKNWSFQGSRDVTISSSWSITAGIELHASINVSA
PtIP-96Cg  (170)  PVTLDSMSDSNNSASMPKNWSFQGSRDVTISSSWNITAGIELHASINVSA
PtIP-96Ch  (172)  PVPLDSLSHSNNSASLPKNWPFQGSPKGTISSSWSILAGIELPASINVSA
PtIP-96Da  (170)  PVTLDSMSNNNNSGSLPSNWAFRGSREVTMSSTWSVTAGIELHASVTVTA
PtIP-96Db  (170)  PVTLDSMSDSNNAGTISKNWTFGGSRSVTISSSWAITAGIELHASITVTA
PtIP-96Dc  (170)  PVTLDSMSDSNNAGTISKNWTFGGSRSVTISSSWAITAGIELHASITVTA
PtIP-96Dd  (170)  PVTLDSMSDSNNAGTISKNWTFGGSRSVTISSSWAITAGIELHASITVTA
PtIP-96De  (170)  PITLDSYSDANQSGSISKNWSFEGSREVTVSSSWSVTAGIEFHASVTVSA
PtIP-96Df  (172)  PITLDSYSDANQSGSISKNWSFEGSREVTVSSSWSVTAGIEFHASVTVSA
PtIP-96Ea  (169)  PVTLDSYNDSNNAGSISKNWTFSGSRTVTISSSWTLTSGIEAHASVTVQA
PtIP-96Eb  (169)  PVTLDSYNDSNNAGSISKNWTFSGSRTVTISSSWTLTSGIEAHASVTVQA
PtIP-96Ec  (169)  PVTLDSFNDSNNAGTISKNWTFSGSRTVTISSSWSLTSGIETHASVSVQA
PtIP-96Ed  (170)  PVTLDSYSDSNNAGSISKNWTFSGSREVKISSSWTVTTGIEYHASITVQA
PtIP-96Ee  (169)  PVTLDSFNDSNNAGTISKNWTFSGSRTVTISSSWSLTSGIETHASVSVQA
PtIP-96Ef  (169)  PVTLDSYNDSNNAGTISKNWTFSGSRTVTISSSWSLTSGIETHASVSVQA
PtIP-96Eg  (169)  PVTLDSFNDSNNAGTISKNWTFSGSRTVTISSSWSLTSGIETHASVSVQA
PtIP-96Eh  (169)  PVTLDSFNDSNNAGTISKNWTFSGSRTVTISSSWSLTSGIETHASVSVQA
PtIP-96Ei  (169)  PVTLDSFNDSNNAGTISKNWTFSGSRTVTISSSWSLTSGIETHASVSVQA
PtIP-96Ej  (169)  PVTLDSFNDSNNAGTISKNWTFSGSRTVTISSSWSLTSGIETHASVSVQA
PtIP-96Ek  (169)  PVTLDSYNDSNNAGTISKNWTFSGSRTVTISSSWSLTSGIETHASVSVQA
PtIP-96El  (169)  PVTLDSFNDSNNAGTISKNWTFSGSRTVTISSSWSLTSGIETHASVSVQA
PtIP-96Em  (169)  PVTLDSYNDSNNAGTISKNWTFSGSRTVTISSSWSLTSGIETHASVSVQA
PtIP-96En  (169)  PVTLDSFNDSNNAGTISKNWTFSGSRTVTISSSWSLTSGIETHASVSVQA
PtIP-96Eo  (170)  PVTLDSLTDNNAGTIAKNWALRGSREVTMSSTWSVTSGIELYASVTVTA
PtIP-96Ep  (170)  PVTLDSLTDNNAGTIAKNWALRGSREVTMSSTWSVTSGIELYASVTVTA
PtIP-96Eq  (170)  PVTLDSLTDSNNAGTISKNWALRGSREVTMSSTWSVTSGIELYASVTVTA
PtIP-96Er  (169)  PVTLDSYNDANNAGTISKSWTFSGSRTVTVSESWTLTAGIEVHATVSVQA
PtIP-96Es  (169)  PVTLDSYNDANNAGTISKSWTFSGSRTVTVSESWTLTAGIEVHATVSVQA
PtIP-96Et  (169)  PVTLDSYNDSNNAGTISKNWTFSGSRTVTISSSWTLTSGIEAHATVSVQA
PtIP-96Eu  (169)  PVTLDSFNDSNNAGTISKNWTFSGSRTVTISSSWSLTSGIETHASVSVQA
PtIP-96Ev  (169)  PVTLDSYNDSNNAGTISKNWTFSGSRTVTISSSWTLTSGIEAHATVSVQA
PtIP-96Ha  (249)  PTALDTFRFRNNS-STPRDWDFSRNMSRSTERTWSITVDLTVHASITVSA
PtIP-96Hd  (249)  PTALDTFRFRNNS-STPRDWDFSRNMSRSTERTWSITVDLTVHASITVSA
PtIP-96He  (250)  PTALDTFRFRNNS-STPRDWDFSRNMSRSTERTWSITVDLTVHASITVSA
PtIP-96Hf  (249)  PTALDTFRFRNNS-STPRDWDFSRNMSRSTERTWSITVDLTVHASITVSA
PtIP-96Hg  (249)  PTALDTFRFRNNS-STPRDWDFSRNMSRSTERTWSITVDLTVHASITVSA
PtIP-96Hh  (249)  PTALDTFRFRNNS-STPRDWDFSRNMSRSTERTWSITVDLTVHAIITVSA
PtIP-96Hi  (249)  PTALDTFRFRNNS-STPRDWDFSRNMSRSTERTWSITVDLTVHASITVSA
PtIP-96Hj  (250)  PTALDTFRFRNNS-STPRDWDFSRNMSRSTERTWSITVDLTVHASITVSA
```

Fig. 1G

```
                   301                                                350
PtIP-96Aa  (220)   GIPLVANVEGQYGWAISTSSTYTINHSETRTLQWQNSGVLEPGQWISLQA
PtIP-96Ab  (220)   GIPLVANVEGQYGWAISTSSTYTINHSETRTLQWQNSGVLEPGQWISLQA
PtIP-96Ac  (220)   GIPLVANVEGQYGWAISTSSTYTINHSETRTIQWQNSGVLEPGQWISLQA
PtIP-96Ad  (220)   GIPLVANVEGQYGWAISTSSTYTINHSETRTLQWQNSGVLEPGQWISLQA
PtIP-96Ae  (220)   GIPLVANVEGQYGWAISTSSTYTINHSETRTLQWQNSGVLEPGQWISLQA
PtIP-96Af  (220)   GIPLVANVEGQYGWAISTSSTYTINHSETRTLQWQNSGVLEPGQWISLQA
PtIP-96Ag  (220)   GIPLVANVEGQYGWGISTSSTYTINHSETRTLQWQNSGVLEPGQWISLQA
PtIP-96Ah  (220)   GIPLVANVEGQYGWAISTSSTYTINHSETRTLQWQNSGVLEPGQWISLQA
PtIP-96Ca  (222)   GVPMLANVDVQYGWTISSTSSYSLSHSETRSLSWQNSGVLEPGQWVSLQA
PtIP-96Cb  (222)   GVPMLANVDVQYGWTISSTSSYSLSHSETRSLSWQNSGVLEPGQWVSLQA
PtIP-96Cc  (220)   GVPMLANVDVQYGWTISSTSSYSLSHSETRSLSWQNSGVLEPGQWVSLQA
PtIP-96Cd  (222)   GVPMLANVDVQYGWTISSTSSYSLSHSETRSLSWQNSGVLEPGQWVSLQA
PtIP-96Ce  (220)   GVPMLANVDVQYGWTISSTSSYSLSHSETRSLSWQNSGVLEPGQWVSLQA
PtIP-96Cf  (220)   GVPMLANVDVQYGWTISSTSSYSLSHSETRSLSWQNSGVLEPGQWVSLQA
PtIP-96Cg  (220)   GVPMLANVDVQYGWTISSTSSYSLSHSETRSLSWQNSGVLEPGQWVSLQA
PtIP-96Ch  (222)   GVPMLANVDVQYGWTISSTSSYSLSHSETRSLSWQNSGVLEPGQWVSLQA
PtIP-96Da  (220)   GIPTVAEVQGQYGWAVSTSTFSITHTETETRSLQWEVSGVLQPGEWISLQA
PtIP-96Db  (220)   GIPTVAEVQGEYGWSISSSSTYTISHEETRTLSWENSGVLQPGEWISLQA
PtIP-96Dc  (220)   GIPTVAEVQGEYGWSISSSSTYTISHEETRTLSWENSGVLQPGEWISLQA
PtIP-96Dd  (220)   GIPTVAEVQGEYGWSISSSSTYTISHEETRTLSWENSGVLQPGEWISLQA
PtIP-96De  (220)   GIPLVLDVDGEFGWAISASATYTINSSETRTLKWNNSGVLEPGQWISLQA
PtIP-96Df  (222)   GIPLVLDVDGEFGWAISASATYTINSSETRTLKWNNSGVLEPGQWISLQA
PtIP-96Ea  (219)   GIPSVAEVSGEFGWSVSVSGSYTSTQEESRTLTWNQSGTLEPGQWISIQA
PtIP-96Eb  (219)   GLPSVAEVSGEFGWSVSVSGSYTSTQEESRTLTWNQSGTLEPGQWISIQA
PtIP-96Ec  (219)   GIPMVAEVSGEFGWSVSVSGTYATTQEESRTLTWNQSGTLEPGQWISLQA
PtIP-96Ed  (220)   GIPLVAEVSGEFGWSVSVTGSYTITHEETRTLSWDQSGTLQPGQWISIQA
PtIP-96Ee  (219)   GIPMVAEVSGEYGWSVSVSGTYATTQEESRTLAWDQSGTLQPGQWISLQA
PtIP-96Ef  (219)   GIPMVAEVSGEFGWSVSVSGTYATTQEESRTLTWNQSGTLEPGQWISLQA
PtIP-96Eg  (219)   GIPMVAEVSGEYGWSVSVSGTYATTQEESRTLAWDQSGTLQPGQWISLQA
PtIP-96Eh  (219)   GIPMVAEVSGEYGWSVSVSGTYATTQEESRTLAWDQSGTLQPGQWISLQA
PtIP-96Ei  (219)   GIPMVAEVSGEYGWSVSVSGTYATTQEESRTLAWDQSGTLQPGQWISLQA
PtIP-96Ej  (219)   GIPMVAEVSGEYGWSVSVSGTYATTQEESRTLAWDQSGTLQPGQWISLQA
PtIP-96Ek  (219)   GIPMVAEVSGEYGWSVSVSGTYATTQEESRTLAWDQSGTLQPGQWISLQA
PtIP-96El  (219)   GIPMVAEVSGEYGWSVSVSGTYATTQEESRTLAWDQSGTLQPGQWISLQA
PtIP-96Em  (219)   GIPMVAEVSGEFGWSVSVSGTYATTQEESRTLTWNQSGTLEPGQWISLQA
PtIP-96En  (219)   GIPMVAEVSGEYGWSVSVSGTYATTQEESRTLAWDQSGTLQPGQWISLQA
PtIP-96Eo  (220)   GVPTVAEVQGEFGWKVSTSATYSITYQETRSLQWEQSGVLQPGEWISIQA
PtIP-96Ep  (220)   GVPTVAEVQGEFGWKVSTSATYSITYQETRSLQWEQSGVLQPGEWISIQA
PtIP-96Eq  (220)   GVPTVAEVQGEFGWRVSTSATYSITHTETRTLQWEQSGVLQPGEWISLQA
PtIP-96Er  (219)   GIPLVAEVNGEYGWSLSTTGSYATTQEESRTLSWNQSGTLEPGQWISIQA
PtIP-96Es  (219)   GIPLVAEVNGEYGWSLSTTGSYATTQEESRTLTWNQSGTLEPGQWISLQA
PtIP-96Et  (219)   GIPLVAEVSGEFGWSLSVTGSYTITQEESRTLTWNQSGTLEPGQWISLQA
PtIP-96Eu  (219)   GIPMVAEVSGEYGWSVSVSGTYATTQEESRTLAWDQSGTLQPGQWISLQA
PtIP-96Ev  (219)   GIPLVAEVSGEFGWSLSVTGSYTTTQEESRTLTWNQSGTLEPGQWISLQA
PtIP-96Ha  (298)   GFPGIANVSGQYGWEIGVTGHFETTETSEHDLSWSVGGRVQPGDVVDLTA
PtIP-96Hd  (298)   GFPGIANVSGQYGWEIGATGHFETTETSEHDLSWSVSGRVQPGEFVDLTA
PtIP-96He  (299)   GFPGIANVSGQYGWEIGATGHFETTETSEHDLSWSVSGRVQPGDVVDLTA
PtIP-96Hf  (298)   GFPGIANVSGQYGWEIGATGHFETTETSEHDLSWSVSGIVQPGDVVDLTA
PtIP-96Hg  (298)   GFPGIANVSGQYGWEIGATGHFETTETSEHDLSWSVSGIVQPGDVVDLTA
PtIP-96Hh  (298)   GFPGIANVSGQYGWEIGATGHFETTETSEHDLSWSVSGRVQPGDVVDLTA
PtIP-96Hi  (298)   GFPGIANVSGQYGWEIGATGHFETTETSEHDLSWSVSGIVQPGDVVDLTA
PtIP-96Hj  (299)   GFPGIANVSGQYGWEIGATGHFETTETSEHDLSWSVSGRVQPGDVVDLTA
```

Fig. 1H

```
              351                                                         400
PtIP-96Aa (270) LTRRGTITLPYQATMQITLQNGTVETYPITAQMAGVDYISVEIVSQGTRD
PtIP-96Ab (270) LTRRGTITLPYQATMQITLQNGTVETYPITAQMAGVDYISVEIVSQGTRD
PtIP-96Ac (270) LTRRGTITLPYQATMQITLQNGTVETYPITAQMAGVDYISVEIVSQGTRD
PtIP-96Ad (270) LTRRGTITLPYQATMQITLQNGTVETYPITAQMAGVDYISVEIVSQGTRD
PtIP-96Ae (270) LTRRGTITLPYQATMQITLQNGTVETYPITAQMSGVDYISVEIVSQGTRD
PtIP-96Af (270) LTRRGTITLPYQATMQITLQNGTVETYPITAQMAGVDYISVEIVSQGTRD
PtIP-96Ag (270) LTRRGTITLPYQATMQITLQNGTVETYPITAQMAGVDYISVEIVSQGTRD
PtIP-96Ah (270) LTRRGTITLPYQATMQITLQNGTVETYPITAQMAGVDYISVEIVSQGTRD
PtIP-96Ca (272) LTRRGTITLPYQATMQITLQNGVVETYPIAAQMAGVDFISVEIVSLGTKD
PtIP-96Cb (272) LTRRGTITLPYQATMQITLQNGVVETYPIAAQMAGVDFISVEIVSLGTKD
PtIP-96Cc (270) LTRRGTITLPYQATMQITLQNGVVETYPIAAQMAGVDFISVEIVSLGTKD
PtIP-96Cd (272) LTRRGTITLPYQATMQITLQNGVVETYPIAAQMAGVDFISVEIVSLGTKD
PtIP-96Ce (270) LTRRGTITLPYQATMQITLQNGVVETYPIAAQMAGVDFISVEIVSLGTKD
PtIP-96Cf (270) LTRRGTITLPYQATMQITLQNGVVETYPIAAQMAGVDFISVEIVSLGTKD
PtIP-96Cg (270) LTRRGTITLPYQATMQITLQNGVVETYPIAAQMAGVDFISVEIVSLGTKD
PtIP-96Ch (272) LTRRGTITLPYQATMQITLQNGVVETYPIAAQMAGVDFISVEIVSLGTKD
PtIP-96Da (270) LTRRGVISLPYQATMQITLQNGAVETYPITAMMAGVDYISVELVHLLDWP
PtIP-96Db (270) LTRRGTISLPYQATMQITLQNGALETYPITAIMAGVDYINVQIVSTGTRH
PtIP-96Dc (270) LTRRGTISLPYQATMQITLQNGALETYPITAIMAGVDYINVQIVSTGTRH
PtIP-96Dd (270) LTRRGTISLPYQATMQITLQNGALETYPITAIMAGVDYINVQIVSTGTRH
PtIP-96De (270) VTRKGTINIPYQANMQITLQNGVIETYALAGQMAGVDYIDVQVVNDGTKN
PtIP-96Df (272) VTRKGTINIPYQANMQITLQNGVIETYALAGQMAGVDYIDVQVVNDGTKN
PtIP-96Ea (269) TTRRGTITLPYQGTMEITLQSGTVEQYPISSMYSGVDYISVDITNTGTRA
PtIP-96Eb (269) TTRRGTITLPYQGTMEITLQSGTVEQYPISSMYSGVDYISVDITNTGTRA
PtIP-96Ec (269) TTRRGTITLPFQATMEITLLSGTIEQYAISSMYSGVDYISVDITNTGTRA
PtIP-96Ed (270) TTRRGNITVPYQGTMEITLQSGQVESYPISSMYSGVDYISVEITNTGTKA
PtIP-96Ee (269) TTRRGTITLPFQATMEITLQSGTIEQYAISSMYSGVDYISVDITNTGSRA
PtIP-96Ef (269) TTRRGTITLPFQATMEITLLSGTIEQYAISSMYSGVDYISVDITNTGTRA
PtIP-96Eg (269) TTRRGTITLPFQATMEITLQSGTIEQYAISSMYSGVDYISVDITNTGSRA
PtIP-96Eh (269) TTQRGTITLPFQATMEITLQSGTIEQYAISSMYSGVDYISVDITNTGSRA
PtIP-96Ei (269) TTRRGTITLPFQATMEITLQSGTIEQYAISSMYSGVDYISVDITNTGSRA
PtIP-96Ej (269) TTRRGTITLPFQATMEITLLSGTIEQYAISSMYSGVDYISVDITNTGSRA
PtIP-96Ek (269) TTRRGTITLPFQATMEITLQSGTIEQYAISSMYSGVDYISVDITNTGSRA
PtIP-96El (269) TTRRGTITLPFQATMEITLQSGTIEQYAISSMYSGVDYISVDITNTGSRA
PtIP-96Em (269) TTRRGTITLPFQATMEITLLSGTIEQYAISSMYSGVDYISVDITNTGSRA
PtIP-96En (269) TTRRGTITLPFQATMEITLQSGTIEQVISSMYSGVDYISVDITNTGSRA
PtIP-96Eo (270) LTRRGTISLPYQGTMQITLQSGTVETYPISALMAGVDYISVEIVNLGTYV
PtIP-96Ep (270) LTRRGTISLPYQGTMQITLQSGTVETYPISALMAGVDYISVEIVNLGTYV
PtIP-96Eq (270) LTRRGNISLPYQGTMQITLQSGTVETYPISALMAGVDYINVEIVNLGTFV
PtIP-96Er (269) TTRRGTITLPYQGTMEITLQSGTKEQYPISSTYTGVDYISVDIVSIGSRV
PtIP-96Es (269) TTRRGTITLPYQGTMEITLQSGTKEQYPISSTYTGVDYISVDIVSIGSRV
PtIP-96Et (269) TTRRGTITLPYQGTMEITLQSGTVEQYPISSMYAGVDYISVDITNTGTRA
PtIP-96Eu (269) TTRRGTITLPFQATMEITLQSGTIEQYAISSMYSGVDYISVDITNTGSRA
PtIP-96Ev (269) TTRRGTITLPYQGTMEITLQSGTVEQYPISSMYAGVDYISVDITNTGTRA
PtIP-96Ha (348) LTRTGTLNIPYEGTMVVRMRNGASESYAVRGTYRGLSYIGTKINDNST--
PtIP-96Hd (348) LTRTGTLNIPYEGTMVVRMRNGASESYAVRGTYRGLSYIGTKINDNST--
PtIP-96He (349) LTRTGTLNIPYEGTMVVRMRNGASESYAVRGTYRGLSYIGTKINDNST--
PtIP-96Hf (348) LTRTGTLNIPYEGTMVVRMRNGASESYAVRGTYRGLSYIGTKINDNST--
PtIP-96Hg (348) LTRTGTLNIPYEGTMVVRMRNGASESYAVRGTYRGLSYIGTKINDNST--
PtIP-96Hh (348) LTRTGTLNIPYEGTMVVRMRNGASESYAVRGTYRGLSYIGTKINDNST--
PtIP-96Hi (348) LTRTGTLNIPYEGTMVVRMRNGASESYAVRGTYRGLSYIGTKINDNST--
PtIP-96Hj (349) LTRTGTLNIPYEGTMVVRMRNGASESYAVRGTYRGLSYIDTKINDNST-
```

Fig. 1I

```
                    401                                              450
PtIP-96Aa  (320)  LGSDHLAINKDVRYIAAANGAAVGTTTTNAPPHYVHPIRGAPIVEPVKFS
PtIP-96Ab  (320)  LGSDHLAINKDVRYIAAANGGAVGTTTTNAPPHYVHPIRGAPIVEPVKFS
PtIP-96Ac  (320)  LGSDHLAINKDVRYIAAANGAAVGTTTTNAPPHYVHPIRGAPIVEPVKFS
PtIP-96Ad  (320)  LGSDHLAINKDVRYIAAANGAAVGTTTTNAPPHYVHPIRGAPIVETVKFS
PtIP-96Ae  (320)  LGSDHLAINKDVRYIAAANGAAVGTTTTNAPPHYVHPIRGAPIVEPVKFS
PtIP-96Af  (320)  LGSDHLAINKDVRYIAAANGAAVGTTTTNAPPHYVHPIRGAPIVEPVKFS
PtIP-96Ag  (320)  LGSDHLAINKDVRYIAAANGAAVGTTTTNAPPHYVHPIRGAPIVEPVKFS
PtIP-96Ah  (320)  LGSDHLAINKDVHYIAAANGAAVGTTTTNAPPHYVHPIRGAPIVEPVKFS
PtIP-96Ca  (322)  VGSGHSATNKDVGRIVAN-----GTATTSAPPQYVR--------P-VKLS
PtIP-96Cb  (322)  VGSGHSATNKDVGRIVAN-----GTATTSAPPQYVR--------P-VKLS
PtIP-96Cc  (320)  VGSGHSATNKDVGRIVAN-----GTATTSAPPQYVR--------P-VKLS
PtIP-96Cd  (322)  VGSGHSATNKDVGRIVAN-----GTATTSAPPQYVR--------P-VKLS
PtIP-96Ce  (320)  VGSGHSATNKDVGRIVAN-----GTATTSAPPQYVR--------P-VKLS
PtIP-96Cf  (320)  VGSGHSATNKDVGRIVAN-----GTATTSAPPQYVR--------P-VKLS
PtIP-96Cg  (320)  VGSGHSATNKDVGRIVAN-----GTATTSAPPQYVR--------P-VKLS
PtIP-96Ch  (322)  VGSGHSATNKDVGRIVAN-----GTATTSAPPQYVR--------P-VKLS
PtIP-96Da  (320)  T-------------------------------------------------
PtIP-96Db  (320)  LDYDHVRSAGGRR---------LVSAISNKGSLPTAATTSVIAPPRYVHP
PtIP-96Dc  (320)  LDYDHVRSAGGRR---------LVSAISNKGSLPTAATTSVIAPPRYVHP
PtIP-96Dd  (320)  LDYDHVRSAGGRR---------LVSAISNKGSLPTAATTSVIAPPRYVHP
PtIP-96De  (320)  AGHVSTTAAKGTTGTTTA-------ARMGALANSVRHVRAASIPRPVKFS
PtIP-96Df  (322)  AGHVSTTAAKGTTGTTTA-------ARMGALANSVRHVRAASIPRPVKFS
PtIP-96Ea  (319)  LKQVEVQATDQQSQ------------------------------------
PtIP-96Eb  (319)  LKQVEVQATDQQSQ------------------------------------
PtIP-96Ec  (319)  SDHVEVEATEQQVQG-----------------------------------
PtIP-96Ed  (320)  ANQVDDQAADPSLTTTTD--------------------------------
PtIP-96Ee  (319)  LDQVEVKTTEQQVEG-----------------------------------
PtIP-96Ef  (319)  SDHVEVEATEQQVQG-----------------------------------
PtIP-96Eg  (319)  LDQVEVKTTEQQVEG-----------------------------------
PtIP-96Eh  (319)  LDQVEVKTTEQQVEG-----------------------------------
PtIP-96Ei  (319)  LDQVEVKTTEQQVEG-----------------------------------
PtIP-96Ej  (319)  LDQVEVKTTEQQVEG-----------------------------------
PtIP-96Ek  (319)  LDQVEVKTTEQQVEG-----------------------------------
PtIP-96El  (319)  LDQVEVKTTEQQVEG-----------------------------------
PtIP-96Em  (319)  LDQVEVKTTEQQVEG-----------------------------------
PtIP-96En  (319)  LDQVEVKTTEQQVEG-----------------------------------
PtIP-96Eo  (320)  SSNNISGEAIPRQLPVSSF-SLPATNIANGAAWAGANANGALAAGTRALI
PtIP-96Ep  (320)  SSNNISGEAIPRQLPVSSF-SLPATNIANGAAWAGANANGALAAGTRALI
PtIP-96Eq  (320)  ASNNISAGEFIPRQPISLP-AATTNTNANGAWTN----AGALAGTTRAVI
PtIP-96Er  (319)  LNQAKVEATNKKAL------------------------------------
PtIP-96Es  (319)  LNQAKVEATNKKAL------------------------------------
PtIP-96Et  (319)  LNRVETEAIDQQAR------------------------------------
PtIP-96Eu  (319)  LDQVEVKTTEQQVEG-----------------------------------
PtIP-96Ev  (319)  LNRVETEAIDQQAR------------------------------------
PtIP-96Ha  (396)  --------------------------------------------------
PtIP-96Hd  (396)  --------------------------------------------------
PtIP-96He  (397)  --------------------------------------------------
PtIP-96Hf  (396)  --------------------------------------------------
PtIP-96Hg  (396)  --------------------------------------------------
PtIP-96Hh  (396)  --------------------------------------------------
PtIP-96Hi  (396)  --------------------------------------------------
PtIP-96Hj  (397)  --------------------------------------------------
```

Fig. 1J

```
                    451                                                    500
PtIP-96Aa   (370)   VGATYINDTDN-------------------------------ITQEVDTT
PtIP-96Ab   (370)   VGATYINDTDN-------------------------------ITQEVDTT
PtIP-96Ac   (370)   VGATYINDTDN-------------------------------ITQEVDTT
PtIP-96Ad   (370)   VGATYINDTDN-------------------------------ITQEVDTT
PtIP-96Ae   (370)   VGATYINDTDN-------------------------------ITQEVDTT
PtIP-96Af   (370)   VGATYINDTDN-------------------------------ITQEVDTT
PtIP-96Ag   (370)   VGATYINDTDN-------------------------------ITQEVDTT
PtIP-96Ah   (370)   VGATYINDTDN-------------------------------ITQEVDTT
PtIP-96Ca   (358)   VGATYINDTNN-------------------------------ITQEVDST
PtIP-96Cb   (358)   VGATYINDTNN-------------------------------ITQEVDST
PtIP-96Cc   (356)   VGATYINDTNN-------------------------------ITQEVDST
PtIP-96Cd   (358)   VGATYINDTNN-------------------------------ITQEVDST
PtIP-96Ce   (356)   VGATYINDTNN-------------------------------ITQEVDST
PtIP-96Cf   (356)   VGATYINDTNN-------------------------------ITQEVDST
PtIP-96Cg   (356)   VGATYINDTNN-------------------------------ITQEVDST
PtIP-96Ch   (358)   VGATYINDTNN-------------------------------ITQEVDST
PtIP-96Da   (321)   --------------------------------------------------
PtIP-96Db   (361)   VNIPAVPYTS------------VIEP--VKVVATRAAPTSINDDNIKQE
PtIP-96Dc   (361)   VNIPAVLYTS------------VIEP--VKVVATRAAPTSINDDNIKQE
PtIP-96Dd   (361)   VNIPAVPYTS------------VIEP--VKVVATRAAPTSINDDNIKQE
PtIP-96De   (363)   AGATYINDTTNN------------------------------ITQEVHSS
PtIP-96Df   (365)   AGATYINDTTNN------------------------------ITQEVHSS
PtIP-96Ea   (333)   ------------------------------------------EGDHNVQ
PtIP-96Eb   (333)   ------------------------------------------EGDHNVQ
PtIP-96Ec   (334)   ------------------------------------------VKDQSVQ
PtIP-96Ed   (338)   ------T--K--------------------------------DGEVLEQ
PtIP-96Ee   (334)   ------------------------------------------VEDQNVQ
PtIP-96Ef   (334)   ------------------------------------------VKDQSVQ
PtIP-96Eg   (334)   ------------------------------------------VEDQNVQ
PtIP-96Eh   (334)   ------------------------------------------VEDQNVQ
PtIP-96Ei   (334)   ------------------------------------------VEDQNVQ
PtIP-96Ej   (334)   ------------------------------------------VEDQNVQ
PtIP-96Ek   (334)   ------------------------------------------VEDQNVQ
PtIP-96El   (334)   ------------------------------------------VEDQNVQ
PtIP-96Em   (334)   ------------------------------------------VEDQNVQ
PtIP-96En   (334)   ------------------------------------------VEDQNVQ
PtIP-96Eo   (369)   NGEPIKPHYSNVLPHTLTTPQDQDHQLSVIKPHYKNILELVHLLDWPT--
PtIP-96Ep   (369)   NGEPIKPHYSNVLPHTLTTPQDQDHQLSVIKPHYKNILDGDNTNYQPQPQ
PtIP-96Eq   (365)   NEEPIKPHYT---------SNQDHQLSVIKPHYKNINIQDGDNTTYQPQ
PtIP-96Er   (333)   ------------------------------------------EGDPNVQ
PtIP-96Es   (333)   ------------------------------------------EGDPNVQ
PtIP-96Et   (333)   ------------------------------------------EGDQNVQ
PtIP-96Eu   (334)   ------------------------------------------VEDQNVQ
PtIP-96Ev   (333)   ------------------------------------------EGDQNVQ
PtIP-96Ha   (396)   --------------------------------------------------
PtIP-96Hd   (396)   --------------------------------------------------
PtIP-96He   (397)   --------------------------------------------------
PtIP-96Hf   (396)   --------------------------------------------------
PtIP-96Hg   (396)   --------------------------------------------------
PtIP-96Hh   (396)   --------------------------------------------------
PtIP-96Hi   (396)   --------------------------------------------------
PtIP-96Hj   (397)   --------------------------------------------------
```

Fig. 1K

```
                  501              520
PtIP-96Aa  (389)  AATSVEELTLVY--------
PtIP-96Ab  (389)  AATSVEELTLVY--------
PtIP-96Ac  (389)  AATSVEELTLVY--------
PtIP-96Ad  (389)  AATSVEELTLVY--------
PtIP-96Ae  (389)  AATSVEELTLVY--------
PtIP-96Af  (389)  AATSVEELTLVY--------
PtIP-96Ag  (389)  AATSVEELTLVY--------
PtIP-96Ah  (389)  AATSVEELTLVY--------
PtIP-96Ca  (377)  -ATSVEELTLMH--------
PtIP-96Cb  (377)  -ATSVEELTLMH--------
PtIP-96Cc  (375)  -ATSVEELTLMH--------
PtIP-96Cd  (377)  -ATSVEELTLVY--------
PtIP-96Ce  (375)  -ATSVEELTLMH--------
PtIP-96Cf  (375)  -ATSVEELTLMH--------
PtIP-96Cg  (375)  -ATSVEELTLMH--------
PtIP-96Ch  (377)  -ATSVEELTLMH--------
PtIP-96Da  (321)  --------------------
PtIP-96Db  (396)  PLVATEERTLVY--------
PtIP-96Dc  (396)  PLVATEERTLVY--------
PtIP-96Dd  (396)  PLVATEERTLVY--------
PtIP-96De  (383)  APTGVEELTLVY--------
PtIP-96Df  (385)  APTGVEELTLVY--------
PtIP-96Ea  (340)  PDKEVEERKVLFTE------
PtIP-96Eb  (340)  PDKEVEERKVLFTE------
PtIP-96Ec  (341)  PNKEAKECTLLFAE------
PtIP-96Ed  (347)  PDKEVQESKLIYPS------
PtIP-96Ee  (341)  PNKEAKECTLLFAE------
PtIP-96Ef  (341)  PNKEAKECTLLFAE------
PtIP-96Eg  (341)  PNKEAKECTLLFAE------
PtIP-96Eh  (341)  PNKEAKECTLLFAE------
PtIP-96Ei  (341)  PNKEAKECTLLFAE------
PtIP-96Ej  (341)  PNKEAKECTLLFAE------
PtIP-96Ek  (341)  PNKEAKECTLLFAE------
PtIP-96El  (341)  PNKEAKECTLLFAE------
PtIP-96Em  (341)  PNKEAKECTLLFAE------
PtIP-96En  (341)  PNKEAKECTLLFAE------
PtIP-96Eo  (417)  --------------------
PtIP-96Ep  (419)  PQGVVEERTLVL--------
PtIP-96Eq  (405)  --GVVEERSLVF--------
PtIP-96Er  (340)  PSKEVQECKLLYIE------
PtIP-96Es  (340)  PSKEVQECKLLYIE------
PtIP-96Et  (340)  PSKDVQECKLLFTD------
PtIP-96Eu  (341)  PNKEAKECTLLFAEGAAYPY
PtIP-96Ev  (340)  PSKDVQECKLLFND------
PtIP-96Ha  (396)  --------------------
PtIP-96Hd  (396)  --------------------
PtIP-96He  (397)  --------------------
PtIP-96Hf  (396)  --------------------
PtIP-96Hg  (396)  --------------------
PtIP-96Hh  (396)  --------------------
PtIP-96Hi  (396)  --------------------
PtIP-96Hj  (397)  --------------------
```

Fig. 2A

```
                 1                                                  50
PtIP-96Aa  (1)   MSIHQTPVTLIGGRGGAAFTYNAGASGRILRRIGVWAGGSQLRGIRVWWT
PtIP-96Ab  (1)   MSIHQTPVTLIGGRGGAAFTYNAGASGRILRRIGVWAGGSQLRGIRVWWT
PtIP-96Ah  (1)   MSIYQTPVTLIGGRGGAAFTYNAGASGRILRRIGVWAGGSQLRGIRVWWT
PtIP-96Ag  (1)   MSIHQTPVTLIGGRGGAAFTYNAGASGRILRRIGVWAGGSQLRGIRVWWT
PtIP-96Ac  (1)   MSIHQTPVTLIGGRGGAAFTYNAGASGRILRRIGVWAGGSQLRGIRVWWT
PtIP-96Ad  (1)   MSIHQTPVTLIGGRGGAAFTYNAGASGRILRRIGVWAGGSQLRGIRVWWT
PtIP-96Ae  (1)   MSIHQTPVTLIGGRGGAAFTYNAGASGRILRRIGVWAGGSQLRGIRVWWT
PtIP-96Af  (1)   MSIHQTPVTLIGGRGGAAFTYNAGASGRILRRIGVWAGGSQLRGIRVWWT
PtIP-96Ag  (1)   MSIHQTPVTLIGGRGGAAFTYNAGASGRILRRIGVWAGGSQLRGIRVWWT
PtIP-96Ah  (1)   MSIYQTPVTLIGGRGGAAFTYNAGASGRILRRIGVWAGGSQLRGIRVWWT 51                                                 100
PtIP-96Aa  (51)  GLDSPITYGTPNVGSYQEFTFQDGERITSLSLWGNGAGTRSGGIRFYTTT
PtIP-96Ab  (51)  GLDSPITYGTPNVGSYQEFTFQDGERITSLSLWGNGAGTRSGGIRFYTTT
PtIP-96Ah  (51)  GLDSPITYGTPNVGSYQEFTFQDGERITSLSLWGNGAGTRSGGIRFYTTT
PtIP-96Ag  (51)  GLDSPITYGTPNVGSYQEFTFQDGERITSLSLWGNGAGTRSGGIRFYTTT
PtIP-96Ac  (51)  GLDSPITYGTPNVGSYQEFTFQDGERITSLSLWGNGAGTRSGGIRFYTTT
PtIP-96Ad  (51)  GLDSPITYGTPNVGSYQEFTFQDGERITSLSLWGNGAGTRSGGIRFYTTT
PtIP-96Ae  (51)  GLDSPITYGTPNVGSYQEFTFQDGERITSLSLWGNGAGTRSCGIRFYTTT
PtIP-96Af  (51)  GLDSPITYGTPNVGSYQEFTFQDGERITSLSLWGNGAGTRSGGIRFYTTT
PtIP-96Ag  (51)  GLDSPITYGTPNVGSYQEFTFQDGERITSLSLWGNGAGTRSGGIRFYTTT
PtIP-96Ah  (51)  GLDSPITYGTPNVGSYQEFTFQDGERITSLSLWGNGAGTRSGGIRFYTTT 101                                                150
PtIP-96Aa  (101) GRRFFHHMTSWGLKQEYPVDVVDGVCVGLTGRQGADIDALGFMFLRTMTS
PtIP-96Ab  (101) GRRFFHHMTSWGLKQEYPVDVVDGVCVGLTGRQGADIDALGFMFLRTMTS
PtIP-96Ah  (101) GRRFFHHMTSWGLKQEYPVDVVDGVCVGLTGRQGADIDALGFMFLRTMTS
PtIP-96Ag  (101) GRRFFHHMTSWGLKQEYPVDVVDGVCVGLTGRQGADIDALGFMFLRTMTS
PtIP-96Ac  (101) GRRFFHHMTSWGLKQEYPVDVVDGVCVGLTGRQGADIDALGFMCLRTMTS
PtIP-96Ad  (101) GRRFFHHMTSWGLKQEYPVDVVDGVCVGLTGRQGADIDALGFMCLRTMTS
PtIP-96Ae  (101) GRRFFHHMTSWGLKQEYPVDVVDGVCVGLTGRQGADIDALGFMCLRTMTS
PtIP-96Af  (101) GRRFFHHMTSWGLKQEYPVDVVDGVCVGLTGRQGADIDALGFMCLRTMTS
PtIP-96Ah  (101) GRRFFHHMTSWGLKQEYPVDVVDGVCVGLTGRQGADIDALGFMFLRTMTS
PtIP-96Ag  (101) GRRFFHHMTSWGLKQEYPVDVVDGVCVGLTGRQGADIDALGFMFLRTMTS 151                                                200
PtIP-96Aa  (151) ARMINVKYPTLGLETAGIVPVTLDFMSDSNNASSISKTWSFQGSREVTVS
PtIP-96Ab  (151) ARMINVKYPTLGLETAGIVPVTLDFMSDSNNAGSISKTWSFQGSREVTVS
PtIP-96Ah  (151) ARMINVKYPTLGLETAGIVPVTLDFMSDSNNAGSISKTWSFQGSREVTVS
PtIP-96Ag  (151) ARMINVKYPTLGLETAGIVPVTLDFMSDSNNASSISKTWSFQGSREVTVS
PtIP-96Ac  (151) ARMINVKYPTLGLETAGIVTVTLDFMSDSNNASSISKTWSFQGSREVTVS
PtIP-96Ad  (151) ARMINVKYPTLGLETAGIVPVTLDFMSDSNNASSISKTWSFQGSREVTVS
PtIP-96Ae  (151) ARMINVKYPTLGLETAGIVPVTLDFMSDSNNASSISKTWSFQGSREVTVS
PtIP-96Af  (151) ARMINVKYPTLGLETAGIVPVTLDFMSDSNNASSISKTWSFQGSREVTVS
PtIP-96Ag  (151) ARMINVKYPTLGLETAGIVPVTLDFMSDSNNASSISKTWSFQGSREVTVS
PtIP-96Ah  (151) ARMINVKYPTLGLETAGIVPVTLDFMSDSNNAGSISKTWSFQGSREVTVS
```

Fig. 2B

```
               201                                                250
PtIP-96Aa (201) SSWSTTTGIELHASITVSAGIPLVANVEGQYGWAISTSSTYTTNHSETRT
PtIP-96Ab (201) SSWSTTTGIELHASITVSAGIPLVANVEGQYGWAISTSSTYTTNHSETRT
PtIP-96Ah (201) SSWSTTTGIELHASITVSAGIPLVANVEGQYGWAISTSSTYTTNHSETRT
PtIP-96Ag (201) SSWSTTTGIELHASITVSAGIPLVANVEGQYGWGISTSSTYTTNHSETRT
PtIP-96Ac (201) SSWSTTTGIELHASITVSAGIPLVANVEGQYGWAISTSSTYTTNHSETRT
PtIP-96Ad (201) SSWSTTTGIELHASITVSAGIPLVANVEGQYGWAISTSSTYTTNHSETRT
PtIP-96Ae (201) SSWSTTTGIELHASITVSAGIPLVANVEGQYGWAISTSSTYTTNHSETRT
PtIP-96Af (201) SSWSTTTGIELHASITVSAGIPLVANVEGQYGWAISTSSTYTTNHSETRT
PtIP-96Ag (201) SSWSTTTGIELHASITVSAGIPLVANVEGQYGWGISTSSTYTTNHSETRT
PtIP-96Ah (201) SSWSTTTGIELHASITVSAGIPLVANVEGQYGWAISTSSTYTTNHSETRT 251                                                300
PtIP-96Aa (251) LQWQNSGVLEPGQWISLQALTRRGTITLPYQATMQITLQNGTVFTYPITA
PtIP-96Ab (251) LQWQNSGVLEPGQWISLQALTRRGTITLPYQATMQITLQNGTVFTYPITA
PtIP-96Ah (251) LQWQNSGVLEPGQWISLQALTRRGTITLPYQATMQITLQNGTVFTYPITA
PtIP-96Ag (251) LQWQNSGVLEPGQWISLQALTRRGTITLPYQATMQITLQNGTVFTYPITA
PtIP-96Ac (251) IQWQNSGVLEPGQWISLQALTRRGTITLPYQATMQITLQNGTVFTYPITA
PtIP-96Ad (251) LQWQNSGVLEPGQWISLQALTRRGTITLPYQATMQITLQNGTVFTYPITA
PtIP-96Ae (251) LQWQNSGVLEPGQWISLQALTRRGTITLPYQATMQITLQNGTVFTYPITA
PtIP-96Af (251) LQWQNSGVLEPGQWISLQALTRRGTITLPYQATMQITLQNGTVFTYPITA
PtIP-96Ag (251) LQWQNSGVLEPGQWISLQALTRRGTITLPYQATMQITLQNGTVFTYPITA
PtIP-96Ah (251) LQWQNSGVLEPGQWISLQALTRRGTITLPYQATMQITLQNGTVFTYPITA 301                                                350
PtIP-96Aa (301) QYAGVDYTSVEIVSQGTRDLGSDHLAINKDVRYIAAANGAAVGTTTTNAP
PtIP-96Ab (301) QYAGVDYTSVEIVSQGTRDLGSDHLAINKDVRYIAAANGGAVGTTTTNAP
PtIP-96Ah (301) QYAGVDYTSVEIVSQGTRDLGSDHLAINKDVHYIAAANGAAVGTTTTNAP
PtIP-96Ag (301) QYAGVDYTSVEIVSQGTRDLGSDHLAINKDVRYIAAANGAAVGTTTTNAP
PtIP-96Ac (301) QYAGVDYTSVEIVSQGTRDLGSDHLAINKDVRYIAAANGAAVGTTTTNAP
PtIP-96Ad (301) QYAGVDYTSVEIVSQGTRDLGSDHLAINKDVRYIAAANGAAVGTTTTNAP
PtIP-96Ae (301) QYSGVDYTSVEIVSQGTRDLGSDHLAINKDVRYIAAANGAAVGTTTTNAP
PtIP-96Af (301) QYAGVDYTSVEIVSQGTRDLGSDHLAINKDVRYIAAANGAAVGTTTTNAP
PtIP-96Ag (301) QYAGVDYTSVEIVSQGTRDLGSDHLAINKDVRYIAAANGAAVGTTTTNAP
PtIP-96Ah (301) QYAGVDYTSVEIVSQGTRDLGSDHLAINKDVHYIAAANGAAVGTTTTNAP 351                                                400
PtIP-96Aa (351) PHYVHPIRGAPIVEPVKFSVGATYINDTDNITQEVDTTAATSVEELTLVY
PtIP-96Ab (351) PHYVHPIRGAPIVEPVKFSVGATYINDTDNITQEVDTTAATSVEELTLVY
PtIP-96Ah (351) PHYVHPIRGAPIVEPVKFSVGATYINDTDNITQEVDTTAATSVEELTLVY
PtIP-96Ag (351) PHYVHPIRGAPIVEPVKFSVGATYINDTDNITQEVDTTAATSVEELTLVY
PtIP-96Ac (351) PHYVHPIRGAPIVEPVKFSVGATYINDTDNITQEVDTTAATSVEELTLVY
PtIP-96Ad (351) PHYVHPIRGAPIVEIVKFSVGATYINDTDNITQEVDTTAATSVEELTLVY
PtIP-96Ae (351) PHYVHPIRGAPIVEPVKFSVGATYINDTDNITQEVDTTAATSVEELTLVY
PtIP-96Af (351) PHYVHPIRGAPIVEPVKFSVGATYINDTDNITQEVDTTAATSVEELTLVY
PtIP-96Ag (351) PHYVHPIRGAPIVEPVKFSVGATYINDTDNITQEVDTTAATSVEELTLVY
PtIP-96Ah (351) PHYVHPIRGAPIVEPVKFSVGATYINDTDNITQEVDTTAATSVEELTLVY
```

Fig. 3A

```
                    1                                                50
PtIP-96Ca     (1)   MSTAIFQTPVHVIGGQGGSEFFYNAGASGRILRRIGVWAGRSFLGGIRSW
PtIP-96Cb     (1)   MSTAIFQTPVHVIGGQGGSEFFYNAGASGRILSRIGVWAGRSFLGGIRSW
PtIP-96Cc     (1)   --MSIHQTPVHVIGGQGGSEFFYNAGASGRILRRIGVWAGRSFLGGIRSW
PtIP-96Cd     (1)   MSTAIFQTPVHVIGGQGGSEFFYNAGASGRILRRIGVWAGRSFLGGIRSW
PtIP-96Ce     (1)   --MSIYQTPVHVIGGQGGSEFFYNAGASGRILRRIGVWAGRSFLGGIRSW
PtIP-96Cf     (1)   --MSIYQTPVHVIGGQGGSEFFYNAGASGRILRRIGVWAGRSFLGGIRSW
PtIP-96Cg     (1)   --MSIYQTPVHVIGGQGGSEFFYNAGASGRILRRIGVWAGRSFLGGIRSW
PtIP-96Ch     (1)   MSTAIFQTPVHVIGGQGGSEFFYNAGASGRILRRIGVWAGRSFLGGIRSW 51                                               100
PtIP-96Ca    (51)   WTGLDSPITYGTPNSGSYREFTFEDGERITSLSLWGNGIGTRSGGIRFNT
PtIP-96Cb    (51)   WTGLDSPITYGTPNSGSYREFTFEDGERITSLSLWGNGIGTRSGGIRFNT
PtIP-96Cc    (49)   WTGLDSPITYGTPNSGSYREFTFEDGERITSLSLWGNGIGTRSGGIRFNT
PtIP-96Cd    (51)   WTGLDSPITYGTPNSGSYREFTFEDGERITSLSLWGNGIGTRSGGIRFNT
PtIP-96Ce    (49)   WTGLDSPITYGTPNSGSYREFTFEDGERITSLSLWGNGIGTRSGGIRFNT
PtIP-96Cf    (49)   WTGLDSPITYGTPNSGSYREFTFEDGERITSLSLWGNGIGTRSGGIRFNT
PtIP-96Cg    (49)   WTGLDSPITYGTPNSGSYREFTFEDGERITSLSLWGNGIGTRSGGIRFNT
PtIP-96Ch    (51)   WTGLDSPITYGTPNSGSYREFTFEDGERITSLSLWGNGIGTRSGGIRFNT 101                                              150
PtIP-96Ca   (101)   STGRQFFHHMTSWSLQQEYAIDVASGLCVGLWGRHGVEIDSLGFMFLRPI
PtIP-96Cb   (101)   STGRQFFHHMTSWSLQQEYAIDVASGLCVGLWGRHGVEIDSLGFMFLRPI
PtIP-96Cc    (99)   STGRQFFHHMTSWSLQQEYAIDVASGLCVGLWGRHGVEIDSLGFMFLRPI
PtIP-96Cd   (101)   STGRQFFHHMTSWSLQQEYAIDVASGLCVGLWGRHGVEIDSLGFMFLRPI
PtIP-96Ce    (99)   STGRQFFHHMTSWSLQQEYAIDVASGLCVGLWGRHGVEIDSLGFMFLRPI
PtIP-96Cf    (99)   STGRQFFHHMTSWSLQQEYAIDVASVLCVGLWGRHGVEIDSLGFMFLRPI
PtIP-96Cg    (99)   STGRQFFHHMTSWSLQQEYAIDVASGLCVGLWGRHGVEIDSLGFMFLRPI
PtIP-96Ch   (101)   STGRQFFHHMTSWSLQQEYAIDVASGLCVGLWGRHGVEIDSLGFMFLRPI 151                                              200
PtIP-96Ca   (151)   ASARMINVRYPTLGLETAGIVPVTLDSMSDSNNSASMPKNWSFQGSRDVT
PtIP-96Cb   (151)   ASARMINVRYPTLGLETAGIVPVTLDSMSDSNNSASMPKNWSFQGSRDVT
PtIP-96Cc   (149)   ASARMINVRYPTLGLETAGIVPVTLDSMSDSNNSASMPKNWSFQGSRDVT
PtIP-96Cd   (151)   ASARMINVRYPTLGLETAGIVPVTLDSMSDSNNSASMPKNWSFQGSRDVT
PtIP-96Ce   (149)   ASARMINVRYPTLGLETAGIVPVTLDSMSDSNNSASMPKNWSFQGSRDVT
PtIP-96Cf   (149)   ASARMINVRYPTLGLETAGIVPVTLDSMSDSNNSASMPKNWSFQGSRDVT
PtIP-96Cg   (149)   ASARMINVRYPTLGLETAGIVPVTLDSMSDSNNSASMPKNWSFQGSRDVT
PtIP-96Ch   (151)   ASARMINVRYPTLGLETAGIVPVPLDSLSHSNNSASLPKNWPFQGSPKGT
```

Fig. 3B

```
                201                                                250
PtIP-96Ca (201) ISSSWSITAGIELHASINVSAGVPMLANVDVQYGWTISSTSSYSTSHSET
PtIP-96Cb (201) ISSSWSITAGIELHASINVSAGVPMLANVDVQYGWTISSTSSYSTSHSET
PtIP-96Cc (199) ISSSWSITAGIELHASINVSAGVPMLANVDVQYGWTISSTSSYSTSHSET
PtIP-96Cd (201) ISSSWSITAGIELHASINVSAGVPMLANVDVQYGWTISSTSSYSTSHSET
PtIP-96Ce (199) ISSSWSITAGIELHASINVSAGVPMLANVDVQYGWTISSTSSYSTSHSET
PtIP-96Cf (199) ISSSWSITAGIELHASINVSAGVPMLANVDVQYGWTISSTSSYSTSHSET
PtIP-96Cg (199) ISSSWNITAGIELHASINVSAGVPMLANVDVQYGWTISSTSSYSTSHSET
PtIP-96Ch (201) ISSSWSILAGIELPASINVSAGVPMLANVDVQYGWTISSTSSYSTSHSET 251                                                300
PtIP-96Ca (251) RSLSWQNSGVLEPGQWVSLQALTRRGTITLPYQATMQITLQNGVVFTYPI
PtIP-96Cb (251) RSLSWQNSGVLEPGQWVSLQALTRRGTITLPYQATMQITLQNGVVFTYPI
PtIP-96Cc (249) RSLSWQNSGVLEPGQWVSLQALTRRGTITLPYQATMQITLQNGVVFTYPI
PtIP-96Cd (251) RSLSWQNSGVLEPGQWVSLQALTRRGTITLPYQATMQITLQNGVVFTYPI
PtIP-96Ce (249) RSLSWQNSGVLEPGQWVSLQALTRRGTITLPYQATMQITLQNGVVFTYPI
PtIP-96Cf (249) RSLSWQNSGVLEPGQWVSLQALTRRGTITLPYQATMQITLQNGVVFTYPI
PtIP-96Cg (249) RSLSWQNSGVLEPGQWVSLQALTRRGTITLPYQATMQITLQNGVVFTYPI
PtIP-96Ch (251) RSLSWQNSGVLEPGQWVSLQALTRRGTITLPYQATMQITLQNGVVFTYPI 301                                                350
PtIP-96Ca (301) AAQYAGVDFTSVEIVSLGTKDVGSGHSATNKDVGRIVANGTATTSAPPQY
PtIP-96Cb (301) AAQYAGVDFTSVEIVSLGTKDVGSGHSATNKDVGRIVANGTATTSAPPQY
PtIP-96Cc (299) AAQYAGVDFTSVEIVSLGTKDVGSGHSATNKDVGRIVANGTATTSAPPQY
PtIP-96Cd (301) AAQYAGVDFTSVEIVSLGTKDVGSGHSATNKDVGRIVANGTATTSAPPQY
PtIP-96Ce (299) AAQYAGVDFTSVEIVSLGTKDVGSGHSATNKDVGRIVANGTATTSAPPQY
PtIP-96Cf (299) AAQYAGVDFTSVEIVSLGTKDVGSGHSATNKDVGRIVANGTATTSAPPQY
PtIP-96Cg (299) AAQYAGVDFTSVEIVSLGTKDVGSGHSATNKDVGRIVANGTATTSAPPQY
PtIP-96Ch (301) AAQYAGVDFTSVEIVSLGTKDVGSGHSATNKDVGRIVANGTATTSAPPQY 351                                       388
PtIP-96Ca (351) VRPVKLSVGATYINDTNNITQEVDSTATSVEELTLMH-
PtIP-96Cb (351) VRPVKLSVGATYINDTNNITQEVDSTATSVEELTLMH-
PtIP-96Cc (349) VRPVKLSVGATYINDTNNITQEVDSTATSVEELTLMH-
PtIP-96Cd (351) VRPVKLSVGATYINDTNNITQEVDSTATSVEELTLVY-
PtIP-96Ce (349) VRPVKLSVGATYINDTNNITQEVDSTATSVEELTLMH-
PtIP-96Cf (349) VRPVKLSVGATYINDTNNITQEVDSTATSVEELTLMH-
PtIP-96Cg (349) VRPVKLSVGATYINDTNNITQEVDSTATSVEELTLMH-
PtIP-96Ch (351) VRPVKLSVGATYINDTNNITQEVDSTATSVEELTLMH-
```

Fig. 4A

```
              1                                                    50
PtIP-96Ea  (1) MALYQTPVYVIGGQGGNSFTYDQSRNGKVLTKIGVWAGEWQLRGIRVWMS
PtIP-96Eb  (1) MALYQTPVYVIGGQGGNSFTYDQSRNGKVLTKIGVWAGEWQLRGIRVWMS
PtIP-96Ec  (1) MSLVQTPVYVIGGQGGNAFTYDQSRNGRILRRIGVWAGEWQLRGIRVWMT
PtIP-96Ef  (1) MSLVQTPVYVIGGQGGNAFSYDQSRNGRILRRIGVWAGEWQLRGIRVWMT
PtIP-96Er  (1) MALYQTPVSIIGGQGGTSFTYDQSPNGKIMRKIGVWAGEWQLRGIRIWVS
PtIP-96Es  (1) MALYQTPVSIIGGQGGTSFTYDQSPNGKIMRKIGVWAGEWQLRGIRIWVS
PtIP-96Et  (1) MALYQTPVYVIGGQGGNSFTYDQSRNGKVLRKIGVWAGEWQLRGIRVWMS
PtIP-96Ev  (1) MALYQTPVYVIGGQGGNSFTYDQSRNGKVLRKIGVWAGEWQLRGIRVWMS
PtIP-96Em  (1) MSLVQTPVYVIGGQGGNAFSYDQSRNGRILRRIGVWAGEWQLRGIRVWMT
PtIP-96Ek  (1) MSLVQTPVYVIGGQGGNAFSYDQSRNGRILRRIGVWAGEWQLRGIRVWMT
PtIP-96El  (1) MSLVQTPVYVIGGQGGNAFSYDQSRNGRILRRIGVWAGEWQLRGIRVWMT
PtIP-96Eg  (1) MSLVQTPVYVIGGQGGNAFSYDQSRNGRILRRIGVWAGEWQLRGIRVWMT
PtIP-96Ej  (1) MSLVQTPVYVIGGQGGNAFTYDQSRNGRILRRIGVWAGEWQLRGIRVWMT
PtIP-96Ei  (1) MSLVQTPVYVIGGQGGNAFTYDQSRNGRILRRIGVWAGEWQLRGIRVWMT
PtIP-96Eu  (1) MALYQTPVYVIGGQGGNAFTYDQSRNGRILRRIGVWAGEWQLRGIRVWMT
PtIP-96Eh  (1) MSLVQTPVYVIGGQGGNAFTYDQSRNGRILRRIGVWAGEWQLRGIRVWMT
PtIP-96En  (1) MSLVQTPVYVIGGQGGNAFTYDQSRNGRILRRIGVWAGEWQLRGIRVWMT
PtIP-96Ee  (1) MSLVQTPVYVIGGQGGNAFTYDQSRNGRILRRIGVWAGEWQLRGIRVWMT 51                                                   100
PtIP-96Ea (51) GSDSPTTFGTASGSYSEYTFAAGERITRLSLWGNGAGTRSGAIRFYTTTG
PtIP-96Eb (51) GSDSPTTFGTASGSYSEYTFAAGERITRLSLWGNGAGTRSGAIRFYTTTG
PtIP-96Ec (51) GTDTPATFGTATGSYSEYTFADGERITRLSLWGNGAGTRSGGIRFYTTTG
PtIP-96Ef (51) GTDTPATFGTATGSYSEYTFTDGERITRLSLWGNGAGTRSGGIRFYTTTG
PtIP-96Er (51) GSDDPTTFGTASGSYNEYTFADGETITSLSLWGNGAGTRSGAIRFYTSTG
PtIP-96Es (51) GSDDPTTFGTASGSYNEYTFADGETITSLSLWGNGAGTRSGAIRFYTSTG
PtIP-96Et (51) GSDSPATFGTASGSYNEYTFADGERITRLSLWGNGAGTRSGGIRFYTTTG
PtIP-96Ev (51) GSDSPATFGTASGSYNEYTFADGERITRLSLWGNGAGTRSGGIRFYTTTG
PtIP-96Em (51) GTDTPATFGTATGSYSEYTFTDGERITRLSLWGNGAGTRSGGIRFYTTTG
PtIP-96Ek (51) GTDTPATFGTATGSYSEYTFTDGERITRLSLWGNGAGTRSGGIRFYTTTG
PtIP-96El (51) GTDTPATFGTATGSYSEYTFTDGERITRLSLWGNGAGTRSGGIRFYTTTG
PtIP-96Eg (51) GTDTPATFGTATGSYSEYTFADGERITRLSLWGNGAGTRSGGIRFYTTTG
PtIP-96Ej (51) GTDTPATFGTATGSYSEYTFADGERITRLSLWGNGAGTRSGGIRFYTTTG
PtIP-96Ei (51) GTDTPATFGTATGSYSEYTFADGERITRLSLWGNGAGTRSGGIRFYTTTG
PtIP-96Eu (51) GTDTPATFGTATGSYSEYTFADGERITRLSLWGNGAGTRSGGIRFYTTTG
PtIP-96Eh (51) GTDTPATFGTATGSYSEYTFADGERITRLSLWGNGAGTRSGGIRFYTTTG
PtIP-96En (51) GTDTPATFGTATGSYSEYTFADGERITRLSLWGNGAGTRSGGIRFYTTTG
PtIP-96Ee (51) GTDTPATFGTATGSYSEYTFADGERITRLSLWGNGAGTRSGGIRFYTTTG
```

Fig. 4B

```
              101                                                150
PtIP-96Ea (100) GSFFPKMTSWDLKTEYPIDVASGLCVGIIGRASADIDSLGFMFLRTIASS
PtIP-96Eb (100) GSFFPKMTSWDLKTEYPIDVASGLCVGIIGRASADIDSLGFMFLRTIASS
PtIP-96Ec (101) GSFFHKMTSWGLQTEYPIDVASGLCVGIMGRANVDVDSLGVLFLRTIASA
PtIP-96Ef (101) GSFFHKMTSWGLQTEYPIDVASGLCVGIMGRANVDVDSLGVLFLRTIASA
PtIP-96Er (101) GSFFPKMTSWGLKTEYPIDVASGLCVGIMGRAGDDIDALGFLFLRTITSA
PtIP-96Es (101) GSFFPKMTSWDLKTEYPIDVASGLCVGIMGRAGDDIDALGFLFLRTITSA
PtIP-96Et (101) GSFFAKMTSWGLQTEYPIDVASGLCVGILGRANVDIDSLGFMFLRTIASA
PtIP-96Ev (101) GSFFAKMTSWGLQTEYPIDVASGLCVGILGRANVDIDSLGFMFLRTIASA
PtIP-96Em (101) GSFFHKMTSWGLQTEYPIDVASGLCVGIMGRANVDVDSLGVLFLRTIASA
PtIP-96Ek (101) GSFFHKMTSWGLQTEYPIDVASGLCVGIMGRANVDVDSLGVLFLRTIASA
PtIP-96El (101) GSFFHKMTSWGLQTEYPIDVASGLCVGIMGRANVDVDSLGVLFLRTIASA
PtIP-96Eg (101) GSFFHKMTSWGLQTEYPIDVASGLCVGIMGRANVDVDSLGVLFLRTIASA
PtIP-96Ej (101) GSFFHKMTSWGLQTEYPIDVASGLCVGIMGRANVDVDSLGVLFLRTIASA
PtIP-96Ei (101) GSFFHKMTSWGLQTEYPIDVASGLCVGIMGRANVDVDSLGVLFLRTIASA
PtIP-96Eu (101) GSFFHKMTSWGLQTEYPIDVASGLCVGIMGRANVDVDSLGVLFLRTIASA
PtIP-96Eh (101) GSFFHKMTSWGLQTEYPIDVASGLCVGIMGRANVDVDSLGVLFLRTIASA
PtIP-96En (101) GSFFHKMTSWGLQTEYPIDVASGLCVGIMGRANVDVDSLGVLFLRTIASA
PtIP-96Ee (101) GSFFHKMTSWGLQTEYPIDVASGLCVGIMGRANVDVDSLGVLFLRTIASA 151                                                200
PtIP-96Ea (150) RMINVSYPTLGLEQAGIIPVTLDSYNDSNNAGSISKNWTFSGSRTVTISS
PtIP-96Eb (150) RMINVSYPTLGLEQAGIIPVTLDSYNDSNNAGSISKNWTFSGSRTVTISS
PtIP-96Ec (151) RMINVSYPTLGLEQAGIIPVTLDSFNDSNNAGTISKNWTFSGSRTVTISS
PtIP-96Ef (151) RMINVSYPTLGLEQAGIIPVTLDSYNDSNNAGTISKNWTFSGSRTVTISS
PtIP-96Er (151) RMINVTYPTLGLEEAAIIPVTLDSYNDANNAGTISKSWTFSGSRTVTVSE
PtIP-96Es (151) RMINVTYPTLGLEEAAIIPVTLDSYNDANNAGTISKSWTFSGSRTVTVSE
PtIP-96Et (151) RMINVSYPTLGLEQAGIVPVTLDSYNDSNNAGTISKNWTFSGSRTVTISS
PtIP-96Ev (151) RMINVSYPTLGLEQAGIVPVTLDSYNDSNNAGTISKNWTFSGSRTVTISS
PtIP-96Em (151) RMINVSYPTLGLEQAGIIPVTLDSYNDSNNAGTISKNWTFSGSRTVTISS
PtIP-96Ek (151) RMINVSYPTLGLEQAGIIPVTLDSYNDSNNAGTISKNWTFSGSRTVTISS
PtIP-96El (151) RMINVSYPTLGLEQAGIIPVTLDSFNDSNNAGTISKNWTFSGSRTVTISS
PtIP-96Eg (151) RMINVSYPTLGLEQAGIIPVTLDSFNDSNNAGTISKNWTFSGSRTVTISS
PtIP-96Ej (151) RMINVSYPTLGLEQAGIIPVTLDSFNDSNNAGTISKNWTFSGSRTVTISS
PtIP-96Ei (151) RMINVSYPTLGLEQAGIIPVTLDSFNDSNNAGTISKNWTFSGSRTVTISS
PtIP-96Eu (151) RMINVSYPTLGLEQAGIIPVTLDSFNDSNNAGTISKNWTFSGSRTVTISS
PtIP-96Eh (151) RMINVSYPTLGLEQAGIIPVTLDSFNDSNNAGTISKNWTFSGSRTVTISS
PtIP-96En (151) RMINVSYPTLGLEQAGIIPVTLDSFNDSNNAGTISKNWTFSGSRTVTISS
PtIP-96Ee (151) RMINVSYPTLGLEQAGIIPVTLDSFNDSNNAGTISKNWTFSGSRTVTISS
```

Fig. 4C

```
                  201                                               250
PtIP-96Ea  (200)  SWTLTSGIEAHASVTVQAGIPSVAEVSGEFGWSVSVSGSYTSTQEESRTL
PtIP-96Eb  (200)  SWTLTSGIEAHASVTVQAGLPSVAEVSGEFGWSVSVSGSYTSTQEESRTL
PtIP-96Ec  (201)  SWSLTSGIETHASVSVQAGIPMVAEVSGEFGWSVSVSGTYATTQEESRTL
PtIP-96Ef  (201)  SWSLTSGIETHASVSVQAGIPMVAEVSGEFGWSVSVSGTYATTQEESRTL
PtIP-96Er  (201)  SWTLTAGIEVHATVSVQAGIPLVAEVNGEYGWSLSTTGSYATTQEESRTL
PtIP-96Es  (201)  SWTLTAGIEVHATVSVQAGIPLVAEVNGEYGWSLSTTGSYATTQEESRTL
PtIP-96Et  (201)  SWTLTSGIEAHATVSVQAGIPLVAEVSGEFGWSLSVTGSYTTTQEESRTL
PtIP-96Ev  (201)  SWTLTSGIEAHATVSVQAGIPLVAEVSGEFGWSLSVTGSYTTTQEESRTL
PtIP-96Em  (201)  SWSLTSGIETHASVSVQAGIPMVAEVSGEFGWSVSVSGTYATTQEESRTL
PtIP-96Ek  (201)  SWSLTSGIETHASVSVQAGIPMVAEVSGEYGWSVSVSGTYATTQEESRTL
PtIP-96El  (201)  SWSLTSGIETHASVSVQAGIPMVAEVSGEYGWSVSVSGTYATTQEESRTL
PtIP-96Eg  (201)  SWSLTSGIETHASVSVQAGIPMVAEVSGEYGWSVSVSGTYATTQEESRTL
PtIP-96Ej  (201)  SWSLTSGIETHASVSVQAGIPMVAEVSGEYGWSVSVSGTYATTQEESRTL
PtIP-96Ei  (201)  SWSLTSGIETHASVSVQAGIPMVAEVSGEYGWSVSVSGTYATTQEESRTL
PtIP-96Eu  (201)  SWSLTSGIETHASVSVQAGIPMVAEVSGEYGWSVSVSGTYATTQEESRTL
PtIP-96Eh  (201)  SWSLTSGIETHASVSVQAGIPMVAEVSGEYGWSVSVSGTYATTQEESRTL
PtIP-96En  (201)  SWSLTSGIETHASVSVQAGIPMVAEVSGEYGWSVSVSGTYATTQEESRTL
PtIP-96Ee  (201)  SWSLTSGIETHASVSVQAGIPMVAEVSGEYGWSVSVSGTYATTQEESRTL 251                                               300
PtIP-96Ea  (250)  TWNQSGTLEPGQWISIQATTRRGTITLPYQGTMEITLQSGTVFQYPISSM
PtIP-96Eb  (250)  TWNQSGTLEPGQWISIQATTRRGTITLPYQGTMEITLQSGTVFQYPISSM
PtIP-96Ec  (251)  TWNQSGTLEPGQWISLQATTRRGTITLPFQATMEITLLSGTIFQYAISSM
PtIP-96Ef  (251)  TWNQSGTLEPGQWISLQATTRRGTITLPFQATMEITLLSGTIFQYAISSM
PtIP-96Er  (251)  SWNQSGTLEPGQWISIQATTRRGTITLPYQGTMEITLQSGTKFQYPISST
PtIP-96Es  (251)  SWNQSGTLEPGQWISIQATTRRGTITLPYQGTMEITLQSGTKFQYPISST
PtIP-96Et  (251)  TWNQSGTLEPGQWISLQATTRRGTITLPYQGTMEITLQSGTVFQYPISSM
PtIP-96Ev  (251)  TWNQSGTLEPGQWISLQATTRRGTITLPYQGTMEITLQSGTVFQYPISSM
PtIP-96Em  (251)  TWNQSGTLEPGQWISLQATTRRGTITLPFQATMEITLLSGTIFQYAISSM
PtIP-96Ek  (251)  AWDQSGTLQPGQWISLQATTRRGTITLPFQATMEITLQSGTIFQYAISSM
PtIP-96El  (251)  AWDQSGTLQPGQWISLQATTRRGTITLPFQATMEITLQSGTIFQYAISSM
PtIP-96Eg  (251)  AWDQSGTLQPGQWISLQATTRRGTITLPFQATMEITLQSGTIFQYAISSM
PtIP-96Ej  (251)  AWDQSGTLQPGQWISLQATTRRGTITLPFQATMEITLLSGTIFQYAISSM
PtIP-96Ei  (251)  AWDQSGTLQPGQWISLQATTRRGTITLPFQATMEITLQSGTIFQYAISSM
PtIP-96Eu  (251)  AWDQSGTLQPGQWISLQATTRRGTITLPFQATMEITLQSGTIFQYAISSM
PtIP-96Eh  (251)  AWDQSGTLQPGQWISLQATTQRGTITLPFQATMEITLQSGTIFQYAISSM
PtIP-96En  (251)  AWDQSGTLQPGQWISLQATTRRGTITLPFQATMEITLQSGTIFQYVISSM
PtIP-96Ee  (251)  AWDQSGTLQPGQWISLQATTRRGTITLPFQATMEITLQSGTIFQYAISSM
```

Fig. 4D

```
              301                                                350
PtIP-96Ea (300) YSGVDYTSVDITNTGTRALKQVEVQATDQQSQ-EGDHNVQPDKEVEERKV
PtIP-96Eb (300) YSGVDYTSVDITNTGTRALKQVEVQATDQQSQ-EGDHNVQPDKEVEERKV
PtIP-96Ec (301) YSGVDYTSVDITNTGTRASDHVEVEATEQQVQGVKDQSVQPNKEAKECTL
PtIP-96Ef (301) YSGVDYTSVDITNTGTRASDHVEVEATEQQVQGVKDQSVQPNKEAKECTL
PtIP-96Er (301) YTGVDYTSVDIVSIGSRVLNQAKVEATNKKAL-EGDPNVQPSKEVQECKL
PtIP-96Es (301) YTGVDYTSVDIVSIGSRVLNQAKVEATNKKAL-EGDPNVQPSKEVQECKL
PtIP-96Et (301) YAGVDYTSVDITNTGTRALNRVETEAIDQQAR-EGDQNVQPSKDVQECKL
PtIP-96Ev (301) YAGVDYTSVDITNTGTRALNRVETEAIDQQAR-EGDQNVQPSKDVQECKL
PtIP-96Em (301) YSGVDYTSVDITNTGSRALDQVEVKTTEQQVEGVEDQNVQPNKEAKECTL
PtIP-96Ek (301) YSGVDYTSVDITNTGSRALDQVEVKTTEQQVEGVEDQNVQPNKEAKECTL
PtIP-96El (301) YSGVDYTSVDITNTGSRALDQVEVKTTEQQVEGVEDQNVQPNKEAKECTL
PtIP-96Eg (301) YSGVDYTSVDITNTGSRALDQVEVKTTEQQVEGVEDQNVQPNKEAKECTL
PtIP-96Ej (301) YSGVDYTSVDITNTGSRALDQVEVKTTEQQVEGVEDQNVQPNKEAKECTL
PtIP-96Ei (301) YSGVDYTSVDITNTGSRALDQVEVKTTEQQVEGVEDQNVQPNKEAKECTL
PtIP-96Eu (301) YSGVDYTSVDITNTGSRALDQVEVKTTEQQVEGVEDQNVQPNKEAKECTL
PtIP-96Eh (301) YSGVDYTSVDITNTGSRALDQVEVKTTEQQVEGVEDQNVQPNKEAKECTL
PtIP-96En (301) YSGVDYTSVDITNTGSRALDQVEVKTTEQQVEGVEDQNVQPNKEAKECTL
PtIP-96Ee (301) YSGVDYTSVDITNTGSRALDQVEVKTTEQQVEGVEDQNVQPNKEAKECTL

351
PtIP-96Ea (350) LFTE------
PtIP-96Eb (350) LFTE------
PtIP-96Ec (351) LFAE------
PtIP-96Ef (351) LFAE------
PtIP-96Er (350) LYIE------
PtIP-96Es (350) LYIE------
PtIP-96Et (350) LFTD------
PtIP-96Ev (350) LFND------
PtIP-96Em (351) LFAE------
PtIP-96Ek (351) LFAE------
PtIP-96El (351) LFAE------
PtIP-96Eg (351) LFAE------
PtIP-96Ej (351) LFAE------
PtIP-96Ei (351) LFAE------
PtIP-96Eu (351) LFAEGAAYPY
PtIP-96Eh (351) LFAE------
PtIP-96En (351) LFAE------
PtIP-96Ee (351) LFAE------
```

Fig. 5

```
                    1                                                  50
PtIP-96Eo    (1)    MSIYQTPVSVIGGTGGSAFSYNAGASGRILRKIGVWAGGWYLGGIRVWWT
PtIP-96Ep    (1)    MSIYQTPVSVIGGTGGSAFSYNAGASGRILRKIGVWAGGWYLGGIRVWWT
PtIP-96Eq    (1)    MSIYQTPISVIGGTGGSAFSYNAGASGRILRKIGVWAGGWYLGGIRVWWT 51                                                 100
PtIP-96Eo   (51)    GLDTPSTFGTANVGSYKEYTFEDGERITSLSLWGNGAGTRSGGIRFRTTK
PtIP-96Ep   (51)    GLDTPSTFGTANVGSYKEYTFEDGERITSLSLWGNGAGTRSGGIRFRTTK
PtIP-96Eq   (51)    GLDTPSTFGTANVGSYKEYTFEDGERITSLSLWGNGAGTRSGGIRFRTTK 101                                                150
PtIP-96Eo  (101)    GSEFFHYMTSWGLKQEYPMDVASGLCVGVIGRHGEHIDSLGFMFLRSIAS
PtIP-96Ep  (101)    GSEFFHYMTSWGLKQEYPMDVASGLCVGVIGRHGEHIDSLGFMFLRSIAS
PtIP-96Eq  (101)    GSEFFHYMTSWGLKQEYPIDVAAGLCVGVIGRHGEHIDSLGFMFLRSIAS 151                                                200
PtIP-96Eo  (151)    ARMINVSYPTLALETAGIVPVTLDSLTDNNNAGTIAKNWALRGSREVTMS
PtIP-96Ep  (151)    ARMINVSYPTLALETAGIVPVTLDSLTDNNNAGTIAKNWALRGSREVTMS
PtIP-96Eq  (151)    ARMINVSYPTLALETAGIVPVTLDSLTDSNNAGTISKNWALRGSREVTMS 201                                                250
PtIP-96Eo  (201)    STWSVTSGIELYASVTVTAGVPTVAEVQGEFGWKVSTSATYSTTYQETRS
PtIP-96Ep  (201)    STWSVTSGIELYASVTVTAGVPTVAEVQGEFGWKVSTSATYSTTYQETRS
PtIP-96Eq  (201)    STWSVTSGIELYASVTVTAGVPTVAEVQGEFGWRVSTSATYSTTHTETRT 251                                                300
PtIP-96Eo  (251)    LQWEQSGVLQPGEWISIQALTRRGTISLPYQGTMQITLQSGTVFTYPISA
PtIP-96Ep  (251)    LQWEQSGVLQPGEWISIQALTRRGTISLPYQGTMQITLQSGTVFTYPISA
PtIP-96Eq  (251)    LQWEQSGVLQPGEWISLQALTRRGNISLPYQGTMQITLQSGTVFTYPISA 301                                                350
PtIP-96Eo  (301)    LYAGVDYTSVEIVNLGTYVSSNNIS-GEAIPRQLPVSSFSLPATNIANGA
PtIP-96Ep  (301)    LYAGVDYTSVEIVNLGTYVSSNNIS-GEAIPRQLPVSSFSLPATNIANGA
PtIP-96Eq  (301)    LYAGVDYTNVEIVNLGTFVASNNISAGEFIPRQP----ISLPAATTNTNA 351                                                400
PtIP-96Eo  (350)    AWAGANANGALAAGTRALINGEPIKPHYSNVLPHTLTTPQDQDHQLSVIK
PtIP-96Ep  (350)    AWAGANANGALAAGTRALINGEPIKPHYSNVLPHTLTTPQDQDHQLSVIK
PtIP-96Eq  (347)    NGAWTNAG-ALAGTTRAVINEEPIKPHYT---------SNQDHQLSVIK 401                      434
PtIP-96Eo  (400)    PHYK--NILELVHLLDWPT---------------
PtIP-96Ep  (400)    PHYK--NILDGDNTNYQPQPQPQGVVEERTLVL-
PtIP-96Eq  (386)    PHYKNINIQDGDNTTYQPQ----GVVEERSLVF-
```

Fig. 6A

```
                        1                                                50
PtIP-96Ha    (1)   MQYGLANTEASPLIEKFQALMEGGIDESILATKLVGAEGDASHLPPPGET
PtIP-96Hb    (1)   MQYGLANMEASPLIEKFQSLMEGGIDESILATKLVGAEGDASHLPPPGET
PtIP-96Hc    (1)   MQYGRANMEASPLIEKFQSLMEGGIDESILATKLVGAEGDASHLPPPGET
PtIP-96Hd    (1)   MQYGLANTEASPLIEKFQALMEGGIDESILATKLVGAEGDASRVPPPGET
PtIP-96Hf    (1)   MQYGLANTEASPLIEKFQALMEGGIDESILATKLVGAEGDASRVPPPGET
PtIP-96Hg    (1)   MQYGLANTEASPLIEKFQALMEGGIDESILATKLVGAEGDASRVPPPGET
PtIP-96Hh    (1)   MQYGLANMEASPLIEKFQSLMEGGIDESILATKLVGAEGDASHLPPPGET
PtIP-96Hi    (1)   MQYGLANMEASPLIEKFQSLMEGGIDESILATKLVGAEGDASHLPPPGET
PtIP-96He    (1)   MQYGLANTEASPLIEKFQALMEGGIDESILATKLVGAEGDASHLPPPGET
PtIP-96Hj    (1)   MQYGLANTEASPLIEKFQALMEGGIDESILATKLVGAEGDASHLPPPGET 51                                               100
PtIP-96Ha   (51)   PSEDGAGKDPPNESLETEDVEEHADDSKARSAS-VTAPLRFIGGPGGSQR
PtIP-96Hb   (51)   PSEDGAGKDPPNESLETEDVEEHADDSKARSAS-VMAPLRFIGGPGGSQR
PtIP-96Hc   (51)   PSEDGAGKDPPNESLETEDVEEHADDSKARSAS-VTAPLRFIGGTGGSQR
PtIP-96Hd   (51)   PSEDGAGKDPPNESLETEDVEEHADDSKARSAS-VTAPLRFIGGTGGSQR
PtIP-96Hf   (51)   PGEDGAGKDPPNESLETEDVEEHADDSKARSAS-VTAPLRFIGGPGGSQR
PtIP-96Hg   (51)   PGEDGAGKDPPNESLETEDVEEHADDSKARSAS-VTAPLRFIGGPGGSQR
PtIP-96Hh   (51)   PSEDGAGKDPPNESLETEDVEEHADDSKARSAS-VTAPLRFIGGPGGSQR
PtIP-96Hi   (51)   PSEDGAGKDPPNESLETEDVEEHADDSKARSAS-VTAPLRFIGGPGGSQR
PtIP-96He   (51)   PSEDGAGKDPPNESLETEDVEEHADDSKARSASSVTAPLRFIGGTGGSQR
PtIP-96Hj   (51)   PSEDGAGKDPPNESLETEDVEEHADDSKARSASSVTAPLRFIGGTGGSQR 101                                              150
PtIP-96Ha  (100)   SVRGWTNGRVITRMRVYRARGTIKAYQIWLTDSAPQTHGVPGNSDFAEYT
PtIP-96Hb  (100)   SVRGWTNGRVITRMRVYRARGTIKAYQIWLTDSAPQTHGVPGNSDFAEYT
PtIP-96Hc  (100)   SVRGWTNGRVITRMRVYRARGTIKAYRIWLTDSGPETHGVPGNSDFAEYT
PtIP-96Hd  (100)   SVRGWTNGRVITRMRVYRARGTIKAYRIWLTDSGPETHGVPGNSDFAEYT
PtIP-96Hf  (100)   SVRGWTNGRVITRMRVYRARGTIKAYQIWLTDSGPETHGVPGNSDFAEYT
PtIP-96Hg  (100)   SVRGWTNGRVITRMRVYRARGTIKAYQIWLTDSGPETHGVPGNSDFAEYT
PtIP-96Hh  (100)   SVRGWTNGRVITRMRVYRARGTIKAYQIWLTDSAPQTHGVPGNSDFAEYT
PtIP-96Hi  (100)   SVRGWTNGRVITRMRVYRARGTIKAYQIWLTDSGPETHGVPGNSDFAEYT
PtIP-96He  (101)   SVRGWTNGRVITRMRVYRARGTIKAYRIWLTDSGPETHGVPGNSDFAEYT
PtIP-96Hj  (101)   SVRGWTNGRVITRMRVYRARGTIKAYRIWLTDSGPETHGVPGNSDFAEYT 151                                              200
PtIP-96Ha  (150)   FRTGERLTRLTLWGNGMGTRAGWIEFETSLGGRFSYGMSHWSLRTPYPVD
PtIP-96Hb  (150)   FRTGERLTRLTLWGNGMGTRAGWIEFETSLGGRFSYGMSHWSLRTPYPVD
PtIP-96Hc  (150)   FRTGERLTRLTLWGNGIGTRAGWIEFETSLGGRFSYGMSHWSLRTPYPVD
PtIP-96Hd  (150)   FRTGERLTRLTLWGNGIGTRAGWIEFETSLGGRFSYGMSHWSLRTPYPVD
PtIP-96Hf  (150)   FRTGERLTRLTLWGNGIGTRAGWIEFETSLGGRFSYGMSHWSLRTPYPVD
PtIP-96Hg  (150)   FRTGERLTRLTLWGNGIGTRAGWIEFETSLGGRFSYGMSHWSLRTSYPVD
PtIP-96Hh  (150)   FRTGERLTRLTLWGNGMGTRAGWIEFETSLGGRFSYGMSHWSLRTPYPVD
PtIP-96Hi  (150)   FRTGERLTRLTLWGNGIGTRAGWIEFETSLGGRFSYGMSHWSLRTPYPVD
PtIP-96He  (151)   FRTGERLTRLTLWGNGIGTRAGWIEFETSLGGRFSYGMSHWSLRTPYPVD
PtIP-96Hj  (151)   FRTGERLTRLTLWGNGIGTRAGWIEFETSLGGRFSYGMSHWSLRTPYPVD
```

Fig. 6B

```
                     201                                               250
PtIP-96Ha   (200)    VGSGILVGYIFNAGEDVDAHGFWFLNHIEQAELTNVRYPTLGFDTAGIVP
PtIP-96Hb   (200)    VGSGILVGYIFNAGEDVDAHGFWFLNHIEQAELTNVRYPTLGFDTAGIVP
PtIP-96Hc   (200)    VGSGILVGYIFNAGEDVDAHGFWFLNHIQQAELTNVRYPTLGFDTAGIVP
PtIP-96Hd   (200)    VGSGILVGYIFNAGEDVDAHGFWFLNHIQQAELTNVRYPTLGFDTAGIVP
PtIP-96Hf   (200)    VGSGILVGYIFNAGEDVDAHGFWFLNHIEQAELTNVRYPTLGFDTAGIVP
PtIP-96Hg   (200)    VGSGILVGYIFNAGEDVDAHGFWFLNHIEQAELTNVRYPTLGFDTAGIVP
PtIP-96Hh   (200)    VGSGILVGYIFNAGEDVDAHGFWFLNHIEQAELTNVRYPTLGFDTAGIVP
PtIP-96Hi   (200)    VGSGILVGYIFNAGEDVDAHGFWFLNHIEQAELTNVRYPTFGFDTAGIVP
PtIP-96He   (201)    VGSGILVGYIFNAGEEVDAHGFWFLNHIQQAELTNVRYPTLGFDTAGIVP
PtIP-96Hj   (201)    VGSGILVGYIFNAGEEVDAHGFWFLNHIQQAELTNVRYPTLGFDTAGIVP 251                                               300
PtIP-96Ha   (250)    TALDTFRFRNNSSTPRDWDFSRNMSRSTERTWSITVDLTVHASITVSAGF
PtIP-96Hb   (250)    TALDTFRFRNNSSTPRDWDFSRNMSRSTERTWSITVDLTVHASITVSAGF
PtIP-96Hc   (250)    TALDTFRFRNNSSTPRDWDFSRNMSRSTERTWSITVDLTVHASITVSAGF
PtIP-96Hd   (250)    TALDTFRFRNNSSTPRDWDFSRNMSRSTERTWSITVDLTVHASITVSAGF
PtIP-96Hf   (250)    TALDTFRFRNNSSTPRDWDFSRNMSRSTERTWSITVDLTVHASITVSAGF
PtIP-96Hg   (250)    TALDTFRFRNNSSTPRDWDFSRNMSRSTERTWSITVDLTVHASITVSAGF
PtIP-96Hh   (250)    TALDTFRFRNNSSTPRDWDFSRNMSRSTERTWSITVDLTVHAIITVSAGF
PtIP-96Hi   (250)    TALDTFRFRNNSSTPRDWDFSRNMSRSTERTWSITVDLTVHASITVSAGF
PtIP-96He   (251)    TALDTFRFRNNSSTPRDWDFSRNMSRSTERTWSITVDLTVHASITVSAGF
PtIP-96Hj   (251)    TALDTFRFRNNSSTPRDWDFSRNMSRSTERTWSITVDLTVHASITVSAGF 301                                               350
PtIP-96Ha   (300)    PGIANVSGQYGWEIGVTGHFETTETSEHDLSWSVGGRVQPGDVVDLTALT
PtIP-96Hb   (300)    PGIANVSGQYGWEIGATGHFETTETSEHDLSWSVSGRVQPGDVVDLTALT
PtIP-96Hc   (300)    PGIANVSGQYGWEIGATGHFETTETSEHDLSWSVSGRVQPGEFVDLTALT
PtIP-96Hd   (300)    PGIANVSGQYGWEIGATGHFETTETSEHDLSWSVSGRVQPGEFVDLTALT
PtIP-96Hf   (300)    PGIANVSGQYGWEIGATGHFETTETSEHDLSWSVSGIVQPGDVVDLTALT
PtIP-96Hg   (300)    PGIANVSGQYGWEIGATGHFETTETSEHDLSWSVSGIVQPGDVVDLTALT
PtIP-96Hh   (300)    PGIANVSGQYGWEIGATGHFETTETSEHDLSWSVSGRVQPGDVVDLTALT
PtIP-96Hi   (300)    PGIANVSGQYGWEIGATGHFETTETSEHDLSWSVSGIVQPGDVVDLTALT
PtIP-96He   (301)    PGIANVSGQYGWEIGATGHFETTETSEHDLSWSVSGRVQPGDVVDLTALT
PtIP-96Hj   (301)    PGIANVSGQYGWEIGATGHFETTETSEHDLSWSVSGRVQPGDVVDLTALT 351                                          396
PtIP-96Ha   (350)    RTGTLNIPYEGTMVVRMRNGASFSYAVRGTYRGLSYTGTKINDNST
PtIP-96Hb   (350)    RTGTLNIPYEGTMVVRMRNGASFSYAVRGTYRGLSYTGTKINDNST
PtIP-96Hc   (350)    RTGTLNIPYEGTMVVRMRNGASFSYAVRGTYRGLSYTGTKINDNST
PtIP-96Hd   (350)    RTGTLNIPYEGTMVVRMRNGASFSYAVRGTYRGLSYTGTKINDNST
PtIP-96Hf   (350)    RTGTLNIPYEGTMVVRMRNGASFSYAVRGTYRGLSYTGTKINDNST
PtIP-96Hg   (350)    RTGTLNIPYEGTMVVRMRNGASFSYAVRGTYRGLSYTGTKINDNST
PtIP-96Hh   (350)    RTGTLNIPYEGTMVVRMRNGASFSYAVRGTYRGLSYTGTKINDNST
PtIP-96Hi   (350)    RTGTLNIPYEGTMVVRMRNGASFSYAVRGTYRGLSYTGTKINDNST
PtIP-96He   (351)    RTGTLNIPYEGTMVVRMRNGASFSYAVRGTYRGLSYTGTKINDNST
PtIP-96Hj   (351)    RTGTLNIPYEGTMVVRMRNGASFSYAVRGTYRGLSYTDTKINDNST
```

Fig. 7A

```
                    1                                                  50
PtIP-96Da    (1)   --MSIVQSPIHVIGGSGGSAFSYNAGTNGRILRRIGVWAGGWFLGGIRAW
PtIP-96De    (1)   --MSIYQTPVSLIGGQGGTAFTYNAGESGRVLRRIGVWAVDSALRGIRVW
PtIP-96Df    (1)   MSTAIFQTPVSLIGGQGGTAFTYNAGESGRVLRRIGVWAVDSALRGIRVW
PtIP-96Dc    (1)   --MSIFQTPVHVIGGQGGGAFSYNAGASGRVLRRIGVWAGGWYLGGIRLW
PtIP-96Db    (1)   --MSIFQTPVHVIGGQGGGAFSYNAGASGRVLRRIGVWAGGWYLGGIRLW
PtIP-96Dd    (1)   --MSIFQTTVHVIGGQGGGAFSYNAGASGRVLRRIGVWAGGWYLGGIRLW 51                                                100
PtIP-96Da   (49)   WTGLDNPVLFGTANVGSYKEFTFEDGERITSLSLWGNGAGTRSGGIRFRT
PtIP-96De   (49)   WTGLDSPLTYGTANSGFYKEFSFQVGERITSLSLWGNGAGTRSGAIRFYT
PtIP-96Df   (51)   WTGLDSPLTYGTANSGFYKEFSFQVGERITSLSLWGNGAGTRSGAIRFYT
PtIP-96Dc   (49)   WTGLDDSITYGTANSGSYREFTFEDGERITSLSLWGNGAGTRSGGIRFRT
PtIP-96Db   (49)   WTGLDDSITYGTANSGSYREFTFEDGERITSLSLWGNGAGTRSGGIRFRT
PtIP-96Dd   (49)   WTGLDDSITYGTANSGSYREFTFEDGERITSLSLWGNGAGTRSGGIRFRT 101                                               150
PtIP-96Da   (99)   TTGREFFHYMTSWGLKQEYPIDVASGLCVGLIGRHGEHIDSLGFMFLRSI
PtIP-96De   (99)   STGREFFHYMTSWGLKQEYPIDVVDGLCVGVTGRHGTDIDALGFMFLRTM
PtIP-96Df  (101)   STGREFFHYMTSWGLKQEYPIDVVDGLCVGVTGRHGTDIDALGFMFLRTM
PtIP-96Dc   (99)   TGGREFFHYMTSWGLQQEYPIDVASGLCVGVIGRHGDHIDSLGFMFLRTI
PtIP-96Db   (99)   TGGREFFHYMTSWGLQQEYPIDVASGLCVGVIGRHGDHIDSLGFMFLRTI
PtIP-96Dd   (99)   TGGREFFHYMTSWGLQQEYPIDVASGLCVGVIGRHGDHIDSLGFMFLRTI 151                                               200
PtIP-96Da  (149)   ASARMINVSYPTLGLETAGIVPVTLDSMSNNNNSGSLPSNWAFRGSREVT
PtIP-96De  (149)   TSARMVDVTYPTLGFDTAGIAPITLDSYSDANQSGSISKNWSFEGSREVT
PtIP-96Df  (151)   TSARMVDVTYPTLGFDTAGIAPITLDSYSDANQSGSISKNWSFEGSREVT
PtIP-96Dc  (149)   ASARMINVSYPTLDLETAGIVPVTLDSMSDSNNAGTISKNWTFGGSRSVT
PtIP-96Db  (149)   ASARMINVSYPTLDLETAGIVPVTLDSMSDSNNAGTISKNWTFGGSRSVT
PtIP-96Dd  (149)   ASARMINVSYPTLDLETAGIVPVTLDSMSDSNNAGTISKNWTFGGSRSVT 201                                               250
PtIP-96Da  (199)   MSSTWSVTAGIELHASVTVTAGIPTVAEVQGQYGWAVSTSSTFSTTHTET
PtIP-96De  (199)   VSSSWSVTAGIEFHASVTVSAGIPLVLDVDGEFGWAISASATYTTNSSET
PtIP-96Df  (201)   VSSSWSVTAGIEFHASVTVSAGIPLVLDVDGEFGWAISASATYTTNSSET
PtIP-96Dc  (199)   ISSSWAITAGIELHASITVTAGIPTVAEVQGEYGWSISSSSTYTTSHEET
PtIP-96Db  (199)   ISSSWAITAGIELHASITVTAGIPTVAEVQGEYGWSISSSSTYTTSHEET
PtIP-96Dd  (199)   ISSSWAITAGIELHASITVTAGIPTVAEVQGEYGWSISSSSTYTTSHEET
```

Fig. 7B

```
              251                                              300
PtIP-96Da (249) RSLQWEVSGVLQPGEWISLQALTRRGVISLPYQATMQITLQNGAVFTYPI
PtIP-96De (249) RTLKWNNSGVLEPGQWISLQAVTRKGTINIPYQANMQITLQNGVIFTYAL
PtIP-96Df (251) RTLKWNNSGVLEPGQWISLQAVTRKGTINIPYQANMQITLQNGVIFTYAL
PtIP-96Dc (249) RTLSWENSGVLQPGEWISLQALTRRGTISLPYQATMQITLQNGALFTYPI
PtIP-96Db (249) RTLSWENSGVLQPGEWISLQALTRRGTISLPYQATMQITLQNGALFTYPI
PtIP-96Dd (249) RTLSWENSGVLQPGEWISLQALTRRGTISLPYQATMQITLQNGALFTYPI 301                                              350
PtIP-96Da (299) TAMYAGVDYTSVELVHLLDWPT----------------------------
PtIP-96De (299) AGQYAGVDYTDVQVVNDGTKNAGHVSTTAAKGTTGTTTAARMGALANSVR
PtIP-96Df (301) AGQYAGVDYTDVQVVNDGTKNAGHVSTTAAKGTTGTTTAARMGALANSVR
PtIP-96Dc (299) TALYAGVDYTNVQIVSTGTRHLDYDHVRSAGGRRLVSAISNKGSLPTAAT
PtIP-96Db (299) TALYAGVDYTNVQIVSTGTRHLDYDHVRSAGGRRLVSAISNKGSLPTAAT
PtIP-96Dd (299) TALYAGVDYTNVQIVSTGTRHLDYDHVRSAGGRRLVSAISNKGSLPTAAT 351                                              400
PtIP-96Da (321) --------------------------------------------------
PtIP-96De (349) HVRAASIPRPVKFSAGATYINDTTNNITQEVHSSAPTGVEELTLVY----
PtIP-96Df (351) HVRAASIPRPVKFSAGATYINDTTNNITQEVHSSAPTGVEELTLVY----
PtIP-96Dc (349) TSVIAPPRYVHPVNIPAVLYTSVIEPVKVVATRAAPTSINDDNIKQEPLV
PtIP-96Db (349) TSVIAPPRYVHPVNIPAVPYTSVIEPVKVVATRAAPTSINDDNIKQEPLV
PtIP-96Dd (349) TSVIAPPRYVHPVNIPAVPYTSVIEPVKVVATRAAPTSINDDNIKQEPLV

401
PtIP-96Da (321) ----------
PtIP-96De (395) ----------
PtIP-96Df (397) ----------
PtIP-96Dc (399) ATEERTLVY-
PtIP-96Db (399) ATEERTLVY-
PtIP-96Dd (399) ATEERTLVY-
```

INSECTICIDAL PROTEINS AND METHODS FOR THEIR USE

This application is a 371 (National Stage) of PCT/US15/55502 filed Oct. 14, 2015, which claims the benefit of U.S. Provisional Application No. 62/064,810 filed Oct. 16, 2014, which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "6584WOPCT_sequence_listing" created on Sep. 14, 2015, and having a size of 255 kilobytes and is filed concurrently with the specification. The sequence listing contained in this ASCII formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of Bt. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

Compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues and seeds.

In particular, isolated or recombinant nucleic acid molecules are provided encoding Pteridophyta and Lycopodiophyta Insecticidal Protein-96 (PtIP-96) polypeptides including amino acid substitutions, deletions, insertions, fragments thereof. Additionally, amino acid sequences corresponding to the PtIP-96 polypeptides are encompassed. Provided are isolated or recombinant nucleic acid molecules capable of encoding PtIP-96 polypeptides of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. Also provided are isolated or recombinant PtIP-96 polypeptides of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO:

100, SEQ ID NO: 102, SEQ ID NO: 104, SEQ ID NO: 106 or SEQ ID NO: 108 as well as amino acid substitutions, deletions, insertions, fragments thereof and combinations thereof.

Methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

Methods for detecting the nucleic acids and polypeptides of the embodiments in a sample are also included. A kit for detecting the presence of a PtIP-96 polypeptide or detecting the presence of a polynucleotide encoding a PtIP-96 polypeptide in a sample is provided. The kit may be provided along with all reagents and control samples necessary for carrying out a method for detecting the intended agent, as well as instructions for use.

The compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of PtIP-96 polypeptides.

BRIEF DESCRIPTION OF THE FIGURES

FIG. 1A-1K shows an amino acid sequence alignment, using the ALIGNX® module of the Vector NTI® suite, of the PtIP-96 polypeptides: PtIP-96Aa (SEQ ID NO: 9); PtIP-96Ab (SEQ ID NO: 12); PtIP-96Ac (SEQ ID NO: 14); PtIP-96Ad (SEQ ID NO: 16); PtIP-96Ae (SEQ ID NO: 18); PtIP-96Af (SEQ ID NO: 20); PtIP-96Ag (SEQ ID NO: 22); PtIP-96Ah (SEQ ID NO: 24); PtIP-96Ca (SEQ ID NO: 26); PtIP-96Cb (SEQ ID NO: 28); PtIP-96Cc (SEQ ID NO: 30); PtIP-96Cd (SEQ ID NO: 32); PtIP-96Ce (SEQ ID NO: 34); PtIP-96Cf (SEQ ID NO: 36); PtIP-96Cg (SEQ ID NO: 38); PtIP-96Ch (SEQ ID NO: 40); PtIP-96 Da (SEQ ID NO: 42); PtIP-96Db (SEQ ID NO: 44); PtIP-96Dc (SEQ ID NO: 46); PtIP-96Dd (SEQ ID NO: 52); PtIP-96De (SEQ ID NO: 48); PtIP-96Df (SEQ ID NO: 50); PtIP-96Ea (SEQ ID NO: 7); PtIP-96Eb (SEQ ID NO: 8); PtIP-96Ec (SEQ ID NO: 6); PtIP-96Ed (SEQ ID NO: 54); PtIP-96Ee (SEQ ID NO: 56); PtIP-96Ef (SEQ ID NO: 58); PtIP-96Eg (SEQ ID NO: 60); PtIP-96Eh (SEQ ID NO: 62); PtIP-96Ei (SEQ ID NO: 64); PtIP-96Ej (SEQ ID NO: 66); PtIP-96Ek (SEQ ID NO: 68); PtIP-96El (SEQ ID NO: 70); PtIP-96Em (SEQ ID NO: 72); PtIP-96En (SEQ ID NO: 74); PtIP-96Eo (SEQ ID NO: 76); PtIP-96Ep (SEQ ID NO: 78); PtIP-96Eq (SEQ ID NO: 80); PtIP-96Er (SEQ ID NO: 82); PtIP-96Es (SEQ ID NO: 84); PtIP-96Et (SEQ ID NO: 86); PtIP-96Eu (SEQ ID NO: 88); PtIP-96Ev (SEQ ID NO: 90); PtIP-96Ha (SEQ ID NO: 10); PtIP-96Hd (SEQ ID NO: 96); PtIP-96He (SEQ ID NO: 98); PtIP-96Hf (SEQ ID NO: 100); PtIP-96Hg (SEQ ID NO: 102); PtIP-96Hh (SEQ ID NO: 104); PtIP-96Hi (SEQ ID NO: 106); PtIP-96Hj (SEQ ID NO: 108). Conserved amino acid positions between the PtIP-96 polypeptide homologs are highlighted. Non-conservative amino acids differences between the PtIP-96 polypeptide homologs are highlighted.

FIG. 2A-2B shows an amino acid sequence alignment, using the ALIGNX® module of the Vector NTI® suite, of the PtIP-96 polypeptides: PtIP-96Aa (SEQ ID NO: 9); PtIP-96Ab (SEQ ID NO: 12); PtIP-96Ac (SEQ ID NO: 14); PtIP-96Ad (SEQ ID NO: 16); PtIP-96Ae (SEQ ID NO: 18); PtIP-96Af (SEQ ID NO: 20); PtIP-96Ag (SEQ ID NO: 22); and PtIP-96Ah (SEQ ID NO: 24). The amino acid sequence diversity between the PtIP-96 polypeptide homologs is highlighted.

FIG. 3A-3B shows an amino acid sequence alignment, using the ALIGNX® module of the Vector NTI® suite, of the PtIP-96 polypeptides: PtIP-96Ca (SEQ ID NO: 26); PtIP-96Cb (SEQ ID NO: 28); PtIP-96Cc (SEQ ID NO: 30); PtIP-96Cd (SEQ ID NO: 32); PtIP-96Ce (SEQ ID NO: 34); PtIP-96Cf (SEQ ID NO: 36); PtIP-96Cg (SEQ ID NO: 38); and PtIP-96Ch (SEQ ID NO: 40). The amino acid sequence diversity between the PtIP-96 polypeptide homologs is highlighted.

FIG. 4A-4D shows an amino acid sequence alignment, using the ALIGNX® module of the Vector NTI® suite, of the PtIP-96 polypeptides: PtIP-96Ea (SEQ ID NO: 7); PtIP-96Eb (SEQ ID NO: 8); PtIP-96Ec (SEQ ID NO: 6); PtIP-96Ed (SEQ ID NO: 54); PtIP-96Ee (SEQ ID NO: 56); PtIP-96Ef (SEQ ID NO: 58); PtIP-96Eg (SEQ ID NO: 60); PtIP-96Eh (SEQ ID NO: 62); PtIP-96Ei (SEQ ID NO: 64); PtIP-96Ej (SEQ ID NO: 66); PtIP-96Ek (SEQ ID NO: 68); PtIP-96El (SEQ ID NO: 70); PtIP-96Em (SEQ ID NO: 72); PtIP-96En (SEQ ID NO: 74); PtIP-96Er (SEQ ID NO: 82); PtIP-96Es (SEQ ID NO: 84); PtIP-96Et (SEQ ID NO: 86); PtIP-96Eu (SEQ ID NO: 88); and PtIP-96Ev (SEQ ID NO: 90). The amino acid sequence diversity between the PtIP-96 polypeptide homologs is highlighted.

FIG. 5 shows an amino acid sequence alignment, using the ALIGNX® module of the Vector NTI® suite, of the PtIP-96 polypeptides: PtIP-96Eo (SEQ ID NO: 76); PtIP-96Ep (SEQ ID NO: 78); and PtIP-96Eq (SEQ ID NO: 80). The amino acid sequence diversity between the PtIP-96 polypeptide homologs is highlighted.

FIG. 6A-6B shows an amino acid sequence alignment, using the ALIGNX® module of the Vector NTI® suite, of the PtIP-96 polypeptides: PtIP-96Ha (SEQ ID NO: 10); PtIP-96Hb (SEQ ID NO: 92); PtIP-96Hc (SEQ ID NO: 94); PtIP-96Hd (SEQ ID NO: 96); PtIP-96He (SEQ ID NO: 98); PtIP-96Hf (SEQ ID NO: 100); PtIP-96Hg (SEQ ID NO: 102); PtIP-96Hh (SEQ ID NO: 104); PtIP-96Hi (SEQ ID NO: 106); and PtIP-96Hj (SEQ ID NO: 108). The amino acid sequence diversity between the PtIP-96 polypeptide homologs is highlighted.

FIG. 7A-7B shows an amino acid sequence alignment, using the ALIGNX® module of the Vector NTI® suite, of the PtIP-96 polypeptides: PtIP-96 Da (SEQ ID NO: 42); PtIP-96Db (SEQ ID NO: 44); PtIP-96Dc (SEQ ID NO: 46); PtIP-96Dd (SEQ ID NO: 52); PtIP-96De (SEQ ID NO: 48); and PtIP-96Df (SEQ ID NO: 50). The amino acid sequence diversity between the PtIP-96 polypeptide homologs is highlighted.

DETAILED DESCRIPTION

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding PtIP-96 polypeptides. In particular, the nucleic acid sequences of the embodiments are useful for preparing plants and microorganisms that possess pesticidal activity. Thus, transformed bacteria, plants, plant cells, plant tissues and seeds are provided. The compositions are pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered PtIP-96 polypeptides by methods known in the art, such as site directed mutagenesis, domain swapping or DNA shuffling. The PtIP-96 find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Péchy-Tarr, (2008) *Environmental Microbiology* 10:2368-2386; GenBank Accession No. EU400157); from *Pseudomonas Taiwanensis* (Liu, et al., (2010) *J. Agric. Food Chem.*, 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of U.S. Ser. No. 13/839,702; a PIP-47 polypeptide of PCT Serial Number PCT/US14/51063, a PIP-72 polypeptide of PCT Serial Number PCT/US14/55128, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic cyt1 and cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476, 781, 7,105,332, 7,378,499 and 7,462,760; a Cry9 protein such as such as members of the Cry9A, Cry9B, Cry9C, Cry9D, Cry9E and Cry9F families; a Cry15 protein of Naimov, et al., (2008) *Applied and Environmental Microbiology*, 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923, 602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI- 023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1DA & Cry1BE (US2012/0331590); Cry1DA & Cry1Fa (US2012/0331589); Cry1AB & Cry1BE (US2012/0324606); Cry1Fa & Cry2Aa and Cry1I & Cry1E (US2012/0324605); Cry34Ab/35Ab and Cry6Aa (US20130167269); Cry34Ab/VCry35Ab & Cry3Aa (US20130167268); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

In some aspects the PtIP-96 polypeptide include amino acid sequences deduced from the full-length nucleic acid sequences disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of PtIP-96 polypeptides. The protein resulting from translation of these PtIP-96 polypeptide genes allows cells to control or kill pests that ingest it.

Nucleic Acid Molecules, and Variants and Fragments Thereof

One aspect pertains to isolated or recombinant nucleic acid molecules comprising nucleic acid sequences encoding PtIP-96 polypeptides or biologically active portions thereof, as well as nucleic acid molecules sufficient for use as hybridization probes to identify nucleic acid molecules encoding proteins with regions of sequence homology. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant"

when used to refer to nucleic acid molecules excludes isolated chromosomes. For example, in various embodiments, the recombinant nucleic acid molecule encoding PtIP-96 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

Isolated nucleic acid molecule encoding PtIP-96 polypeptides are contemplated having one or more change in the nucleic acid sequence compared to the native or genomic nucleic acid sequence. The change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding a PtIP-96 polypeptide is a non-genomic sequence.

A variety of polynucleotides that encode PtIP-96 polypeptides or related proteins are contemplated. Such polynucleotides are useful for production of PtIP-96 polypeptides in host cells when operably linked to suitable promoter, transcription termination and/or polyadenylation sequences. Such polynucleotides are also useful as probes for isolating homologous or substantially homologous polynucleotides that encode PtIP-96 polypeptides or related proteins.

Polynucleotides Encoding PtIP-96 Polypeptides

One source of polynucleotides that encode PtIP-96 polypeptides or related proteins is a fern or other primitive plant species which contains a PtIP-96 polynucleotide of SEQ ID NO: 1, SEQ ID NO: 2, SEQ ID NO: 3, SEQ ID NO: 4, SEQ ID NO: 15, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25; SEQ ID NO: 27; SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107 or SEQ ID NO: 109, encoding a PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108. The polynucleotides of SEQ ID NO: 1, SEQ ID NO: 2, SEQ ID NO: 3, SEQ ID NO: 4, SEQ ID NO: 15, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25; SEQ ID NO: 27; SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107 or SEQ ID NO: 109 can be used to express PtIP-96 polypeptides in bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode PtIP-96 polypeptides or related proteins. Such probes can be used to identify homologous or substantially homologous polynucleotides derived from Pteridophyta and Lycopodiophyta species.

Polynucleotides that encode PtIP-96 polypeptides can also be synthesized de novo from a PtIP-96 polypeptide sequence. The sequence of the polynucleotide gene can be deduced from a PtIP-96 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of PtIP-96 polypeptide sequences that can be used to obtain corresponding nucleotide encoding sequences include, but are not limited to the PtIP-96 polypeptides of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108. Furthermore, synthetic PtIP-96 polynucleotide sequences of the disclosure can be designed so that they will be expressed in plants. U.S. Pat. No. 5,500,365 describes a method for synthesizing plant genes to improve the expression level of the protein encoded by the synthesized gene. This method relates to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein. A similar method for obtaining enhanced expression of transgenes in monocotyledonous plants is disclosed in U.S. Pat. No. 5,689,052.

The nucleic acid molecule encoding a PtIP-96 polypeptide can be a polynucleotide having the sequence set forth in SEQ ID NO: 1, SEQ ID NO: 2, SEQ ID NO: 3, SEQ ID NO: 4, SEQ ID NO: 15, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25; SEQ ID NO: 27; SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107 or SEQ ID NO: 109, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

The nucleic acid molecule encoding the PtIP-96 polypeptide can be a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

In some embodiments the nucleic acid molecules encoding a PtIP-96 polypeptide is a non-genomic nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity, to the nucleic acid sequence of SEQ ID NO: 1, SEQ ID NO: 2, SEQ ID NO: 3, SEQ ID NO: 4, SEQ ID NO: 15, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25; SEQ ID NO: 27; SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107 or SEQ ID NO: 109, wherein the PtIP-96 polypeptide has insecticidal activity.

In some embodiments the nucleic acid molecule encodes a PtIP-96 polypeptide comprising an amino acid sequence of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments the nucleic acid molecule encoding the PtIP-96 polypeptide is derived from a fern species in the Division Pteridophyta or other primitive plant of the Division Lycopodiophyta The phylogeny of ferns as used herein is based on the classification for extant ferns by A. R. Smith et al, *TAXON,* 55:705-731 (2006). The consensus phylogeny based on the classification by A. R. Smith is shown in FIG. 1. Other phylogenic classifications of extant ferns are known to one skilled in the art. Additional information on the phylogeny of ferns can be found at mobot.org/MOBOT/research/APweb/ (which can be accessed using the "www" prefix) and Schuettpelz E. and Pryer K. M., *TAXON* 56: 1037-1050 (2007) based on three plastid genes. Additional fern and other primitive plant species can be found at homepages.caverock.net.nz/~bj/fern/list.htm (which can be accessed using the http:// prefix).

In some embodiments the nucleic acid molecule encoding the PtIP-96 polypeptide is derived from a fern species in the Class Psilotopsida. In some embodiments the nucleic acid molecule encoding the PtIP-96 polypeptide is derived from a fern species in the Class Psilotopsida, Order Psilotales. In some embodiments the nucleic acid molecule encoding PtIP-96 polypeptide is derived from a fern species in the Class Psilotopsida, Order Ophioglossales. In some embodiments the nucleic acid molecule encoding the PtIP-96 polypeptide is derived from a fern species in the Class Psilotopsida, Order Ophioglossales, Family Psilotaceae. In some embodiments the nucleic acid molecule encoding the PtIP-96 polypeptide is derived from a fern species in the Class Psilotopsida, Order Ophioglossales Family Ophioglossaceae. In some embodiments the nucleic acid molecule encoding the PtIP-96 polypeptide is derived from a fern species in the Genus *Ophioglossum* L., *Botrychium, Botrypus, Helminthostachys, Ophioderma, Cheiroglossa, Sceptridium* or *Mankyua*. In some embodiments the nucleic acid molecule encoding the PtIP-96 polypeptide is derived from a fern species in the *Ophioglossum* L. Genus is selected from but not limited to *Ophioglossum califomicum, Ophioglossum coriaceum, Ophioglossum costatum, Ophioglossum crotalophoroides, Ophioglossum engelmannii, Ophioglossum falcatum, Ophioglossum gomezianum, Ophioglossum gramineum, Ophioglossum kawamurae, Ophioglossum lusitanicum, Ophioglossum namegatae, Ophioglossum nudicaule, Ophioglossum palmatum, Ophioglossum parvum, Ophioglossum pedunculosum, Ophioglossum pendulum, Ophioglossum petiolatum, Ophioglossum pusillum, Ophioglossum reticulatum, Ophioglossum richardsiae, Ophioglossum thermale,* and *Ophioglossum vulgatum*.

In some embodiments the nucleic acid molecule encoding the PtIP-96 polypeptide is derived from a fern species in the Order Polypodiales, Family Polypodiaceae, Genus *Campyloneurum*, Genus *Drynaria*, Genus *Lepisorus*, Genus *Microgramma*, Genus *Microsorum*, Genus *Neurodium*, Genus *Niphidium*, Genus *Pecluma* M.G., Genus *Phlebodium*, Genus *Phymatosorus*, Genus *Platycerium*, Genus *Pleopeltis*, Genus *Polypodium* L or Genus *Colysis*.

In some embodiments the nucleic acid molecule encoding the PtIP-96 polypeptide is derived from a fern species in the *Colysis* Genus selected from but not limited to *Colysis ampla, Colysis digitata, Colysis diversifolia, Colysis elegans Colysis elliptica, Colysis flexiloba, Colysis hemionitidea, Colysis hemitoma, Colysis henryi, Colysis insignis, Colysis intermedia, Colysis leveillei, Colysis longipes, Colysis pedunculata, Colysis pentaphylla, Colysis pothifolia, Colysis pteropus, Colysis shintenensis, Colysis simplicifrons, Colysis triphylla, Colysis wrightii,* and *Colysis×shintenensis*.

In some embodiments the nucleic acid molecule encoding the PtIP-96 polypeptide is derived from a fern species in the Order Polypodiales, Family Pteridaceae, Genus *Adiantaceae* selected from but not limited to *Adiantum aethiopicum, Adiantum aleuticum, Adiantum bonatianum, Adiantum cajennense, Adiantum capillus-junonis, Adiantum capillus-veneris, Adiantum caudatum, Adiantum chienii, Adiantum chilense, Adiantum cuneatum, Adiantum cunninghamii, Adiantum davidii, Adiantum diaphanum, Adiantum edentulum, Adiantum edgeworthii, Adiantum excisum, Adiantum fengianum, Adiantum fimbriatum, Adiantum flabellulatum, Adiantum formosanum, Adiantum formosum, Adiantum fulvum, Adiantum gravesii, Adiantum hispidulum, Adiantum induratum, Adiantum jordanii, Adiantum juxtapositum, Adiantum latifolium, Adiantum leveillei, Adiantum lianxianense, Adiantum malesianum, Adiantum mariesii, Adiantum monochlamys, Adiantum myriosorum, Adiantum obliquum, Adiantum ogasawarense, Adiantum pedatum, Adiantum pentadactylon, Adiantum peruvianum, Adiantum philippense, Adiantum princeps, Adiantum pubescens, Adiantum raddianum, Adiantum raddianum, Adiantum reniforme, Adiantum roborowskii, Adiantum serratodentatum, Adiantum sinicum, Adiantum soboliferum, Adiantum subcordatum, Adiantum tenerum, Adiantum terminatum, Adiantum tetraphyllum, Adiantum venustum, Adiantum viridescens,* and *Adiantum viridimontanum*.

In some embodiments the nucleic acid molecule encoding the PtIP-96 polypeptide is derived from a fern species in the Order Polypodiales, Family Dryopteridaceae Genus *Polystichum* selected from but not limited to *Polystichum acanthophyllum, Polystichum acrostichoides, Polystichum aculeatum, Polystichum acutidens, Polystichum acutipinnulum, Polystichum alcicorne, Polystichum aleuticum, Polystichum andersonii, Polystichum atkinsonii, Polystichum australiense, Polystichum bakerianum, Polystichum biaristatum, Polystichum bomiense, Polystichum bonseyi, Polystichum brachypterum, Polystichum braunii, Polystichum brachypterum, Polystichum calderonense, Polystichum califomicum, Polystichum capillipes, Polystichum castaneum, Polystichum chilense, Polystichum christii, Polystichum chunii, Polystichum craspedosorum, Polystichum cyclolobum, Polystichum cystostegia, Polystichum deltodon, Polystichum dielsii, Polystichum discretum, Polystichum drepanum, Polystichum dudleyi, Polystichum duthiei, Polystichum echinatum, Polystichum erosum, Polystichum excellens, Polystichum eximium, Polystichum falcatipinnum, Polystichum falcinellum, Polystichum fallax, Polystichum formosanum, Polystichum glandulosum, Polystichum gongboense, Polystichum grandifrons, Polystichum gymnocarpium, Polystichum haleakalense, Polystichum hancockii, Polystichum hecatopteron, Polystichum herbaceurn, Polystichum imbricans, Polystichum incongruum, Polystichum kruckebergiil, Polystichum kwakiutlii, Polystichum lachenense, Polystichum lanceolatum, Polystichum lemmonii, Polystichum lentum, Polystichum lonchitis, Polystichum longidens, Polystichum longipaleatum, Polystichum longipes, Polystichum luctuosum, Polystichum macleae, Polystichum macrochlaenum, Polystichum makinoi, Polystichum martini, Polystichum mayebarae, Polystichum mediocre, Polystichum medogense, Polystichum microchlamys, Polystichum mohrioides, Polystichum mollissimum, Polystichum monticola, Polystichum moorei, Polystichum morii, Polystichum moupinense, Polystichum munitum, Polystichum muricatum, Polystichum nakenense, Polystichum neolobatum, Polystichum nepalense, Polystichum ningshenense, Polystichum obliquum, Polystichum omeiense, Polystichum ordinatum, Polystichum orientalitibeticum, Polystichum paramoupinense, Polystichum parvipinnulum, Polystichum piceopaleaceum, Polystichum polyblepharum, Polystichum prescottianurn, Polystichum prionolepis, Polystichum proliferum, Polystichum pseudocastaneum, Polystichum pseudomakinoi, Polystichum punctiferum, Polystichum pungens, Polystichum qamdoense, Polystichum retrosopaleaceurn, Polystichum rhombiforme, Polystichum rhomboidea, Polystichum richardii, Polystichum rigens, Polystichum rotundiloburn, Polystichum scopulinum, Polystichum semifertile, Polystichum setiferum, Polystichum setigerum, Polystichum shensiense, Polystichum silvaticum, Polystichum simplicipinnum, Polystichum sinense, Polystichum squarrosum, Polystichum stenophyllum, Polystichum stimulans, Polystichum submite, Polystichum tacticopterum,*

*Polystichum thomsoni, Polystichum tibeticum, Polystichum transvaalense, Polystichum tripteron, Polystichum tsus-simense, Polystichum vestitum, Polystichum wattii, Polystichum whiteleggei, Polystichum xiphophyllum, Polystichum yadongense*, and *Polystichum yunnanense*.

In some embodiments the nucleic acid molecule encoding the PtIP-96 polypeptide is derived from a fern species in the Order Polypodiales, Family Dryopteridaceae Genus *Cyrtomium* selected from but not limited to *Cyrtomium aequibasis, Cyrtomium balansae, Cyrtomium brevicuneatum, Cyrtomium calcicola, Cyrtomium caryotideum, Cyrtomium caudatum, Cyrtomium confertifolium, Cyrtomium conforme, Cyrtomium coriaceum, Cyrtomium cuneatum, Cyrtomium devexiscapulae, Cyrtomium dubium, Cyrtomium falcatum, Cyrtomium falcipinnum, Cyrtomium fengianum, Cyrtomium fortunei, Cyrtomium fraxinellum, Cyrtomium houi, Cyrtomium integrum, Cyrtomium laetevirens, Cyrtomium latifalcatum, Cyrtomium lonchitoides, Cyrtomium longipes, Cyrtomium macrophyllum, Cyrtomium maximum, Cyrtomium mediocre, Cyrtomium megaphyllum, Cyrtomium micropterum, Cyrtomium moupingense, Cyrtomium neocatyotideum, Cyrtomium nephrolepioides, Cyrtomium nervosum, Cyrtomium obliquum, Cyrtomium omeiense, Cyrtomium ovale, Cyrtomium pseudocaudipinnurn, Cyrtomium recurvum, Cyrtomium retrosopaleaceurn, Cyrtomium salicipinnurn, Cyrtomium serratum, Cyrtomium shandongense, Cyrtomium simile, Cyrtomium sinicum, Cyrtomium sinningense, Cyrtomium spectabile, Cyrtomium taiwanianum, Cyrtomium takusicola, Cyrtomium tengii, Cyrtomium trapezoideum, Cyrtomium tsinglingense, Cyrtomium uniseriale, Cyrtomium urophyllum, Cyrtomium vittatum, Cyrtomium wangianum, Cyrtomium yiangshanense, Cyrtomium yuanum*, and *Cyrtomium yunnanense*.

In some embodiments the nucleic acid molecule encoding the PtIP-96 polypeptide is derived from a fern species in the Order Polypodiales, Family Polypodiaceae, Genus *Platycerium*, selected from but not limited to *Platycerium andinum, Platycerium alcicorne, Platycerium bifurcatum, Platycerium coronarium, Platycerium elephantotis, Platycerium ellisii, Platycerium grande, Platycerium hillii, Platycerium holttumii, Platycerium madagascariense, Platycerium quadridichotomum, Platycerium ridleyi, Platycerium stemaria, Platycerium superbum, Platycerium veitchii, Platycerium wallichii, Platycerium wandae, Platycerium wilhelminae-reginae*, and *Platycerium willinkii*.

In some embodiments the nucleic acid molecule encoding the PtIP-96 polypeptide is derived from a fern species in the Order Polypodiales, Family Polypodiaceae, Genus *Aglaomorpha* selected from but not limited to *Aglaomorpha acuminata, Aglaomorpha brooksii, Aglaomorpha cornucopia, Aglaomorpha coronans, Aglaomorpha drynarioides, Aglaomorpha heraclea, Aglaomorpha hieronymi, Aglaomorpha latipinna, Aglaomorpha meyeniana, Aglaomorpha nectarifera, Aglaomorpha novoguineensis, Aglaomorpha parkinsoni, Aglaomorpha pilosa*, and *Aglaomorpha splendens*.

In some embodiments the nucleic acid molecule encoding the PtIP-96 polypeptide is derived from a fern species in the Order Cyatheales, Family Cyatheaceae, Genus *Cyathea*, Subgenus *Cyathea*, selected from but not limited to *Cyathea acutidens, Cyathea aemula, Cyathea alata, Cyathea albomarginata, Cyathea alphonsiana, Cyathea alstonii, Cyathea amazonica, Cyathea andina, Cyathea arborea, Cyathea armata, Cyathea ars, Cyathea aspera, Cyathea atahuallpa, Cyathea aterrima, Cyathea atrovirens, Cyathea australis Cyathea barringtonii, Cyathea×bernardii, Cyathea bettinae, Cyathea bicrenata, Cyathea bipinnata, Cyathea boliviana, Cyathea borinquena, Cyathea bradei, Cyathea brevistipes, Cyathea brunnescens, Cyathea×calolepis, Cyathea caracasana, Cyathea cicatricosa, Cyathea concordia, Cyathea conformis, Cyathea conjugata, Cyathea corallifera, Cyathea costaricensis, Cyathea cranhamii, Cyathea cyatheoides, Cyathea cyclodium, Cyathea cystolepis, Cyathea darienensis, Cyathea decomposita, Cyathea decorata, Cyathea decurrens, Cyathea delgadii, Cyathea demissa, Cyathea dichromatolepis, Cyathea dissimilis, Cyathea dissoluta, Cyathea divergens, Cyathea dombeyi, Cyathea dudleyi, Cyathea ebenina, Cyathea estelae, Cyathea falcata, Cyathea frigida, Cyathea fulva, Cyathea furfuracea, Cyathea gardneri, Cyathea gibbosa, Cyathea glauca, Cyathea gracilis, Cyathea halonata, Cyathea harrisii, Cyathea haughtii, Cyathea hemiepiphytica, Cyathea hirsuta, Cyathea hodgeana, Cyathea holdridgeana, Cyathea howeana, Cyathea impar, Cyathea intramarginalis, Cyathea jamaicensis, Cyathea kalbreyeri, Cyathea lasiosora, Cyathea latevagens, Cyathea lechleri, Cyathea leucofolis, Cyathea×lewisii, Cyathea lockwoodiana, Cyathea macrocarpa, Cyathea macrosora, Cyathea marginalis, Cyathea microdonta, Cyathea microphylla, Cyathea microphylla, Cyathea mucilagina, Cyathea multiflora, Cyathea multisegmenta, Cyathea myosuroides, Cyathea nanna, Cyathea nesiotica, Cyathea nigripes, Cyathea nodulifera, Cyathea notabilis, Cyathea onusta, Cyathea palaciosii, Cyathea paladensis, Cyathea pallescens, Cyathea parianensis, Cyathea parva, Cyathea parvula, Cyathea pauciflora, Cyathea petiolata, Cyathea phalaenolepis, Cyathea phalerata, Cyathea phegopteroides, Cyathea pilosissima, Cyathea pinnula, Cyathea platylepis, Cyathea poeppigii, Cyathea praecincta, Cyathea pseudonanna, Cyathea pubens, Cyathea punctata, Cyathea pungens, Cyathea robertsiana, Cyathea rufa, Cyathea ruiziana, Cyathea sagittifolia, Cyathea schiedeana, Cyathea schlimii, Cyathea senilis, Cyathea simplex, Cyathea sipapoensis, Cyathea speciosa, Cyathea squamulosa, Cyathea steyermarkii, Cyathea stipularis, Cyathea stokesii, Cyathea stolzei, Cyathea straminea, Cyathea subtropica, Cyathea suprastrigosa, Cyathea surinamensis, Cyathea tenera, Cyathea tortuosa, Cyathea trichiata, Cyathea tryonorum, Cyathea ursina, Cyathea valdecrenata, Cyathea venezuelensis, Cyathea villosa, Cyathea weatherbyana, Cyathea wendlandii, Cyathea werffii, Cyathea williamsii*.

In some embodiments the nucleic acid molecule encoding the PtIP-96 polypeptide is derived from a fern species in the Order Polypodiales, Family Davalliaceae, Genus *Davallia* selected from but not limited to *Davallia angustata, Davallia assamica, Davallia brassii, Davallia brevipes, Davallia canariensis, Davallia corniculata, Davallia denticulata, Davallia embolostegia, Davallia falcinella, Davallia graeffei, Davallia griffithiana, Davallia heterophylla, Davallia leptocarpa, Davallia parvula, Davallia pectinata, Davallia pentaphylla, Davallia repens, Davallia rouffaeriensis, Davallia seramensis, Davallia sessilifolia, Davallia sessilifolioides, Davallia solida, Davallia speciosa, Davallia tasmanii, Davallia trichomanoides, Davallia triphylla, Davallia undulata, Davallia wagneriana*, and *Davallia yunnanensis*.

In some embodiments the nucleic acid molecule encoding the PtIP-96 polypeptide is derived from a fern species in the Order Schizaeales, Family Lygodiaceae, Genus *Lygodium*, selected from but not limited to *Lygodium altum, Lygodium articulatum, Lygodium boivini Kuhn, Lygodium borneense Alderw., Lygodium circinnatum, Lygodium colaniae, Lygodium conforme, Lygodium cubense, Lygodium dimorphum, Lygodium flexuosum, Lygodium giganteum, Lygodium heterodoxum, Lygodium hians, Lygodium japonicum, Lygo-*

*dium kerstenii, Lygodium lanceolatum, Lygodium longifolium, Lygodium merrillii, Lygodium microphyllum, Lygodium oligostachyum, Lygodium palmatum, Lygodium pedicellatum, Lygodium polystachyum, Lygodium radiatum, Lygodium reticulatum, Lygodium salicifolium, Lygodium smithianum, Lygodium subareolatum, Lygodium trifurcatum, Lygodium venustum, Lygodium versteegii, Lygodium volubile, Lygodium×fayae, Lygodium×lancetillanum*, and *Lygodium yunnanense.*

In some embodiments the nucleic acid molecule encoding the PtIP-96 polypeptide is derived from a species in the Class Isoetopsida or Class Lycopodiopsida.

In some embodiments the nucleic acid molecule encoding the PtIP-96 polypeptide is derived from a species in the Class Isoetopsida Order Selaginales. In some embodiments the nucleic acid molecule encoding the PtIP-96 polypeptide is derived from a species in the Class Isoetopsida, Order Selaginales, Family Selaginellaceae. In some embodiments the nucleic acid molecule encoding the PtIP-96 polypeptide is derived from a clubmoss species in the Genus *Selaginella*. In some embodiments the nucleic acid molecule encoding the PtIP-96 polypeptide is derived from a *Selaginella* species selected from but not limited to *Selaginella acanthonota, Selaginella apoda, Selaginella arbuscula, Selaginella arenicola, Selaginella arizonica, Selaginella armata, Selaginella asprella, Selaginella biformis, Selaginella bigelovii, Selaginella braunii, Selaginella cinerascens, Selaginella cordifolia, Selaginella deflexa, Selaginella delicatula, Selaginella densa, Selaginella douglasii, Selaginella eatonii, Selaginella eclipes, Selaginella eremophila, Selaginella erythropus, Selaginella flabellata, Selaginella hansenii, Selaginella heterodonta, Selaginella kraussiana, Selaginella krugii, Selaginella laxifolia, Selaginella lepidophylla, Selaginella leucobtyoides, Selaginella ludoviciana, Selaginella mutica, Selaginella oregana, Selaginella ovifolia, Selaginella pallescens, Selaginella peruviana, Selaginella pilifera, Selaginella plana, Selaginella plumosa, Selaginella pulcherrima, Selaginella rupestris, Selaginella rupincola, Selaginella scopulorum, Selaginella selaginoides, Selaginella sibirica, Selaginella standleyi, Selaginella stellata, Selaginella subcaulescens, Selaginella substipitata, Selaginella tenella, Selaginella tortipila, Selaginella uliginosa, Selaginella umbrosa, Selaginella uncinata, Selaginella underwoodii, Selaginella utahensis, Selaginella victoriae, Selaginella viridissima, Selaginella wallacei, Selaginella watsonii, Selaginella weatherbiana, Selaginella willdenowii, Selaginella wrightii* and *Selaginella×neomexicana.*

In some embodiments the nucleic acid molecule encoding the PtIP-96 polypeptide is derived from a species in the Class Lycopodiopsida, Order Lycopodiales, Family Huperziaceae, Genus *Huperzia* selected from but not limited to *Huperzia acerosa, Huperzia appressa, Huperzia arctica, Huperzia attenuata, Huperzia australiana, Huperzia balansae, Huperzia billardieri, Huperzia brachiata, Huperzia bradeorum, Huperzia brevifolia, Huperzia campiana, Huperzia capellae, Huperzia capillaris, Huperzia carinata, Huperzia chamaeleon, Huperzia compacta, Huperzia crassa, Huperzia cumingii, Huperzia cuneifolia, Huperzia curvifolia, Huperzia dacrydioides, Huperzia dentata, Huperzia dichaeoides, Huperzia dichotoma, Huperzia ericifolia, Huperzia eversa, Huperzia filiformis, Huperzia foliacea, Huperzia fordii, Huperzia funiformis, Huperzia hastata, Huperzia heteroclita, Huperzia hippuridea, Huperzia hippuris, Huperzia hoffmannii, Huperzia holstii, Huperzia homocarpa, Huperzia horizontalis, Huperzia hystrix, Huperzia lancifolia, Huperzia lindenii, Huperzia linifolia, Huperzia lockyeri, Huperzia lucidula, Huperzia mannii, Huperzia megastachya, Huperzia mesoamericana, Huperzia mingcheensis, Huperzia mollicoma, Huperzia myrsinites, Huperzia nummularifolia, Huperzia nutans, Huperzia ophioglossoides, Huperzia pflanzii, Huperzia phlegmaria, Huperzia phlegmarioides, Huperzia pithyodes, Huperzia pittieri, Huperzia polycarpos, Huperzia polydactyla, Huperzia porophila, Huperzia prolifera, Huperzia reflexa, Huperzia rosenstockiana, Huperzia rufescens, Huperzia salvinioides, Huperzia sarmentosa, Huperzia selago, Huperzia serrata, Huperzia sieboldii, Huperzia squarrosa, Huperzia subulata, Huperzia talamancana, Huperzia tauri, Huperzia taxifolia, Huperzia tenuis, Huperzia tetragona, Huperzia tetrasticha, Huperzia tubulosa, Huperzia unguiculata, Huperzia varia, Huperzia verticillata*, and *Huperzia wilson.*

In some embodiments the nucleic acid molecule encoding the PtIP-96 polypeptide is derived from a species in the Class Lycopodiopsida, Order Lycopodiales, Family Lycopodiaceae, Genus *Lycopodium* selected from but not limited to selected from but not limited to *Lycopodium alpinum L., Lycopodium annotinum L., Lycopodium clavatum L., Lycopodium complanatum L., Lycopodium dendroideum Michx., Lycopodium digitatum, Lycopodium×habereri, Lycopodium hickeyi, Lycopodium×issleri, Lycopodium lagopus, Lycopodium obscurum L., Lycopodium phlegmaria L., Lycopodium sabinifolium, Lycopodium sitchense, Lycopodium tristachyum, Lycopodium venustulum, Lycopodium venustulum* var. *venustulum, Lycopodium venustulum* var. *verticale, Lycopodium volubile* and *Lycopodium xzeilleri.*

Also provided are nucleic acid molecules that encode transcription and/or translation products that are subsequently spliced to ultimately produce functional PtIP-96 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate a PtIP-96 polypeptide encoding sequence. An example of trans splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length PtIP-96 polypeptide, but rather encode a fragment or fragments of a PtIP-96 polypeptide. These polynucleotides can be used to express a functional PtIP-96 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding PtIP-96 polypeptides are also encompassed by the embodiments. "Fragment" as used herein refers to a portion of the nucleic acid sequence encoding a PtIP-96 polypeptide. A fragment of a nucleic acid sequence may encode a biologically active portion of a PtIP-96 polypeptide or it may be a fragment that can be used as a hybridization probe or PCR primer using methods disclosed below. Nucleic acid molecules that are fragments of a nucleic acid sequence encoding a PtIP-96 polypeptide comprise at least about 150, 180, 210, 240, 270, 300, 330 or 360, contiguous nucleotides or up to the number of nucleotides present in a full-length nucleic acid sequence encoding a PtIP-96 polypeptide disclosed herein, depending upon the intended use. “Contiguous nucleotides” is used herein to refer to nucleotide residues that are immediately adjacent to one another. Fragments of the nucleic acid sequences of the embodiments will encode protein fragments that retain the biological activity of the PtIP-96Aa polypeptide and, hence, retain insecticidal activity. “Retains insecticidal activity” is used herein to refer to a polypeptide having at least about 10%, at least about 30%, at least about 50%, at least about 70%, 80%, 90%, 95% or higher of the insecticidal activity of the full-length PtIP-96Aa polypeptide (SEQ ID NO: 9). In some embodiments, the insecticidal activity is Lepidoptera activity. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata howardi*, and the Mexican corn rootworm, *D. virgifera zeae*. In one embodiment, the insecticidal activity is against a *Diabrotica* species.

In some embodiments a fragment of a nucleic acid sequence encoding a PtIP-96 polypeptide encoding a biologically active portion of a protein will encode at least about 15, 20, 30, 50, 75, 100, 125, contiguous amino acids or up to the total number of amino acids present in a full-length PtIP-96 polypeptide of the embodiments. In some embodiments, the fragment is an N-terminal and/or a C-terminal truncation of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or variants thereof, e.g., by proteolysis, insertion of a start codon, deletion of the codons encoding the deleted amino acids with the concomitant insertion of a stop codon or by insertion of a stop codon in the coding sequence.

In some embodiments the PtIP-96 polypeptide is encoded by a nucleic acid sequence sufficiently homologous to the nucleic acid sequence of SEQ ID NO: 1, SEQ ID NO: 2, SEQ ID NO: 3, SEQ ID NO: 4, SEQ ID NO: 15, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25; SEQ ID NO: 27; SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107 or SEQ ID NO: 109. “Sufficiently homologous” is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account codon degeneracy, amino acid similarity, reading frame positioning, and the like. In some embodiments the sequence homology is against the full length sequence of the polynucleotide encoding a PtIP-96 polypeptide or against the full length sequence of a PtIP-96 polypeptide.

In some embodiments the nucleic acid encoding a PtIP-96 polypeptide is selected from any one of SEQ ID NO: 1, SEQ ID NO: 2, SEQ ID NO: 3, SEQ ID NO: 4, SEQ ID NO: 15, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25; SEQ ID NO: 27; SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107 or SEQ ID NO: 109.

In some embodiments the nucleic acid encodes a PtIP-96 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two amino acid sequences or of two nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of SEQ ID NO: 1). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

The embodiments also encompass nucleic acid molecules encoding PtIP-96 polypeptide variants. "Variants" of the PtIP-96 polypeptide encoding nucleic acid sequences include those sequences that encode the PtIP-96 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the PtIP-96 polypeptides disclosed as discussed below.

The present disclosure provides isolated or recombinant polynucleotides that encode any of the PtIP-96 polypeptides disclosed herein. Those having ordinary skill in the art will readily appreciate that due to the degeneracy of the genetic code, a multitude of nucleotide sequences encoding PtIP-96 polypeptides of the present disclosure exist.

The skilled artisan will further appreciate that changes can be introduced by mutation of the nucleic acid sequences thereby leading to changes in the amino acid sequence of the encoded PtIP-96 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produces by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene,* 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortie, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA,* 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a fern species in the Division Pteridophyta or a clubmoss species in the Genus *Selaginella*. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential PtIP-96 polypeptides from fern or moss collections, the fern or moss cell lysates can be screened with antibodies generated against a PtIP-96 polypeptides and/or PtIP-96 polypeptides using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of PtIP-96 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to PtIP-96 polypeptides) with sequence information of PtIP-96 polypeptides of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 and their homologs. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known PtIP-96 polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding a PtIP-96 polypeptide of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding a PtIP-96 polypeptide, disclosed herein or one or more portions thereof may be used as a probe capable of specifically hybridizing to corresponding nucleic acid sequences encoding PtIP-96 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Proteins and Variants and Fragments Thereof In another aspect PtIP-96 polypeptides are encompassed by the disclosure. "Pteridophyta Insecticidal Protein-96" "PtIP-96 polypeptide", and "PtIP-96 protein" as used herein interchangeably refers to a polypeptide having insecticidal activity including but not limited to insecticidal activity against one or more insect pests of the Lepidoptera and/or Coleoptera orders, and is sufficiently homologous to the protein of SEQ ID NO: 10. A variety of PtIP-96 polypeptides are contemplated. Sources of PtIP-96 polypeptides or related proteins are fern species or other primitive plants selected from but not limited to a fern species in the Division Pteridophyta or a clubmoss species in the Genus *Selaginella*.

"Sufficiently homologous" is used herein to refer to an amino acid sequence that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments the sequence homology is against the full length sequence of a PtIP-96 polypeptide. In some embodiments the PtIP-96 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108. One of skill in the art will recognize that these values can be appropriately adjusted to determine corresponding homology of proteins taking into account amino acid similarity and the like. In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX® module of the Vector NTI® Program Suite (Invitrogen Corporation, Carlsbad, Calif.) with all default parameters.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

A "recombinant protein" is used herein to refer to a protein that is no longer in its natural environment, for example in vitro or in a recombinant bacterial or plant host cell. A PtIP-96 polypeptide that is substantially free of cellular material includes preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to a PtIP-96 polypeptide and that exhibit insecticidal activity. "Fragments" or "biologically active portions" of PtIP-96 polypeptides includes fragments comprising amino acid sequences sufficiently identical to the amino acid sequence set forth in SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, wherein the PtIP-96 polypeptide has insecticidal activity. Such biologically active portions can be prepared by recombinant techniques and evaluated for insecticidal activity. In some embodiments, the PtIP-96 polypeptide fragment is an N-terminal and/or a C-terminal truncation of at least about 1, 2, 3, 4, 5, 6, 7, 8, 9, 10, 11, 12, 13, 14, 15, 16, 17, 18, 19, 20, 25, 26, 27, 28, 29, 30, 31, 32, 33, 34 or more amino acids from the N-terminus and/or C-terminus relative to SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, e.g., by proteolysis, by insertion of a start codon, by deletion of the codons encoding the deleted amino acids and concomitant insertion of a start codon, and/or insertion of a stop codon.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the parental amino acid sequence.

PtIP-96 Polypeptides

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 81%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 9, SEQ ID NO: 12, SEQ ID NO: 14, SEQ ID NO: 16, SEQ ID NO: 18, SEQ ID NO: 20, SEQ ID NO: 22 or SEQ ID NO: 24, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 26; SEQ ID NO: 28; SEQ ID NO: 30, SEQ ID NO: 32, SEQ ID NO: 34, SEQ ID NO: 36, SEQ ID NO: 38 or SEQ ID NO: 40, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 42, SEQ ID NO: 44, SEQ ID NO: 46, SEQ ID NO: 48, SEQ ID NO: 50 or SEQ ID NO: 52, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 82, SEQ ID NO: 84, SEQ ID NO: 86, SEQ ID NO: 88 or SEQ ID NO: 90, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 76, SEQ ID NO: 78, or SEQ ID NO: 80, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88 or SEQ ID NO: 90, wherein the PtIP-96 polypeptide has insecticidal activity.

In some embodiments a PtIP-96 polypeptide comprises an amino acid sequence having at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 10, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, wherein the PtIP-96 polypeptide has insecticidal activity.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 9, SEQ ID NO: 12, SEQ ID NO: 14, SEQ ID NO: 16, SEQ ID NO: 18, SEQ ID NO: 20, SEQ ID NO: 22 or SEQ ID NO: 24.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 26; SEQ ID NO: 28; SEQ ID NO: 30, SEQ ID NO: 32, SEQ ID NO: 34, SEQ ID NO: 36, SEQ ID NO: 38 or SEQ ID NO: 40.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 42, SEQ ID NO: 44, SEQ ID NO: 46, SEQ ID NO: 48, SEQ ID NO: 50 or SEQ ID NO: 52.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88 or SEQ ID NO: 90.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 82, SEQ ID NO: 84, SEQ ID NO: 86, SEQ ID NO: 88 or SEQ ID NO: 90.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 76, SEQ ID NO: 78 or SEQ ID NO: 80.

In some embodiments a PtIP-96 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 10, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments a PtIP-96 polypeptide comprises an amino acid sequence of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments a PtIP-96 polypeptide comprises an amino acid sequence of SEQ ID NO: 9, SEQ ID NO: 12, SEQ ID NO: 14, SEQ ID NO: 16, SEQ ID NO: 18, SEQ ID NO: 20, SEQ ID NO: 22 or SEQ ID NO: 24 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 9, SEQ ID NO: 12, SEQ ID NO: 14, SEQ ID NO: 16, SEQ ID NO: 18, SEQ ID NO: 20, SEQ ID NO: 22 or SEQ ID NO: 24.

In some embodiments a PtIP-96 polypeptide comprises an amino acid sequence of SEQ ID NO: 26; SEQ ID NO: 28; SEQ ID NO: 30, SEQ ID NO: 32, SEQ ID NO: 34, SEQ ID NO: 36, SEQ ID NO: 38 or SEQ ID NO: 40 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 26; SEQ ID NO: 28; SEQ ID NO: 30, SEQ ID NO: 32, SEQ ID NO: 34, SEQ ID NO: 36, SEQ ID NO: 38 or SEQ ID NO: 40.

In some embodiments a PtIP-96 polypeptide comprises an amino acid sequence of SEQ ID NO: 42, SEQ ID NO: 44, SEQ ID NO: 46, SEQ ID NO: 48, SEQ ID NO: 50 or SEQ ID NO: 52 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 42, SEQ ID NO: 44, SEQ ID NO: 46, SEQ ID NO: 48, SEQ ID NO: 50 or SEQ ID NO: 52.

In some embodiments a PtIP-96 polypeptide comprises an amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88 or SEQ ID NO: 90 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88 or SEQ ID NO: 90.

In some embodiments a PtIP-96 polypeptide comprises an amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 82, SEQ ID NO: 84, SEQ ID NO: 86, SEQ ID NO: 88 or SEQ ID NO: 90 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 82, SEQ ID NO: 84, SEQ ID NO: 86, SEQ ID NO: 88 or SEQ ID NO: 90.

In some embodiments a PtIP-96 polypeptide comprises an amino acid sequence of SEQ ID NO: 76, SEQ ID NO: 78 or SEQ ID NO: 80 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 76, SEQ ID NO: 78 or SEQ ID NO: 80.

In some embodiments a PtIP-96 polypeptide comprises an amino acid sequence of SEQ ID NO: 10, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino acid substitutions compared to the native amino acid at the corresponding position of the polypeptide of SEQ ID NO: 10, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments the sequence identity is across the entire length of the polypeptide calculated using ClustalW algorithm in the ALIGNX® module of the Vector NTI® Program Suite (Invitrogen Corporation, Carlsbad, Calif.) with all default parameters.

In some embodiments the PtIP-96 polypeptide comprises an amino acid sequence of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

In some embodiments the PtIP-96 polypeptide comprises an amino acid sequence of SEQ ID NO: 9, SEQ ID NO: 12, SEQ ID NO: 14, SEQ ID NO: 16, SEQ ID NO: 18, SEQ ID NO: 20, SEQ ID NO: 22 or SEQ ID NO: 24.

In some embodiments the PtIP-96 polypeptide comprises an amino acid sequence of SEQ ID NO: 26; SEQ ID NO: 28; SEQ ID NO: 30, SEQ ID NO: 32, SEQ ID NO: 34, SEQ ID NO: 36, SEQ ID NO: 38 or SEQ ID NO: 40.

In some embodiments the PtIP-96 polypeptide comprises an amino acid sequence of SEQ ID NO: 42, SEQ ID NO: 44, SEQ ID NO: 46, SEQ ID NO: 48, SEQ ID NO: 50 or SEQ ID NO: 52.

In some embodiments the PtIP-96 polypeptide comprises an amino acid sequence of SEQ ID NO: 7, SEQ ID NO: 8, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88 or SEQ ID NO: 90.

In some embodiments the PtIP-96 polypeptide comprises an amino acid sequence of SEQ ID NO: 10, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

Phylogenetic, Sequence Motif, and Structural Analyses for Insecticidal Protein Families The sequence and structure analysis method employed is composed of four components: phylogenetic tree construction, protein sequence motifs finding, secondary structure prediction, and alignment of protein sequences and secondary structures. Details about each component are illustrated below.

1) Phylogenetic Tree Construction

The phylogenetic analysis can be performed using the software MEGA5. Protein sequences were subjected to ClustalW version 2 analysis (Larkin M. A et al (2007) *Bioinformatics* 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

2) Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, Calif., 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

3) Secondary Structure Prediction

PSIPRED, top ranked secondary structure prediction method (Jones D T. (1999) *J. Mol. Biol.* 292: 195-202), can be installed in a local Linux server, and used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

4) Alignment of Protein Sequences and Secondary Structures

A customized script was developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments the PtIP-96 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the PtIP-96 polypeptide has increased digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In another aspect the PtIP-96 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273:10567-10577; Cotton, et al., (1999) *J. Am. Chem. Soc.* 121:1100-1101; Evans, et al., (1999) *J. Biol. Chem.* 274:18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207: 187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.*, 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another aspect the PtIP-96 polypeptide may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of the PtIP-96 polypeptide and the 3' intein coding sequence is linked to the 5' end of the second fragment coding for the C-terminal part of the PtIP-96 polypeptide.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J Biol Chem.* 275(13):9091-4 and of the DnaE gene from *Nostoc punctiforme* (see, Iwai, et al., (2006) *FEBS Lett.* 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.il/~pietro/inteins/Inteinstable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta.* 1387: 422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol.* 47:61-73) and hedgehog (Hog) auto-processing domains (the latter is combined with inteins when referred to as the Hog/intein superfamily or HINT family (see, Dassa, et al., (2004) *J Biol Chem.* 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry.* 46(1):322-30). Other such mixtures of disparate split intein partners have been shown to be unreactive one with another (see, Brenzel, et al., (2006) *Biochemistry.* 45(6):1571-8). However, it is within the ability of a person skilled in the relevant art to determine whether a particular pair of polypeptides is able to associate with each other to provide a functional intein, using routine methods and without the exercise of inventive skill.

In another aspect the PtIP-96 polypeptide is a circular permuted variant. In certain embodiments the PtIP-96 polypeptide is a circular permuted variant of the polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) *Proteins: Struct., Funct. & Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted PtIP-96 polypeptides with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted PtIP-96 polypeptides with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another aspect fusion proteins are provided that include within its amino acid sequence an amino acid sequence comprising a PtIP-96 polypeptide including but not limited to the polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108, and active fragments thereof.

Methods for design and construction of fusion proteins (and polynucleotides encoding same) are known to those of skill in the art. Polynucleotides encoding a PtIP-96 polypeptide may be fused to signal sequences which will direct the localization of the PtIP-96 polypeptide to particular compartments of a prokaryotic or eukaryotic cell and/or direct the secretion of the PtIP-96 polypeptide of the embodiments from a prokaryotic or eukaryotic cell. For example, in *E. coli*, one may wish to direct the expression of the protein to the periplasmic space. Examples of signal sequences or proteins (or fragments thereof) to which the PtIP-96 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the PtIP-96 polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art (see, U.S. Pat.

No. 7,193,133). Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the PtIP-96 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine codon of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9.

In some embodiments fusion proteins are provide comprising a PtIP-96 polypeptide and an insecticidal polypeptide joined by an amino acid linker. In some embodiments fusion proteins are provided represented by a formula selected from the group consisting of:

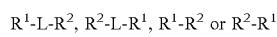

wherein $R^1$ is a PtIP-96 polypeptide, $R^2$ is a protein of interest. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$ or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker is from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

In another aspect chimeric PtIP-96 polypeptides are provided that are created through joining two or more portions of PtIP-96 genes, which originally encoded separate PtIP-96 proteins to create a chimeric gene. The translation of the chimeric gene results in a single chimeric PtIP-96 polypeptide with regions, motifs or domains derived from each of the original polypeptides. In certain embodiments the chimeric protein comprises portions, motifs or domains of PtIP-96 polypeptides of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 in any combination.

It is recognized that DNA sequences may be altered by various methods, and that these alterations may result in DNA sequences encoding proteins with amino acid sequences different than that encoded by the wild-type (or native) pesticidal protein. In some embodiments a PtIP-96 polypeptide may be altered in various ways including amino acid substitutions, deletions, truncations and insertions of one or more amino acids, including up to 2, 3, 4, 5, 6, 7, 8, 9, 10, 15, 20, 25, 30, 35, 40, 45, 50, 55, 60, 65, 70, 75, 80, 85, 90, 100, 105, 110, 115, 120, 125, 130, 135, 140, 145 or more amino acid substitutions, deletions and/or insertions or combinations thereof compared to any one of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108.

Methods for such manipulations are generally known in the art. For example, amino acid sequence variants of a PtIP-96 polypeptide can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a PtIP-96 polypeptide to confer pesticidal activity may be improved by the use of such techniques upon the compositions of this disclosure.

For example, conservative amino acid substitutions may be made at one or more, PtIP-, nonessential amino acid residues. A "nonessential" amino acid residue is a residue that can be altered from the wild-type sequence of a PtIP-96 without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5);

asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0+0.1); glutamate (+3.0+0.1); serine (+0.3); asparagine (+0.2); glutamine (+0.2); glycine (0); threonine (−0.4); proline (−0.5+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different PtIP-96 polypeptide coding regions can be used to create a new PtIP-96 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered PtIP-96 polypeptides. Domains may be swapped between PtIP-96 polypeptides resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Alignment of PtIP-96 homologs (FIG. 1) allows for identification of residues that are highly conserved among natural homologs in this family.

Compositions

Compositions comprising a PtIP-96 polypeptide of the disclosure are also embraced. In some embodiments the composition comprises a PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108. In some embodiments the composition comprises a PtIP-96 fusion protein.

Antibodies

Antibodies to a PtIP-96 polypeptide of the embodiments or to variants or fragments thereof are also encompassed. The antibodies of the disclosure include polyclonal and monoclonal antibodies as well as fragments thereof which retain their ability to bind to PtIP-96 polypeptide found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. PtIP-96 polypeptide antibodies or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing a PtIP-96 polypeptide as antigens.

A kit for detecting the presence of a PtIP-96 polypeptide or detecting the presence of a nucleotide sequence encoding a PtIP-96 polypeptide in a sample is provided. In one embodiment, the kit provides antibody-based reagents for detecting the presence of a PtIP-96 polypeptide in a tissue sample. In another embodiment, the kit provides labeled nucleic acid probes useful for detecting the presence of one or more polynucleotides encoding PtIP-96 polypeptide. The kit is provided along with appropriate reagents and controls for carrying out a detection method, as well as instructions for use of the kit.

Receptor Identification and Isolation

Receptors to the PtIP-96 polypeptide of the embodiments or to variants or fragments thereof are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the PtIP-96 polypeptide using the brush-border membrane vesicles from susceptible insects. In addition to the radioactive labeling method listed in the cited literatures, PtIP-96 polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled PtIP-96 polypeptide can be incubated with blotted membrane of BBMV and labeled the PtIP-96 polypeptide can be identified with the labeled reporters. Identification of protein band(s) that interact with the PtIP-96 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the PtIP-96 polypeptide. Receptor function for insecticidal activity by the PtIP-96 polypeptide can be verified by accomplished by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the PtIP-96 polypeptide gene sequence to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, and Liu H et al. *Mol Bio Rep* 37:677-684, 2010, herein incorporated by reference. A *Zea maize* codon usage table can be also found at kazusa.or.jp/codon/cgi-bin/showcodon.cgi?species=4577, which can be accessed using the www prefix.

A *Glycine max* codon usage table is shown in Table 4 and can also be found at kazusa.or.jp/codon/cgi-bin/showcodon.cgi?species=3847&aa=1&style=N, which can be accessed using the www prefix.

In some embodiments the recombinant nucleic acid molecule encoding a PtIP-96 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research*, 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) are well known to one skilled in the art also include chimeric CTPs comprising but not limited to, an N-terminal domain, a central domain or a C-terminal domain from a CTP from *Oryza sativa* 1-deoxy-D xyulose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The PtIP-96 polypeptide gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann.* *Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4:645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced PtIP-96 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524;

Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed roIC and roID root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and roIB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters.

For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608, 144; 5,604,121; 5,569,597; 5,466,785; 5,399,680; 5,268, 463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.*

6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Lec1 transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the PtIP-96 polynucleotide or variants and fragments thereof directly into the plant or the introduction of the PtIP-96 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the PtIP-96 polypeptide polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for Agrobacterium-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from Agrobacterium to plant cells. This plasmid often contains the virulence functions (Vir genes) that allow infection of plant cells by Agrobacterium, and transfer of DNA by cleavage at border sequences and vir-mediated DNA transfer, as is understood in the art (Hellens and Mullineaux, (2000) Trends in Plant Science 5:446-451). Several types of Agrobacterium strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) The Plant Journal 6:271-282; Ishida, et al., (1996) Nature Biotechnology 14:745-750). Explants are typically transferred to a fresh supply of the same medium and cultured routinely. A general description of the techniques and methods for generating transgenic plants are found in Ayres and Park, (1994) Critical Reviews in Plant Science 13:219-239 and Bommineni and Jauhar, (1997) Maydica 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) Plant Cell Reports 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired PtIP-96 polypeptide. It is also recognized that such a viral polyprotein, comprising at least a portion of the amino acid sequence of a PtIP-96 of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931; herein incorporated by reference.

Methods for transformation of chloroplasts are known in the art. See, for example, Svab, et al., (1990) Proc. Natl. Acad. Sci. USA 87:8526-8530; Svab and Maliga, (1993) Proc. Natl. Acad. Sci. USA 90:913-917; Svab and Maliga, (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) Proc. Natl. Acad. Sci. USA 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus effiotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the PtIP-96 polypeptide.

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the PtIP-96 polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests. Transgenes useful for stacking include but are not limited to:
1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. *tomato* encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens*, 7:1-13), from *Pseudomonas protegens* strain CHA0 and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; a PIP-1 polypeptide of US Patent Publication US20140007292; an AfIP-1A and/or AfIP-1B polypeptide of US Patent Publication US20140033361; a PHI-4 polypeptide of U.S. Ser. No. 13/839,702; a PIP-47 polypeptide of PCT Serial Number PCT/US14/51063, a PIP-72 polypeptide of PCT Serial Number PCT/US14/55128, and 5-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of 5-endotoxin genes and the *B. thuringiensis* cytolytic Cyt1 and Cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of 5-endotoxins also include but are not limited to Cry1A proteins of U.S. Pat. Nos. 5,880,275 and 7,858, 849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+ Cry2Ab, Cry1Ab, Cry1A.105, Cry1F, Cry1Fa2, Cry1F+ Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/ vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/

0035765 and incorporated by reference for this purpose. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 5,094,945; 4,940,835; 5,866,775; 6,225,114; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837, and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic Such as:

(A) Altered fatty acids, for example, by (1) Down-regulation of stearoyl-ACP to increase stearic acid content of the plant. See, Knultzon, et al., (1992) *Proc.*

*Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391, 348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that confers male fertility to be transcribed.

(A) Introduction of a deacetylase gene under the control of a tapetum-specific promoter and with the application of the chemical N-Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014 and 6,265,640, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. Nos. 6,177,275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(o) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiment the stacked trait may be a trait or event that has received regulatory approval including but not limited to the events with regulatory approval that are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments the stacked trait may be in the form of silencing of one or more polynucleotides of interest resulting in suppression of one or more target pest polypeptides. In some embodiments the silencing is achieved through the use of a suppression DNA construct.

In some embodiments one or more polynucleotide encoding the polypeptides of the PtIP-96 polypeptide or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) *Nature* 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) *Trends Genet.* 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein, et al., (2001) *Nature* 409:363). Short interfering RNAs derived from dicer activity are typically about 21 to about 23 nucleotides in length and comprise about 19 base pair duplexes (Elbashir, et al., (2001) *Genes Dev.* 15:188). Dicer has also been implicated in the excision of 21- and 22-nucleotide small temporal RNAs (stRNAs) from precursor RNA of conserved structure that are implicated in translational control (Hutvagner, et al., (2001) *Science* 293: 834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) *Genes Dev.* 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) *Science* 297:1818-1819; Volpe, et al., (2002) *Science* 297: 1833-1837; Jenuwein, (2002) *Science* 297:2215-2218 and Hall, et al., (2002) *Science* 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and Lygus can be found in US Patent Application Publication 2011/0301223 and US Patent Application Publication 2009/0192117.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubulin Homologous Sequence.

Use in Pesticidal Control

General methods for employing strains comprising a nucleic acid sequence of the embodiments or a variant thereof, in pesticide control or in engineering other organisms as pesticidal agents are known in the art. See, for example U.S. Pat. No. 5,039,523 and EP 0480762A2.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the PtIP-96 polypeptide and desirably provide for improved protection of the pesticide from environmental degradation and inactivation.

Alternatively, the PtIP-96 polypeptides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated PtIP-96 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agrochemical composition that contains at least one of the PtIP-96 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, lndoxacarb, Forthiazate, Fenamiphos, Cadusaphos, Pyriproxifen, Fen butatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caligi-* nosellus Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrotestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schaffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (*Bagrada* Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant PtIP-96 polypeptide. In some embodiments methods are provided for killing an insect pest, comprising contacting the insect pest with an insecticidally-effective amount of a recombinant pesticidal protein of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or a variant thereof.

In some embodiments methods are provided for controlling an insect pest population, comprising contacting the insect pest population, either simultaneously or sequentially, with an insecticidally-effective amount of a recombinant PtIP-96 polypeptide. In some embodiments methods are provided for controlling an insect pest population, comprising contacting the insect pest population with an insecticidally-effective amount of a recombinant PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or a variant thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of a recombinant PtIP-96 polypeptide. In some embodiments methods are provided for controlling an insect pest population resistant to a pesticidal protein, comprising contacting the insect pest population with an insecticidally-effective amount of a recombinant PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or a variant thereof.

In some embodiments methods are provided for protecting a plant from an insect pest, comprising expressing in the plant or cell thereof at least one recombinant polynucleotide encoding a PtIP-96 polypeptide. In some embodiments methods are provided for protecting a plant from an insect pest, comprising expressing in the plant or cell thereof a recombinant polynucleotide encoding PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or variants thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the PtIP-96 polypeptide of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management the at least one of the insecticidal proteins comprise a PtIP-96 polypeptide insecticidal to insects in the order Lepidoptera and/or Coleoptera.

In some embodiments the methods of controlling Lepidoptera and/or Coleoptera insect infestation in a transgenic plant and promoting insect resistance management the at least one of the insecticidal proteins comprises a PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or variants thereof, insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant a PtIP-96 polypeptide and a Cry protein insecticidal to insects in the order Lepidoptera and/or Coleoptera having different modes of action.

In some embodiments the methods of controlling Lepidoptera and/or Coleoptera insect infestation in a transgenic plant and promoting insect resistance management comprise in the transgenic plant a PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or variants thereof and a Cry protein insecticidal to insects in the order Lepidoptera and/or Coleoptera having different modes of action.

Also provided are methods of reducing likelihood of emergence of Lepidoptera and/or Coleoptera insect resistance to transgenic plants expressing in the plants insecticidal proteins to control the insect species, comprising expression of a PtIP-96 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise a PtIP-96 polypeptide and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise a PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or variants thereof and a Cry protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the PtIP-96 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the PtIP-96 polypeptide of SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26; SEQ ID NO: 28; SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106 or SEQ ID NO: 108 or variant thereof does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant.

"Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a PtIP-96 polypeptide disclosed herein. Expression of the PtIP-96 polypeptide results in a reduced ability of a pest to infest or feed on the plant, thus improving plant yield.

Methods of Processing

Further provided are methods of processing a plant, plant part or grain to obtain a food or feed product comprising a PtIP-96 polypeptide. The plants, plant parts or seeds provided herein, can be processed to yield oil, protein products and/or by-products that are derivatives obtained by processing that have commercial value. Non-limiting examples include transgenic seeds comprising a nucleic acid molecule encoding a PtIP-96 polypeptide which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds.

The following examples are offered by way of illustration and not by way of limitation.

EXPERIMENTALS

Example 1—Identification of an Insecticidal Protein Active from the *Selaginella kraussiana*

The amino acid sequence of SEQ ID NO: 9 was identified by BLAST (Basic Local Alignment Search Tool; Altschul, et al., (1993) J. Mol. Biol. 215:403-410; see also ncbi.nlm.nih.gov/BLAST/, which can be accessed using the www prefix) when polynucleotide sequences encoding the PtIP-65 insecticidal polypeptides of PCT publication WO2015/120270 were searched against the *Selaginella kraussiana* transcriptome in an internal DUPONT PIONEER database. The transcriptome sequences were used to design primers to clone the PtIP-96Aa cDNA sequence. This clone was produced by polymerase chain reaction using the KOD Hot Start DNA Polymerase® PCR kit (Novagen, Merck KGaA, Darmstadt, Germany) and the total RNA from *Selaginella kraussiana* (sample Id. PS-8780) as the template. The cloned PCR product was confirmed by sequencing. Based on the DNA sequencing, the PtIP-96Aa polynucleotide sequence is shown as SEQ ID NO: 4 and the encoded polypeptide sequence as SEQ ID NO: 9.

Bioassays against the three pest species, Soybean Looper (SBL) (*Chrysodeixis includens*), Corn Earworm (CEW) (*Helicoverpa zea*) and European Corn Borer (ECB) (*Ostrinia nubialis*) were conducted using a plant tissue protein extract from *Selaginella kraussiana* sample PS-8780, overlaid onto an agar-based Lepidoptera diet (Southland Products Inc., Lake Village, Ark.) in a 96-well plate format. Six replicates were used per sample. Samples were allowed to dry on top of the diet and two to five neonate insects were placed into each well of the treated plate. After four days of incubation at 27° C. larvae were scored for mortality or severity of stunting. The scores were recorded numerically as dead (3), severely stunted (2) (little or no growth but alive and equivalent to a $1^{st}$ instar larvae), stunted (1) (growth to second instar but not equivalent to controls), or normal (0). Subjecting the sample to proteinase K and heat treatments resulted in loss of activity indicating that the active principle was proteinaceous in nature. Bioassay results are shown in Table 1.

TABLE 1

|  | CEW | ECB | SBL |
|---|---|---|---|
| PS-8780 protein extract | + | + | + |

Example 2 Transcriptomic Sequencing of *Selaginella kraussiana*

A transcriptome for *Selaginella kraussiana* from sample Id. PS-8780 was prepared as follows. Total RNAs were isolated from frozen tissues by use of the Qiagen® RNeasy® kit for total RNA isolation. Sequencing libraries from the resulting total RNAs were prepared using the TruSeq™ mRNA-Seq kit and protocol from Illumina®, Inc. (San Diego, Calif.). Briefly, mRNAs were isolated via attachment to oligo(dT) beads, fragmented to a mean size of 180 nt, reverse transcribed into cDNA by random hexamer prime, end repaired, 3' A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and five hour anneal at 68° C. Annealed library was treated with 2 ul of DSN enzyme for 25 minutes, purified by Qiagen® MinElute® columns according to manufacturer protocols, and amplified twelve cycles using Illumina® adapter specific primers. Final products were purified with Ampure® XP beads (Beckman Genomics, Danvers, Mass.) and checked for quality and quantity on the Agilent Bioanalyzer® DNA 7500 chip.

Normalized transcript libraries were sequenced according to manufacturer protocols on the Illumina® Genome Analyzer IIx. Each library was hybridized to two flowcell lanes and amplified, blocked, linearized and primer hybridized using the Illumina® clonal cluster generation process on cBot®. Sequencing was completed on the Genome Analyzer IIx, generating sixty million 75 bp paired end reads per normalized library.

Example 3—Identification of PtIP-96 Polypeptide Homologs

Gene identities conducted by BLAST in an internal DUPONT PIONEER transcriptome database of ferns and other primitive plants identified homologs for PtIP-96Aa polypeptide (SEQ ID NO: 4). The PtIP-96Aa polypeptide homologs and the organism they were identified from are shown in Table 2. In some cases the homologs were identified from pooled samples of fern isolates and/or species identified in Table 2 as "mix1" mix3" and "mix4". The ferns in the pooled samples are shown in Table 3.

TABLE 2

| Sample ID | Species | name | n.a. sequence | a.a. sequence |
|---|---|---|---|---|
| PS-9145 | *Ophioglossum pendulum* | PtIP-96Ec | SEQ ID NO: 1 | SEQ ID NO: 6 |
| PS-9427 | *Colysis wrightii 'Monstifera'* | PtIP-96Ea | SEQ ID NO: 2 | SEQ ID NO: 7 |
| PS-7897 | *Colysis wrightii* | PtIP-96Eb | SEQ ID NO: 3 | SEQ ID NO: 8 |
| PS-7896 | *Selaginella victoriae* | PtIP-96Ha | SEQ ID NO: 5 | SEQ ID NO: 10 |
| PS-8780 | *Selaginella kraussiana 'Variegata'* | PtIP-96Aa | SEQ ID NO: 4 | SEQ ID NO: 9 |
| PS-8780CF | *Selaginella kraussiana 'Variegata'* | PtIP-96Ab | SEQ ID NO: 11 | SEQ ID NO: 12 |
| PS-8780CF | *Selaginella kraussiana 'Variegata'* | PtIP-96Ac | SEQ ID NO: 13 | SEQ ID NO: 14 |
| PS-8780CF | *Selaginella kraussiana 'Variegata'* | PtIP-96Ad | SEQ ID NO: 15 | SEQ ID NO: 16 |
| PS-8780CF | *Selaginella kraussiana 'Variegata'* | PtIP-96Ae | SEQ ID NO: 17 | SEQ ID NO: 18 |
| PS-8780CF | *Selaginella kraussiana 'Variegata'* | PtIP-96Af | SEQ ID NO: 19 | SEQ ID NO: 20 |
| PS-12342-2 | *Adiantum raddianum 'Gracillimum'* | PtIP-96Ag | SEQ ID NO: 21 | SEQ ID NO: 22 |
| PS-2-2 | *Cyathea australis* | PtIP-96Ah | SEQ ID NO: 23 | SEQ ID NO: 24 |
| mix1 | *Adiantum/Cyrtomium* | PtIP-96Ca | SEQ ID NO: 25 | SEQ ID NO: 26 |
| mix1 | *Adiantum/Cyrtomium* | PtIP-96Cb | SEQ ID NO: 27 | SEQ ID NO: 28 |
| PS-12342-1 | *Adiantum raddianum 'Gracillimum'* | PtIP-96Cc | SEQ ID NO: 29 | SEQ ID NO: 30 |
| PS-12342-4 | *Adiantum raddianum 'Gracillimum'* | PtIP-96Cd | SEQ ID NO: 31 | SEQ ID NO: 32 |
| PS-2-3 | *Adiantum raddianum 'Fragrans'* | PtIP-96Ce | SEQ ID NO: 33 | SEQ ID NO: 34 |
| PS-3-1 | *Adiantum raddianum 'Fritz Luthi'* | PtIP-96Cf | SEQ ID NO: 35 | SEQ ID NO: 36 |
| PS-3-2 | *Adiantum raddianum 'Fritz Luthi'* | PtIP-96Cg | SEQ ID NO: 37 | SEQ ID NO: 38 |
| PS-3-3 | *Adiantum raddianum 'Fritz Luthi'* | PtIP-96Ch | SEQ ID NO: 39 | SEQ ID NO: 40 |
| PS-11707 | *Cyrtomium falcatum* | PtIP-96Da | SEQ ID NO: 41 | SEQ ID NO: 42 |
| PS-5-1 | *Cyathea australis* | PtIP-96Db | SEQ ID NO: 43 | SEQ ID NO: 44 |
| PS-5-2 | *Cyathea australis* | PtIP-96Dc | SEQ ID NO: 45 | SEQ ID NO: 46 |
| PS-2-1 | *Adiantum raddianum 'Fragrans'* | PtIP-96De | SEQ ID NO: 47 | SEQ ID NO: 48 |
| PS-2-4 | *Adiantum raddianum 'Fragrans'* | PtIP-96Df | SEQ ID NO: 49 | SEQ ID NO: 50 |
| PS-5-3 | *Cyathea australis* | PtIP-96Dd | SEQ ID NO: 51 | SEQ ID NO: 52 |
| PS-9224AF | *Lygodium flexuosum* | PtIP-96Ed | SEQ ID NO: 53 | SEQ ID NO: 54 |
| PS-9135AF | *Platycerium bifurcatum* | PtIP-96Ee | SEQ ID NO: 55 | SEQ ID NO: 56 |
| PS-9135AF | *Platycerium bifurcatum* | PtIP-96Ef | SEQ ID NO: 57 | SEQ ID NO: 58 |
| mix3 | *Platycerium/Huperzia/Lygodium* | PtIP-96Eg | SEQ ID NO: 59 | SEQ ID NO: 60 |
| mix3 | *Platycerium/Huperzia/Lygodium* | PtIP-96Eh | SEQ ID NO: 61 | SEQ ID NO: 62 |
| PS-9135AF | *Platycerium bifurcatum* | PtIP-96Ew | SEQ ID NO: 109 | SEQ ID NO: 1 |
| PS-9135AF | *Platycerium bifurcatum* | PtIP-96Ei | SEQ ID NO: 63 | SEQ ID NO: 64 |
| PS-9135AF | *Platycerium bifurcatum* | PtIP-96Ej | SEQ ID NO: 65 | SEQ ID NO: 66 |
| PS-9135AF | *Platycerium bifurcatum* | PtIP-96Ek | SEQ ID NO: 67 | SEQ ID NO: 68 |
| PS-9135AF | *Platycerium bifurcatum* | PtIP-96El | SEQ ID NO: 69 | SEQ ID NO: 70 |
| PS-9135AF | *Platycerium bifurcatum* | PtIP-96Em | SEQ ID NO: 71 | SEQ ID NO: 72 |
| PS-9135AF | *Platycerium bifurcatum* | PtIP-96En | SEQ ID NO: 73 | SEQ ID NO: 74 |
| PS-13327-1 | *Polystichium tsus-simense* | PtIP-96Eo | SEQ ID NO: 75 | SEQ ID NO: 76 |
| PS-13327-2 | *Polystichium tsus-simense* | PtIP-96Ep | SEQ ID NO: 77 | SEQ ID NO: 78 |
| PS-11698 | *Davallia fejeensis* | PtIP-96Eq | SEQ ID NO: 79 | SEQ ID NO: 80 |
| PS-9210-1 | *Aglaomorpha meyeniana 'Roberts'* | PtIP-96Er | SEQ ID NO: 81 | SEQ ID NO: 82 |
| PS-9210-2 | *Aglaomorpha meyeniana* | PtIP-96Es | SEQ ID NO: 83 | SEQ ID NO: 84 |
| PS-9210-3 | *Aglaomorpha meyeniana* | PtIP-96Et | SEQ ID NO: 85 | SEQ ID NO: 86 |
| PS-9210-4 | *Aglaomorpha meyeniana* | PtIP-96Eu | SEQ ID NO: 87 | SEQ ID NO: 88 |
| PS-9210-5 | *Aglaomorpha meyeniana* | PtIP-96Ev | SEQ ID NO: 89 | SEQ ID NO: 90 |
| mix4 | *Selaginella victoriae* | PtIP-96Hb | SEQ ID NO: 91 | SEQ ID NO: 92 |
| mix4 | *Selaginella victoriae* | PtIP-96Hc | SEQ ID NO: 93 | SEQ ID NO: 94 |
| mix4 | *Selaginella victoriae* | PtIP-96Hd | SEQ ID NO: 95 | SEQ ID NO: 96 |
| mix4 | *Selaginella victoriae* | PtIP-96He | SEQ ID NO: 97 | SEQ ID NO: 98 |
| mix4 | *Selaginella victoriae* | PtIP-96Hf | SEQ ID NO: 99 | SEQ ID NO: 100 |
| mix4 | *Selaginella victoriae* | PtIP-96Hg | SEQ ID NO: 101 | SEQ ID NO: 102 |
| mix4 | *Selaginella victoriae* | PtIP-96Hh | SEQ ID NO: 103 | SEQ ID NO: 104 |
| mix4 | *Selaginella victoriae* | PtIP-96Hi | SEQ ID NO: 105 | SEQ ID NO: 106 |
| mix4 | *Selaginella victoriae* | PtIP-96Hj | SEQ ID NO: 107 | SEQ ID NO: 108 |

TABLE 3

| Mix1: | PS-12343 | *Adiantum raddianum* 'Pacific Maid' |
|---|---|---|
|  | PS-8570 | *Adiantum capillus-veneris* L. |
|  | PS-12344 | *Adiantum hispidulum* |
|  | PS-12353 | *Cyrtomium fortunei* |
| Mix3: | PS-9135AF | *Platycerium bifurcatum* |
|  | PS-9141AF | *Huperzia salvinioides* |
|  | PS-9092AF | *Platycerium wandae* |
| Mix4: | PS-10890 | *Selaginella victoriae* |
|  | PS-10887 | *Selaginella victoriae* |
|  | PS-7896DF | *Selaginella victoriae* | cDNAs were generated from source organisms with identified homologs by reverse transcription from total RNA or synthesized based upon the sequence assembled from the transcriptome. The cDNA derived genes, encoding the PtIP-96 homologs, were PCR amplified from their respective cDNAs using primers designed to the coding sequences of each homolog and subcloned into a plant transient expression vector. Cloned PCR products were confirmed by sequencing.

The percent amino acid sequence identity between the PtIP-96 polypeptide homologs calculated using the Needleman-Wunsch algorithm, as implemented in the Needle program (EMBOSS tool suite), are presented as a matrix table in Table 4a-4e. The void portions of the matrix table are not shown.

TABLE 4a

|  | PtIP-96Aa SEQ ID NO: 9 | PtIP-96Ab SEQ ID NO: 12 | PtIP-96Ac SEQ ID NO: 14 | PtIP-96Ad SEQ ID NO: 16 | PtIP-96Ae SEQ ID NO: 18 | PtIP-96Af SEQ ID NO: 20 | PtIP-96Ag SEQ ID NO: 22 | PtIP-96Ah SEQ ID NO: 24 | PtIP-96Ca SEQ ID NO: 26 | PtIP-96Cb SEQ ID NO: 28 | PtIP-96Cc SEQ ID NO: 30 |
|---|---|---|---|---|---|---|---|---|---|---|---|
| PtIP-96Ec SEQ ID NO: 6 | 56.3 | 56.5 | 55.5 | 56.0 | 56.0 | 56.0 | 56.3 | 56.5 | 55.5 | 55.2 | 56.3 |
| PtIP-96Aa SEQ ID NO: 9 | — | 99.5 | 99.2 | 99.5 | 99.2 | 99.8 | 99.8 | 99.2 | 75.4 | 75.1 | 76.5 |
| PtIP-96Ab SEQ ID NO: 12 | — | — | 98.8 | 99.0 | 98.8 | 99.2 | 99.2 | 99.2 | 75.4 | 75.1 | 76.5 |
| PtIP-96Ac SEQ ID NO: 14 | — | — | — | 99.2 | 99.0 | 99.5 | 99.0 | 98.5 | 74.6 | 74.4 | 75.8 |
| PtIP-96Ad SEQ ID NO: 16 | — | — | — | — | 99.2 | 99.8 | 99.2 | 98.8 | 75.1 | 74.9 | 76.2 |
| PtIP-96Ae SEQ ID NO: 18 | — | — | — | — | — | 99.5 | 99.0 | 98.5 | 74.6 | 74.4 | 75.8 |
| PtIP-96Af SEQ ID NO: 20 | — | — | — | — | — | — | 99.5 | 99.0 | 75.1 | 74.9 | 76.2 |
| PtIP-96Ag SEQ ID NO: 22 | — | — | — | — | — | — | — | 99.0 | 75.4 | 75.1 | 76.5 |
| PtIP-96Ah SEQ ID NO: 24 | — | — | — | — | — | — | — | — | 75.4 | 75.1 | 76.2 |
| PtIP-96Ca SEQ ID NO: 26 | — | — | — | — | — | — | — | — | — | 99.7 | 98.7 |
| PtIP-96Cb SEQ ID NO: 28 | — | — | — | — | — | — | — | — | — | — | 98.4 |

TABLE 4b

|  | PtIP-96Cd SEQ ID NO: 32 | PtIP-96Ce SEQ ID NO: 34 | PtIP-96Cf SEQ ID NO: 36 | PtIP-96Cg SEQ ID NO: 38 | PtIP-96Ch SEQ ID NO: 40 | PtIP-96Da SEQ ID NO: 42 | PtIP-96Db SEQ ID NO: 44 | PtIP-96Dc SEQ ID NO: 46 | PtIP-96Dd SEQ ID NO: 52 | PtIP-96De SEQ ID NO: 48 | PtIP-96Df SEQ ID NO: 50 |
|---|---|---|---|---|---|---|---|---|---|---|---|
| PtIP-96Ec SEQ ID NO: 6 | 55.5 | 56.3 | 56.0 | 56.0 | 54.0 | 60.3 | 57.3 | 57.3 | 57.1 | 53.5 | 52.8 |
| PtIP-96Aa SEQ ID NO: 9 | 75.9 | 76.2 | 76.0 | 76.0 | 73.4 | 60.0 | 70.1 | 69.9 | 69.9 | 71.8 | 70.9 |
| PtIP-96Ab SEQ ID NO: 12 | 75.9 | 76.2 | 76.0 | 76.0 | 73.4 | 60.3 | 70.4 | 70.1 | 70.1 | 72.0 | 71.2 |
| PtIP-96Ac SEQ ID NO: 14 | 75.1 | 75.5 | 75.2 | 75.2 | 72.6 | 59.3 | 69.4 | 69.2 | 69.2 | 71.0 | 70.2 |
| PtIP-96Ad SEQ ID NO: 16 | 75.6 | 76.0 | 75.8 | 75.8 | 73.1 | 59.8 | 69.7 | 69.4 | 69.4 | 71.3 | 70.4 |
| PtIP-96Ae SEQ ID NO: 18 | 75.1 | 75.5 | 75.2 | 75.2 | 72.6 | 59.3 | 69.4 | 69.2 | 69.2 | 71.0 | 70.2 |
| PtIP-96Af SEQ ID NO: 20 | 75.6 | 76.0 | 75.8 | 75.8 | 73.1 | 59.8 | 69.9 | 69.7 | 69.7 | 71.5 | 70.7 |
| PtIP-96Ag SEQ ID NO: 22 | 75.9 | 76.2 | 76.0 | 76.0 | 73.4 | 59.8 | 70.1 | 69.9 | 69.9 | 71.5 | 70.7 |
| PtIP-96Ah SEQ ID NO: 24 | 75.9 | 76.5 | 76.2 | 76.2 | 73.4 | 60.3 | 70.1 | 69.9 | 69.9 | 72.3 | 71.2 |
| PtIP-96Ca SEQ ID NO: 26 | 99.5 | 98.7 | 98.4 | 98.4 | 97.4 | 61.8 | 68.8 | 68.8 | 68.5 | 64.9 | 66.2 |
| PtIP-96Cb SEQ ID NO: 28 | 99.2 | 98.4 | 98.2 | 98.2 | 97.2 | 61.5 | 68.5 | 68.5 | 68.3 | 64.6 | 65.9 |
| PtIP-96Cc SEQ ID NO: 30 | 98.2 | 99.7 | 99.5 | 99.5 | 96.1 | 62.6 | 69.3 | 69.3 | 69.1 | 65.7 | 64.9 |
| PtIP-96Cd SEQ ID NO: 32 | — | 98.2 | 97.9 | 97.9 | 96.9 | 61.8 | 69.2 | 69.2 | 69.0 | 65.4 | 66.7 |

TABLE 4b-continued

|  | PtIP-96Cd SEQ ID NO: 32 | PtIP-96Ce SEQ ID NO: 34 | PtIP-96Cf SEQ ID NO: 36 | PtIP-96Cg SEQ ID NO: 38 | PtIP-96Ch SEQ ID NO: 40 | PtIP-96Da SEQ ID NO: 42 | PtIP-96Db SEQ ID NO: 44 | PtIP-96Dc SEQ ID NO: 46 | PtIP-96Dd SEQ ID NO: 52 | PtIP-96De SEQ ID NO: 48 | PtIP-96Df SEQ ID NO: 50 |
|---|---|---|---|---|---|---|---|---|---|---|---|
| PtIP-96Ce SEQ ID NO: 34 | — | — | 99.7 | 99.7 | 96.1 | 62.6 | 69.3 | 69.3 | 69.1 | 66.0 | 64.9 |
| PtIP-96Cf SEQ ID NO: 36 | — | — | — | 99.5 | 95.9 | 62.4 | 69.1 | 69.1 | 68.9 | 65.7 | 64.6 |
| PtIP-96Cg SEQ ID NO: 38 | — | — | — | — | 95.9 | 62.4 | 69.3 | 69.3 | 69.1 | 65.7 | 64.6 |
| PtIP-96Ch SEQ ID NO: 40 | — | — | — | — | — | 60.5 | 67.1 | 67.1 | 66.8 | 63.1 | 64.4 |
| PtIP-96Da SEQ ID NO: 42 | — | — | — | — | — | — | 63.9 | 63.9 | 63.6 | 55.3 | 54.5 |
| PtIP-96Db SEQ ID NO: 44 | — | — | — | — | — | — | — | 99.8 | 99.8 | 62.8 | 62.3 |
| PtIP-96Dc SEQ ID NO: 46 | — | — | — | — | — | — | — | — | 99.5 | 62.8 | 62.3 |
| PtIP-96Dd SEQ ID NO: 52 | — | — | — | — | — | — | — | — | — | 62.6 | 62.0 |
| PtIP-96De SEQ ID NO: 48 | — | — | — | — | — | — | — | — | — | — | 98.7 |

TABLE 4c

|  | PtIP-96Ea SEQ ID NO: 7 | PtIP-96Eb SEQ ID NO: 8 | PtIP-96Ed SEQ ID NO: 54 | PtIP-96Ee SEQ ID NO: 56 | PtIP-96Ef SEQ ID NO: 58 | PtIP-96Eg SEQ ID NO: 60 | PtIP-96Eh SEQ ID NO: 62 | PtIP-96Ei SEQ ID NO: 64 | PtIP-96Ej SEQ ID NO: 66 | PtIP-96Ek SEQ ID NO: 68 | PtIP-96El SEQ ID NO: 70 |
|---|---|---|---|---|---|---|---|---|---|---|---|
| PtIP-96Ec SEQ ID NO: 6 | 83.9 | 83.6 | 73.3 | 96.3 | 99.2 | 96.0 | 96.0 | 96.3 | 96.6 | 95.5 | 95.8 |
| PtIP-96Aa SEQ ID NO: 9 | 56.2 | 56.0 | 58.2 | 55.8 | 56.0 | 55.6 | 55.6 | 55.8 | 55.6 | 55.6 | 55.6 |
| PtIP-96Ab SEQ ID NO: 12 | 56.5 | 56.2 | 58.4 | 56.0 | 56.3 | 55.8 | 55.8 | 56.0 | 55.8 | 55.8 | 55.8 |
| PtIP-96Ac SEQ ID NO: 14 | 55.5 | 55.2 | 57.4 | 55.1 | 55.3 | 54.8 | 54.8 | 55.1 | 54.8 | 54.8 | 54.8 |
| PtIP-96Ad SEQ ID NO: 16 | 56.0 | 55.8 | 56.6 | 55.6 | 55.8 | 55.3 | 55.3 | 55.6 | 55.3 | 55.3 | 55.3 |
| PtIP-96Ae SEQ ID NO: 18 | 56.0 | 55.8 | 57.9 | 55.6 | 55.8 | 55.3 | 55.3 | 55.6 | 55.3 | 55.3 | 55.3 |
| PtIP-96Af SEQ ID NO: 20 | 56.0 | 55.8 | 57.9 | 55.6 | 55.8 | 55.3 | 55.3 | 55.6 | 55.3 | 55.3 | 55.3 |
| PtIP-96Ag SEQ ID NO: 22 | 56.2 | 56.0 | 58.2 | 55.8 | 56.0 | 55.6 | 55.6 | 55.8 | 55.6 | 55.6 | 55.6 |
| PtIP-96Ah SEQ ID NO: 24 | 56.8 | 56.5 | 58.8 | 56.0 | 56.3 | 55.8 | 55.8 | 56.0 | 55.8 | 55.8 | 55.8 |
| PtIP-96Ca SEQ ID NO: 26 | 54.1 | 54.1 | 55.5 | 54.6 | 55.5 | 54.6 | 54.4 | 54.6 | 54.4 | 54.6 | 54.6 |
| PtIP-96Cb SEQ ID NO: 28 | 54.1 | 54.1 | 55.3 | 54.4 | 55.2 | 54.4 | 54.1 | 54.4 | 54.1 | 54.4 | 54.4 |
| PtIP-96Cc SEQ ID NO: 30 | 54.4 | 54.4 | 56.3 | 55.4 | 56.3 | 55.4 | 55.2 | 55.4 | 55.2 | 55.4 | 55.4 |
| PtIP-96Cd SEQ ID NO: 32 | 54.1 | 54.1 | 55.5 | 54.6 | 55.5 | 54.6 | 54.4 | 54.6 | 54.4 | 54.6 | 54.6 |
| PtIP-96Ce SEQ ID NO: 34 | 54.7 | 54.7 | 56.6 | 55.4 | 55.4 | 55.2 | 55.2 | 55.2 | 55.2 | 55.4 | 55.4 |
| PtIP-96Cf SEQ ID NO: 36 | 54.4 | 54.4 | 56.3 | 55.2 | 56.0 | 55.2 | 54.9 | 55.2 | 54.9 | 55.2 | 55.2 |
| PtIP-96Cg SEQ ID NO: 38 | 54.7 | 54.7 | 56.6 | 55.2 | 56.0 | 55.2 | 54.9 | 55.2 | 54.9 | 55.2 | 55.2 |
| PtIP-96Ch SEQ ID NO: 40 | 52.6 | 52.6 | 54.0 | 53.1 | 54.0 | 53.1 | 52.8 | 53.1 | 52.8 | 53.1 | 53.1 |
| PtIP-96Da SEQ ID NO: 42 | 58.3 | 58.0 | 60.6 | 61.1 | 60.6 | 61.4 | 60.8 | 61.1 | 60.8 | 61.4 | 61.4 |
| PtIP-96Db SEQ ID NO: 44 | 55.2 | 54.9 | 57.4 | 57.8 | 57.6 | 58.0 | 57.6 | 57.8 | 57.6 | 58.0 | 58.0 |
| PtIP-96Dc SEQ ID NO: 46 | 55.2 | 54.9 | 57.4 | 57.8 | 57.6 | 58.0 | 57.6 | 57.8 | 57.6 | 58.0 | 58.0 |
| PtIP-96Dd SEQ ID NO: 52 | 54.9 | 54.7 | 57.1 | 57.6 | 57.3 | 57.8 | 57.3 | 57.6 | 57.3 | 57.8 | 57.8 |
| PtIP-96De SEQ ID NO: 48 | 54.6 | 54.3 | 55.9 | 52.8 | 53.5 | 52.5 | 52.5 | 52.8 | 52.5 | 52.8 | 52.5 |
| PtIP-96Df SEQ ID NO: 50 | 54.0 | 53.8 | 54.9 | 52.0 | 52.8 | 51.8 | 51.8 | 52.0 | 51.8 | 52.0 | 51.8 |
| PtIP-96Ea SEQ ID NO: 7 | — | 99.7 | 77.8 | 83.4 | 83.6 | 83.1 | 83.1 | 83.4 | 83.1 | 83.1 | 82.8 |

TABLE 4c-continued

| | PtIP-96Ea SEQ ID NO: 7 | PtIP-96Eb SEQ ID NO: 8 | PtIP-96Ed SEQ ID NO: 54 | PtIP-96Ee SEQ ID NO: 56 | PtIP-96Ef SEQ ID NO: 58 | PtIP-96Eg SEQ ID NO: 60 | PtIP-96Eh SEQ ID NO: 62 | PtIP-96Ei SEQ ID NO: 64 | PtIP-96Ej SEQ ID NO: 66 | PtIP-96Ek SEQ ID NO: 68 | PtIP-96El SEQ ID NO: 70 |
|---|---|---|---|---|---|---|---|---|---|---|---|
| PtIP-96Eb SEQ ID NO: 8 | — | — | 77.5 | 83.1 | 83.3 | 82.8 | 82.8 | 83.1 | 82.8 | 82.8 | 82.5 |
| PtIP-96Ed SEQ ID NO: 54 | — | — | — | 73.3 | 73.9 | 73.6 | 73.1 | 73.3 | 73.1 | 73.9 | 73.6 |
| PtIP-96Ee SEQ ID NO: 56 | — | — | — | — | 95.5 | 99.7 | 99.7 | 100 | 99.7 | 99.2 | 99.4 |
| PtIP-96Ef SEQ ID NO: 58 | — | — | — | — | — | 95.8 | 95.2 | 95.5 | 95.8 | 96.3 | 96.0 |
| PtIP-96Eg SEQ ID NO: 60 | — | — | — | — | — | — | 99.4 | 99.7 | 99.4 | 99.4 | 99.7 |
| PtIP-96Eh SEQ ID NO: 62 | — | — | — | — | — | — | — | 99.7 | 99.4 | 98.9 | 99.2 |
| PtIP-96Ei SEQ ID NO: 64 | — | — | — | — | — | — | — | — | 99.7 | 99.2 | 99.4 |
| PtIP-96Ej SEQ ID NO: 66 | — | — | — | — | — | — | — | — | — | 98.9 | 99.2 |
| PtIP-96Ek SEQ ID NO: 68 | — | — | — | — | — | — | — | — | — | — | 99.7 |

TABLE 4d

| | PtIP-96Em SEQ ID NO: 72 | PtIP-96En SEQ ID NO: 74 | PtIP-96Eo SEQ ID NO: 76 | PtIP-96Ep SEQ ID NO: 78 | PtIP-96Eq SEQ ID NO: 80 | PtIP-96Er SEQ ID NO: 82 | PtIP-96Es SEQ ID NO: 84 | PtIP-96Et SEQ ID NO: 86 | PtIP-96Eu SEQ ID NO: 88 | PtIP-96Ev SEQ ID NO: 90 |
|---|---|---|---|---|---|---|---|---|---|---|
| PtIP-96Ec SEQ ID NO: 6 | 96.9 | 96.0 | 56.1 | 54.3 | 56.4 | 76.3 | 74.6 | 85.6 | 94.2 | 85.6 |
| PtIP-96Aa SEQ ID NO: 9 | 55.3 | 55.8 | 59.1 | 62.8 | 62.2 | 54.9 | 54.6 | 55.9 | 57.0 | 55.6 |
| PtIP-96Ab SEQ ID NO: 12 | 55.6 | 56.0 | 59.3 | 62.8 | 62.7 | 55.1 | 55.6 | 55.7 | 57.2 | 54.7 |
| PtIP-96Ac SEQ ID NO: 14 | 54.6 | 55.1 | 58.4 | 62.1 | 61.5 | 54.1 | 53.8 | 55.1 | 56.2 | 54.8 |
| PtIP-96Ad SEQ ID NO: 16 | 55.1 | 55.6 | 59.2 | 62.6 | 62.1 | 54.6 | 54.3 | 55.6 | 57.5 | 55.3 |
| PtIP-96Ae SEQ ID NO: 18 | 55.1 | 55.6 | 58.4 | 62.1 | 61.5 | 54.4 | 54.1 | 55.1 | 56.8 | 54.8 |
| PtIP-96Af SEQ ID NO: 20 | 55.1 | 55.6 | 58.9 | 62.6 | 62.0 | 54.6 | 54.3 | 55.6 | 56.8 | 55.3 |
| PtIP-96Ag SEQ ID NO: 22 | 55.3 | 55.8 | 59.1 | 62.8 | 62.2 | 54.9 | 54.6 | 55.9 | 57.0 | 55.6 |
| PtIP-96Ah SEQ ID NO: 24 | 55.6 | 56.0 | 59.3 | 63.3 | 62.7 | 55.4 | 55.1 | 55.9 | 57.5 | 54.9 |
| PtIP-96Ca SEQ ID NO: 26 | 54.4 | 54.6 | 56.0 | 54.2 | 57.5 | 54.9 | 54.5 | 56.3 | 55.2 | 56.3 |
| PtIP-96Cb SEQ ID NO: 28 | 54.1 | 54.4 | 55.7 | 54.0 | 57.2 | 54.6 | 54.2 | 56.1 | 54.9 | 56.1 |
| PtIP-96Cc SEQ ID NO: 30 | 55.2 | 55.4 | 56.7 | 54.9 | 58.2 | 55.2 | 54.8 | 56.6 | 55.4 | 56.6 |
| PtIP-96Cd SEQ ID NO: 32 | 54.4 | 54.6 | 56.0 | 54.2 | 57.5 | 54.9 | 54.5 | 56.3 | 55.2 | 56.3 |
| PtIP-96Ce SEQ ID NO: 34 | 55.2 | 55.4 | 56.9 | 55.1 | 58.5 | 55.4 | 55.0 | 56.9 | 55.7 | 56.9 |
| PtIP-96Cf SEQ ID NO: 36 | 54.9 | 55.2 | 56.7 | 54.9 | 58.2 | 55.2 | 54.8 | 56.6 | 55.4 | 56.6 |
| PtIP-96Cg SEQ ID NO: 38 | 54.9 | 55.2 | 56.7 | 54.9 | 58.2 | 55.4 | 55.0 | 56.9 | 55.4 | 56.9 |
| PtIP-96Ch SEQ ID NO: 40 | 52.8 | 53.1 | 55.0 | 53.3 | 56.5 | 53.4 | 53.0 | 54.8 | 53.6 | 54.8 |
| PtIP-96Da SEQ ID NO: 42 | 60.6 | 61.1 | 64.2 | 62.1 | 64.7 | 56.5 | 55.1 | 58.8 | 59.6 | 58.8 |
| PtIP-96Db SEQ ID NO: 44 | 57.3 | 57.8 | 65.4 | 66.2 | 69.1 | 54.3 | 54.3 | 56.6 | 57.7 | 56.8 |
| PtIP-96Dc SEQ ID NO: 46 | 57.3 | 57.8 | 65.6 | 66.4 | 68.7 | 54.3 | 54.3 | 56.6 | 57.7 | 56.8 |
| PtIP-96Dd SEQ ID NO: 52 | 57.1 | 57.6 | 65.2 | 66.0 | 68.9 | 54.0 | 54.0 | 56.3 | 57.5 | 56.5 |
| PtIP-96De SEQ ID NO: 48 | 53.3 | 52.5 | 57.9 | 54.4 | 59.7 | 53.4 | 53.4 | 53.8 | 53.3 | 53.2 |
| PtIP-96Df SEQ ID NO: 50 | 52.5 | 51.8 | 56.9 | 53.5 | 58.7 | 52.9 | 52.9 | 53.3 | 52.8 | 52.7 |
| PtIP-96Ea SEQ ID NO: 7 | 83.9 | 83.4 | 54.4 | 52.7 | 54.1 | 80.7 | 79.4 | 89.8 | 82.5 | 89.5 |

TABLE 4d-continued

| | PtIP-96Em SEQ ID NO: 72 | PtIP-96En SEQ ID NO: 74 | PtIP-96Eo SEQ ID NO: 76 | PtIP-96Ep SEQ ID NO: 78 | PtIP-96Eq SEQ ID NO: 80 | PtIP-96Er SEQ ID NO: 82 | PtIP-96Es SEQ ID NO: 84 | PtIP-96Et SEQ ID NO: 86 | PtIP-96Eu SEQ ID NO: 88 | PtIP-96Ev SEQ ID NO: 90 |
|---|---|---|---|---|---|---|---|---|---|---|
| PtIP-96Eb SEQ ID NO: 8 | 83.7 | 83.1 | 54.4 | 52.7 | 54.1 | 80.5 | 79.2 | 89.5 | 82.3 | 89.2 |
| PtIP-96Ed SEQ ID NO: 54 | 73.3 | 73.3 | 55.3 | 53.5 | 58.5 | 72.5 | 70.8 | 77.8 | 72.1 | 77.8 |
| PtIP-96Ee SEQ ID NO: 56 | 97.7 | 99.7 | 55.2 | 53.4 | 56.0 | 77.2 | 75.4 | 84.8 | 97.8 | 84.8 |
| PtIP-96Ef SEQ ID NO: 58 | 97.7 | 95.2 | 56.4 | 54.5 | 56.6 | 76.1 | 74.3 | 85.4 | 93.3 | 85.4 |
| PtIP-96Eg SEQ ID NO: 60 | 98.0 | 99.4 | 55.4 | 53.6 | 56.3 | 76.9 | 75.1 | 84.5 | 97.5 | 84.5 |
| PtIP-96Eh SEQ ID NO: 62 | 97.5 | 99.4 | 54.9 | 53.1 | 55.8 | 76.9 | 75.1 | 84.5 | 97.5 | 84.5 |
| PtIP-96Ei SEQ ID NO: 64 | 97.7 | 99.7 | 55.2 | 53.4 | 56.0 | 77.2 | 75.4 | 84.8 | 97.8 | 84.8 |
| PtIP-96Ej SEQ ID NO: 66 | 98.0 | 99.4 | 54.9 | 53.1 | 55.8 | 76.9 | 75.1 | 84.5 | 97.5 | 84.5 |
| PtIP-96Ek SEQ ID NO: 68 | 98.6 | 98.9 | 55.4 | 53.6 | 56.3 | 76.9 | 75.1 | 84.5 | 96.9 | 84.5 |
| PtIP-96El SEQ ID NO: 70 | 98.3 | 99.2 | 55.4 | 53.6 | 56.3 | 76.6 | 74.9 | 84.2 | 97.2 | 84.2 |
| PtIP-96Em SEQ ID NO: 72 | — | 97.5 | 55.2 | 53.4 | 56.0 | 76.9 | 75.1 | 85.4 | 95.6 | 85.4 |
| PtIP-96En SEQ ID NO: 74 | — | — | 55.2 | 53.4 | 56.0 | 77.2 | 75.4 | 84.8 | 97.5 | 84.8 |
| PtIP-96Eo SEQ ID NO: 76 | — | — | — | 94.7 | 83.0 | 51.9 | 51.7 | 55.5 | 55.2 | 55.6 |
| PtIP-96Ep SEQ ID NO: 78 | — | — | — | — | 86.7 | 50.2 | 50.1 | 53.7 | 53.4 | 53.8 |
| PtIP-96Eq SEQ ID NO: 80 | — | — | — | — | — | 51.8 | 52.4 | 55.7 | 55.3 | 56.5 |
| PtIP-96Er SEQ ID NO: 82 | — | — | — | — | — | — | 97.8 | 83.0 | 76.5 | 83.0 |
| PtIP-96Es SEQ ID NO: 84 | — | — | — | — | — | — | — | 81.1 | 76.0 | 81.1 |
| PtIP-96Et SEQ ID NO: 86 | — | — | — | — | — | — | — | — | 83.9 | 99.7 |
| PtIP-96Eu SEQ ID NO: 88 | — | — | — | — | — | — | — | — | — | 83.9 |

TABLE 4e

| | PtIP-96Ha SEQ ID NO: 10 | PtIP-96Hb SEQ ID NO: 92 | PtIP-96Hc SEQ ID NO: 94 | PtIP-96Hd SEQ ID NO: 96 | PtIP-96He SEQ ID NO: 98 | PtIP-96Hf SEQ ID NO: 100 | PtIP-96Hg SEQ ID NO: 102 | PtIP-96Hh SEQ ID NO: 104 | PtIP-96Hi SEQ ID NO: 106 | PtIP-96Hj SEQ ID NO: 108 |
|---|---|---|---|---|---|---|---|---|---|---|
| PtIP-96Ec SEQ ID NO: 6 | 29.4 | 29.4 | 29.7 | 29.7 | 29.6 | 29.4 | 29.4 | 29.2 | 29.2 | 29.6 |
| PtIP-96Aa SEQ ID NO: 9 | 27.0 | 27.2 | 27.8 | 27.8 | 27.6 | 27.6 | 27.6 | 27.0 | 27.4 | 27.6 |
| PtIP-96Ab SEQ ID NO: 12 | 26.8 | 27.0 | 27.6 | 27.6 | 27.4 | 27.4 | 27.4 | 26.8 | 27.2 | 27.4 |
| PtIP-96Ac SEQ ID NO: 14 | 26.4 | 26.6 | 27.2 | 27.2 | 27.0 | 27.0 | 27.0 | 26.4 | 26.8 | 27.0 |
| PtIP-96Ad SEQ ID NO: 16 | 26.8 | 27.0 | 27.6 | 27.6 | 27.4 | 27.4 | 27.4 | 26.8 | 27.2 | 27.4 |
| PtIP-96Ae SEQ ID NO: 18 | 26.6 | 26.8 | 27.4 | 27.4 | 27.2 | 27.2 | 27.2 | 26.6 | 27.0 | 27.2 |
| PtIP-96Af SEQ ID NO: 20 | 26.8 | 27.0 | 27.6 | 27.6 | 27.4 | 27.4 | 27.4 | 26.8 | 27.2 | 27.4 |
| PtIP-96Ag SEQ ID NO: 22 | 27.0 | 27.2 | 27.8 | 27.8 | 27.6 | 27.6 | 27.6 | 27.0 | 27.4 | 27.6 |
| PtIP-96Ah SEQ ID NO: 24 | 26.8 | 27.0 | 27.6 | 27.6 | 27.4 | 27.4 | 27.4 | 26.8 | 27.2 | 27.4 |
| PtIP-96Ca SEQ ID NO: 26 | 28.8 | 29.0 | 29.8 | 29.8 | 30.0 | 29.6 | 29.6 | 28.8 | 29.4 | 30.0 |
| PtIP-96Cb SEQ ID NO: 28 | 28.8 | 29.0 | 29.8 | 29.8 | 30.0 | 29.6 | 29.6 | 28.8 | 29.4 | 30.0 |
| PtIP-96Cc SEQ ID NO: 30 | 28.8 | 29.0 | 29.8 | 29.8 | 30.0 | 29.6 | 29.6 | 28.8 | 29.3 | 30.0 |
| PtIP-96Cd SEQ ID NO: 32 | 28.8 | 29.0 | 29.8 | 29.8 | 30.0 | 29.6 | 29.6 | 28.8 | 29.4 | 30.0 |
| PtIP-96Ce SEQ ID NO: 34 | 28.8 | 29.0 | 29.8 | 29.8 | 30.0 | 29.6 | 29.6 | 28.8 | 29.3 | 30.0 |

TABLE 4e-continued

| | PtIP-96Ha SEQ ID NO: 10 | PtIP-96Hb SEQ ID NO: 92 | PtIP-96Hc SEQ ID NO: 94 | PtIP-96Hd SEQ ID NO: 96 | PtIP-96He SEQ ID NO: 98 | PtIP-96Hf SEQ ID NO: 100 | PtIP-96Hg SEQ ID NO: 102 | PtIP-96Hh SEQ ID NO: 104 | PtIP-96Hi SEQ ID NO: 106 | PtIP-96Hj SEQ ID NO: 108 |
|---|---|---|---|---|---|---|---|---|---|---|
| PtIP-96Cf SEQ ID NO: 36 | 28.5 | 28.8 | 29.6 | 29.6 | 29.8 | 29.3 | 29.3 | 28.5 | 29.1 | 29.8 |
| PtIP-96Cg SEQ ID NO: 38 | 28.5 | 28.8 | 29.6 | 29.6 | 29.8 | 29.3 | 29.3 | 28.5 | 29.1 | 29.8 |
| PtIP-96Ch SEQ ID NO: 40 | 28.4 | 28.6 | 29.4 | 29.4 | 29.6 | 29.2 | 29.2 | 28.4 | 29.0 | 29.6 |
| PtIP-96Da SEQ ID NO: 42 | 34.3 | 34.6 | 35.1 | 35.1 | 35.0 | 34.6 | 34.6 | 34.3 | 34.3 | 35.0 |
| PtIP-96Db SEQ ID NO: 44 | 26.9 | 27.1 | 27.2 | 27.2 | 27.0 | 26.8 | 26.8 | 26.9 | 26.6 | 27.0 |
| PtIP-96Dc SEQ ID NO: 46 | 26.9 | 27.1 | 27.2 | 27.2 | 27.0 | 26.8 | 26.8 | 26.9 | 26.6 | 27.0 |
| PtIP-96Dd SEQ ID NO: 52 | 26.7 | 26.9 | 27.0 | 27.0 | 26.8 | 26.6 | 26.6 | 26.7 | 26.4 | 26.8 |
| PtIP-96De SEQ ID NO: 48 | 25.9 | 26.3 | 26.9 | 26.9 | 26.7 | 26.7 | 26.7 | 26.1 | 26.5 | 26.9 |
| PtIP-96Df SEQ ID NO: 50 | 25.9 | 26.4 | 26.9 | 26.9 | 26.7 | 26.7 | 26.7 | 26.2 | 26.5 | 26.9 |
| PtIP-96Ea SEQ ID NO: 7 | 29.0 | 29.0 | 29.3 | 29.3 | 28.7 | 29.0 | 29.0 | 28.8 | 28.8 | 28.7 |
| PtIP-96Eb SEQ ID NO: 8 | 29.0 | 29.0 | 29.3 | 29.3 | 28.7 | 29.0 | 29.0 | 28.8 | 28.8 | 28.7 |
| PtIP-96Ed SEQ ID NO: 54 | 28.9 | 28.9 | 29.1 | 29.1 | 29.0 | 28.9 | 28.9 | 28.6 | 28.6 | 29.0 |
| PtIP-96Ee SEQ ID NO: 56 | 29.7 | 29.7 | 29.9 | 29.9 | 29.8 | 29.7 | 29.7 | 29.4 | 29.4 | 29.8 |
| PtIP-96Ef SEQ ID NO: 58 | 29.4 | 29.4 | 29.7 | 29.7 | 29.6 | 29.4 | 29.4 | 29.2 | 29.2 | 29.6 |
| PtIP-96Eg SEQ ID NO: 60 | 29.9 | 29.9 | 30.1 | 30.1 | 30.0 | 29.9 | 29.9 | 29.7 | 29.7 | 30.0 |
| PtIP-96Eh SEQ ID NO: 62 | 29.4 | 29.4 | 29.7 | 29.7 | 29.6 | 29.4 | 29.4 | 29.2 | 29.2 | 29.6 |
| PtIP-96Ei SEQ ID NO: 64 | 29.7 | 29.7 | 29.9 | 29.9 | 29.8 | 29.7 | 29.7 | 29.4 | 29.4 | 29.8 |
| PtIP-96Ej SEQ ID NO: 66 | 29.7 | 29.7 | 29.9 | 29.9 | 29.8 | 29.7 | 29.7 | 29.4 | 29.4 | 29.8 |
| PtIP-96Ek SEQ ID NO: 68 | 29.7 | 29.7 | 29.9 | 29.9 | 29.8 | 29.7 | 29.7 | 29.4 | 29.4 | 29.8 |
| PtIP-96El SEQ ID NO: 70 | 29.9 | 29.9 | 30.1 | 30.1 | 30.0 | 29.9 | 29.9 | 29.7 | 29.7 | 30.0 |
| PtIP-96Em SEQ ID NO: 72 | 29.2 | 29.2 | 29.4 | 29.4 | 29.4 | 29.2 | 29.2 | 29.0 | 29.0 | 29.4 |
| PtIP-96En SEQ ID NO: 74 | 29.4 | 29.4 | 29.7 | 29.7 | 29.6 | 29.4 | 29.4 | 29.2 | 29.2 | 29.6 |
| PtIP-96Eo SEQ ID NO: 76 | 25.3 | 25.5 | 26.1 | 26.1 | 25.9 | 25.5 | 25.5 | 25.3 | 25.3 | 25.9 |
| PtIP-96Ep SEQ ID NO: 78 | 24.6 | 24.8 | 25.3 | 25.3 | 25.1 | 24.8 | 24.8 | 24.6 | 24.6 | 25.1 |
| PtIP-96Eq SEQ ID NO: 80 | 25.4 | 25.6 | 26.2 | 26.2 | 26.0 | 25.6 | 25.6 | 25.4 | 25.4 | 26.0 |
| PtIP-96Er SEQ ID NO: 82 | 29.0 | 29.3 | 29.5 | 29.5 | 29.0 | 29.3 | 29.3 | 29.3 | 29.0 | 29.0 |
| PtIP-96Es SEQ ID NO: 84 | 28.6 | 28.8 | 29.0 | 29.0 | 28.5 | 28.8 | 28.8 | 28.8 | 28.6 | 28.5 |
| PtIP-96Et SEQ ID NO: 86 | 29.3 | 29.3 | 29.5 | 29.5 | 29.0 | 29.3 | 29.3 | 29.3 | 29.0 | 29.0 |
| PtIP-96Eu SEQ ID NO: 88 | 29.3 | 29.3 | 29.5 | 29.5 | 29.0 | 29.3 | 29.3 | 29.0 | 29.0 | 29.0 |
| PtIP-96Ev SEQ ID NO: 90 | 29.3 | 29.3 | 29.5 | 29.5 | 29.0 | 29.3 | 29.3 | 29.3 | 29.0 | 29.0 |
| PtIP-96Ha SEQ ID NO: 10 | — | 98.7 | 96.7 | 97.0 | 97.5 | 97.7 | 97.5 | 98.7 | 97.7 | 97.2 |
| PtIP-96Hb SEQ ID NO: 92 | — | — | 97.5 | 96.7 | 97.2 | 97.5 | 97.2 | 99.5 | 98.5 | 97.0 |
| PtIP-96Hc SEQ ID NO: 94 | — | — | — | 98.7 | 98.2 | 97.0 | 96.7 | 97.5 | 98.0 | 98.0 |
| PtIP-96Hd SEQ ID NO: 96 | — | — | — | — | 98.5 | 98.2 | 98.0 | 96.7 | 97.2 | 98.2 |
| PtIP-96He SEQ ID NO: 98 | — | — | — | — | — | 97.7 | 97.5 | 97.2 | 97.7 | 99.7 |
| PtIP-96Hf SEQ ID NO: 100 | — | — | — | — | — | — | 99.7 | 97.5 | 98.5 | 97.5 |
| PtIP-96Hg SEQ ID NO: 102 | — | — | — | — | — | — | — | 97.2 | 98.2 | 97.2 |
| PtIP-96Hh SEQ ID NO: 104 | — | — | — | — | — | — | — | — | 98.5 | 97.0 |

TABLE 4e-continued

|  | PtIP-96Ha SEQ ID NO: 10 | PtIP-96Hb SEQ ID NO: 92 | PtIP-96Hc SEQ ID NO: 94 | PtIP-96Hd SEQ ID NO: 96 | PtIP-96He SEQ ID NO: 98 | PtIP-96Hf SEQ ID NO: 100 | PtIP-96Hg SEQ ID NO: 102 | PtIP-96Hh SEQ ID NO: 104 | PtIP-96Hi SEQ ID NO: 106 | PtIP-96Hj SEQ ID NO: 108 |
|---|---|---|---|---|---|---|---|---|---|---|
| PtIP-96Hi SEQ ID NO: 106 | — | — | — | — | — | — | — | — |  | 97.5 |

Example 4—Identification of PtIP-96 Homologs by Protein Purification

PtIP-96 polypeptide homologs may also be identified by protein purification, mass spectroscopy (MS) and PCR cloning from *Selaginella kraussiana* or other club mosses and ferns.

Plant tissue is collected, flash frozen in liquid $N_2$ and stored at −80° C. After storage it is ground to a fine powder at liquid $N_2$ temperatures with a Geno Ball Mill (SPEX, Metuchen, N.J.). To extract protein, 20 mL of 50 mM Tris buffer, pH 8.0, 150 mM KCl, 2.5 mM EDTA, 1.5% polyvinylpolypyrrolidone (PVPP) and protease inhibitor cocktail (Roche Diagnostics, Germany) is added to every 5 g fresh weight of tissue. The homogenate is centrifuged to remove cell debris, filtered through 0.22 um filters and desalted using 10 ml Zeba Spin Desalting columns (Thermo Scientific, IL.)

For protein purification, the plant material is ground to a fine powder at liquid $N_2$ temperatures with a Geno Ball Mill (SPEX, Metuchen, N.J.). Protein is extracted in 100 mM Tris buffer, pH 8.0, 150 mM KCl, 2.5 mM EDTA, 1.5% PVPP and protease inhibitor cocktail (Roche Diagnostics, Germany). The extracted material is centrifuged to remove cell debris, filtered through Miracloth® (Calbiochem) and ammonium sulfate added to 35% and allowed to equilibrate. The suspension is centrifuged and the resulting pellet is resuspended in a small volume of 20 mM Tris buffer, pH 8. After clarification by centrifugation it is desalted using a Sephadex G25 column (GE, Piscataway, N.J.) equilibrated in 20 mM Tris buffer, pH 8. The desalted protein fraction pool is loaded onto a 1 ml Mono Q column (GE, Piscataway, N.J.) and eluted with a linear (60 CV (column volumes) gradient from 0 M to 0.7 M NaCl in 20 mM Tris, pH 8.0, Fractions active against SBL and ECB are combined and desalted into 25 mM MOPS, pH 6.7. The active fraction is loaded onto a 4 mL Mono P column (Buffer A: 25 mM MOPS, pH 6.7; Buffer B: Polybuffer 74, pH 4) using a 4 CV linear gradient (0% Buffer B) followed by a 15 CV 100% Buffer B wash.

Protein identification is performed by MS analysis after protein digestion with trypsin. Proteins for MS identification are obtained after running the sample on an LDS-PAGE gel stained with Brilliant Blue G-250 Stain. Bands of interest are excised from the gel, de-stained, reduced with dithiothreitol and then alkylated with iodoacetamide. Following overnight digestion with trypsin, samples are analyzed by nano-liquid chromatography/electrospray tandem mass spectrometry (nano-LC/ES-MSMS) on a Thermo Q Exactive Orbitrap mass spectrometer (Thermo Fisher Scientific) interfaced with an Eksigent NanoLC Ultra 1-D Plus nano-lc system and a nanolc-as2 autosampler (AB Sciex). The protein identification is performed by searching the nano-LC/MSMS data against an in-house transcriptome database containing the transcripts from the source plant materials and the public protein database Swiss-Prot using the Mascot search engine (Matrix Science).

Example 5: Transient Expression in Leaves and Insect Bioassay

The PtIP-96 polypeptides were expressed in a transient expression system under control of a viral promoter dMMV and/or AtUBQ10 (Day, et. al., (1999) *Plant Mol. Biol.* 40:771-782; Norris S R et al (1993) *Plant Mol Biol.* 21(5): 895-906) was utilized. The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, the unifoliate stage of bush bean (common bean, *Phaseolus vulgaris*) or soybean (*Glycine max*), were agro-infiltrated with normalized bacterial cell cultures of test and control strains. After 4 to 7 days leaf disks were excised from each plantlet and infested with 2 neonates of Soybean Looper (SBL) (*Chrysodeixis includens*), 2 neonates of Corn Earworm (CEW) (*Helicoverpa zea*), or 4 neonates of European Corn Borer (ECB) (*Ostrinia nubialis*) alone. Control leaf discs were generated with *Agrobacterium* containing only a DsRed2 fluorescence marker (Clontech™, 1290 Terra Bella Ave. Mountain View, Calif. 94043) expression vector. Leaf discs from non-infiltrated plants were included as a second control. The consumption of green leaf tissue was scored two (CEW) or three (ECB, SBL, FAW) days after infestation. The transiently expressed PtIP-96 polypeptides protected leaf discs from consumption by the infested insects while total green tissue consumption was observed for the negative control and untreated tissue (Table 5). nd=not determined

TABLE 5

| polypeptide | Sequence identifier | SBL | CEW | ECB | VBC |
|---|---|---|---|---|---|
| PtIP-96Aa | SEQ ID NO: 9 | ++ | ++ | + | − |
| PtIP-96Ab | SEQ ID NO: 12 | ++ | ++ | ++ | ++ |
| PtIP-96Ac | SEQ ID NO: 14 | + | ++ | nd | nd |
| PtIP-96Ad | SEQ ID NO: 16 | ++ | ++ | ++ | ++ |
| PtIP-96Ae | SEQ ID NO: 18 | + | − | nd | nd |
| PtIP-96Af | SEQ ID NO: 20 | ++ | ++ | nd | nd |
| PtIP-96Ca | SEQ ID NO: 26 | ++ | ++ | ++ | ++ |
| PtIP-96Cb | SEQ ID NO: 28 | ++ | ++ | nd | nd |
| PtIP-96Da | SEQ ID NO: 42 | + | + | + | + |
| PtIP-96Db | SEQ ID NO: 44 | ++ | ++ | nd | − |
| PtIP-96Dc | SEQ ID NO: 46 | ++ | ++ | nd | + |
| PtIP-96Dd | SEQ ID NO: 52 | + | + | nd | + |
| PtIP-96De | SEQ ID NO: 48 | + | + | nd | − |
| PtIP-96Df | SEQ ID NO: 50 | + | + | nd | − |
| PtIP-96Eb | SEQ ID NO: 8 | nd | ++ | − | + |
| PtIP-96Ea | SEQ ID NO: 7 | nd | ++ | − | + |
| PtIP-96Ec | SEQ ID NO: 6 | nd | ++ | + | ++ |
| PtIP-96Ew | SEQ ID NO: 6 | nd | ++ | ++ | ++ |
| PtIP-96Ee | SEQ ID NO: 56 | nd | ++ | + | ++ |
| PtIP-96Ef | SEQ ID NO: 58 | nd | ++ | + | ++ |
| PtIP-96Eg | SEQ ID NO: 60 | nd | ++ | + | ++ |
| PtIP-96Eh | SEQ ID NO: 62 | nd | ++ | + | ++ |
| PtIP-96Ei | SEQ ID NO: 64 | nd | ++ | + | ++ |
| PtIP-96Ej | SEQ ID NO: 66 | nd | ++ | ++ | ++ |
| PtIP-96Ek | SEQ ID NO: 68 | nd | ++ | ++ | ++ |
| PtIP-96El | SEQ ID NO: 70 | nd | ++ | + | ++ |

TABLE 5-continued

| polypeptide | Sequence identifier | SBL | CEW | ECB | VBC |
|---|---|---|---|---|---|
| PtIP-96Em | SEQ ID NO: 72 | nd | ++ | + | ++ |
| PtIP-96En | SEQ ID NO: 74 | nd | ++ | ++ | ++ |
| PtIP-96Ed | SEQ ID NO: 54 | – | ++ | + | ++ |
| PtIP-96Ha | SEQ ID NO: 10 | nd | + | ++ | nd |
| PtIP-96Hb | SEQ ID NO: 92 | – | + | nd | nd |
| PtIP-96Hc | SEQ ID NO: 94 | – | + | nd | nd |
| PtIP-96Hd | SEQ ID NO: 96 | – | + | nd | nd |
| PtIP-96He | SEQ ID NO: 98 | – | + | nd | nd |
| PtIP-96Hf | SEQ ID NO: 100 | – | + | nd | nd |
| PtIP-96Hg | SEQ ID NO: 102 | – | + | nd | nd |
| PtIP-96Hh | SEQ ID NO: 104 | – | + | nd | nd |
| PtIP-96Hi | SEQ ID NO: 106 | – | + | nd | nd |
| PtIP-96Hj | SEQ ID NO: 108 | – | – | nd | nd |

Example 6: *Agrobacterium*-Mediated Transformation of Maize and Regeneration of Transgenic Plants For *Agrobacterium*-mediated transformation of maize with the PtIP-96 polynucleotides of the disclosure the method of Zhao can be used (U.S. Pat. No. 5,981,840 and PCT Patent Publication Number WO 1998/32326; the contents of which are hereby incorporated by reference). Briefly, immature embryos are isolated from maize and the embryos contacted with a suspension of *Agrobacterium* under conditions whereby the bacteria are capable of transferring the nucleotide sequence to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformation (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 7: Transformation and Regeneration of Soybean (*Glycine max*)

Transgenic soybean lines generated by the method of particle gun bombardment (Klein et al., *Nature* (London) 327:70-73 (1987); U.S. Pat. No. 4,945,050) using a BIO-RAD Biolistic PDS1000/He instrument and either plasmid or fragment DNA. The following stock solutions and media are used for transformation and regeneration of soybean plants:

Stock Solutions:
Sulfate 100× Stock:
  37.0 g $MgSO_4.7H_2O$, 1.69 g $MnSO_4.H_2O$, 0.86 g $ZnSO_4.7H_2O$, 0.0025 g $CuSO_4.5H_2O$
Halides 100× Stock:
  30.0 g $CaCl_2.2H_2O$, 0.083 g KI, 0.0025 g $CoCl_2.6H_2O$
P, B, Mo 100× Stock:
  18.5 g $KH_2PO_4$, 0.62 g $H_3BO_3$, 0.025 g $Na_2MoO_4.2H_2O$
Fe EDTA 100× Stock:
  3.724 g $Na_2EDTA$, 2.784 g $FeSO_4.7H_2O$
2,4-D Stock:
  10 mg/mL Vitamin
B5 vitamins, 1000× Stock:
  100.0 g myo-inositol, 1.0 g nicotinic acid, 1.0 g pyridoxine HCl, 10 g thiamine.HCL.
Media (Per Liter):
SB199 Solid Medium:
  1 package MS salts (Gibco/BRL—Cat. No. 11117-066), 1 mL B5 vitamins 1000× stock, 30 g Sucrose, 4 ml 2, 4-D (40 mg/L final concentration), pH 7.0, 2 gm Gelrite
SB1 Solid Medium:
  1 package MS salts (Gibco/BRL—Cat. No. 11117-066), 1 mL B5 vitamins 1000× stock, 31.5 g Glucose, 2 mL 2, 4-D (20 mg/L final concentration), pH 5.7, 8 g TC agar
SB196:
  10 mL of each of the above stock solutions 1-4, 1 mL B5 Vitamin stock, 0.463 g (NH4)2 SO4, 2.83 g KNO3, 1 mL 2,4 D stock, 1 g asparagine, 10 g Sucrose, pH 5.7
SB71-4:
  Gamborg's B5 salts, 20 g sucrose, 5 g TC agar, pH 5.7.
SB103:
  1 pk. Murashige & Skoog salts mixture, 1 mL B5 Vitamin stock, 750 mg MgCl2 hexahydrate, 60 g maltose, 2 g gelrite, pH 5.7.
SB166:
  SB103 supplemented with 5 g per liter activated charcoal.
Soybean Embryogenic Suspension Culture Initiation:
  Pods with immature seeds from available soybean plants 45-55 days after planting are picked, removed from their shells and placed into a sterilized magenta box. The soybean seeds are sterilized by shaking them for 15 min in a 5% Clorox® solution with 1 drop of Ivory™ soap (i.e., 95 mL of autoclaved distilled water plus 5 mL Clorox® and 1 drop of soap, mixed well). Seeds are rinsed using 2 L sterile distilled water and those less than 3 mm are placed on individual microscope slides. The small end of the seed is cut and the cotyledons pressed out of the seed coat. Cotyledons are transferred to plates containing SB199 medium (25-30 cotyledons per plate) for 2 weeks, then transferred to SB1 for 2-4 weeks. Plates are wrapped with fiber tape. After this time, secondary embryos are cut and placed into SB196 liquid medium for 7 days.
Culture Conditions:
  Soybean embryogenic suspension cultures (cv. 93Y21) were maintained in 50 mL liquid medium SB196 on a rotary shaker, 100-150 rpm, 26° C. on 16:8 h day/night photoperiod at light intensity of 80-100 µE/m2/s. Cultures are subcultured every 7-14 days by inoculating up to ½ dime size quantity of tissue (clumps bulked together) into 50 mL of fresh liquid SB196.
Preparation of DNA for Bombardment:
  In particle gun bombardment procedures it is possible to use purified 1) entire plasmid DNA; or 2) DNA fragments containing only the recombinant DNA expression cassette(s) of interest. For every seventeen bombardment transformations, 85 µL of suspension is prepared containing 1 to 90 picograms of plasmid DNA per base pair of each DNA plasmid. DNA plasmids or fragments are co-precipitated onto gold particles as follows. The DNAs in suspension are added to 50 µL of a 10-60 mg/mL 0.6 µm gold particle suspension and then combined with 50 µL $CaCl_2$ (2.5 M) and 20 µL spermidine (0.1 M). The mixture is vortexed for 5 sec, spun in a microfuge for 5 sec, and the supernatant removed. The DNA-coated particles are then washed once with 150 µL of 100% ethanol, vortexed and spun in a microfuge, and then resuspended in 85 µL of anhydrous ethanol. Five µL of the DNA-coated gold particles are then loaded on each macrocarrier disc.

Tissue Preparation and Bombardment with DNA:

Approximately 100 mg of two-week-old suspension culture is placed in an empty 60 mm×15 mm petri plate and the residual liquid removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Following bombardment, the tissue from each plate is divided between two flasks, placed back into liquid media, and cultured as described above.

Selection of Transformed Embryos and Plant Regeneration:

After bombardment, tissue from each bombarded plate is divided and placed into two flasks of SB196 liquid culture maintenance medium per plate of bombarded tissue. Seven days post bombardment, the liquid medium in each flask is replaced with fresh SB196 culture maintenance medium supplemented with 100 ng/ml selective agent (selection medium). For selection of transformed soybean cells the selective agent used can be a sulfonylurea (SU) compound with the chemical name, 2-chloro-N-((4-methoxy-6 methy-1,3,5-triazine-2-yl)aminocarbonyl) benzenesulfonamide (common names: DPX-W4189 and Chlorsulfuron). Chlorsulfuron is the active ingredient in the DuPont sulfonylurea herbicide, GLEAN®. The selection medium containing SU is replaced every two weeks for 8 weeks. After the 8 week selection period, islands of green, transformed tissue are observed growing from untransformed, necrotic embryogenic clusters. These putative transgenic events are isolated and kept in SB196 liquid medium with SU at 100 ng/ml for another 5 weeks with media changes every 1-2 weeks to generate new, clonally propagated, transformed embryogenic suspension cultures. Embryos spend a total of around 13 weeks in contact with SU. Suspension cultures are subcultured and maintained as clusters of immature embryos and also regenerated into whole plants by maturation and germination of individual somatic embryos.

Somatic embryos became suitable for germination after four weeks on maturation medium (1 week on SB166 followed by 3 weeks on SB103). They are then removed from the maturation medium and dried in empty petri dishes for up to seven days. The dried embryos are then planted in SB71-4 medium where they are allowed to germinate under the same light and temperature conditions as described above. Germinated embryos are transferred to potting medium and grown to maturity for seed production.

Example 8—Particle Bombardment Transformation and Regeneration of Transgenic Plants Immature maize embryos from greenhouse donor plants are bombarded with a plasmid containing a nucleotide sequence encoding the insecticidal protein. The ears are husked and surface sterilized in 30% Clorox® bleach plus 0.5% Micro detergent for 20 minutes and rinsed two times with sterile water. The immature embryos are excised and placed embryo axis side down (scutellum side up), 25 embryos per plate, on 560Y medium for 4 hours and then aligned within the 2.5 cm target zone in preparation for bombardment. A plasmid vector DNA comprising the nucleotide sequence encoding the insecticidal protein operably linked to a promoter is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$ and 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed and 105 µl of 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment. The sample plates are bombarded at level #4 in a particle gun. All samples receive a single shot at 650 PSI, with a total of ten aliquots taken from each tube of prepared particles/DNA Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of a PtIP-96 polypeptide by assays known in the art, such as, for example, immunoassays and Western blotting.

Transgenic maize plants positive for expression of the insecticidal proteins are tested for pesticidal activity using standard bioassays known in the art. Such methods include, for example, root excision bioassays and whole plant bioassays. See, e.g., US Patent Application Publication Number US 2003/0120054 and International Publication Number WO 2003/018810.

Bombardment medium (560Y) comprises 4.0 g/l N6 basal salts (SIGMA C-1416), 1.0 ml/l Eriksson's Vitamin Mix (1000 times SIGMA-1511), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000 times SIGMA-1511), 0.5 mg/l thiamine HCl, 30.0 g/l sucrose and 2.0 mg/l 2,4-D (brought to volume with D-I $H_2O$ following adjustment to pH 5.8 with KOH); 3.0 g/l Gelrite (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite (added after bringing to volume with D-I H₂O) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL and 0.40 g/l glycine brought to volume with polished D-I H₂O), 0.1 g/l myo-inositol and 40.0 g/l sucrose (brought to volume with polished D-I H₂O after adjusting pH to 5.6) and 6 g/l bacto-agar (added after bringing to volume with polished D-I H₂O), sterilized and cooled to 60° C.

Example 9 Insect Control Efficacy of Stable Transformed Soybean and Corn Plants Against Broad Spectrum of Lepidopteran Insects Leaf discs are excised from the transformed plants and tested for insecticidal activity of PtIP-96 polypeptides against the Soy Bean Looper (SBL) (*Chrysodeixis includens*), Corn Earworm, (CEW) (*Helicoverpa zea*), European Corn Borer (ECB) (*Ostrinia nubialis*), Velvet Bean Caterpillar (VBC) (*Anticarsia gemmatalis*) and Fall Armyworm (*Spodoptera frugiperda*).

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. A recombinant PtIP-96 polypeptide comprising an amino acid sequence having at least 95% sequence identity to SEQ ID NO: 26, wherein the PtIP-96 polypeptide has insecticidal activity against Corn Earworm and is operably liked to a heterologous transit or signal sequence.

2. The recombinant PtIP-96 polypeptide of claim 1, wherein the PtIP-96 polypeptide has at least 98% sequence identity to the amino acid sequence of SEQ ID NO: 26.

3. A recombinant polynucleotide encoding a PtIP-96 polypeptide having at least 95% sequence identity to the amino acid sequence of SEQ ID NO: 26, and having insecticidal activity against Corn Earworm, wherein the polynucleotide is operably linked to a heterologous regulatory element.

4. The recombinant polynucleotide of claim 3, wherein the polynucleotide is a non-genomic polynucleotide.

5. The recombinant polynucleotide of claim 4, wherein the polynucleotide is a cDNA.

6. The recombinant polynucleotide of claim 4, wherein the polynucleotide is synthetic polynucleotide.

7. The recombinant polynucleotide of claim 6, wherein the polynucleotide has codons optimized for expression in an agriculturally important crop.

8. A transgenic plant or plant cell comprising the polynucleotide of claim 3.

9. A DNA construct comprising the polynucleotide of claim 3 operably linked to a heterologous regulatory element.

10. A transgenic plant or plant cell comprising the DNA construct of claim 9.

11. A composition comprising the PtIP-96 polypeptide of claim 1.

12. A fusion protein comprising the PtIP-96 polypeptide of claim 1.

13. A method for controlling an insect pest population, comprising contacting the insect pest population with the PtIP-96 polypeptide claim 1.

14. A method of inhibiting growth or killing an insect pest, comprising contacting the insect pest with a composition comprising the PtIP-96 polypeptide of claim 1.

15. A method of controlling Lepidoptera and/or Coleoptera insect infestation in a transgenic plant and providing insect resistance management, comprising expressing in the plant the PtIP-96 polypeptide of claim 1.

16. A method for controlling an insect pest population, comprising contacting the insect pest population with the transgenic plant or plant cell of claim 10.

17. A method of inhibiting growth or killing an insect pest, comprising transforming a plant with the DNA construct of claim 9.

18. The method of claim 17, further comprising contacting the insect pest with the transgenic plant or plant cell.

19. The method of claim 17, wherein the insect pest is Corn Earworm (*Helicoverpa zea*).

20. The method of claim 16, 17, 18 or 19, wherein the insect pest or insect pest population is resistant to at least one Bt toxin.

21. The recombinant PtIP-96 polypeptide of claim 1, wherein the PtIP-96 polypeptide is selected from SEQ ID NO: 26, SEQ ID NO: 28, SEQ ID NO: 30, SEQ ID NO: 32, SEQ ID NO: 34, SEQ ID NO: 36, and SEQ ID NO: 38.

22. The recombinant polynucleotide of claim 3, wherein the encoded a PtIP-96 polypeptide has at least 98% sequence identity to the amino acid sequence of SEQ ID NO: 26.

23. The recombinant polynucleotide of claim 3, wherein the encoded a PtIP-96 polypeptide is selected from SEQ ID NO: 26, SEQ ID NO: 28, SEQ ID NO: 30, SEQ ID NO: 32, SEQ ID NO: 34, SEQ ID NO: 36, and SEQ ID NO: 38.

* * * * *

SEQUENCE LISTING

```
<160> NUMBER OF SEQ ID NOS: 109

<210> SEQ ID NO 1
<211> LENGTH: 1065
<212> TYPE: DNA
<213> ORGANISM: Ophioglossum pendulum

<400> SEQUENCE: 1
atgtcgctgg ttcagacacc cgtgtatgtc atcggagggc aaggaggcaa tgcgtttact    60
tacgatcaga gcagaaacgg gaggatcctg cggaggattg gggtgtgggc gggcgagtgg   120
caactgcgcg gaatccgcgt gtggatgacg ggcaccgaca ccccggccac tttcggcacg   180
gccacgggct cttacagtga atataccttc gcggatggcg agcgcatcac ccgcttgtcc   240 ttgtgggca acggggctgg tacacgttca ggaggcatca gattctacac cacaacagga   300
ggttctttct tccataaaat gacatcttgg ggcttacaaa ccgagtatcc aatcgacgtg   360
gcatctggtc tttgtgtggg gatcatggga cgagctaatg ttgatgtgga ttcattgggt   420
gttttgttct taagaaccat agcatctgct cgtatgatca atgtaagcta ccctaccttg   480
ggcttagagc aagccggaat catccctgtt acacttgatt ccttcaatga ctccaacaat   540
gcaggtacta tttccaaaaa ttggactttc tcgggtagcc gaaccgtgac aatatcatca   600
tcatggtctc tcacttcagg gatagagaca catgcaagtg tgagcgtgca agcagggatc   660
cccatggttg cagaagtgag tggagagttt ggatggtctg ttagtgtatc tgggacctat   720
gcaaccactc aagaggaaag tcgaaccctā acttggaacc aatctggaac cctagagcct   780
gggcaatgga tctcactcca agctaccact cgaagaggaa ccatcacatt accctttcaa   840
gcaaccatgg aaatcacttt gctgtctgga acgatctttc aatatgccat ctcctctatg   900
tactccggtg tggattatac tagtgtggat ataactaaca ctggaactag agcatcagat   960
catgttgagg tcgaagctac tgagcaacaa gtccaagggg tcaaagatca aagtgtacaa  1020
cctaataaag aagctaaaga gtgcacactc ctctttgctg aataa              1065
```

```
<210> SEQ ID NO 2
<211> LENGTH: 1062
<212> TYPE: DNA
<213> ORGANISM: Colysis wrightii

<400> SEQUENCE: 2
atggcgttgt atcagacacc tgtgtatgtg atcggagggc aaggtggcaa ctcgtttact      60
tacgatcaga gcaggaacgg gaaggtgttg acgaagattg gggtgtgggc tggcgagtgg     120
cagctgcgcg gcatccgggt ttggatgtct ggctccgata gcccgaccac ctttggcaca     180
gcctcgggct cttactctga atacacattt gcagctggcg agcgcatcac ccggttgtct     240
ttgtggggca acggtgctgg tacgcggtct ggagccatta gattctacac gacaactgga     300
ggctcatttt tcccaaaaat gacatcttgg gacttaaaga ctgagtatcc aattgatgtg     360
gcatccggtc tttgtgtggg gatcatagga cgagctagtg ctgacattga ttcattgggg     420
tttatgtttc tcagaaccat agcatcttct cgcatgatca atgtaagcta cccaaccttg     480
ggcttagagc aagctggaat tatccccgtc acgcttgatt cgtacaacga ctctaataat     540
gcaggttcta tttccaagaa ttggactttc tctggtagcc gaacagttac aatatcatca     600
tcatggacac tcacttcagg gatagaggca catgctagtg tgaccgttca gcaggaatc      660 ccctcggttg cagaagtgag cggagagttt ggatggtcag tgagtgtaag tggaagctac     720
acaagcaccc aagaggagag tcgaaccctc acttggaacc aatccggaac cctagagcca     780
ggacaatgga tttccatcca agctaccact cggagaggaa ccatcacctt gccctatcag     840
gggaccatgg agatcaccct acaatctgga actgtgtttc aatacccta  tcctctatg      900 tattccggtg tggattatac tagtgttgac ataaccaaca ctggaactag agcattgaag     960
caagttgagg ttcaagctac tgatcaacaa tcccaggaag gagatcacaa tgtacaacct    1020
gataaagaag tcgaagaaag aaaagtcctc tttactgagt ag                       1062

<210> SEQ ID NO 3
<211> LENGTH: 1062
<212> TYPE: DNA
<213> ORGANISM: Colysis wrightii

<400> SEQUENCE: 3
atggcgttgt atcagacacc tgtgtatgtg atcggagggc aaggtggcaa ctcgtttact      60
tacgatcaga gcaggaacgg gaaggtgttg acgaagattg gggtgtgggc tggcgagtgg     120
cagctgcgcg gcatccgggt ttggatgtct ggctccgata gcccgaccac ctttggcaca     180
gcctcgggct cttactctga atacacattt gcagctggcg agcgcatcac ccggttgtct     240
ttgtggggca acggtgctgg tacgcggtct ggagccatta gattctacac gacaactgga     300
ggctcatttt tcccaaaaat gacatcttgg gacttaaaga ctgagtatcc aattgatgtg     360
gcatccggtc tttgtgtggg gatcatagga cgagctagtg ctgacattga ttcattgggg     420
tttatgtttc tcagaaccat agcatcttct cgcatgatca atgtaagcta cccaaccttg     480
ggcttagagc aagctggaat tatccccgtc acgcttgatt cgtacaacga ctctaataat     540
gcaggttcta tttccaagaa ttggactttc tctggtagcc gaacagttac aatatcatca     600
tcatggacac tcacttcagg gatagaggca catgctagtg tgaccgttca gcaggtctc      660 ccctcggttg cagaagtgag cggagagttt ggatggtcag tgagtgtaag tggaagctac     720
acaagcaccc aagaggagag tcgaaccctc acttggaacc aatccggaac cctagagcca     780
ggacaatgga tttccatcca agctaccact cggagaggaa ccatcacctt gccctatcag     840
```

```
gggaccatgg agatcaccct acaatctgga actgtgtttc aatacccctat atcctctatg    900 tattccggtg tggattatac tagtgttgac ataaccaaca ctggaactag agcattgaag    960
caagttgagg ttcaagctac tgatcaacaa tcccaggaag gagatcacaa tgtacaacct   1020
gataaagaag tcgaagaaag aaaagtcctc tttactgagt ag                       1062
```

<210> SEQ ID NO 4
<211> LENGTH: 1203
<212> TYPE: DNA
<213> ORGANISM: Selaginella kraussiana

<400> SEQUENCE: 4

```
atgtcgatcc atcaaacacc cgtgaccctc atcggaggaa gaggcggagc ggcgttcacg     60
tacaatgcag gcgcgagcgg ccgcatcttg aggaggatcg agtatgggc cggcgggtcg    120 cagctgcgag gcatccgagt gtggtggact ggcctggatt cccccattac ttacggcact    180
cctaacgttg gctcctacca ggagttcacc tttcaggatg cgagcgtat caccagtctc    240 tctctatggg gcaatggagc aggtacacgc agtggtggca ttaggttcta cacgaccacg    300
ggaaggcggt ttttccacca catgaccctc tggggcctga agcaagagta tccagttgac    360
gtagtggatg cgtgtgcgt aggcttgact ggaaggcagg gtgccgacat cgatgccttg    420
ggcttcatgt tcctacgcac catgaccctc gctcgcatga tcaatgtgaa gtaccctacc    480
ctcggcctgg agacggcagg cattgtgcca gtcacgctgg acttcatgag cgacagcaac    540
aatgctagct ccatttccaa gacttggtcc ttccaaggaa gccgagaggt gaccgtatcc    600
tcctcctgga gtaccaccac gggcattgag cttcatgcga gcatcaccgt atcggcaggg    660
atccctctcg tggccaatgt cgaagggcaa tacggatggg ccatcagcac aagctccacc    720
tacactacca accactcgga gactcgcacc cttcagtggc agaattcggg cgtcttggag    780
cccggtcagt ggatctctct gcaagccctc acgcggagag gaaccatcac cctaccctac    840
caagccacca tgcaaatcac cctccagaac ggcaccgttt tcacctaccc aatcactgct    900
cagtacgcag gagtggatta ccagcgtc gagattgtga gccagggaac aagagattta    960
ggctctgatc acttggccat caacaaggat gtccgctaca tcgctgctgc caatggtgca   1020
gctgttggta caactacaac taacgcaccg ccccactacg tccaccctat ccgaggagcg   1080
cctattgttg aacccgtcaa gtttagtgta ggtgcaactt acatcaatga caccgacaat   1140
atcactcagg aagttgacac tactgcagct actagtgtgg aagagcttac ccttgtgtac   1200
tag                                                                  1203
```

<210> SEQ ID NO 5
<211> LENGTH: 1188
<212> TYPE: DNA
<213> ORGANISM: Selaginella victoriae

<400> SEQUENCE: 5

```
atgcaatatg gcctggccaa tactgaagca agcccccctga tcgagaagtt ccaagctcta     60
atggaaggcg gcatagatga gagcatcctt gcgactaagc ttgttggtgc tgaaggagat    120
gcttctcatt tgccaccacc tggagagacg cctagtgagg atggtgccgg caaggatcca    180
cccaatgaat cgctggagac tgaagatgta gaggagcatg ctgatgatag caaagcccgt    240
tctgctagtg tcacggcccc tctgcgcttc ataggcggcc ccgtgggtc gcaacgttcc    300 gtccgaggat ggaccaacgg cagggtcatc accaggatgc gtgtctacag ggcccggggg    360
actatcaaag cgtaccagat ctggctcaca gactctgctc cccagactca tggtgttcct    420
```

| | | |
|---|---|---|
| gggaacagcg acttcgccga gtacacgttc cgcaccggag agcgtcttac aagattaaca | 480 | |
| ctgtggggaa acggaatggg cactcgtgct ggatggatcg agtttgagac gagcttgggt | 540 | |
| ggaaggtttt catatggcat gagccattgg tcgctgagaa ctccttaccc tgtcgacgtc | 600 | |
| ggttctggca tccttgtggg ctacattttt aatgctggag aggacgtcga tgcacacggc | 660 | |
| ttctggtttc tcaaccacat tgagcaggcc gagctcacca atgtgaggta tccgactctt | 720 | |
| ggatttgaca cggcaggtat tgtacccacg gccctggata ccttccggtt cagaaacaac | 780 | |
| tcatccacgc caagagactg ggacttcagc cggaacatga gcaggagcac tgagcggaca | 840 | |
| tggtcgatca ccgtggatct tactgtccat gcgagcatca cggtgagtgc agggtttcca | 900 | |
| ggcattgcaa acgtgagtgg tcagtatgga tgggagattg gggtgacggg ccatttcgaa | 960 | |
| acaacagaga cgtccgagca cgacttgagc tggagcgtgg gtgggagagt ccagcctggg | 1020 | |
| gatgttgtcg atctcactgc gctcactcgg actggaactc ttaacattcc ttacgaaggt | 1080 | |
| acgatggtgg tgaggatgag aaatggtgcc tccttcagct atgccgtgcg tggaacctac | 1140 | |
| agaggcctta gctataccgg cacaaaaata aacgacaact caacttaa | 1188 | |

<210> SEQ ID NO 6
<211> LENGTH: 354
<212> TYPE: PRT
<213> ORGANISM: Ophioglossum pendulum

<400> SEQUENCE: 6

Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
                20                  25                  30

Ile Gly Val Trp Ala Gly Glu Trp Gln Leu Arg Gly Ile Arg Val Trp
            35                  40                  45

Met Thr Gly Thr Asp Thr Pro Ala Thr Phe Gly Thr Ala Thr Gly Ser
        50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Phe Gly Trp Ser Val Ser Val Ser Gly Thr Tyr
225                 230                 235                 240

```
Ala Thr Thr Gln Glu Glu Ser Arg Thr Leu Thr Trp Asn Gln Ser Gly
            245                 250                 255

Thr Leu Glu Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Leu
            275                 280                 285

Ser Gly Thr Ile Phe Gln Tyr Ala Ile Ser Ser Met Tyr Ser Gly Val
            290                 295                 300

Asp Tyr Thr Ser Val Asp Ile Thr Asn Thr Gly Thr Arg Ala Ser Asp
305                 310                 315                 320

His Val Glu Val Glu Ala Thr Glu Gln Gln Val Gln Gly Val Lys Asp
                325                 330                 335

Gln Ser Val Gln Pro Asn Lys Glu Ala Lys Glu Cys Thr Leu Leu Phe
            340                 345                 350

Ala Glu

<210> SEQ ID NO 7
<211> LENGTH: 353
<212> TYPE: PRT
<213> ORGANISM: Colysis wrightii

<400> SEQUENCE: 7

Met Ala Leu Tyr Gln Thr Pro Val Tyr Val Ile Gly Gly Gln Gly Gly
1               5                   10                  15

Asn Ser Phe Thr Tyr Asp Gln Ser Arg Asn Gly Lys Val Leu Thr Lys
            20                  25                  30

Ile Gly Val Trp Ala Gly Glu Trp Gln Leu Arg Gly Ile Arg Val Trp
        35                  40                  45

Met Ser Gly Ser Asp Ser Pro Thr Thr Phe Gly Thr Ala Ser Gly Ser
    50                  55                  60

Tyr Ser Glu Tyr Thr Phe Ala Ala Gly Glu Arg Ile Thr Arg Leu Ser
65                  70                  75                  80

Leu Trp Gly Asn Gly Ala Gly Thr Arg Ser Gly Ala Ile Arg Phe Tyr
                85                  90                  95

Thr Thr Thr Gly Gly Ser Phe Phe Pro Lys Met Thr Ser Trp Asp Leu
            100                 105                 110

Lys Thr Glu Tyr Pro Ile Asp Val Ala Ser Gly Leu Cys Val Gly Ile
        115                 120                 125

Ile Gly Arg Ala Ser Ala Asp Ile Asp Ser Leu Gly Phe Met Phe Leu
    130                 135                 140

Arg Thr Ile Ala Ser Ser Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
                165                 170                 175

Asp Ser Asn Asn Ala Gly Ser Ile Ser Lys Asn Trp Thr Phe Ser Gly
            180                 185                 190

Ser Arg Thr Val Thr Ile Ser Ser Trp Thr Leu Thr Ser Gly Ile
        195                 200                 205

Glu Ala His Ala Ser Val Thr Val Gln Ala Gly Ile Pro Ser Val Ala
    210                 215                 220

Glu Val Ser Gly Glu Phe Gly Trp Ser Val Ser Val Ser Gly Ser Tyr
225                 230                 235                 240

Thr Ser Thr Gln Glu Glu Ser Arg Thr Leu Thr Trp Asn Gln Ser Gly
                245                 250                 255
```

```
Thr Leu Glu Pro Gly Gln Trp Ile Ser Ile Gln Ala Thr Thr Arg Arg
        260                 265                 270

Gly Thr Ile Thr Leu Pro Tyr Gln Gly Thr Met Glu Ile Thr Leu Gln
        275                 280                 285

Ser Gly Thr Val Phe Gln Tyr Pro Ile Ser Ser Met Tyr Ser Gly Val
        290                 295                 300

Asp Tyr Thr Ser Val Asp Ile Thr Asn Thr Gly Thr Arg Ala Leu Lys
305                 310                 315                 320

Gln Val Glu Val Gln Ala Thr Asp Gln Gln Ser Gln Glu Gly Asp His
                325                 330                 335

Asn Val Gln Pro Asp Lys Glu Val Glu Arg Lys Val Leu Phe Thr
                340                 345                 350

Glu

<210> SEQ ID NO 8
<211> LENGTH: 353
<212> TYPE: PRT
<213> ORGANISM: Colysis wrightii

<400> SEQUENCE: 8

Met Ala Leu Tyr Gln Thr Pro Val Tyr Val Ile Gly Gly Gln Gly Gly
1               5                   10                  15

Asn Ser Phe Thr Tyr Asp Gln Ser Arg Asn Gly Lys Val Leu Thr Lys
                20                  25                  30

Ile Gly Val Trp Ala Gly Glu Trp Gln Leu Arg Gly Ile Arg Val Trp
            35                  40                  45

Met Ser Gly Ser Asp Ser Pro Thr Thr Phe Gly Thr Ala Ser Gly Ser
    50                  55                  60

Tyr Ser Glu Tyr Thr Phe Ala Ala Gly Glu Arg Ile Thr Arg Leu Ser
65                  70                  75                  80

Leu Trp Gly Asn Gly Ala Gly Thr Arg Ser Gly Ala Ile Arg Phe Tyr
                85                  90                  95

Thr Thr Thr Gly Gly Ser Phe Phe Pro Lys Met Thr Ser Trp Asp Leu
            100                 105                 110

Lys Thr Glu Tyr Pro Ile Asp Val Ala Ser Gly Leu Cys Val Gly Ile
        115                 120                 125

Ile Gly Arg Ala Ser Ala Asp Ile Asp Ser Leu Gly Phe Met Phe Leu
    130                 135                 140

Arg Thr Ile Ala Ser Ser Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
                165                 170                 175

Asp Ser Asn Asn Ala Gly Ser Ile Ser Lys Asn Trp Thr Phe Ser Gly
            180                 185                 190

Ser Arg Thr Val Thr Ile Ser Ser Trp Thr Leu Thr Ser Gly Ile
        195                 200                 205

Glu Ala His Ala Ser Val Thr Val Gln Ala Gly Leu Pro Ser Val Ala
    210                 215                 220

Glu Val Ser Gly Glu Phe Gly Trp Ser Val Ser Val Ser Gly Ser Tyr
225                 230                 235                 240

Thr Ser Thr Gln Glu Glu Ser Arg Thr Leu Thr Trp Asn Gln Ser Gly
                245                 250                 255

Thr Leu Glu Pro Gly Gln Trp Ile Ser Ile Gln Ala Thr Thr Arg Arg
            260                 265                 270
```

```
Gly Thr Ile Thr Leu Pro Tyr Gln Gly Thr Met Glu Ile Thr Leu Gln
            275                 280                 285

Ser Gly Thr Val Phe Gln Tyr Pro Ile Ser Ser Met Tyr Ser Gly Val
290                 295                 300

Asp Tyr Thr Ser Val Asp Ile Thr Asn Thr Gly Thr Arg Ala Leu Lys
305                 310                 315                 320

Gln Val Glu Val Gln Ala Thr Asp Gln Ser Gln Glu Gly Asp His
            325                 330                 335

Asn Val Gln Pro Asp Lys Glu Val Glu Glu Arg Lys Val Leu Phe Thr
            340                 345                 350

Glu

<210> SEQ ID NO 9
<211> LENGTH: 400
<212> TYPE: PRT
<213> ORGANISM: Selaginella kraussiana

<400> SEQUENCE: 9

Met Ser Ile His Gln Thr Pro Val Thr Leu Ile Gly Gly Arg Gly Gly
1               5                   10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
        35                  40                  45

Trp Thr Gly Leu Asp Ser Pro Ile Thr Tyr Gly Thr Pro Asn Val Gly
    50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Val Asp Gly Val Cys Val Gly
        115                 120                 125

Leu Thr Gly Arg Gln Gly Ala Asp Ile Asp Ala Leu Gly Phe Met Phe
    130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
                165                 170                 175

Ser Asp Ser Asn Asn Ala Ser Ser Ile Ser Lys Thr Trp Ser Phe Gln
            180                 185                 190

Gly Ser Arg Glu Val Thr Val Ser Ser Ser Trp Ser Thr Thr Thr Gly
        195                 200                 205

Ile Glu Leu His Ala Ser Ile Thr Val Ser Ala Gly Ile Pro Leu Val
    210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Leu Gln Trp Gln Asn Ser
                245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
        275                 280                 285
```

Gln Asn Gly Thr Val Phe Thr Tyr Pro Ile Thr Ala Gln Tyr Ala Gly
            290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Asn Ala Pro Pro His
            340                 345                 350

Tyr Val His Pro Ile Arg Gly Ala Pro Ile Val Glu Pro Val Lys Phe
            355                 360                 365

Ser Val Gly Ala Thr Tyr Ile Asn Asp Thr Asp Asn Ile Thr Gln Glu
            370                 375                 380

Val Asp Thr Thr Ala Ala Thr Ser Val Glu Glu Leu Thr Leu Val Tyr
385                 390                 395                 400

<210> SEQ ID NO 10
<211> LENGTH: 395
<212> TYPE: PRT
<213> ORGANISM: Selaginella victoriae

<400> SEQUENCE: 10

Met Gln Tyr Gly Leu Ala Asn Thr Glu Ala Ser Pro Leu Ile Glu Lys
1               5                   10                  15

Phe Gln Ala Leu Met Glu Gly Gly Ile Asp Glu Ser Ile Leu Ala Thr
            20                  25                  30

Lys Leu Val Gly Ala Gly Gly Asp Ala Ser His Leu Pro Pro Pro Gly
        35                  40                  45

Glu Thr Pro Ser Glu Asp Gly Ala Gly Lys Asp Pro Pro Asn Glu Ser
    50                  55                  60

Leu Glu Thr Glu Asp Val Glu His Ala Asp Asp Ser Lys Ala Arg
65                  70                  75                  80

Ser Ala Ser Val Thr Ala Pro Leu Arg Phe Ile Gly Gly Pro Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp
        115                 120                 125

Leu Thr Asp Ser Ala Pro Gln Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Met Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn

```
                 260                 265                 270
Met Ser Arg Ser Thr Glu Arg Thr Trp Ser Ile Thr Val Asp Leu Thr
            275                 280                 285

Val His Ala Ser Ile Thr Val Ser Ala Gly Phe Pro Gly Ile Ala Asn
        290                 295                 300

Val Ser Gly Gln Tyr Gly Trp Glu Ile Gly Val Thr Gly His Phe Glu
305                 310                 315                 320

Thr Thr Glu Thr Ser Glu His Asp Leu Ser Trp Ser Val Gly Gly Arg
                325                 330                 335

Val Gln Pro Gly Asp Val Val Asp Leu Thr Ala Leu Thr Arg Thr Gly
            340                 345                 350

Thr Leu Asn Ile Pro Tyr Glu Gly Thr Met Val Val Arg Met Arg Asn
        355                 360                 365

Gly Ala Ser Phe Ser Tyr Ala Val Arg Gly Thr Tyr Arg Gly Leu Ser
        370                 375                 380

Tyr Thr Gly Thr Lys Ile Asn Asp Asn Ser Thr
385                 390                 395
```

<210> SEQ ID NO 11
<211> LENGTH: 1200
<212> TYPE: DNA
<213> ORGANISM: Selaginella kraussiana

<400> SEQUENCE: 11

```
atgtcgatcc atcaaacacc cgtgaccctc atcggaggaa gaggcggagc ggcgttcacg      60
tacaatgcag gcgcgagcgg ccgcatcttg aggaggatcg gagtatgggc cggcgggtcg     120
cagctgcgag gcatccgagt gtggtggact ggcctggatt ccccccattac ttacggcact    180
cctaacgttg gctcctacca ggagttcacc tttcaggatg cgagcgtat caccagtctc      240
tctctatggg gcaatggagc aggtacacgc agtggtggca ttaggttcta cacgaccacg     300
ggaaggcggt ttttccacca catgaccctc tggggcctga agcaagagta tccagttgac     360
gtagtggatg gcgtgtgcgt aggcttgact ggaaggcagg gtgccgacat cgatgccttg     420
ggcttcatgt tcctacgcac catgaccctcc gctcgcatga tcaatgtgaa gtaccctacc     480
ctcggcctgg agacggcagg cattgtgcca gtcacgctgg acttcatgag cgacagcaac    540
aatgctggct ccatttccaa gacttggtcc ttccaaggaa gccgagaggt gaccgtatcc     600
tcctcctgga gtaccaccac gggcattgag cttcatgcga gcatcaccgt atcggcaggg    660
atccctctcg tggccaatgt cgaagggcaa tacggatggg ccatcagcac aagctccacc    720
tacactacca accactcgga gactcgcacc cttcagtggc agaattcggg cgtcttggag     780
cccggtcagt ggatctctct gcaagccctc acgcggagag gaaccatcac cctaccctac    840
caggccacca tgcaaatcac cctccagaac ggcaccgttt tcacctaccc aatcactgct   900
cagtacgcag gagtggatta ccagccgtc gagattgtga ccagggaac aagagattta      960
ggctctgatc acttggccat caacaaggat gtccgctaca tcgctgctgc caatggtgga   1020
gctgttggta caactacaac taacgcaccg ccccactacg tccaccctat ccgaggagcg   1080
cctattgttg aacccgtcaa gtttagtgta ggtgcaactt acatcaatga caccgacaat   1140
atcactcagg aagttgacac tactgcagct actagtgtgg aagagcttac ccttgtgtac   1200
```

<210> SEQ ID NO 12
<211> LENGTH: 400
<212> TYPE: PRT
<213> ORGANISM: Selaginella kraussiana

<400> SEQUENCE: 12

```
Met Ser Ile His Gln Thr Pro Val Thr Leu Ile Gly Gly Arg Gly Gly
1               5                   10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
        35                  40                  45

Trp Thr Gly Leu Asp Ser Pro Ile Thr Tyr Gly Thr Pro Asn Val Gly
50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Asp Gly Val Cys Val Gly
        115                 120                 125

Leu Thr Gly Arg Gln Gly Ala Asp Ile Asp Ala Leu Gly Phe Met Phe
    130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
                165                 170                 175

Ser Asp Ser Asn Asn Ala Gly Ser Ile Ser Lys Thr Trp Ser Phe Gln
            180                 185                 190

Gly Ser Arg Glu Val Thr Val Ser Ser Ser Trp Ser Thr Thr Thr Gly
        195                 200                 205

Ile Glu Leu His Ala Ser Ile Thr Val Ser Ala Gly Ile Pro Leu Val
    210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Leu Gln Trp Gln Asn Ser
                245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Thr Val Phe Thr Tyr Pro Ile Thr Ala Gln Tyr Ala Gly
    290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Gly Ala Val Gly Thr Thr Thr Asn Ala Pro His
            340                 345                 350

Tyr Val His Pro Ile Arg Gly Ala Pro Ile Val Glu Pro Val Lys Phe
        355                 360                 365

Ser Val Gly Ala Thr Tyr Ile Asn Asp Thr Asp Asn Ile Thr Gln Glu
    370                 375                 380

Val Asp Thr Thr Ala Ala Thr Ser Val Glu Glu Leu Thr Leu Val Tyr
385                 390                 395                 400
```

```
<210> SEQ ID NO 13
<211> LENGTH: 1200
<212> TYPE: DNA
<213> ORGANISM: Selaginella kraussiana

<400> SEQUENCE: 13
atgtcgatcc atcaaacacc cgtgaccctc atcggaggaa gaggcggagc ggcgttcacg      60
tacaatgcag gcgcgagcgg ccgcatcttg aggaggatcg gagtatgggc cggcgggtcg     120
cagctgcgag gcatccgagt gtggtggact ggcctggatt ccccattac ttacggcact      180 cctaacgttg gctcctacca ggagttcacc tttcaggatg gcgagcgtat caccagtctc     240
tctctatggg gcaatggagc aggtacacgc agtggtggca ttaggttcta cacgaccacg     300
ggaaggcggt ttttccacca catgacctct tggggcctga agcaagagta tccagttgac     360
gtagtggatg gcgtgtgcgt aggcttgact ggaaggcagg gtgccgacat cgatgccttg     420
ggcttcatgt gcctacgcac catgacctcc gctcgcatga tcaatgtgaa gtaccctacc     480
ctcggcctgg agacggcagg cattgtgaca gtcacgctgg acttcatgag cgacagcaac     540
aatgctagct ccatttccaa gacgtggtcc ttccaaggaa gccgagaggt gaccgtatcc     600
tcctcctgga gtaccaccac gggcattgag cttcatgcga gcatcaccgt atcggcaggg     660
atccctctcg tggccaatgt cgaagggcaa tacggatggg ccatcagcac aagctccacc     720
tacactacca accactcgga gactcgcacc attcagtggc agaattcggg cgtcttggag     780
cccggtcagt ggatctctct gcaagccctc acgcggagag gaaccatcac cctaccctac     840
caagccacca tgcaaatcac cctccagaac ggcaccgttt tcacctaccc aatcactgct     900
cagtacgcag gagtggatta taccagcgtc gagattgtga gccagggaac aagagattta     960
ggctctgatc acttggccat caacaaggat gtccgctaca tcgctgctgc aaatggtgca    1020
gctgttggta caactacaac taacgcaccg ccccactacg tccaccctat ccgaggagcg    1080
cctattgttg aacccgtcaa gtttagtgta ggtgcaactt acatcaatga caccgacaat    1140
atcactcagg aagttgacac tactgcagct actagtgtgg aagagcttac ccttgtgtac    1200

<210> SEQ ID NO 14
<211> LENGTH: 400
<212> TYPE: PRT
<213> ORGANISM: Selaginella kraussiana

<400> SEQUENCE: 14

Met Ser Ile His Gln Thr Pro Val Thr Leu Ile Gly Gly Arg Gly Gly
1               5                   10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
        35                  40                  45

Trp Thr Gly Leu Asp Ser Pro Ile Thr Tyr Gly Thr Pro Asn Val Gly
    50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Val Asp Gly Val Cys Val Gly
        115                 120                 125
```

Leu Thr Gly Arg Gln Gly Ala Asp Ile Asp Ala Leu Gly Phe Met Cys
130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Thr Val Thr Leu Asp Phe Met
            165                 170                 175

Ser Asp Ser Asn Asn Ala Ser Ser Ile Ser Lys Thr Trp Ser Phe Gln
            180                 185                 190

Gly Ser Arg Glu Val Thr Val Ser Ser Trp Ser Thr Thr Thr Gly
            195                 200                 205

Ile Glu Leu His Ala Ser Ile Thr Val Ser Ala Gly Ile Pro Leu Val
210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Ile Gln Trp Gln Asn Ser
                245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
            275                 280                 285

Gln Asn Gly Thr Val Phe Thr Tyr Pro Ile Thr Ala Gln Tyr Ala Gly
290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Asn Ala Pro Pro His
            340                 345                 350

Tyr Val His Pro Ile Arg Gly Ala Pro Ile Val Glu Pro Val Lys Phe
            355                 360                 365

Ser Val Gly Ala Thr Tyr Ile Asn Asp Thr Asp Asn Ile Thr Gln Glu
            370                 375                 380

Val Asp Thr Thr Ala Ala Thr Ser Val Glu Glu Leu Thr Leu Val Tyr
385                 390                 395                 400

<210> SEQ ID NO 15
<211> LENGTH: 1200
<212> TYPE: DNA
<213> ORGANISM: Selaginella kraussiana

<400> SEQUENCE: 15

```
atgtcgatcc atcaaacacc cgtgaccctc atcggaggaa gaggcggagc ggcgttcacg      60
tacaatgcag gcgcgagcgg ccgcatcttg aggaggatcg gagtatgggc cggcgggtcg     120
cagctgcgag gcatccgagt gtggtggact ggcctggatt cccccattac ttacggcact     180
cctaacgttg gctcctacca ggagttcacc tttcaggatg cgagcgtat  caccagtctc     240
tctctatggg gcaatggagc aggtacacgc agtggtggca ttaggttcta cacgaccacg     300
ggaaggcggt ttttccacca catgaccctct tggggcctga agcaagagta tccagttgac     360
gtagtggatg gcgtgtgcgt aggcttgact ggaaggcagg gtgccgacat cgatgccttg     420
ggcttcatgt gcctacgcac catgacctcc gctcgcatga tcaatgtgaa gtaccctacc     480
ctcggcctgg agacggcagg cattgtgcca gtcacgctgg acttcatgag cgacagcaac     540
aatgctagct ccatttccaa gacgtggtcc ttccaaggaa gccgagaggt gaccgtatcc     600
```

```
tcctcctgga gtaccaccac gggcattgag cttcatgcga gcatcaccgt atcggcaggg      660
atccctctcg tggccaatgt cgaagggcaa tacggatggg ccatcagcac aagctccacc      720
tacactacca accactcgga gactcgcacc cttcagtggc agaattcggg cgtcttggag      780
cccggtcagt ggatctctct gcaagccctc acgcggagag gaaccatcac cctaccctac      840
caagccacca tgcaaatcac cctccagaac ggcaccgttt tcacctaccc aatcactgct      900
cagtacgcag gagtggatta taccagcgtc gagattgtga gccagggaac aagagattta      960
ggctctgatc acttggccat caacaaggat gtccgctaca tcgctgctgc caatggtgca     1020
gctgttggta caactacaac taacgcaccg ccccactacg tccaccctat ccgaggagcg     1080
cctattgttg aaaccgtcaa gtttagtgta ggtgcaactt acatcaatga caccgacaat     1140
atcactcagg aagttgacac tactgcagct actagtgtgg aagagcttac ccttgtgtac     1200
```

<210> SEQ ID NO 16
<211> LENGTH: 400
<212> TYPE: PRT
<213> ORGANISM: Selaginella kraussiana

<400> SEQUENCE: 16

```
Met Ser Ile His Gln Thr Pro Val Thr Leu Ile Gly Gly Arg Gly Gly
1               5                   10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
        35                  40                  45

Trp Thr Gly Leu Asp Ser Pro Ile Thr Tyr Gly Thr Pro Asn Val Gly
    50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Val Asp Gly Val Cys Val Gly
        115                 120                 125

Leu Thr Gly Arg Gln Gly Ala Asp Ile Asp Ala Leu Gly Phe Met Cys
    130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
                165                 170                 175

Ser Asp Ser Asn Asn Ala Ser Ser Ile Ser Lys Thr Trp Ser Phe Gln
            180                 185                 190

Gly Ser Arg Glu Val Thr Val Ser Ser Trp Ser Thr Thr Thr Gly
        195                 200                 205

Ile Glu Leu His Ala Ser Ile Thr Val Ser Ala Gly Ile Pro Leu Val
    210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Leu Gln Trp Gln Asn Ser
                245                 250                 255

Gly Val Leu Glu Pro Gly Gln Trp Ile Ser Leu Gln Ala Leu Thr Arg
            260                 265                 270
```

```
Arg Gly Thr Ile Thr Leu Pro Tyr Gln Ala Thr Met Gln Ile Thr Leu
            275                 280                 285

Gln Asn Gly Thr Val Phe Thr Tyr Pro Ile Thr Ala Gln Tyr Ala Gly
        290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Asn Ala Pro Pro His
            340                 345                 350

Tyr Val His Pro Ile Arg Gly Ala Pro Ile Val Glu Thr Val Lys Phe
        355                 360                 365

Ser Val Gly Ala Thr Tyr Ile Asn Asp Thr Asp Asn Ile Thr Gln Glu
370                 375                 380

Val Asp Thr Thr Ala Ala Thr Ser Val Glu Glu Leu Thr Leu Val Tyr
385                 390                 395                 400

<210> SEQ ID NO 17
<211> LENGTH: 1200
<212> TYPE: DNA
<213> ORGANISM: Selaginella kraussiana

<400> SEQUENCE: 17
atgtcgatcc atcaaacacc cgtgaccctc atcggaggaa gaggcggagc ggcgttcacg      60
tacaatgcag gcgcgagcgg ccgcatcttg aggaggatcg gagtatgggc cggcgggtcg     120
cagctgcgag gcatccgagt gtggtggact ggcctggatt cccccattac ttacggcact     180
cctaacgttg gctcctacca ggagttcacc tttcaggatg gcgagcgtat caccagtctc     240
tctctatggg gcaatggagc aggtacacgc agttgtggca ttaggttcta cacgaccacg     300
ggaaggcggt ttttccacca catgacctct tggggcctga agcaagagta ccagttgac     360 gtagtggatg gcgtgtgcgt aggcttgact ggaaggcagg gtgccgacat cgatgccttg     420
ggcttcatgt gcctacgcac catgacctcc gctcgcatga tcaatgtgaa gtaccctacc     480
ctcggcctgg agacggcagg cattgtgcca gtcacgctgg acttcatgag cgacagcaac     540
aatgctagct ccatttccaa gacgtggtcc ttccaaggaa gccgagaggt gaccgtatcc     600
tcctcctgga gtaccaccac gggcattgag cttcatgcga gcatcaccgt atcggcaggg     660
atccctctcg tggccaatgt cgaagggcaa tacggatggg ccatcagcac aagctccacc     720
tacactacca accactcgga gactcgcacc cttcagtggc agaattcggg cgtcttggag     780
cccggtcagt ggatctctct gcaagccctc acgcggagag gaaccatcac cctaccctac     840
caagccacca tgcaaatcac cctccagaac ggcaccgttt tcacctaccc aatcactgct     900
cagtactcag gagtggatta taccagcgtc gagattgtga gccagggaac aagagattta     960
ggctctgatc acttggccat caacaaggat gtccgctaca tcgctgctgc caatggtgca    1020
gctgttggta caactacaac taacgcaccg cccactacg tccaccctat ccgaggagcg    1080
cctattgttg aacccgtcaa gtttagtgta ggtgcaactt acatcaatga caccgacaat    1140
atcactcagg aagttgacac tactgcagct actagtgtgg aagagcttac ccttgtgtac    1200

<210> SEQ ID NO 18
<211> LENGTH: 400
<212> TYPE: PRT
<213> ORGANISM: Selaginella kraussiana

<400> SEQUENCE: 18
```

Met Ser Ile His Gln Thr Pro Val Thr Leu Ile Gly Arg Gly Gly
1               5                   10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
            35                  40                  45

Trp Thr Gly Leu Asp Ser Pro Ile Thr Tyr Gly Thr Pro Asn Val Gly
        50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Cys Gly Ile Arg Phe
                85                  90                  95

Tyr Thr Thr Thr Gly Arg Arg Phe Phe His His Met Thr Ser Trp Gly
                100                 105                 110

Leu Lys Gln Glu Tyr Pro Val Asp Val Asp Gly Val Cys Val Gly
            115                 120                 125

Leu Thr Gly Arg Gln Gly Ala Asp Ile Asp Ala Leu Gly Phe Met Cys
        130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
                165                 170                 175

Ser Asp Ser Asn Asn Ala Ser Ser Ile Ser Lys Thr Trp Ser Phe Gln
            180                 185                 190

Gly Ser Arg Glu Val Thr Val Ser Ser Trp Ser Thr Thr Thr Gly
            195                 200                 205

Ile Glu Leu His Ala Ser Ile Thr Val Ser Ala Gly Ile Pro Leu Val
210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Leu Gln Trp Gln Asn Ser
            245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Thr Val Phe Thr Tyr Pro Ile Thr Ala Gln Tyr Ser Gly
        290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Asn Ala Pro Pro His
            340                 345                 350

Tyr Val His Pro Ile Arg Gly Ala Pro Ile Val Glu Pro Val Lys Phe
                355                 360                 365

Ser Val Gly Ala Thr Tyr Ile Asn Asp Thr Asp Asn Ile Thr Gln Glu
        370                 375                 380

Val Asp Thr Thr Ala Ala Thr Ser Val Glu Glu Leu Thr Leu Val Tyr
385                 390                 395                 400

<210> SEQ ID NO 19
<211> LENGTH: 1200

```
<212> TYPE: DNA
<213> ORGANISM: Selaginella kraussiana

<400> SEQUENCE: 19
atgtcgatcc atcaaacacc cgtgaccctc atcggaggaa gaggcggagc ggcgttcacg      60
tacaatgcag gcgcgagcgg ccgcatcttg aggaggatcg gagtatgggc cggcgggtcg     120
cagctgcgag gcatccgagt gtggtggact ggcctggatt cccccattac ttacggcact     180
cctaacgttg gctcctacca ggagttcacc tttcaggatg gcgagcgtat caccagtctc     240
tctctatggg gcaatggagc aggtacacgc agtggtggca ttaggttcta cacgaccacg     300
ggaaggcggt ttttccacca catgacctct tggggcctga agcaagagta tccagttgac     360
gtagtggatg gcgtgtgcgt aggcttgact ggaaggcagg gtgccgacat cgatgccttg     420
ggcttcatgt gcctacgcac catgacctcc gctcgcatga tcaatgtgaa gtaccctacc     480
ctcggcctgg agacggcagg cattgtgcca gtcacgctgg acttcatgag cgacagcaac     540
aatgctagct ccatttccaa gacgtggtcc ttccaaggaa gccgagaggt gaccgtatcc     600
tcctcctgga gtaccaccac gggcattgag cttcatgcga gcatcaccgt atcggcaggg     660
atccctctcg tggccaatgt cgaagggcaa tacggatggg ccatcagcac aagctccacc     720
tacactacca accactcgga gactcgcacc cttcagtggc agaattcggg cgtcttggag     780
cccggtcagt ggatctctct gcaagccctc acgcggagag gaaccatcac cctaccctac     840
caagccacca tgcaaatcac cctccagaac ggcaccgttt tcacctaccc aatcactgct     900
cagtacgcag gagtggatta taccagcgtc gagattgtga gccagggaac aagagattta     960
ggctctgatc acttggccat caacaaggat gtccgctaca tcgctgctgc caatggtgca    1020
gctgttggta caactacaac taacgcaccg ccccactacg tccaccctat ccgaggagcg    1080
cctattgttg aacccgtcaa gtttagtgta ggtgcaactt acatcaatga caccgacaat    1140
atcactcagg aagttgacac tactgcagct actagtgtgg aagagcttac ccttgtgtac    1200

<210> SEQ ID NO 20
<211> LENGTH: 400
<212> TYPE: PRT
<213> ORGANISM: Selaginella kraussiana

<400> SEQUENCE: 20

Met Ser Ile His Gln Thr Pro Val Thr Leu Ile Gly Gly Arg Gly Gly
1               5                  10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
        35                  40                  45

Trp Thr Gly Leu Asp Ser Pro Ile Thr Tyr Gly Thr Pro Asn Val Gly
    50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Asp Gly Val Cys Val Gly
        115                 120                 125

Leu Thr Gly Arg Gln Gly Ala Asp Ile Asp Ala Leu Gly Phe Met Cys
    130                 135                 140
```

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
            165                 170                 175

Ser Asp Ser Asn Asn Ala Ser Ser Ile Ser Lys Thr Trp Ser Phe Gln
        180                 185                 190

Gly Ser Arg Glu Val Thr Val Ser Ser Ser Trp Ser Thr Thr Thr Gly
    195                 200                 205

Ile Glu Leu His Ala Ser Ile Thr Val Ser Ala Gly Ile Pro Leu Val
210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Leu Gln Trp Gln Asn Ser
                245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Thr Val Phe Thr Tyr Pro Ile Thr Ala Gln Tyr Ala Gly
    290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Asn Ala Pro Pro His
            340                 345                 350

Tyr Val His Pro Ile Arg Gly Ala Pro Ile Val Glu Pro Val Lys Phe
        355                 360                 365

Ser Val Gly Ala Thr Tyr Ile Asn Asp Thr Asp Asn Ile Thr Gln Glu
    370                 375                 380

Val Asp Thr Thr Ala Ala Thr Ser Val Glu Glu Leu Thr Leu Val Tyr
385                 390                 395                 400

<210> SEQ ID NO 21
<211> LENGTH: 1200
<212> TYPE: DNA
<213> ORGANISM: Adiantum raddianum

<400> SEQUENCE: 21
atgtcgatcc atcaaacacc cgtgaccctc atcggaggaa gaggcggagc ggcgttcacg    60
tacaatgcag gcgcgagcgg ccgcatcttg aggaggatcg agtatgggc cggcgggtcg    120 cagctgcgag gcatccgagt gtggtggact ggcctggatt cccccattac ttacggcact    180
cctaacgttg gctcctacca ggagttcacc tttcaggatg gcgagcgtat caccagtctc    240
tctctatggg gcaatggagc aggtacacgc agtggtggca ttaggttcta acgaccacg    300 ggaaggcggt ttttccacca catgaccctct tgggcctga agcaagagta tccagttgac    360
gtagtggatg gcgtgtgcgt aggcttgact ggaaggcagg gtgccgacat cgatgccttg    420
ggcttcatgt tcctacgcac catgacctcc gctcgcatga tcaatgtgaa gtaccctacc    480
ctcggcctgg agacggcagg cattgtgcca gtcacgctgg acttcatgag cgacagcaac    540
aatgctagct ccatttccaa gacttggtcc ttccaaggaa gccgagaggt gaccgtatcc    600
tcctcctgga gtaccaccac gggcattgag cttcatgcga gcatcaccgt atcggcaggg    660

-continued

```
atccctctcg tggccaatgt cgaagggcaa tacggatggg gcatcagcac aagctccacc      720
tacactacca accactcgga gactcgcacc cttcagtggc agaattcggg cgtcttggag      780
cccggtcagt ggatctctct gcaagccctc acgcggagag gaaccatcac cctaccctac      840
caagccacca tgcaaatcac cctccagaac ggcaccgttt tcacctaccc aatcactgct      900
cagtacgcag gagtggatta taccagcgtc gagattgtga gccagggaac aagagattta      960
ggctctgatc acttggccat caacaaggat gtccgctaca tcgctgctgc caatggtgca     1020
gctgttggta caactacaac taacgcaccc cccactacg tccaccctat ccgaggagcg      1080
cctattgttg aacccgtcaa gtttagtgta ggtgcaactt acatcaatga caccgacaat     1140
atcactcagg aagttgacac tactgcagct actagtgtgg aagagcttac ccttgtgtac     1200
```

<210> SEQ ID NO 22
<211> LENGTH: 400
<212> TYPE: PRT
<213> ORGANISM: Adiantum raddianum

<400> SEQUENCE: 22

```
Met Ser Ile His Gln Thr Pro Val Thr Leu Ile Gly Gly Arg Gly Gly
1               5                   10                  15

Ala Ala Phe Thr Tyr Asn Ala Gly Ala Ser Gly Arg Ile Leu Arg Arg
            20                  25                  30

Ile Gly Val Trp Ala Gly Gly Ser Gln Leu Arg Gly Ile Arg Val Trp
        35                  40                  45

Trp Thr Gly Leu Asp Ser Pro Ile Thr Tyr Gly Thr Pro Asn Val Gly
    50                  55                  60

Ser Tyr Gln Glu Phe Thr Phe Gln Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Val Asp Gly Val Cys Val Gly
        115                 120                 125

Leu Thr Gly Arg Gln Gly Ala Asp Ile Asp Ala Leu Gly Phe Met Phe
    130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
                165                 170                 175

Ser Asp Ser Asn Asn Ala Ser Ser Ile Ser Lys Thr Trp Ser Phe Gln
            180                 185                 190

Gly Ser Arg Glu Val Thr Val Ser Ser Ser Trp Ser Thr Thr Thr Gly
        195                 200                 205

Ile Glu Leu His Ala Ser Ile Thr Val Ser Ala Gly Ile Pro Leu Val
    210                 215                 220

Ala Asn Val Glu Gly Gln Tyr Gly Trp Gly Ile Ser Thr Ser Ser Thr
225                 230                 235                 240

Tyr Thr Thr Asn His Ser Glu Thr Arg Thr Leu Gln Trp Gln Asn Ser
                245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
        275                 280                 285
```

```
Gln Asn Gly Thr Val Phe Thr Tyr Pro Ile Thr Ala Gln Tyr Ala Gly
    290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Thr Asn Ala Pro Pro His
            340                 345                 350

Tyr Val His Pro Ile Arg Gly Ala Pro Ile Val Glu Pro Val Lys Phe
        355                 360                 365

Ser Val Gly Ala Thr Tyr Ile Asn Asp Thr Asp Asn Ile Thr Gln Glu
    370                 375                 380

Val Asp Thr Thr Ala Ala Thr Ser Val Glu Glu Leu Thr Leu Val Tyr
385                 390                 395                 400

<210> SEQ ID NO 23
<211> LENGTH: 1200
<212> TYPE: DNA
<213> ORGANISM: Cyathea australis

<400> SEQUENCE: 23
atgtcgatct atcaaacacc cgtgaccctc atcggaggaa gaggcggagc ggcgttcacg    60
tacaatgcag gcgcgagcgg ccgcatcttg aggaggatcg gagtatgggc cggcgggtcg   120
caactgcgag gcatccgagt gtggtggact ggcctggatt cccccattac ttacggcact   180
cctaacgttg gctcctacca ggagttcacc tttcaggatg cgagcgtat caccagtctc   240 tctctatggg gcaatggagc aggtacacgc agtggtggca ttaggttcta cacgaccacg   300
ggaaggcggt ttttccacca catgacctct tggggcctga agcaagagta tccagttgac   360
gtagtggatg gcgtgtgcgt aggcttgact ggaaggcagg gtgccgacat cgatgccttg   420
ggcttcatgt tcctacgcac catgacctcc gctcgcatga tcaatgtgaa gtaccctacc   480
ctcggcctgg agacggcagg cattgtgcca gtcacgctgg acttcatgag cgacagcaac   540
aatgctggct ccatttccaa gacttggtcc ttccaaggaa gccgagaggt gaccgtatcc   600
tcctcctgga gtaccaccac gggcattgag cttcatgcga gcatcaccgt atcggcaggg   660
atccctctcg tggccaatgt cgaagggcaa tacggatggg ccatcagcac aagctccacc   720
tacactacca accactcgga gactcgcacc cttcagtggc agaattcggg cgtcttggag   780
cccggtcagt ggatctctct gcaagccctc acgcggagag gaaccatcac cctaccctac   840
caggccacca tgcaaatcac cctccagaac ggcaccgttt tcacctaccc aatcactgct   900
cagtacgcag gagtggatta taccagcgtc gaaattgtga gccagggaac aagagattta   960
ggctctgatc acttggccat caacaaggat gtccactaca tcgctgctgc caatggtgca  1020
gctgttggta caactacaac taacgcaccg ccccactacg tccaccctat ccgaggagcg  1080
cctattgttg aacccgtcaa gtttagtgta ggtgcaactt acatcaatga caccgacaat  1140
atcactcagg aagttgacac tactgcagct actagtgtgg aagagcttac ccttgtctac  1200

<210> SEQ ID NO 24
<211> LENGTH: 400
<212> TYPE: PRT
<213> ORGANISM: Cyathea australis

<400> SEQUENCE: 24

Met Ser Ile Tyr Gln Thr Pro Val Thr Leu Ile Gly Gly Arg Gly Gly
```

```
  1               5               10              15
Ala Ala Phe Thr Tyr Asn Ala Gly Ala Ser Gly Arg Ile Leu Arg Arg
                20              25              30
Ile Gly Val Trp Ala Gly Gly Ser Gln Leu Arg Gly Ile Arg Val Trp
                35              40              45
Trp Thr Gly Leu Asp Ser Pro Ile Thr Tyr Gly Thr Pro Asn Val Gly
                50              55              60
Ser Tyr Gln Glu Phe Thr Phe Gln Asp Gly Glu Arg Ile Thr Ser Leu
 65              70              75              80
Ser Leu Trp Gly Asn Gly Ala Gly Thr Arg Ser Gly Gly Ile Arg Phe
                85              90              95
Tyr Thr Thr Thr Gly Arg Arg Phe Phe His His Met Thr Ser Trp Gly
                100             105             110
Leu Lys Gln Glu Tyr Pro Val Asp Val Val Asp Gly Val Cys Val Gly
                115             120             125
Leu Thr Gly Arg Gln Gly Ala Asp Ile Asp Ala Leu Gly Phe Met Phe
                130             135             140
Leu Arg Thr Met Thr Ser Ala Arg Met Ile Asn Val Lys Tyr Pro Thr
145             150             155             160
Leu Gly Leu Glu Thr Ala Gly Ile Val Pro Val Thr Leu Asp Phe Met
                165             170             175
Ser Asp Ser Asn Asn Ala Gly Ser Ile Ser Lys Thr Trp Ser Phe Gln
                180             185             190
Gly Ser Arg Glu Val Thr Val Ser Ser Ser Trp Ser Thr Thr Thr Gly
                195             200             205
Ile Glu Leu His Ala Ser Ile Thr Val Ser Ala Gly Ile Pro Leu Val
                210             215             220
Ala Asn Val Glu Gly Gln Tyr Gly Trp Ala Ile Ser Thr Ser Ser Thr
225             230             235             240
Tyr Thr Thr Asn His Ser Glu Thr Arg Thr Leu Gln Trp Gln Asn Ser
                245             250             255
Gly Val Leu Glu Pro Gly Gln Trp Ile Ser Leu Gln Ala Leu Thr Arg
                260             265             270
Arg Gly Thr Ile Thr Leu Pro Tyr Gln Ala Thr Met Gln Ile Thr Leu
                275             280             285
Gln Asn Gly Thr Val Phe Thr Tyr Pro Ile Thr Ala Gln Tyr Ala Gly
                290             295             300
Val Asp Tyr Thr Ser Val Glu Ile Val Ser Gln Gly Thr Arg Asp Leu
305             310             315             320
Gly Ser Asp His Leu Ala Ile Asn Lys Asp Val His Tyr Ile Ala Ala
                325             330             335
Ala Asn Gly Ala Ala Val Gly Thr Thr Thr Asn Ala Pro Pro His
                340             345             350
Tyr Val His Pro Ile Arg Gly Ala Pro Ile Val Glu Pro Val Lys Phe
                355             360             365
Ser Val Gly Ala Thr Tyr Ile Asn Asp Thr Asp Asn Ile Thr Gln Glu
                370             375             380
Val Asp Thr Thr Ala Ala Thr Ser Val Glu Glu Leu Thr Leu Val Tyr
385             390             395             400

<210> SEQ ID NO 25
<211> LENGTH: 1161
<212> TYPE: DNA
<213> ORGANISM: Unknown
```

<220> FEATURE:
<223> OTHER INFORMATION: mixture of Adiantum raddianum, Adiantum
      capillus-veneris, Adiantum hispidulum, and Cyrtomium fortunei

<400> SEQUENCE: 25

```
atgtcgacgg ccatctttca aacacccgtg catgtgatag gaggtcaagg cggatctgag    60
ttcttttaca atgcaggcgc gagcgggcgc atcttgagga ggatcggagt gtgggcgggc   120
aggtcgttcc tgggaggcat ccgttcctgg tggacaggcc tggattcccc catcacctac   180
ggcactccta actccggctc ctacagagag ttacttttg aagatggcga gcgcatcacc    240
agtctctccc tatggggcaa tggaataggt acacgcagcg gtggcattag gttcaacacc   300
agcacgggaa ggcagttctt ccaccatatg acctcttgga gcttgcagca agagtacgca   360
atcgatgtag cgtccggctt atgcgtaggc ctgtggggaa ggcacggcgt ggaaatcgat   420
tccttgggct tcatgttcct cgcccccata gcctccgctc gcatgatcaa tgtgagatat   480
cctactctag gcctggagac ggcaggcatt gtgccagtca cgctggactc catgagcgac   540
agcaacaatt ctgcctccat gcccaagaat tggtcattcc aaggcagccg agatgtgacc   600
atatcctcct cttggagtat tactgcgggc attgagcttc atgcctccat caacgtctcg   660
gcggggtcc ctatgctggc caatgtggac gtgcaatatg gatggaccat cagcagcacc    720
tcgtcctata gcaccagcca ctcggagact cgcagcctta gttggcagaa ttccggcgtc   780
ttggagcctg gtcagtgggt ctctctgcaa gccctcacgc ggagaggaac catcacccta   840
ccctaccagg ccaccatgca aatcacccctc cagaacggcg tcgttttcac ctacccaatc  900
gctgctcagt acgcaggagt ggattttaca agcgtcgaga ttgtgagcct agggacaaaa   960
gatgtaggct ctggtcactc ggccaccaac aaggatgtcg ccgcatcgt tgccaatggt   1020
acagctacaa ctagcgcacc gccccaatat gtccgccctg tcaagttaag tgtaggagca  1080
acttacatca atgacaccaa taatatcact caggaagttg acagtacagc tactagtgta  1140
gaagagctta ccctcatgca t                                            1161
```

<210> SEQ ID NO 26
<211> LENGTH: 387
<212> TYPE: PRT
<213> ORGANISM: Unknown
<220> FEATURE:
<223> OTHER INFORMATION: mixture of Adiantum raddianum, Adiantum
      capillus-veneris, Adiantum hispidulum, and Cyrtomium fortunei

<400> SEQUENCE: 26

```
Met Ser Thr Ala Ile Phe Gln Thr Pro Val His Val Ile Gly Gly Gln
1               5                   10                  15

Gly Gly Ser Glu Phe Phe Tyr Asn Ala Gly Ala Ser Gly Arg Ile Leu
            20                  25                  30

Arg Arg Ile Gly Val Trp Ala Gly Arg Ser Phe Leu Gly Gly Ile Arg
        35                  40                  45

Ser Trp Trp Thr Gly Leu Asp Ser Pro Ile Thr Tyr Gly Thr Pro Asn
    50                  55                  60

Ser Gly Ser Tyr Arg Glu Phe Thr Phe Glu Asp Gly Glu Arg Ile Thr
65                  70                  75                  80

Ser Leu Ser Leu Trp Gly Asn Gly Ile Gly Thr Arg Ser Gly Gly Ile
                85                  90                  95

Arg Phe Asn Thr Ser Thr Gly Arg Gln Phe Phe His His Met Thr Ser
            100                 105                 110

Trp Ser Leu Gln Gln Glu Tyr Ala Ile Asp Val Ala Ser Gly Leu Cys
```

|     |     | 115 |     |     | 120 |     |     |     | 125 |     |     |
| --- | --- | --- | --- | --- | --- | --- | --- | --- | --- | --- | --- |

Val Gly Leu Trp Gly Arg His Gly Val Glu Ile Asp Ser Leu Gly Phe
130                 135                     140

Met Phe Leu Arg Pro Ile Ala Ser Ala Arg Met Ile Asn Val Arg Tyr
145                 150                 155                 160

Pro Thr Leu Gly Leu Glu Thr Ala Gly Ile Val Pro Val Thr Leu Asp
                165                 170                 175

Ser Met Ser Asp Ser Asn Asn Ser Ala Ser Met Pro Lys Asn Trp Ser
            180                 185                 190

Phe Gln Gly Ser Arg Asp Val Thr Ile Ser Ser Trp Ser Ile Thr
        195                 200                 205

Ala Gly Ile Glu Leu His Ala Ser Ile Asn Val Ser Ala Gly Val Pro
210                 215                 220

Met Leu Ala Asn Val Asp Val Gln Tyr Gly Trp Thr Ile Ser Ser Thr
225                 230                 235                 240

Ser Ser Tyr Ser Thr Ser His Ser Glu Thr Arg Ser Leu Ser Trp Gln
                245                 250                 255

Asn Ser Gly Val Leu Glu Pro Gly Gln Trp Val Ser Leu Gln Ala Leu
            260                 265                 270

Thr Arg Arg Gly Thr Ile Thr Leu Pro Tyr Gln Ala Thr Met Gln Ile
        275                 280                 285

Thr Leu Gln Asn Gly Val Val Phe Thr Tyr Pro Ile Ala Ala Gln Tyr
290                 295                 300

Ala Gly Val Asp Phe Thr Ser Val Glu Ile Val Ser Leu Gly Thr Lys
305                 310                 315                 320

Asp Val Gly Ser Gly His Ser Ala Thr Asn Lys Asp Val Gly Arg Ile
                325                 330                 335

Val Ala Asn Gly Thr Ala Thr Thr Ser Ala Pro Pro Gln Tyr Val Arg
            340                 345                 350

Pro Val Lys Leu Ser Val Gly Ala Thr Tyr Ile Asn Asp Thr Asn Asn
        355                 360                 365

Ile Thr Gln Glu Val Asp Ser Thr Ala Thr Ser Val Glu Glu Leu Thr
370                 375                 380

Leu Met His
385

```
<210> SEQ ID NO 27
<211> LENGTH: 1161
<212> TYPE: DNA
<213> ORGANISM: Unknown
<220> FEATURE:
<223> OTHER INFORMATION: mixture of Adiantum raddianum, Adiantum
      capillus-veneris, Adiantum hispidulum, and Cyrtomium fortunei

<400> SEQUENCE: 27
atgtcgacgg ccatctttca aacacccgtg catgtgatag gaggtcaagg cggatctgag      60
ttcttttaca atgcaggcgc gagcgggcgc atcttgagta ggatcggagt gtgggcgggc     120
aggtcgttcc tgggaggcat ccgttcctgg tggacaggcc tggattcccc catcacctac     180
ggcactccta actccggctc ctacagagag ttcacttttg aagatggcga gcgcatcacc     240
agtctctccc tatggggcaa tggaataggt acacgcagcg gtggcattag gttcaacacc     300
agcacgggaa ggcagttctt ccaccatatg acctcttgga gcttgcagca agagtacgca     360
atcgatgtag cgtccggctt atgcgtaggc ctgtggggaa ggcacggcgt ggaaatcgat     420
tccttgggct tcatgttcct gcgccccata gcctccgctc gcatgatcaa tgtgagatat     480
```

-continued

```
cctactctag gcctggagac ggcaggcatt gtgccagtca cgctggactc catgagcgac      540
agcaacaatt ctgcctccat gcccaagaat tggtcattcc aaggcagccg agatgtgacc      600
atatcctcct cttggagtat tactgcgggc attgagcttc atgcctccat caacgtctcg      660 gcggggtcc ctatgctggc caatgtggac gtgcaatatg gatggaccat cagcagcacc       720
tcgtcctata gcaccagcca ctcggagact cgcagcctta gttggcagaa ttccggcgtc      780
ttggagcctg gtcagtgggt ctctctgcaa gccctcacgc ggagaggaac catcacccta      840
ccctaccagg ccaccatgca aatcaccctc cagaacggcg tcgttttcac ctacccaatc      900
gctgctcagt acgcaggagt ggattttaca agcgtcgaga ttgtgagcct agggacaaaa      960
gatgtaggct ctggtcactc ggccaccaac aaggatgtcg gccgcatcgt tgccaatggt     1020
acagctacaa ctagcgcacc gccccaatat gtccgccctg tcaagttaag tgtaggagca     1080
acttacatca atgacaccaa taatatcact caggaagttg acagtacagc tactagtgta     1140
gaagagctta ccctcatgca t                                                1161
```

<210> SEQ ID NO 28
<211> LENGTH: 387
<212> TYPE: PRT
<213> ORGANISM: Unknown
<220> FEATURE:
<223> OTHER INFORMATION: mixture of Adiantum raddianum, Adiantum
      capillus-veneris, Adiantum hispidulum, and Cyrtomium fortunei

<400> SEQUENCE: 28

```
Met Ser Thr Ala Ile Phe Gln Thr Pro Val His Val Ile Gly Gly Gln
1               5                  10                  15

Gly Gly Ser Glu Phe Phe Tyr Asn Ala Gly Ala Ser Gly Arg Ile Leu
            20                  25                  30

Ser Arg Ile Gly Val Trp Ala Gly Arg Ser Phe Leu Gly Gly Ile Arg
        35                  40                  45

Ser Trp Trp Thr Gly Leu Asp Ser Pro Ile Thr Tyr Gly Thr Pro Asn
    50                  55                  60

Ser Gly Ser Tyr Arg Glu Phe Thr Phe Glu Asp Gly Glu Arg Ile Thr
65                  70                  75                  80

Ser Leu Ser Leu Trp Gly Asn Gly Ile Gly Thr Arg Ser Gly Gly Ile
                85                  90                  95

Arg Phe Asn Thr Ser Thr Gly Arg Gln Phe Phe His His Met Thr Ser
            100                 105                 110

Trp Ser Leu Gln Gln Glu Tyr Ala Ile Asp Val Ala Ser Gly Leu Cys
        115                 120                 125

Val Gly Leu Trp Gly Arg His Gly Val Glu Ile Asp Ser Leu Gly Phe
    130                 135                 140

Met Phe Leu Arg Pro Ile Ala Ser Ala Arg Met Ile Asn Val Arg Tyr
145                 150                 155                 160

Pro Thr Leu Gly Leu Glu Thr Ala Gly Ile Val Pro Val Thr Leu Asp
                165                 170                 175

Ser Met Ser Asp Ser Asn Asn Ser Ala Ser Met Pro Lys Asn Trp Ser
            180                 185                 190

Phe Gln Gly Ser Arg Asp Val Thr Ile Ser Ser Ser Trp Ser Ile Thr
        195                 200                 205

Ala Gly Ile Glu Leu His Ala Ser Ile Asn Val Ser Ala Gly Val Pro
    210                 215                 220

Met Leu Ala Asn Val Asp Val Gln Tyr Gly Trp Thr Ile Ser Ser Thr
```

```
                225                 230                 235                 240
Ser Ser Tyr Ser Thr Ser His Ser Glu Thr Arg Ser Leu Ser Trp Gln
                245                 250                 255
Asn Ser Gly Val Leu Glu Pro Gly Gln Trp Val Ser Leu Gln Ala Leu
                260                 265                 270
Thr Arg Arg Gly Thr Ile Thr Leu Pro Tyr Gln Ala Thr Met Gln Ile
                275                 280                 285
Thr Leu Gln Asn Gly Val Val Phe Thr Tyr Pro Ile Ala Ala Gln Tyr
                290                 295                 300
Ala Gly Val Asp Phe Thr Ser Val Glu Ile Val Ser Leu Gly Thr Lys
305                 310                 315                 320
Asp Val Gly Ser Gly His Ser Ala Thr Asn Lys Asp Val Gly Arg Ile
                325                 330                 335
Val Ala Asn Gly Thr Ala Thr Thr Ser Ala Pro Pro Gln Tyr Val Arg
                340                 345                 350
Pro Val Lys Leu Ser Val Gly Ala Thr Tyr Ile Asn Asp Thr Asn Asn
                355                 360                 365
Ile Thr Gln Glu Val Asp Ser Thr Ala Thr Ser Val Glu Glu Leu Thr
                370                 375                 380
Leu Met His
385

<210> SEQ ID NO 29
<211> LENGTH: 1155
<212> TYPE: DNA
<213> ORGANISM: Adiantum raddianum

<400> SEQUENCE: 29
atgtcgatcc atcaaacacc cgtgcatgtg ataggaggtc aaggcggatc tgagttcttt      60
tacaatgcag gcgcgagcgg gcgcatcttg aggaggatcg gagtgtgggc gggcaggtcg     120
ttcctgggag gcatccgttc ctggtggaca ggcctggatt cccccatcac ctacggcact     180
cctaactccg gctcctacag agagttcact tttgaagatg gcgagcgcat caccagtctc     240
tccctatggg gcaatggaat aggtacacgc agcggtggca ttaggttcaa caccagcacg     300
ggaaggcagt tcttccacca tatgaccctct tggagcttgc agcaagagta cgcaatcgat     360
gtagcgtccg gcttatgcgt aggcctgtgg ggaaggcacg gcgtggaaat cgattccttg     420
ggcttcatgt tcctgcgccc catagcctcc gctcgcatga tcaatgtgag atatcctact     480
ctaggcctgg agacggcagg cattgtgcca gtcacgctgg actccatgag cgacagcaac     540
aattctgcct ccatgcccaa gaattggtca ttccaaggca gccgagatgt gaccatatcc     600
tcctcttgga gtattactgc gggcattgag cttcatgcct ccatcaacgt ctcggcgggg     660
gtccctatgc tggccaatgt ggacgtgcaa tatggatgga ccatcagcag cacctcgtcc     720
tatagcacca gccactcgga gactcgcagc cttagttggc agaattccgg cgtcttggag     780
cctggtcagt gggtctctct gcaagccctc acgcggagag aaccatcac cctaccctac     840 caggccacca tgcaaatcac cctccagaac ggcgtcgttt tcacctaccc aatcgctgct     900
cagtacgcag gagtggattt tacaagcgtc gagattgtga gcctagggac aaaagatgta     960
ggctctggtc actcggccac caacaaggat gtcggccgca tcgttgccaa tggtacagct    1020
acaactagcg caccgcccca atatgtccgc cctgtcaagt taagtgtagg agcaacttac    1080
atcaatgaca ccaataatat cactcaggaa gttgacagta cagctactag tgtagaagag    1140 cttacccctca tgcat                                                    1155
```

<210> SEQ ID NO 30
<211> LENGTH: 385
<212> TYPE: PRT
<213> ORGANISM: Adiantum raddianum

<400> SEQUENCE: 30

```
Met Ser Ile His Gln Thr Pro Val His Val Ile Gly Gly Gln Gly Gly
1               5                   10                  15

Ser Glu Phe Phe Tyr Asn Ala Gly Ala Ser Gly Arg Ile Leu Arg Arg
            20                  25                  30

Ile Gly Val Trp Ala Gly Arg Ser Phe Leu Gly Gly Ile Arg Ser Trp
        35                  40                  45

Trp Thr Gly Leu Asp Ser Pro Ile Thr Tyr Gly Thr Pro Asn Ser Gly
50                  55                  60

Ser Tyr Arg Glu Phe Thr Phe Glu Asp Gly Glu Arg Ile Thr Ser Leu
65                  70                  75                  80

Ser Leu Trp Gly Asn Gly Ile Gly Thr Arg Ser Gly Gly Ile Arg Phe
                85                  90                  95

Asn Thr Ser Thr Gly Arg Gln Phe Phe His His Met Thr Ser Trp Ser
            100                 105                 110

Leu Gln Gln Glu Tyr Ala Ile Asp Val Ala Ser Gly Leu Cys Val Gly
        115                 120                 125

Leu Trp Gly Arg His Gly Val Glu Ile Asp Ser Leu Gly Phe Met Phe
130                 135                 140

Leu Arg Pro Ile Ala Ser Ala Arg Met Ile Asn Val Arg Tyr Pro Thr
145                 150                 155                 160

Leu Gly Leu Glu Thr Ala Gly Ile Val Pro Val Thr Leu Asp Ser Met
                165                 170                 175

Ser Asp Ser Asn Asn Ser Ala Ser Met Pro Lys Asn Trp Ser Phe Gln
            180                 185                 190

Gly Ser Arg Asp Val Thr Ile Ser Ser Ser Trp Ser Ile Thr Ala Gly
        195                 200                 205

Ile Glu Leu His Ala Ser Ile Asn Val Ser Ala Gly Val Pro Met Leu
210                 215                 220

Ala Asn Val Asp Val Gln Tyr Gly Trp Thr Ile Ser Ser Thr Ser Ser
225                 230                 235                 240

Tyr Ser Thr Ser His Ser Glu Thr Arg Ser Leu Ser Trp Gln Asn Ser
                245                 250                 255

Gly Val Leu Glu Pro Gly Gln Trp Val Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Val Val Phe Thr Tyr Pro Ile Ala Ala Gln Tyr Ala Gly
290                 295                 300

Val Asp Phe Thr Ser Val Glu Ile Val Ser Leu Gly Thr Lys Asp Val
305                 310                 315                 320

Gly Ser Gly His Ser Ala Thr Asn Lys Asp Val Gly Arg Ile Val Ala
                325                 330                 335

Asn Gly Thr Ala Thr Thr Ser Ala Pro Pro Gln Tyr Val Arg Pro Val
            340                 345                 350

Lys Leu Ser Val Gly Ala Thr Tyr Ile Asn Asp Thr Asn Asn Ile Thr
        355                 360                 365

Gln Glu Val Asp Ser Thr Ala Thr Ser Val Glu Glu Leu Thr Leu Met
```

His
385

<210> SEQ ID NO 31
<211> LENGTH: 1206
<212> TYPE: DNA
<213> ORGANISM: Adiantum raddianum

<400> SEQUENCE: 31

```
atgtcgacgg ccatctttca acacccgtg catgtgatag gaggtcaagg cggatctgag      60
ttcttttaca atgcaggcgc gagcgggcgc atcttgagga ggatcggagt gtgggcgggc    120
aggtcgttcc tgggaggcat ccgttcctgg tggacaggcc tggattcccc catcacctac    180
ggcactccta actccggctc ctacagagag ttcacttttg aagatggcga gcgcatcacc    240
agtctctccc tatggggcaa tggaataggt acacgcagcg gtggcattag gttcaacacc    300
agcacgggaa ggcagttctt ccaccatatg acctcttgga gcttgcagca agagtacgca    360
atcgatgtag cgtccggctt atgcgtaggc ctgtggggaa ggcacggcgt ggaaatcgat    420
tccttgggct tcatgttcct cgcccccata gcctccgctc gcatgatcaa tgtgagatat    480
cctactctag gcctggagac ggcaggcatt gtgccagtca cgctggactc catgagcgac    540
agcaacaatt ctgcctccat gcccaagaat tggtcattcc aaggcagccg agatgtgacc    600
atatcctcct cttggagtat tactgcgggc attgagcttc atgcctccat caacgtctcg    660
gcggggtcc ctatgctggc caatgtggac gtgcaatatg gatggaccat cagcagcacc    720
tcgtcctata gcaccagcca ctcggagact cgcagcctta gttggcagaa ttccggcgtc    780
ttggagcctg gtcagtgggt ctctctgcaa gccctcacgc ggagaggaac catcacccta    840
ccctaccagg ccaccatgca aatcaccctc cagaacggcg tcgttttcac ctacccaatc    900
gctgctcagt acgcaggagt ggattttaca agcgtcgaga ttgtgagcct agggacaaaa    960
gatgtaggct ctggtcactc ggccaccaac aaggatgtcg gccgcatcgt tgccaatggt   1020
acagctacaa ctagcgcacc gccccaatat gtccgccctg tcaagttaag tgtaggagca   1080
acttacatca atgacaccaa taatatcact caggaagttg acagtacagc tactagtgta   1140
gaagagctta cccttgtgta ctagacttgt ccatcttctg gattggccaa cttaattaat   1200
gtatga                                                              1206
```

<210> SEQ ID NO 32
<211> LENGTH: 387
<212> TYPE: PRT
<213> ORGANISM: Adiantum raddianum

<400> SEQUENCE: 32

Met Ser Thr Ala Ile Phe Gln Thr Pro Val His Val Ile Gly Gly Gln
1               5                   10                  15

Gly Gly Ser Glu Phe Phe Tyr Asn Ala Gly Ala Ser Gly Arg Ile Leu
            20                  25                  30

Arg Arg Ile Gly Val Trp Ala Gly Arg Ser Phe Leu Gly Gly Ile Arg
        35                  40                  45

Ser Trp Trp Thr Gly Leu Asp Ser Pro Ile Thr Tyr Gly Thr Pro Asn
    50                  55                  60

Ser Gly Ser Tyr Arg Glu Phe Thr Phe Glu Asp Gly Glu Arg Ile Thr
65                  70                  75                  80

Ser Leu Ser Leu Trp Gly Asn Gly Ile Gly Thr Arg Ser Gly Gly Ile

```
                          85                  90                  95
Arg Phe Asn Thr Ser Thr Gly Arg Gln Phe His His Met Thr Ser
                100                 105                 110
Trp Ser Leu Gln Gln Glu Tyr Ala Ile Asp Val Ala Ser Gly Leu Cys
            115                 120                 125
Val Gly Leu Trp Gly Arg His Gly Val Glu Ile Asp Ser Leu Gly Phe
    130                 135                 140
Met Phe Leu Arg Pro Ile Ala Ser Ala Arg Met Ile Asn Val Arg Tyr
145                 150                 155                 160
Pro Thr Leu Gly Leu Glu Thr Ala Gly Ile Val Pro Val Thr Leu Asp
                165                 170                 175
Ser Met Ser Asp Ser Asn Asn Ser Ala Ser Met Pro Lys Asn Trp Ser
                180                 185                 190
Phe Gln Gly Ser Arg Asp Val Thr Ile Ser Ser Ser Trp Ser Ile Thr
            195                 200                 205
Ala Gly Ile Glu Leu His Ala Ser Ile Asn Val Ser Ala Gly Val Pro
    210                 215                 220
Met Leu Ala Asn Val Asp Val Gln Tyr Gly Trp Thr Ile Ser Ser Thr
225                 230                 235                 240
Ser Ser Tyr Ser Thr Ser His Ser Glu Thr Arg Ser Leu Ser Trp Gln
                245                 250                 255
Asn Ser Gly Val Leu Glu Pro Gly Gln Trp Val Ser Leu Gln Ala Leu
            260                 265                 270
Thr Arg Arg Gly Thr Ile Thr Leu Pro Tyr Gln Ala Thr Met Gln Ile
    275                 280                 285
Thr Leu Gln Asn Gly Val Val Phe Thr Tyr Pro Ile Ala Ala Gln Tyr
    290                 295                 300
Ala Gly Val Asp Phe Thr Ser Val Glu Ile Val Ser Leu Gly Thr Lys
305                 310                 315                 320
Asp Val Gly Ser Gly His Ser Ala Thr Asn Lys Asp Val Gly Arg Ile
                325                 330                 335
Val Ala Asn Gly Thr Ala Thr Thr Ser Ala Pro Pro Gln Tyr Val Arg
            340                 345                 350
Pro Val Lys Leu Ser Val Gly Ala Thr Tyr Ile Asn Asp Thr Asn Asn
    355                 360                 365
Ile Thr Gln Glu Val Asp Ser Thr Ala Thr Ser Val Glu Glu Leu Thr
    370                 375                 380
Leu Val Tyr
385

<210> SEQ ID NO 33
<211> LENGTH: 1155
<212> TYPE: DNA
<213> ORGANISM: Adiantum raddianum

<400> SEQUENCE: 33
atgtcgatct atcaaacacc cgtgcatgtg ataggaggtc aaggcggatc tgagttcttt      60
tacaatgcag gcgcgagcgg gcgcatcttg aggaggatcg gagtgtgggc gggcaggtcg     120
ttcctgggag gcatccgttc ctggtggaca ggcctggatt ccccccatca ctacggcact     180
cctaactccg gctcctacag agagttcact tttgaagatg gcgagcgcat caccagtctc     240
tccctatggg gcaatggaat aggtacacgc agcggtggca ttaggttcaa caccagcacg     300
ggaaggcagt tcttccacca tatgacctct tggagcttgc agcaagagta cgcaatcgat     360
```

```
gtagcgtccg gcttatgcgt aggcctgtgg ggaaggcacg gcgtggaaat cgattccttg    420
ggcttcatgt tcctgcgccc catagcctcc gctcgcatga tcaatgtgag atatcctact    480
ctaggcctgg agacggcagg cattgtgcca gtcacgctgg actccatgag cgacagcaac    540
aattctgcct ccatgcccaa gaattggtca ttccaaggca gccgagatgt gaccatatcc    600
tcctcttgga gtattactgc gggcattgag cttcatgcct ccatcaacgt ctcggcgggg    660
gtccctatgc tggccaatgt ggacgtgcaa tatggatgga ccatcagcag cacctcgtcc    720
tatagcacca gccactcgga gactcgcagc cttagttggc agaattccgg cgtcttggag    780
cctggtcagt gggtctctct gcaagccctc acgcggagag gaaccatcac cctaccctac    840
caggccacca tgcaaatcac cctccagaac ggcgtcgttt tcacctaccc aatcgctgct    900
cagtacgcag gagtggattt tacaagcgtc gagattgtga gcctagggac aaaagatgta    960
ggctctggtc actcggccac caacaaggat gtcggccgca tcgttgccaa tggtacagct   1020
acaactagcg caccgcccca atatgtccgc cctgtcaagt taagtgtagg agcaacttac   1080
atcaatgaca ccaataatat cactcaggaa gttgacagta cagctactag tgtagaagag   1140
cttaccctca tgcat                                                   1155
```

<210> SEQ ID NO 34
<211> LENGTH: 385
<212> TYPE: PRT
<213> ORGANISM: Adiantum raddianum

<400> SEQUENCE: 34

```
Met Ser Ile Tyr Gln Thr Pro Val His Val Ile Gly Gly Gln Gly Gly
1               5                   10                  15

Ser Glu Phe Phe Tyr Asn Ala Gly Ala Ser Gly Arg Ile Leu Arg Arg
            20                  25                  30

Ile Gly Val Trp Ala Gly Arg Ser Phe Leu Gly Gly Ile Arg Ser Trp
        35                  40                  45

Trp Thr Gly Leu Asp Ser Pro Ile Thr Tyr Gly Thr Pro Asn Ser Gly
    50                  55                  60

Ser Tyr Arg Glu Phe Thr Phe Glu Asp Gly Glu Arg Ile Thr Ser Leu
65                  70                  75                  80

Ser Leu Trp Gly Asn Gly Ile Gly Thr Arg Ser Gly Gly Ile Arg Phe
                85                  90                  95

Asn Thr Ser Thr Gly Arg Gln Phe Phe His His Met Thr Ser Trp Ser
            100                 105                 110

Leu Gln Gln Glu Tyr Ala Ile Asp Val Ala Ser Gly Leu Cys Val Gly
        115                 120                 125

Leu Trp Gly Arg His Gly Val Glu Ile Asp Ser Leu Gly Phe Met Phe
    130                 135                 140

Leu Arg Pro Ile Ala Ser Ala Arg Met Ile Asn Val Arg Tyr Pro Thr
145                 150                 155                 160

Leu Gly Leu Glu Thr Ala Gly Ile Val Pro Val Thr Leu Asp Ser Met
                165                 170                 175

Ser Asp Ser Asn Asn Ser Ala Ser Met Pro Lys Asn Trp Ser Phe Gln
            180                 185                 190

Gly Ser Arg Asp Val Thr Ile Ser Ser Ser Trp Ser Ile Thr Ala Gly
        195                 200                 205

Ile Glu Leu His Ala Ser Ile Asn Val Ser Ala Gly Val Pro Met Leu
    210                 215                 220

Ala Asn Val Asp Val Gln Tyr Gly Trp Thr Ile Ser Ser Thr Ser Ser
```

```
                225                 230                 235                 240
Tyr Ser Thr Ser His Ser Glu Thr Arg Ser Leu Ser Trp Gln Asn Ser
                    245                 250                 255
Gly Val Leu Glu Pro Gly Gln Trp Val Ser Leu Gln Ala Leu Thr Arg
                260                 265                 270
Arg Gly Thr Ile Thr Leu Pro Tyr Gln Ala Thr Met Gln Ile Thr Leu
            275                 280                 285
Gln Asn Gly Val Val Phe Thr Tyr Pro Ile Ala Ala Gln Tyr Ala Gly
        290                 295                 300
Val Asp Phe Thr Ser Val Glu Ile Val Ser Leu Gly Thr Lys Asp Val
305                 310                 315                 320
Gly Ser Gly His Ser Ala Thr Asn Lys Asp Val Gly Arg Ile Val Ala
                    325                 330                 335
Asn Gly Thr Ala Thr Thr Ser Ala Pro Pro Gln Tyr Val Arg Pro Val
                340                 345                 350
Lys Leu Ser Val Gly Ala Thr Tyr Ile Asn Asp Thr Asn Asn Ile Thr
            355                 360                 365
Gln Glu Val Asp Ser Thr Ala Thr Ser Val Glu Glu Leu Thr Leu Met
        370                 375                 380
His
385

<210> SEQ ID NO 35
<211> LENGTH: 1155
<212> TYPE: DNA
<213> ORGANISM: Adiantum raddianum

<400> SEQUENCE: 35
atgtcgatct atcaaacacc cgtgcatgtg ataggaggtc aaggcggatc tgagttcttt      60
tacaatgcag gcgcgagcgg gcgcatcttg aggaggatcg gagtgtgggc gggcaggtcg     120
ttcctgggag gcatccgttc ctggtggaca ggcctggatt cccccatcac ctacggcact     180
cctaactccg gctcctacag agagttcact tttgaagatg gcgagcgcat caccagtctc     240
tccctatggg gcaatggaat aggtacacgc agcggtggca ttaggttcaa caccagcacg     300
ggaaggcagt tcttccacca tatgacctct tggagcttgc agcaagagta cgcaatcgat     360
gtagcgtccg gcttatgcgt aggcctgtgg ggaaggcacg gcgtggaaat cgattccttg     420
ggcttcatgt tcctgcgccc catagcctcc gctcgcatga tcaatgtgag atatcctact     480
ctaggcctgg agacggcagg cattgtgcca gtcacgctgg actccatgag cgacagcaac     540
aattctgcct ccatgcccaa gaattggtca ttccaaggca gccgagatgt gaccatatcc     600
tcctcttgga gtattactgc gggcattgag cttcatgcct ccatcaacgt ctcggcgggg     660
gtccctatgc tggccaatgt ggacgtgcaa tatggatgga ccatcagcag cacctcgtcc     720
tatagcacca gccactcgga gactcgcagc cttagttggc agaattccgg cgtcttggag     780
cctggtcagt gggtctctct gcaagccctc acgcggagag aaccatcac cctaccctac     840
caggccacca tgcaaatcac cctccagaac ggcgtcgttt tcacctaccc aatcgctgct     900
cagtacgcag gagtggattt tacaagcgtc gagattgtga gcctagggac aaaagatgta     960
ggctctggtc actcggccac caacaaggat gtcggccgca tcgttgccaa tggtacagct    1020
acaactagcg caccgcccca atatgtccgc cctgtcaagt taagtgtagg agcaacttac    1080
atcaatgaca ccaataatat cactcaggaa gttgacagta cagctactag tgtagaagag    1140
cttacccctca tgcat                                                    1155
```

<210> SEQ ID NO 36
<211> LENGTH: 385
<212> TYPE: PRT
<213> ORGANISM: Adiantum raddianum

<400> SEQUENCE: 36

```
Met Ser Ile Tyr Gln Thr Pro Val His Val Ile Gly Gln Gly Gly
1               5                   10                  15

Ser Glu Phe Phe Tyr Asn Ala Gly Ala Ser Gly Arg Ile Leu Arg Arg
            20                  25                  30

Ile Gly Val Trp Ala Gly Arg Ser Phe Leu Gly Gly Ile Arg Ser Trp
        35                  40                  45

Trp Thr Gly Leu Asp Ser Pro Ile Thr Tyr Gly Thr Pro Asn Ser Gly
50                  55                  60

Ser Tyr Arg Glu Phe Thr Phe Glu Asp Gly Glu Arg Ile Thr Ser Leu
65                  70                  75                  80

Ser Leu Trp Gly Asn Gly Ile Gly Thr Arg Ser Gly Gly Ile Arg Phe
                85                  90                  95

Asn Thr Ser Thr Gly Arg Gln Phe Phe His His Met Thr Ser Trp Ser
            100                 105                 110

Leu Gln Gln Glu Tyr Ala Ile Asp Val Ala Ser Val Leu Cys Val Gly
        115                 120                 125

Leu Trp Gly Arg His Gly Val Glu Ile Asp Ser Leu Gly Phe Met Phe
    130                 135                 140

Leu Arg Pro Ile Ala Ser Ala Arg Met Ile Asn Val Arg Tyr Pro Thr
145                 150                 155                 160

Leu Gly Leu Glu Thr Ala Gly Ile Val Pro Val Thr Leu Asp Ser Met
                165                 170                 175

Ser Asp Ser Asn Asn Ser Ala Ser Met Pro Lys Asn Trp Ser Phe Gln
            180                 185                 190

Gly Ser Arg Asp Val Thr Ile Ser Ser Ser Trp Ser Ile Thr Ala Gly
        195                 200                 205

Ile Glu Leu His Ala Ser Ile Asn Val Ser Ala Gly Val Pro Met Leu
    210                 215                 220

Ala Asn Val Asp Val Gln Tyr Gly Trp Thr Ile Ser Ser Thr Ser Ser
225                 230                 235                 240

Tyr Ser Thr Ser His Ser Glu Thr Arg Ser Leu Ser Trp Gln Asn Ser
                245                 250                 255

Gly Val Leu Glu Pro Gly Gln Trp Val Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Val Val Phe Thr Tyr Pro Ile Ala Ala Gln Tyr Ala Gly
    290                 295                 300

Val Asp Phe Thr Ser Val Glu Ile Val Ser Leu Gly Thr Lys Asp Val
305                 310                 315                 320

Gly Ser Gly His Ser Ala Thr Asn Lys Asp Val Gly Arg Ile Val Ala
                325                 330                 335

Asn Gly Thr Ala Thr Thr Ser Ala Pro Pro Gln Tyr Val Arg Pro Val
            340                 345                 350

Lys Leu Ser Val Gly Ala Thr Tyr Ile Asn Asp Thr Asn Asn Ile Thr
        355                 360                 365

Gln Glu Val Asp Ser Thr Ala Thr Ser Val Glu Glu Leu Thr Leu Met
```

His
385

<210> SEQ ID NO 37
<211> LENGTH: 1155
<212> TYPE: DNA
<213> ORGANISM: Adiantum raddianum

<400> SEQUENCE: 37

```
atgtcgatct atcaaacacc cgtgcatgtg ataggaggtc aaggcggatc tgagttcttt      60
tacaatgcag gcgcgagcgg gcgcatcttg aggaggatcg gagtgtgggc gggcaggtcg     120
ttcctgggag gcatccgttc ctggtggaca ggcctggatt cccccatcac ctacggcact     180
cctaactccg gctcctacag agagttcact tttgaagatg gcgagcgcat caccagtctc     240
tccctatggg gcaatggaat aggtacacgc agcggtggca ttaggttcaa caccagcacg     300
ggaaggcagt tcttccacca tatgacctct tggagcttgc agcaagagta cgcaatcgat     360
gtagcgtccg gcttatgcgt aggcctgtgg ggaaggcacg gcgtggaaat cgattccttg     420
ggcttcatgt tcctgcgccc catagcctcc gctcgcatga tcaatgtgag atatcctact     480
ctaggcctgg agacggcagg cattgtgcca gtcacgctgg actccatgag cgacagcaac     540
aattctgcct ccatgcccaa gaattggtca ttccaaggca gccgagatgt gaccatatcc     600
tcctcttgga atattactgc gggcattgag cttcatgcct ccatcaacgt ctcggcgggg     660
gtccctatgc tggccaatgt ggacgtgcaa tatggatgga ccatcagcag cacctcgtcc     720
tatagcacca gccactcgga gactcgcagc cttagttggc agaattccgg cgtcttggag     780
cctggtcagt gggtctctct gcaagccctc acgcggagag gaaccatcac cctaccctac     840
caggccacca tgcaaatcac cctccagaac ggcgtcgttt tcacctaccc aatcgctgct     900
cagtacgcag gagtggattt tacaagcgtc gagattgtga gcctagggac aaaagatgta     960
ggctctggtc actcggccac caacaaggat gtcggccgca tcgttgccaa tggtacagct    1020
acaactagcg caccgcccca atatgtccgc cctgtcaagt taagtgtagg agcaacttac    1080
atcaatgaca ccaataatat cactcaggaa gttgacagta cagctactag tgtagaagag    1140
cttacccctca tgcat                                                    1155
```

<210> SEQ ID NO 38
<211> LENGTH: 385
<212> TYPE: PRT
<213> ORGANISM: Adiantum raddianum

<400> SEQUENCE: 38

Met Ser Ile Tyr Gln Thr Pro Val His Val Ile Gly Gly Gln Gly Gly
1               5                   10                  15

Ser Glu Phe Phe Tyr Asn Ala Gly Ala Ser Gly Arg Ile Leu Arg Arg
            20                  25                  30

Ile Gly Val Trp Ala Gly Arg Ser Phe Leu Gly Gly Ile Arg Ser Trp
        35                  40                  45

Trp Thr Gly Leu Asp Ser Pro Ile Thr Tyr Gly Thr Pro Asn Ser Gly
    50                  55                  60

Ser Tyr Arg Glu Phe Thr Phe Glu Asp Gly Glu Arg Ile Thr Ser Leu
65                  70                  75                  80

Ser Leu Trp Gly Asn Gly Ile Gly Thr Arg Ser Gly Gly Ile Arg Phe
                85                  90                  95

```
Asn Thr Ser Thr Gly Arg Gln Phe Phe His His Met Thr Ser Trp Ser
            100                 105                 110

Leu Gln Gln Glu Tyr Ala Ile Asp Val Ala Ser Gly Leu Cys Val Gly
        115                 120                 125

Leu Trp Gly Arg His Gly Val Glu Ile Asp Ser Leu Gly Phe Met Phe
    130                 135                 140

Leu Arg Pro Ile Ala Ser Ala Arg Met Ile Asn Val Arg Tyr Pro Thr
145                 150                 155                 160

Leu Gly Leu Glu Thr Ala Gly Ile Val Pro Val Thr Leu Asp Ser Met
                165                 170                 175

Ser Asp Ser Asn Asn Ser Ala Ser Met Pro Lys Asn Trp Ser Phe Gln
            180                 185                 190

Gly Ser Arg Asp Val Thr Ile Ser Ser Ser Trp Asn Ile Thr Ala Gly
        195                 200                 205

Ile Glu Leu His Ala Ser Ile Asn Val Ser Ala Gly Val Pro Met Leu
    210                 215                 220

Ala Asn Val Asp Val Gln Tyr Gly Trp Thr Ile Ser Ser Thr Ser Ser
225                 230                 235                 240

Tyr Ser Thr Ser His Ser Glu Thr Arg Ser Leu Ser Trp Gln Asn Ser
                245                 250                 255

Gly Val Leu Glu Pro Gly Gln Trp Val Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Val Val Phe Thr Tyr Pro Ile Ala Ala Gln Tyr Ala Gly
    290                 295                 300

Val Asp Phe Thr Ser Val Glu Ile Val Ser Leu Gly Thr Lys Asp Val
305                 310                 315                 320

Gly Ser Gly His Ser Ala Thr Asn Lys Asp Val Gly Arg Ile Val Ala
                325                 330                 335

Asn Gly Thr Ala Thr Thr Ser Ala Pro Pro Gln Tyr Val Arg Pro Val
            340                 345                 350

Lys Leu Ser Val Gly Ala Thr Tyr Ile Asn Asp Thr Asn Asn Ile Thr
        355                 360                 365

Gln Glu Val Asp Ser Thr Ala Thr Ser Val Glu Glu Leu Thr Leu Met
    370                 375                 380

His
385

<210> SEQ ID NO 39
<211> LENGTH: 1161
<212> TYPE: DNA
<213> ORGANISM: Adiantum raddianum

<400> SEQUENCE: 39
atgtcgacgg ccatctttca aacacccgtg catgtgatag gaggtcaagg cggatctgag       60
ttcttttaca atgcaggcgc gagcgggcgc atcttgagga ggatcggagt gtgggcgggc      120
aggtcgttcc tgggaggcat ccgttcctgg tggacaggcc tggattcccc catcacctac      180
ggcactccta actccggctc ctacagagag ttcacttttg aagatggcga gcgcatcacc      240
agtctctccc tatggggcaa tggaataggt acacgcagcg gtggcattag gttcaacacc      300
agcacgggaa ggcagttctt ccaccatatg acctcttgga gcttgcagca agagtacgca      360
atcgatgtag cgtccggctt atgcgtaggc ctgtggggaa ggcacggcgt ggaaatcgat      420
```

-continued

```
tccttgggct tcatgttcct gcgccccata gcctccgctc gcatgatcaa tgtgagatat      480
cctactctag gcctggagac ggcaggcatt gtgccagtcc cgctggactc cctgagccac      540
agcaacaatt ctgcctccct gcccaagaat tggccattcc agggcagccc aaagggacc      600 atatcctcct cttggagtat actggcgggc attgagcttc ctgcctccat caacgtctcg      660 gcggggtcc ctatgctggc caatgtggac gtgcaatatg gatggaccat cagcagcacc      720
tcgtcctata gcaccagcca ctcggagact cgcagcctta gttggcagaa ttccggcgtc      780
ttggagcctg gtcagtgggt ctctctgcaa gccctcacgc ggagaggaac catcacccta      840
ccctaccagg ccaccatgca aatcaccctc cagaacggcg tcgttttcac ctacccaatc      900
gctgctcagt acgcaggagt ggattttaca agcgtcgaga ttgtgagcct agggacaaaa      960
gatgtaggct ctggtcactc ggccaccaac aaggatgtcg ccgcatcgt tgccaatggt     1020 acagctacaa ctagcgcacc gccccaatat gtccgccctg tcaagttaag tgtaggagca     1080
acttacatca atgacaccaa taatatcact caggaagttg acagtacagc tactagtgta     1140
gaagagctta ccctcatgca t                                               1161
```

<210> SEQ ID NO 40
<211> LENGTH: 387
<212> TYPE: PRT
<213> ORGANISM: Adiantum raddianum

<400> SEQUENCE: 40

```
Met Ser Thr Ala Ile Phe Gln Thr Pro Val His Val Ile Gly Gly Gln
1               5                   10                  15

Gly Gly Ser Glu Phe Phe Tyr Asn Ala Gly Ala Ser Gly Arg Ile Leu
            20                  25                  30

Arg Arg Ile Gly Val Trp Ala Gly Arg Ser Phe Leu Gly Gly Ile Arg
        35                  40                  45

Ser Trp Trp Thr Gly Leu Asp Ser Pro Ile Thr Tyr Gly Thr Pro Asn
    50                  55                  60

Ser Gly Ser Tyr Arg Glu Phe Thr Phe Glu Asp Gly Glu Arg Ile Thr
65                  70                  75                  80

Ser Leu Ser Leu Trp Gly Asn Gly Ile Gly Thr Arg Ser Gly Gly Ile
                85                  90                  95

Arg Phe Asn Thr Ser Thr Gly Arg Gln Phe Phe His His Met Thr Ser
            100                 105                 110

Trp Ser Leu Gln Gln Glu Tyr Ala Ile Asp Val Ala Ser Gly Leu Cys
        115                 120                 125

Val Gly Leu Trp Gly Arg His Gly Val Glu Ile Asp Ser Leu Gly Phe
    130                 135                 140

Met Phe Leu Arg Pro Ile Ala Ser Ala Arg Met Ile Asn Val Arg Tyr
145                 150                 155                 160

Pro Thr Leu Gly Leu Glu Thr Ala Gly Ile Val Pro Val Pro Leu Asp
                165                 170                 175

Ser Leu Ser His Ser Asn Asn Ser Ala Ser Leu Pro Lys Asn Trp Pro
            180                 185                 190

Phe Gln Gly Ser Pro Lys Gly Thr Ile Ser Ser Trp Ser Ile Leu
        195                 200                 205

Ala Gly Ile Glu Leu Pro Ala Ser Ile Asn Val Ser Ala Gly Val Pro
    210                 215                 220

Met Leu Ala Asn Val Asp Val Gln Tyr Gly Trp Thr Ile Ser Ser Thr
225                 230                 235                 240
```

```
Ser Ser Tyr Ser Thr Ser His Ser Glu Thr Arg Ser Leu Ser Trp Gln
                245                 250                 255

Asn Ser Gly Val Leu Glu Pro Gly Gln Trp Val Ser Leu Gln Ala Leu
            260                 265                 270

Thr Arg Arg Gly Thr Ile Thr Leu Pro Tyr Gln Ala Thr Met Gln Ile
        275                 280                 285

Thr Leu Gln Asn Gly Val Val Phe Thr Tyr Pro Ile Ala Ala Gln Tyr
    290                 295                 300

Ala Gly Val Asp Phe Thr Ser Val Glu Ile Val Ser Leu Gly Thr Lys
305                 310                 315                 320

Asp Val Gly Ser Gly His Ser Ala Thr Asn Lys Asp Val Gly Arg Ile
                325                 330                 335

Val Ala Asn Gly Thr Ala Thr Thr Ser Ala Pro Pro Gln Tyr Val Arg
            340                 345                 350

Pro Val Lys Leu Ser Val Gly Ala Thr Tyr Ile Asn Asp Thr Asn Asn
        355                 360                 365

Ile Thr Gln Glu Val Asp Ser Thr Ala Thr Ser Val Glu Glu Leu Thr
    370                 375                 380

Leu Met His
385

<210> SEQ ID NO 41
<211> LENGTH: 960
<212> TYPE: DNA
<213> ORGANISM: Cyrtomium falcatum

<400> SEQUENCE: 41
atgtctattg tacaatcacc cattcacgtg atcggaggct caggcggatc agcgttctca      60
tacaatgcag gtacgaacgg tcgcatcttg aggaggatcg agtgtgggc aggcgggtgg      120 ttcctgggag gcatccgggc gtggtggaca ggccttgata cccagttct gtttggtacg      180 gccaatgtag gctcctacaa ggagttcacc ttcgaggatg cgagcgcat acgagcctc      240 tctctctggg gcaacggtgc aggtacgcgt tctggtggca tcaggttccg cacgaccacc      300
ggaagggagt ttttccacta catgacatca tggggcttga acaagagta cccgatcgat      360 gtagcgtcgg gcttgtgcgt gggcttgata ggcaggcatg gcgagcacat tgatagcctg      420
ggcttcatgt tcctacgctc catagcgtcc gctcgcatga tcaatgtgag ctacccgacc      480
ttgggcctgg agacggcggg catcgtgccc gtcacgctgg actccatgag caacaacaac      540
aattcgggta gcctccccct cgaactgggca ttccgaggca gccgagaggt gacaatgtcc      600
tccacctggt cggtcacagc aggcatagag ctgcatgcca gcgttaccgt gacggcgggg      660
atcccgacgg ttgcggaggt gcaaggtcag tacggatggg cagtgagcac cagctccacc      720
ttctcaacca cccacacgga aactcgcagc ctgcagtggg aggtgtcggg agtcttacag      780
cctggtgagt ggatctctct acaagctctc actaggagag gggtcatatc cctgccctac      840
caggccacca tgcaaatcac cctccagaat ggcgctgtgt ttacctaccc aattactgct      900
atgtacgctg gagtggatta caccagcgtt gaacttgtcc atcttctgga ttggccaact      960

<210> SEQ ID NO 42
<211> LENGTH: 320
<212> TYPE: PRT
<213> ORGANISM: Cyrtomium falcatum

<400> SEQUENCE: 42

Met Ser Ile Val Gln Ser Pro Ile His Val Ile Gly Gly Ser Gly Gly
```

```
              1               5                  10                 15
            Ser Ala Phe Ser Tyr Asn Ala Gly Thr Asn Gly Arg Ile Leu Arg Arg
                           20                  25                 30

Ile Gly Val Trp Ala Gly Gly Trp Phe Leu Gly Gly Ile Arg Ala Trp
                           35                  40                 45

Trp Thr Gly Leu Asp Asn Pro Val Leu Phe Gly Thr Ala Asn Val Gly
                50                      55                  60

Ser Tyr Lys Glu Phe Thr Phe Glu Asp Gly Glu Arg Ile Thr Ser Leu
            65                      70                  75                 80

Ser Leu Trp Gly Asn Gly Ala Gly Thr Arg Ser Gly Gly Ile Arg Phe
                           85                  90                 95

Arg Thr Thr Thr Gly Arg Glu Phe Phe His Tyr Met Thr Ser Trp Gly
                          100                 105                110

Leu Lys Gln Glu Tyr Pro Ile Asp Val Ala Ser Gly Leu Cys Val Gly
                          115                 120                125

Leu Ile Gly Arg His Gly Glu His Ile Asp Ser Leu Gly Phe Met Phe
                          130                 135                140

Leu Arg Ser Ile Ala Ser Ala Arg Met Ile Asn Val Ser Tyr Pro Thr
            145                     150                 155                160

Leu Gly Leu Glu Thr Ala Gly Ile Val Pro Val Thr Leu Asp Ser Met
                              165                 170                175

Ser Asn Asn Asn Ser Gly Ser Leu Pro Ser Asn Trp Ala Phe Arg
                          180                 185                 190

Gly Ser Arg Glu Val Thr Met Ser Ser Thr Trp Ser Val Thr Ala Gly
                          195                 200                205

Ile Glu Leu His Ala Ser Val Thr Val Thr Ala Gly Ile Pro Thr Val
                          210                 215                 220

Ala Glu Val Gln Gly Gln Tyr Gly Trp Ala Val Ser Thr Ser Ser Thr
            225                     230                 235                240

Phe Ser Thr Thr His Thr Glu Thr Arg Ser Leu Gln Trp Glu Val Ser
                              245                 250                255

Gly Val Leu Gln Pro Gly Glu Trp Ile Ser Leu Gln Ala Leu Thr Arg
                          260                 265                270

Arg Gly Val Ile Ser Leu Pro Tyr Gln Ala Thr Met Gln Ile Thr Leu
                          275                 280                 285

Gln Asn Gly Ala Val Phe Thr Tyr Pro Ile Thr Ala Met Tyr Ala Gly
                          290                 295                300

Val Asp Tyr Thr Ser Val Glu Leu Val His Leu Leu Asp Trp Pro Thr
            305                     310                 315                320

<210> SEQ ID NO 43
<211> LENGTH: 1221
<212> TYPE: DNA
<213> ORGANISM: Cyathea australis

<400> SEQUENCE: 43
atgtctatct ttcagacgcc cgtgcatgtg ataggaggtc agggtggagg ggcgttctcg      60
tacaatgcag gcgcgagcgg gcgcgtcttg aggaggatcg gtgtgtgggc gggcggctgg     120
tacctgggag gcatccggtt gtggtggaca ggcctggatg actccattac ctacggcact     180
gctaactccg gctcctacag ggagttcacc ttcgaggatg gcgagcgcat caccagtctc     240
tccctctggg gcaacggagc aggtacacgc agtggtggca tcaggttccg caccaccggg     300
ggaagggagt tcttccacta catgacctct tggggcctcc agcaagagta cccaatagat     360
```

```
gtagcgtcgg gcttgtgcgt gggtgtcatc ggcaggcacg gggatcacat tgattccctg   420
ggcttcatgt tcctgcgcac catagcctcc gctcgcatga tcaatgtcag ctacccaacc   480
ctggacctgg agactgcagg cattgtgcca gtcacgctgg actccatgag cgacagcaac   540
aatgccggca ccatctccaa gaactggaca ttcggaggca gcagaagtgt gaccatatcc   600
tcctcctggg ctatcaccgc aggcattgag ctccatgcca gcatcactgt cacagccggg   660
atccccacgg tggcggaggt gcaaggggaa tacggatggt ccatcagcag cagctccacc   720
tacaccacta gccatgagga gactcgcacc cttagctggg agaattccgg agtcttgcag   780
cccggcgagt ggatctctct gcaagccctc acacggagag gaaccatctc cctgccctac   840
caggctacca tgcaaatcac cctccagaac ggcgccctct tcacctatcc gatcaccgct   900
ctttacgccg gagtcgatta caccaacgtc cagattgtga gcacggggac cagacatcta   960
gattacgatc acgtgcgctc agctggcggc cgccgattag tatcggccat cagcaacaaa  1020
ggcagcttgc cgaccgctgc cactacttct gtgattgcgc cgccccgtta tgtccaccct  1080
gttaacatac cagcagtgcc ttatacgtct gtcattgaac cagtcaaagt tgtggccacg  1140
agagcagcac ctactagcat taatgacgac aacataaagc aggaacctct agtagctacc  1200
gaagagcgta cgcttgtata c                                            1221

<210> SEQ ID NO 44
<211> LENGTH: 407
<212> TYPE: PRT
<213> ORGANISM: Cyathea australis

<400> SEQUENCE: 44

Met Ser Ile Phe Gln Thr Pro Val His Val Ile Gly Gly Gln Gly Gly
1               5                   10                  15

Gly Ala Phe Ser Tyr Asn Ala Gly Ala Ser Gly Arg Val Leu Arg Arg
            20                  25                  30

Ile Gly Val Trp Ala Gly Gly Trp Tyr Leu Gly Gly Ile Arg Leu Trp
        35                  40                  45

Trp Thr Gly Leu Asp Asp Ser Ile Thr Tyr Gly Thr Ala Asn Ser Gly
    50                  55                  60

Ser Tyr Arg Glu Phe Thr Phe Glu Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Arg Thr Thr Gly Gly Arg Glu Phe Phe His Tyr Met Thr Ser Trp Gly
            100                 105                 110

Leu Gln Gln Glu Tyr Pro Ile Asp Val Ala Ser Gly Leu Cys Val Gly
        115                 120                 125

Val Ile Gly Arg His Gly Asp His Ile Asp Ser Leu Gly Phe Met Phe
    130                 135                 140

Leu Arg Thr Ile Ala Ser Ala Arg Met Ile Asn Val Ser Tyr Pro Thr
145                 150                 155                 160

Leu Asp Leu Glu Thr Ala Gly Ile Val Pro Val Thr Leu Asp Ser Met
                165                 170                 175

Ser Asp Ser Asn Asn Ala Gly Thr Ile Ser Lys Asn Trp Thr Phe Gly
            180                 185                 190

Gly Ser Arg Ser Val Thr Ile Ser Ser Trp Ala Ile Thr Ala Gly
        195                 200                 205

Ile Glu Leu His Ala Ser Ile Thr Val Thr Ala Gly Ile Pro Thr Val
    210                 215                 220
```

Ala Glu Val Gln Gly Glu Tyr Gly Trp Ser Ile Ser Ser Ser Thr
225                 230                 235                 240

Tyr Thr Thr Ser His Glu Thr Arg Thr Leu Ser Trp Glu Asn Ser
            245                 250                 255

Gly Val Leu Gln Pro Gly Glu Trp Ile Ser Leu Gln Ala Leu Thr Arg
        260                 265                 270

Arg Gly Thr Ile Ser Leu Pro Tyr Gln Ala Thr Met Gln Ile Thr Leu
        275                 280                 285

Gln Asn Gly Ala Leu Phe Thr Tyr Pro Ile Thr Ala Leu Tyr Ala Gly
290                 295                 300

Val Asp Tyr Thr Asn Val Gln Ile Val Ser Thr Gly Arg His Leu
305                 310                 315                 320

Asp Tyr Asp His Val Arg Ser Ala Gly Gly Arg Arg Leu Val Ser Ala
            325                 330                 335

Ile Ser Asn Lys Gly Ser Leu Pro Thr Ala Ala Thr Thr Ser Val Ile
        340                 345                 350

Ala Pro Pro Arg Tyr Val His Pro Val Asn Ile Pro Ala Val Pro Tyr
        355                 360                 365

Thr Ser Val Ile Glu Pro Val Lys Val Val Ala Thr Arg Ala Ala Pro
    370                 375                 380

Thr Ser Ile Asn Asp Asp Asn Ile Lys Gln Glu Pro Leu Val Ala Thr
385                 390                 395                 400

Glu Glu Arg Thr Leu Val Tyr
                405

<210> SEQ ID NO 45
<211> LENGTH: 1221
<212> TYPE: DNA
<213> ORGANISM: Cyathea australis

<400> SEQUENCE: 45
atgtctatct tcagacgcc cgtgcatgtg ataggaggtc agggtggagg ggcgttctcg      60
tacaatgcag gcgcgagcgg gcgcgtcttg aggaggatcg gtgtgtgggc gggcggctgg    120
tacctgggag gcatccggtt gtggtggaca ggcctggatg actccattac ctacggcact    180
gctaactccg gctcctacag ggagttcacc ttcgaggatg gcgagcgcat caccagtctc    240
tccctctggg caacggagc aggtacacgc agtggtggca tcaggttccg caccaccggg    300
ggaagggagt tcttccacta catgacctct ggggcctcc agcaagagta cccaatagat    360
gtagcgtcgg gcttgtgcgt gggtgtcatc ggcaggcacg gggatcacat tgattccctg    420
ggcttcatgt tcctgcgcac catagcctcc gctcgcatga tcaatgtcag ctacccaacc    480
ctggacctgg agactgcagg cattgtgcca gtcacgctgg actccatgag cgacagcaac    540
aatgccggca ccatctccaa gaactggaca ttcggaggca gcagaagtgt gaccatatcc    600
tcctcctggg ctataccgc aggcattgag ctccatgcca gcatcactgt cacagccggg    660
atccccacgg tggcggaggt gcaaggggaa tacggatggt ccatcagcag cagctccacc    720
tacaccacta gccatgagga gactcgcacc cttagctggg agaattccgg agtcttgcag    780
cccggcgagt ggatctctct gcaagccctc acacggagag gaaccatctc cctgccctac    840
caggctacca tgcaaatcac cctccagaac ggcgccctct tcacctatcc gatcaccgct    900
ctttacgccg gagtcgatta caccaacgtc cagattgtga gcacggggac cagacatcta    960
gattacgatc acgtgcgctc agctggcggc cgccgattag tatcggccat cagcaacaaa   1020

-continued

```
ggcagcttgc cgaccgctgc cactacttct gtgattgcgc cgccccgtta tgtccaccct      1080
gttaacatac cagcagtgct ttatacgtct gtcattgaac cagtcaaagt tgtggccacg      1140
agagcagcac ctactagcat taatgacgac aacataaagc aggaacctct agtagctacc      1200
gaagagcgta cgcttgtata c                                                1221
```

<210> SEQ ID NO 46
<211> LENGTH: 407
<212> TYPE: PRT
<213> ORGANISM: Cyathea australis

<400> SEQUENCE: 46

```
Met Ser Ile Phe Gln Thr Pro Val His Val Ile Gly Gly Gln Gly Gly
1               5                   10                  15

Gly Ala Phe Ser Tyr Asn Ala Gly Ala Ser Gly Arg Val Leu Arg Arg
            20                  25                  30

Ile Gly Val Trp Ala Gly Gly Trp Tyr Leu Gly Gly Ile Arg Leu Trp
        35                  40                  45

Trp Thr Gly Leu Asp Asp Ser Ile Thr Tyr Gly Thr Ala Asn Ser Gly
    50                  55                  60

Ser Tyr Arg Glu Phe Thr Phe Glu Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Arg Thr Thr Gly Gly Arg Glu Phe Phe His Tyr Met Thr Ser Trp Gly
            100                 105                 110

Leu Gln Gln Glu Tyr Pro Ile Asp Val Ala Ser Gly Leu Cys Val Gly
        115                 120                 125

Val Ile Gly Arg His Gly Asp His Ile Asp Ser Leu Gly Phe Met Phe
    130                 135                 140

Leu Arg Thr Ile Ala Ser Ala Arg Met Ile Asn Val Ser Tyr Pro Thr
145                 150                 155                 160

Leu Asp Leu Glu Thr Ala Gly Ile Val Pro Val Thr Leu Asp Ser Met
                165                 170                 175

Ser Asp Ser Asn Asn Ala Gly Thr Ile Ser Lys Asn Trp Thr Phe Gly
            180                 185                 190

Gly Ser Arg Ser Val Thr Ile Ser Ser Ser Trp Ala Ile Thr Ala Gly
        195                 200                 205

Ile Glu Leu His Ala Ser Ile Thr Val Thr Ala Gly Ile Pro Thr Val
    210                 215                 220

Ala Glu Val Gln Gly Glu Tyr Gly Trp Ser Ile Ser Ser Ser Ser Thr
225                 230                 235                 240

Tyr Thr Thr Ser His Glu Glu Thr Arg Thr Leu Ser Trp Glu Asn Ser
                245                 250                 255

Gly Val Leu Gln Pro Gly Glu Trp Ile Ser Leu Gln Ala Leu Thr Arg
            260                 265                 270

Arg Gly Thr Ile Ser Leu Pro Tyr Gln Ala Thr Met Gln Ile Thr Leu
        275                 280                 285

Gln Asn Gly Ala Leu Phe Thr Tyr Pro Ile Thr Ala Leu Tyr Ala Gly
    290                 295                 300

Val Asp Tyr Thr Asn Val Gln Ile Val Ser Thr Gly Thr Arg His Leu
305                 310                 315                 320

Asp Tyr Asp His Val Arg Ser Ala Gly Gly Arg Arg Leu Val Ser Ala
                325                 330                 335
```

```
Ile Ser Asn Lys Gly Ser Leu Pro Thr Ala Ala Thr Thr Ser Val Ile
            340                 345                 350

Ala Pro Pro Arg Tyr Val His Pro Val Asn Ile Pro Ala Val Leu Tyr
        355                 360                 365

Thr Ser Val Ile Glu Pro Val Lys Val Val Ala Thr Arg Ala Ala Pro
        370                 375                 380

Thr Ser Ile Asn Asp Asp Asn Ile Lys Gln Glu Pro Leu Val Ala Thr
385                 390                 395                 400

Glu Glu Arg Thr Leu Val Tyr
                405
```

<210> SEQ ID NO 47
<211> LENGTH: 1182
<212> TYPE: DNA
<213> ORGANISM: Adiantum raddianum

<400> SEQUENCE: 47

```
atgtcgatct atcaaacacc cgtgagcctg atcggaggac aaggcggaac ggcgttcacg      60
tacaatgcag gcgagagcgg gcgcgtcttg aggaggattg gggtgtgggc cgttgactcg     120
gcgttgcgag gcatccgagt gtggtggaca ggcctggatt ccccccttac ttacggcact     180
gctaactccg gcttctacaa ggagttctcc tttcaggttg gcgagcgcat caccagtctc     240
tccctatggg gcaatggagc aggtacacgc agtggtgcca ttaggtttta caccagcacg     300
ggaagggagt tcttccacta catgacctct ggggcctga agcaagagta tccaattgat     360
gtagtggatg gcttgtgcgt aggcgtgaca ggaaggcacg gtaccgacat cgatgccttg     420
ggcttcatgt tcctacgcac catgacctcc gctcgcatgg tcgatgtgac gtatcctacc     480
ctgggcttcg atacggcagg cattgcgcca atcacgctgg actcctacag cgacgccaac     540
caatctggct ccatttcgaa gaattggtcg ttcgaaggca gccgagaggt gaccgtatcc     600
tcctcttgga gtgtcaccgc gggaattgaa tttcacgcca gcgtcaccgt ctcggcgggg     660
atcccgctgg tgctcgacgt ggatggcgag tttggatggg ccatcagtgc aagcgccacc     720
tacaccacca actcctcgga gactcgcacc cttaagtgga ataattccgg cgttttggag     780
cccggtcaat ggatctctct gcaggccgtc acgcggaagg gaaccatcaa catacccttac    840
caggccaaca tgcaaatcac cctccagaac ggcgtcattt tcacctacgc acttgctggt     900
cagtacgccg gagtggacta caccgatgtc caggttgtga tgacgggac caagaacgcc     960
ggtcacgtgt caaccaccgc tgccaaaggc acgactggta caactactgc tgctaggatg    1020
ggcgccctag ccaattccgt ccgccatgtc cgagcagcgt ctattcctag acctgtcaag    1080
ttcagtgcag gagcaactta catcaatgac accaccaaca atatcactca agaagttcac    1140
agtagtgcac ctactggtgt ggaagagctt acccttgtct ac                       1182
```

<210> SEQ ID NO 48
<211> LENGTH: 394
<212> TYPE: PRT
<213> ORGANISM: Adiantum raddianum

<400> SEQUENCE: 48

```
Met Ser Ile Tyr Gln Thr Pro Val Ser Leu Ile Gly Gly Gln Gly Gly
1               5                   10                  15

Thr Ala Phe Thr Tyr Asn Ala Gly Glu Ser Gly Arg Val Leu Arg Arg
            20                  25                  30

Ile Gly Val Trp Ala Val Asp Ser Ala Leu Arg Gly Ile Arg Val Trp
        35                  40                  45
```

Trp Thr Gly Leu Asp Ser Pro Leu Thr Tyr Gly Thr Ala Asn Ser Gly
     50                  55                  60

Phe Tyr Lys Glu Phe Ser Phe Gln Val Gly Glu Arg Ile Thr Ser Leu
 65                  70                  75                  80

Ser Leu Trp Gly Asn Gly Ala Gly Thr Arg Ser Gly Ala Ile Arg Phe
                 85                  90                  95

Tyr Thr Ser Thr Gly Arg Glu Phe Phe His Tyr Met Thr Ser Trp Gly
             100                 105                 110

Leu Lys Gln Glu Tyr Pro Ile Asp Val Val Asp Gly Leu Cys Val Gly
         115                 120                 125

Val Thr Gly Arg His Gly Thr Asp Ile Asp Ala Leu Gly Phe Met Phe
130                 135                 140

Leu Arg Thr Met Thr Ser Ala Arg Met Val Asp Val Thr Tyr Pro Thr
145                 150                 155                 160

Leu Gly Phe Asp Thr Ala Gly Ile Ala Pro Ile Thr Leu Asp Ser Tyr
                 165                 170                 175

Ser Asp Ala Asn Gln Ser Gly Ser Ile Ser Lys Asn Trp Ser Phe Glu
             180                 185                 190

Gly Ser Arg Glu Val Thr Val Ser Ser Trp Ser Val Thr Ala Gly
         195                 200                 205

Ile Glu Phe His Ala Ser Val Thr Val Ser Ala Gly Ile Pro Leu Val
210                 215                 220

Leu Asp Val Asp Gly Glu Phe Gly Trp Ala Ile Ser Ala Ser Ala Thr
225                 230                 235                 240

Tyr Thr Thr Asn Ser Ser Glu Thr Arg Thr Leu Lys Trp Asn Asn Ser
                 245                 250                 255

Gly Val Leu Glu Pro Gly Gln Trp Ile Ser Leu Gln Ala Val Thr Arg
             260                 265                 270

Lys Gly Thr Ile Asn Ile Pro Tyr Gln Ala Asn Met Gln Ile Thr Leu
         275                 280                 285

Gln Asn Gly Val Ile Phe Thr Tyr Ala Leu Ala Gly Gln Tyr Ala Gly
290                 295                 300

Val Asp Tyr Thr Asp Val Gln Val Asn Asp Gly Thr Lys Asn Ala
305                 310                 315                 320

Gly His Val Ser Thr Thr Ala Ala Lys Gly Thr Thr Gly Thr Thr Thr
                 325                 330                 335

Ala Ala Arg Met Gly Ala Leu Ala Asn Ser Val Arg His Val Arg Ala
             340                 345                 350

Ala Ser Ile Pro Arg Pro Val Lys Phe Ser Ala Gly Ala Thr Tyr Ile
         355                 360                 365

Asn Asp Thr Thr Asn Asn Ile Thr Gln Glu Val His Ser Ser Ala Pro
370                 375                 380

Thr Gly Val Glu Glu Leu Thr Leu Val Tyr
385                 390

<210> SEQ ID NO 49
<211> LENGTH: 1190
<212> TYPE: DNA
<213> ORGANISM: Adiantum raddianum

<400> SEQUENCE: 49
atgtcgactt gtccatcttt caaacacccg tgagcctgat cggaggacaa ggcggaacgg    60
cgttcacgta caatgcaggc gagagcgggc gcgtcttgag gaggattggg gtgtgggccg   120

```
ttgactcggc gttgcgaggc atccgagtgt ggtggacagg cctggattcc cccttactt      180 acggcactgc taactccggc ttctacaagg agttctcctt tcaggttggc gagcgcatca      240
ccagtctctc cctatggggc aatggagcag gtacacgcag tggtgccatt aggttttaca      300
ccagcacggg aagggagttc ttccactaca tgacctcttg gggcctgaag caagagtatc      360
caattgatgt agtggatggc ttgtgcgtag gcgtgacagg aaggcacggt accgacatcg      420
atgccttggg cttcatgttc ctacgcacca tgacctccgc tcgcatggtc gatgtgacgt      480
atcctaccct gggcttcgat acggcaggca ttgcgccaat cacgctggac tcctacagcg      540
acgccaacca atctggctcc atttcgaaga attggtcgtt cgaaggcagc cgagaggtga      600
ccgtatcctc ctcttggagt gtcaccgcgg gaattgaatt tcacgccagc gtcaccgtct      660
cggcggggat cccgctggtg ctcgacgtgg atggcgagtt tggatgggcc atcagtgcaa      720
gcgccaccta caccaccaac tcctcggaga ctcgcaccct taagtggaat aattccggcg      780
ttttggagcc cggtcaatgg atctctctgc aggccgtcac gcggaaggga accatcaaca      840
taccttacca ggccaacatg caaatcaccc tccagaacgg cgtcattttc acctacgcac      900
ttgctggtca gtacgccgga gtggactaca ccgatgtcca ggttgtgaat gacgggacca      960
agaacgccgg tcacgtgtca accaccgctg ccaaaggcac gactggtaca actactgctg     1020
ctaggatggg cgccctagcc aattccgtcc gccatgtccg agcagcgtct attcctagac     1080
ctgtcaagtt cagtgcagga gcaacttaca tcaatgacac caccaacaat atcactcaag     1140
aagttcacag tagtgcacct actggtgtgg aagagcttac ccttgtctac                 1190

<210> SEQ ID NO 50
<211> LENGTH: 396
<212> TYPE: PRT
<213> ORGANISM: Adiantum raddianum

<400> SEQUENCE: 50

Met Ser Thr Ala Ile Phe Gln Thr Pro Val Ser Leu Ile Gly Gly Gln
1               5                   10                  15

Gly Gly Thr Ala Phe Thr Tyr Asn Ala Gly Glu Ser Gly Arg Val Leu
            20                  25                  30

Arg Arg Ile Gly Val Trp Ala Val Asp Ser Ala Leu Arg Gly Ile Arg
        35                  40                  45

Val Trp Trp Thr Gly Leu Asp Ser Pro Leu Thr Tyr Gly Thr Ala Asn
    50                  55                  60

Ser Gly Phe Tyr Lys Glu Phe Ser Phe Gln Val Gly Glu Arg Ile Thr
65                  70                  75                  80

Ser Leu Ser Leu Trp Gly Asn Gly Ala Gly Thr Arg Ser Gly Ala Ile
                85                  90                  95

Arg Phe Tyr Thr Ser Thr Gly Arg Glu Phe Phe His Tyr Met Thr Ser
            100                 105                 110

Trp Gly Leu Lys Gln Glu Tyr Pro Ile Asp Val Asp Gly Leu Cys
        115                 120                 125

Val Gly Val Thr Gly Arg His Gly Thr Asp Ile Asp Ala Leu Gly Phe
    130                 135                 140

Met Phe Leu Arg Thr Met Thr Ser Ala Arg Met Val Asp Val Thr Tyr
145                 150                 155                 160

Pro Thr Leu Gly Phe Asp Thr Ala Gly Ile Ala Pro Ile Thr Leu Asp
                165                 170                 175

Ser Tyr Ser Asp Ala Asn Gln Ser Gly Ser Ile Ser Lys Asn Trp Ser
            180                 185                 190
```

```
Phe Glu Gly Ser Arg Glu Val Thr Val Ser Ser Trp Ser Val Thr
            195                 200                 205
Ala Gly Ile Glu Phe His Ala Ser Val Thr Val Ser Ala Gly Ile Pro
    210                 215                 220
Leu Val Leu Asp Val Asp Gly Glu Phe Gly Trp Ala Ile Ser Ala Ser
225                 230                 235                 240
Ala Thr Tyr Thr Thr Asn Ser Ser Glu Thr Arg Thr Leu Lys Trp Asn
                245                 250                 255
Asn Ser Gly Val Leu Glu Pro Gly Gln Trp Ile Ser Leu Gln Ala Val
            260                 265                 270
Thr Arg Lys Gly Thr Ile Asn Ile Pro Tyr Gln Ala Asn Met Gln Ile
        275                 280                 285
Thr Leu Gln Asn Gly Val Ile Phe Thr Tyr Ala Leu Ala Gly Gln Tyr
    290                 295                 300
Ala Gly Val Asp Tyr Thr Asp Val Gln Val Val Asn Asp Gly Thr Lys
305                 310                 315                 320
Asn Ala Gly His Val Ser Thr Thr Ala Ala Lys Gly Thr Thr Gly Thr
                325                 330                 335
Thr Thr Ala Ala Arg Met Gly Ala Leu Ala Asn Ser Val Arg His Val
            340                 345                 350
Arg Ala Ala Ser Ile Pro Arg Pro Val Lys Phe Ser Ala Gly Ala Thr
        355                 360                 365
Tyr Ile Asn Asp Thr Thr Asn Asn Ile Thr Gln Glu Val His Ser Ser
    370                 375                 380
Ala Pro Thr Gly Val Glu Glu Leu Thr Leu Val Tyr
385                 390                 395
```

```
<210> SEQ ID NO 51
<211> LENGTH: 1221
<212> TYPE: DNA
<213> ORGANISM: Cyathea australis

<400> SEQUENCE: 51
atgtctatct tcagacgac cgtgcatgtg ataggaggtc agggtggagg ggcgttctcg      60
tacaatgcag gcgcgagcgg gcgcgtcttg aggaggatcg gtgtgtgggc gggcggctgg    120
tacctgggag gcatccggtt gtggtggaca ggcctggatg actccattac ctacggcact    180
gctaactccg gctcctacag ggagttcacc ttcgaggatg gcgagcgcat caccagtctc    240
tccctctggg gcaacggagc aggtacacgc agtggtggca tcaggttccg caccaccggg    300
ggaagggagt tcttccacta catgacctct tggggcctcc agcaagagta cccaatagat    360
gtagcgtcgg gcttgtgcgt gggtgtcatc ggcaggcacg gggatcacat tgattccctg    420
ggcttcatgt tcctgcgcac catagcctcc gctcgcatga tcaatgtcag ctacccaacc    480
ctggacctgg agactgcagg cattgtgcca gtcacgctgg actccatgag cgacagcaac    540
aatgccggca ccatctccaa gaactggaca ttcggaggca gcagaagtgt gaccatatcc    600
tcctcctggg ctatcaccgc aggcattgag ctccatgcca gcatcactgt cacagccggg    660
atccccacgg tggcggaggt gcaagggaa tacggatggt ccatcagcag cagctccacc    720
tacaccacta gccatgagga gactcgcacc cttagctggg agaattccgg agtcttgcag    780
cccggcgagt ggatctctct gcaagccctc acacggagag gaaccatctc cctgccctac    840
caggctacca tgcaaatcac cctccagaac ggcgccctct tcacctatcc gatcaccgct    900
ctttacgccg gagtcgatta caccaacgtc cagattgtga gcacggggac cagacatcta    960
```

-continued

```
gattacgatc acgtgcgctc agctggcggc cgccgattag tatcggccat cagcaacaaa    1020
ggcagcttgc cgaccgctgc cactacttct gtgattgcgc cgccccgtta tgtccaccct    1080
gttaacatac cagcagtgcc ttatacgtct gtcattgaac cagtcaaagt tgtggccacg    1140
agagcagcac ctactagcat taatgacgac aacataaagc aggaacctct agtagctacc    1200
gaagagcgta cgcttgtata c                                              1221
```

<210> SEQ ID NO 52
<211> LENGTH: 407
<212> TYPE: PRT
<213> ORGANISM: Cyathea australis

<400> SEQUENCE: 52

```
Met Ser Ile Phe Gln Thr Thr Val His Val Ile Gly Gly Gln Gly Gly
1               5                   10                  15

Gly Ala Phe Ser Tyr Asn Ala Gly Ala Ser Gly Arg Val Leu Arg Arg
                20                  25                  30

Ile Gly Val Trp Ala Gly Gly Trp Tyr Leu Gly Gly Ile Arg Leu Trp
            35                  40                  45

Trp Thr Gly Leu Asp Asp Ser Ile Thr Tyr Gly Thr Ala Asn Ser Gly
50                  55                  60

Ser Tyr Arg Glu Phe Thr Phe Glu Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Arg Thr Thr Gly Gly Arg Glu Phe Phe His Tyr Met Thr Ser Trp Gly
            100                 105                 110

Leu Gln Gln Glu Tyr Pro Ile Asp Val Ala Ser Gly Leu Cys Val Gly
        115                 120                 125

Val Ile Gly Arg His Gly Asp His Ile Asp Ser Leu Gly Phe Met Phe
130                 135                 140

Leu Arg Thr Ile Ala Ser Ala Arg Met Ile Asn Val Ser Tyr Pro Thr
145                 150                 155                 160

Leu Asp Leu Glu Thr Ala Gly Ile Val Pro Val Thr Leu Asp Ser Met
                165                 170                 175

Ser Asp Ser Asn Asn Ala Gly Thr Ile Ser Lys Asn Trp Thr Phe Gly
            180                 185                 190

Gly Ser Arg Ser Val Thr Ile Ser Ser Trp Ala Ile Thr Ala Gly
        195                 200                 205

Ile Glu Leu His Ala Ser Ile Thr Val Thr Ala Gly Ile Pro Thr Val
    210                 215                 220

Ala Glu Val Gln Gly Glu Tyr Gly Trp Ser Ile Ser Ser Ser Ser Thr
225                 230                 235                 240

Tyr Thr Thr Ser His Glu Glu Thr Arg Thr Leu Ser Trp Glu Asn Ser
                245                 250                 255

Gly Val Leu Gln Pro Gly Glu Trp Ile Ser Leu Gln Ala Leu Thr Arg
            260                 265                 270

Arg Gly Thr Ile Ser Leu Pro Tyr Gln Ala Thr Met Gln Ile Thr Leu
        275                 280                 285

Gln Asn Gly Ala Leu Phe Thr Tyr Pro Ile Thr Ala Leu Tyr Ala Gly
    290                 295                 300

Val Asp Tyr Thr Asn Val Gln Ile Val Ser Thr Gly Arg His Leu
305                 310                 315                 320
```

```
Asp Tyr Asp His Val Arg Ser Ala Gly Gly Arg Arg Leu Val Ser Ala
            325                 330                 335

Ile Ser Asn Lys Gly Ser Leu Pro Thr Ala Ala Thr Thr Ser Val Ile
        340                 345                 350

Ala Pro Pro Arg Tyr Val His Pro Val Asn Ile Pro Ala Val Pro Tyr
    355                 360                 365

Thr Ser Val Ile Glu Pro Val Lys Val Val Ala Thr Arg Ala Ala Pro
370                 375                 380

Thr Ser Ile Asn Asp Asp Asn Ile Lys Gln Glu Pro Leu Val Ala Thr
385                 390                 395                 400

Glu Glu Arg Thr Leu Val Tyr
            405

<210> SEQ ID NO 53
<211> LENGTH: 1083
<212> TYPE: DNA
<213> ORGANISM: Lygodium flexuosum

<400> SEQUENCE: 53
atgtcgttgt atcagacacc cgtgacaata attgggggcc agggcggcaa ctcatttct      60 tacgagcaga gcagaaacgg gaagatcctg aggaagatcg gggtgtgggc gggcgaatgg     120
caactgcgag gcatccgcat ctggatgagc ggctccgaca gctcagtcac ctacggcaca     180
gccaatgtgg gctcttacaa ggagtacgag ttcaaggatg cgagcgcat acccgtttg      240 tctttatggg gcaatggtgc aggcacacgt tctggaggca ttagattcta caccacaaca     300
ggaggccagt ttttccatta catgacatct tggggcttaa agcaagagta cccaatcgat     360
gtggcatccg gtctttgtgt ggggatcttg gaagagcta atgctgatat tgatgcatta     420
gggttctatt tcctaaagtc catagcatct gctcgcatga tcaatgtaag ctaccctaca     480
ttgagcttag agacagctgg aattattccc gtcacgcttg attcatacag tgactccaat     540
aatgcaggct ctatttcaaa gaattggaca ttctctggta gtcgggaagt gaagatctca     600
tcatcatgga cggtcactac ggggatcgag tatcatgcca gtataactgt tcaagcaggg     660
attccccttg ttgcggaagt gtcaggagag tttggatggt cggtgagtgt cacaggaagc     720
tacacaacca cgcatgagga gactcgaacc cttagctggg atcaatccgg aacccttcaa     780
ccagggcagt ggatctccat ccaagctacc actcggagag gaaacatcac agtaccctac     840
cagggaacca tggagattac cctccagtcc ggccaagtct tttcataccc catctcctca     900
atgtattctg gcgtggatta taccagtgtc gaaataacca cacaggaac taaagcagca     960 aaccaagtcg atgatcaagc tgctgatcca agcctcacca ctacaactga taccaaggat    1020
ggtgaggtac ttgagcagcc agataaagaa gtccaagagt ctaaactcat ctatcctagc    1080
tga                                                                  1083

<210> SEQ ID NO 54
<211> LENGTH: 360
<212> TYPE: PRT
<213> ORGANISM: Lygodium flexuosum

<400> SEQUENCE: 54

Met Ser Leu Tyr Gln Thr Pro Val Thr Ile Ile Gly Gly Gln Gly Gly
1               5                   10                  15

Asn Ser Phe Ser Tyr Glu Gln Ser Arg Asn Gly Lys Ile Leu Arg Lys
            20                  25                  30

Ile Gly Val Trp Ala Gly Glu Trp Gln Leu Arg Gly Ile Arg Ile Trp
```

```
                35                  40                  45
Met Ser Gly Ser Asp Ser Ser Val Thr Tyr Gly Thr Ala Asn Val Gly
    50                  55                  60

Ser Tyr Lys Glu Tyr Glu Phe Lys Asp Gly Glu Arg Ile Thr Arg Leu
 65                  70                  75                  80

Ser Leu Trp Gly Asn Gly Ala Gly Thr Arg Ser Gly Gly Ile Arg Phe
                 85                  90                  95

Tyr Thr Thr Thr Gly Gly Gln Phe Phe His Tyr Met Thr Ser Trp Gly
                100                 105                 110

Leu Lys Gln Glu Tyr Pro Ile Asp Val Ala Ser Gly Leu Cys Val Gly
                115                 120                 125

Ile Leu Gly Arg Ala Asn Ala Asp Ile Asp Ala Leu Gly Phe Tyr Phe
                130                 135                 140

Leu Lys Ser Ile Ala Ser Ala Arg Met Ile Asn Val Ser Tyr Pro Thr
145                 150                 155                 160

Leu Ser Leu Glu Thr Ala Gly Ile Ile Pro Val Thr Leu Asp Ser Tyr
                165                 170                 175

Ser Asp Ser Asn Asn Ala Gly Ser Ile Ser Lys Asn Trp Thr Phe Ser
                180                 185                 190

Gly Ser Arg Glu Val Lys Ile Ser Ser Ser Trp Thr Val Thr Thr Gly
                195                 200                 205

Ile Glu Tyr His Ala Ser Ile Thr Val Gln Ala Gly Ile Pro Leu Val
                210                 215                 220

Ala Glu Val Ser Gly Glu Phe Gly Trp Ser Val Ser Val Thr Gly Ser
225                 230                 235                 240

Tyr Thr Thr Thr His Glu Glu Thr Arg Thr Leu Ser Trp Asp Gln Ser
                245                 250                 255

Gly Thr Leu Gln Pro Gly Gln Trp Ile Ser Ile Gln Ala Thr Thr Arg
                260                 265                 270

Arg Gly Asn Ile Thr Val Pro Tyr Gln Gly Thr Met Glu Ile Thr Leu
                275                 280                 285

Gln Ser Gly Gln Val Phe Ser Tyr Pro Ile Ser Ser Met Tyr Ser Gly
                290                 295                 300

Val Asp Tyr Thr Ser Val Glu Ile Thr Asn Thr Gly Thr Lys Ala Ala
305                 310                 315                 320

Asn Gln Val Asp Asp Gln Ala Ala Asp Pro Ser Leu Thr Thr Thr Thr
                325                 330                 335

Asp Thr Lys Asp Gly Glu Val Leu Glu Gln Pro Asp Lys Glu Val Gln
                340                 345                 350

Glu Ser Lys Leu Ile Tyr Pro Ser
                355                 360

<210> SEQ ID NO 55
<211> LENGTH: 1062
<212> TYPE: DNA
<213> ORGANISM: Platycerium bifurcatum

<400> SEQUENCE: 55
atgtcgctgg ttcagacacc cgtgtatgtc atcggagggc aaggaggcaa tgcgtttact      60
tacgatcaga gcagaaacgg gaggatcctg cggaggattg gggtgtgggc gggcgagtgg     120
caactgcgcg gaatccgcgt gtggatgacg ggcaccgaca ccccggccac tttcggcacg     180
gccacgggct cttacagtga ataccccttc gcggatggcg agcgcatcac ccgcttgtcc     240
ttgtggggca acgggctgg tacacgttca ggaggcatca gattctacac cacaacagga     300
```

```
ggttctttct tccataaaat gacatcttgg ggcttacaaa ccgagtatcc aatcgacgtg    360
gcatctggtc tttgtgtggg gatcatggga cgagctaatg ttgatgtgga ttcattgggt    420
gttttgttct taaggaccat agcatctgct cgtatgatca atgtaagcta ccctaccttg    480
ggcttagagc aagccggaat catccctgtt acacttgatt ccttcaatga ctccaacaat    540
gcaggtacta tttccaaaaa ttggactttc tcgggtagcc gaaccgtgac aatatcatca    600
tcatggtctc tcacttcagg gatagagaca catgcaagtg tgagcgtgca agcagggatc    660
cccatggtcg cagaagtgag tggagagtat ggatggtctg taagtgtatc tgggacctat    720
gcaaccactc aagaggaaag tcgaaccctg catgggacc aatctggaac cctacagcct    780
gggcaatgga tttcactcca agctaccact cgaagaggaa ccatcacatt ccctttcaa    840 gcaaccatgg aaatcacttt gcagtctgga acgatctttc aatatgccat ctcctcaatg    900
tactccggtg tggattatac tagtgtggat ataactaaca ctggaagtag agcattagat    960
caggttgagg tcaaaactac tgagcaacaa gttgaagggg tcgaggatca aaatgtacaa   1020
cctaataaag aagctaaaga gtgcacactc ctctttgctg aa                     1062
```

<210> SEQ ID NO 56
<211> LENGTH: 354
<212> TYPE: PRT
<213> ORGANISM: Platycerium bifurcatum

<400> SEQUENCE: 56

```
Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240
```

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Gln
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Gln Val Glu Gly Val Glu Asp
                325                 330                 335

Gln Asn Val Gln Pro Asn Lys Glu Ala Lys Glu Cys Thr Leu Leu Phe
            340                 345                 350

Ala Glu

<210> SEQ ID NO 57
<211> LENGTH: 1062
<212> TYPE: DNA
<213> ORGANISM: Platycerium bifurcatum

<400> SEQUENCE: 57

```
atgtcgctgg ttcagacacc cgtctatgtc atcggagggc aaggaggcaa tgcgttttct      60
tacgatcaga gcagaaacgg gaggatcctg cggaggatag gggtgtgggc gggcgagtgg     120
caactgcgcg aatccgcgt gtggatgacg ggcaccgaca ccccggccac ctttggcacg     180
gccacgggct cttatagtga atataccttc acggatggcg agcgcatcac ccgcttgtcc     240
ttgtgggca acggggctgg tacacgttct ggaggcatta gattctacac cacaacagga     300
ggttcttttt tccataaaat gacatcttgg ggcttacaga ccgagtatcc aatcgatgtg     360
gcatctggtc tttgtgtggg gatcatggga cgagctaatg ttgatgtgga ttcattgggt     420
gttttgttct taagaaccat agcatctgct cgtatgatca atgtaagcta ccctaccttg     480
ggcttagagc aagccggaat catccctgtt acccttgatt cgtacaatga ctccaacaat     540
gcaggtacta tttccaaaaa ttggactttc tcgggtagcc gaacagtgac aatatcatca     600
tcatggtcgc tcacttcagg gatagagaca catgcaagtg tgagcgtgca agcagggatc     660
cccatggttg cagaagtgag tggagagttt ggatggtctg ttagtgtatc tgggacctat     720
gcaaccactc aagaggaaag tcgaaccctca acttggaacc aatctggaac cctagagcct     780
gggcaatgga tctcactcca agctaccact cgaagaggaa ccatcacatt ccctttcaa     840
gcaaccatgg aaatcacttt gctgtctgga acgatctttc aatatgccat ctcctctatg     900
tactccggtg tggattatac tagtgtggat ataactaaca ctggaactag agcatcagat     960
catgttgagg tcgaagctac tgagcaacaa gtccaagggg tcaaagatca aagtgtacaa    1020
cctaataaag aagctaaaga gtgcacactc ctctttgctg aa                       1062
```

<210> SEQ ID NO 58
<211> LENGTH: 354
<212> TYPE: PRT
<213> ORGANISM: Platycerium bifurcatum

<400> SEQUENCE: 58

Met Ser Leu Val Gln Thr Pro Val Tyr Val Ile Gly Gly Gln Gly Gly
1               5                   10                  15

Asn Ala Phe Ser Tyr Asp Gln Ser Arg Asn Gly Arg Ile Leu Arg Arg
                20                  25                  30

Ile Gly Val Trp Ala Gly Glu Trp Gln Leu Arg Gly Ile Arg Val Trp
            35                  40                  45

Met Thr Gly Thr Asp Thr Pro Ala Thr Phe Gly Thr Ala Thr Gly Ser
 50                  55                  60

Tyr Ser Glu Tyr Thr Phe Thr Asp Gly Glu Arg Ile Thr Arg Leu Ser
 65                  70                  75                  80

Leu Trp Gly Asn Gly Ala Gly Thr Arg Ser Gly Ile Arg Phe Tyr
                85                  90                  95

Thr Thr Thr Gly Gly Ser Phe Phe His Lys Met Thr Ser Trp Gly Leu
                100                 105                 110

Gln Thr Glu Tyr Pro Ile Asp Val Ala Ser Gly Leu Cys Val Gly Ile
            115                 120                 125

Met Gly Arg Ala Asn Val Asp Val Asp Ser Leu Gly Val Leu Phe Leu
130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
            165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
            195                 200                 205

Glu Thr His Ala Ser Val Ser Val Gln Ala Gly Ile Pro Met Val Ala
210                 215                 220

Glu Val Ser Gly Glu Phe Gly Trp Ser Val Ser Val Ser Gly Thr Tyr
225                 230                 235                 240

Ala Thr Thr Gln Glu Glu Ser Arg Thr Leu Thr Trp Asn Gln Ser Gly
                245                 250                 255

Thr Leu Glu Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Leu
            275                 280                 285

Ser Gly Thr Ile Phe Gln Tyr Ala Ile Ser Ser Met Tyr Ser Gly Val
290                 295                 300

Asp Tyr Thr Ser Val Asp Ile Thr Asn Thr Gly Thr Arg Ala Ser Asp
305                 310                 315                 320

His Val Glu Val Glu Ala Thr Glu Gln Gln Val Gln Gly Val Lys Asp
                325                 330                 335

Gln Ser Val Gln Pro Asn Lys Glu Ala Lys Glu Cys Thr Leu Leu Phe
            340                 345                 350

Ala Glu

<210> SEQ ID NO 59
<211> LENGTH: 1062
<212> TYPE: DNA
<213> ORGANISM: Unknown
<220> FEATURE:
<223> OTHER INFORMATION: Mixture of Platycerium bifurcatum, Huperzia
      salvinioides, and Platycerium wandae

<400> SEQUENCE: 59
atgtcgctgg ttcagacacc cgtctatgtc atcggagggc aaggaggcaa tgcgttttct    60
tacgatcaga gcagaaacgg gaggatcctg cggaggatag gggtgtgggc gggcgagtgg   120

-continued

```
caactgcgcg gaatccgcgt gtggatgacg ggcaccgaca ccccggccac tttcggcacg      180
gccacgggct cttacagtga atataccttc gcggatggcg agcgcatcac ccgcttgtcc      240
ttgtggggca acgggctgg tacacgttca ggaggcatca gattctacac cacaacagga      300
ggttctttct tccataaaat gacatcttgg ggcttacaaa ccgagtatcc aatcgacgtg      360
gcatctggtc tttgtgtggg gatcatggga cgagctaatg ttgatgtgga ttcattgggt      420
gttttgttct taaggaccat agcatctgct cgtatgatca atgtaagcta ccctaccttg      480
ggcttagagc aagccggaat catccctgtt acacttgatt ccttcaatga ctccaacaat      540
gcaggtacta tttccaaaaa ttggactttc tcgggtagcc gaaccgtgac aatatcatca      600
tcatggtctc tcacttcagg gatagagaca catgcaagtg tgagcgtgca agcagggatc      660
cccatggtcg cagaagtgag tggagagtat ggatggtctg taagtgtatc tgggacctat      720
gcaaccactc aagaggaaag tcgaaccta gcatgggacc aatctggaac cctacagcct      780
gggcaatgga tttcactcca agctaccact cgaagaggaa ccatcacatt acccttcaa      840 gcaaccatgg aaatcacttt gcagtctgga acgatctttc aatatgccat ctcctcaatg      900
tactccggtg tggattatac tagtgtggat ataactaaca ctggaagtag agcattagat      960
caggttgagg tcaaaactac tgagcaacaa gttgaagggg tcgaggatca aaatgtacaa     1020
cctaataaag aagctaaaga gtgcacactc ctctttgctg aa                       1062
```

<210> SEQ ID NO 60
<211> LENGTH: 354
<212> TYPE: PRT
<213> ORGANISM: Unknown
<220> FEATURE:
<223> OTHER INFORMATION: Mixture of Platycerium bifurcatum, Huperzia
      salvinioides, and Platycerium wandae

<400> SEQUENCE: 60

```
Met Ser Leu Val Gln Thr Pro Val Tyr Val Ile Gly Gly Gln Gly Gly
1               5                  10                  15

Asn Ala Phe Ser Tyr Asp Gln Ser Arg Asn Gly Arg Ile Leu Arg Arg
                20                  25                  30

Ile Gly Val Trp Ala Gly Glu Trp Gln Leu Arg Gly Ile Arg Val Trp
            35                  40                  45

Met Thr Gly Thr Asp Thr Pro Ala Thr Phe Gly Thr Ala Thr Gly Ser
        50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190
```

Ser Arg Thr Val Thr Ile Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Gln
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Gln Val Gly Val Glu Asp
                325                 330                 335

Gln Asn Val Gln Pro Asn Lys Glu Ala Lys Glu Cys Thr Leu Leu Phe
            340                 345                 350

Ala Glu

<210> SEQ ID NO 61
<211> LENGTH: 1062
<212> TYPE: DNA
<213> ORGANISM: Unknown
<220> FEATURE:
<223> OTHER INFORMATION: Mixture of Platycerium bifurcatum, Huperzia
      salvinioides, and Platycerium wandae

<400> SEQUENCE: 61
atgtcgctgg ttcagacacc cgtgtatgtc atcggagggc aaggaggcaa tgcgtttact      60
tacgatcaga gcagaaacgg gaggatcctg cggaggattg gggtgtgggc gggcgagtgg     120
caactgcgcg gaatccgcgt gtggatgacg ggcaccgaca ccccggccac tttcggcacg     180
gccacgggct cttacagtga atataccttc gcggatggcg agcgcatcac ccgcttgtcc     240
ttgtggggca acgggctgg tacacgttca ggaggcatca gattctacac acaacagga      300 ggttcttct  tccataaaat gacatcttgg ggcttacaaa ccgagtatcc aatcgacgtg     360
gcatctggtc tttgtgtggg gatcatggga cgagctaatg ttgatgtgga ttcattgggt     420
gttttgttct taaggaccat agcatctgct cgtatgatca atgtaagcta ccctaccttg     480
ggcttagagc aagccggaat catccctgtt acacttgatt ccttcaatga ctccaacaat     540
gcaggtacta tttccaaaaa ttggactttc tcgggtagcc gaaccgtgac aatatcatca     600
tcatggtctc tcacttcagg gatagagaca catgcaagtg tgagcgtgca agcagggatc     660
cccatggtcg cagaagtgag tggagagtat ggatggtctg taagtgtatc tgggacctat     720
gcaaccactc aagaggaaag tcgaacccta gcatgggacc aatctggaac cctacagcct     780
gggcaatgga tttcactcca agctaccact caaagaggaa ccatcacatt acccttcaa      840 gcaaccatgg aaatcacttt gcagtctgga acgatctttc aatatgccat ctcctcaatg     900
tactccggtg tggattatac tagtgtggat ataactaaca ctggaagtag agcattagat     960
caggttgagg tcaaaactac tgagcaacaa gttgaagggg tcgaggatca aaatgtacaa    1020
cctaataaag aagctaaaga gtgcacactc ctctttgctg aa                       1062

<210> SEQ ID NO 62
<211> LENGTH: 354
<212> TYPE: PRT
<213> ORGANISM: Unknown
<220> FEATURE:
<223> OTHER INFORMATION: Mixture of Platycerium bifurcatum, Huperzia salvinioides, and Platycerium wandae

<400> SEQUENCE: 62

Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Gln Arg
            260                 265                 270

Gly Thr Ile Thr Leu Pro Phe Gln Ala Thr Met Glu Ile Thr Leu Gln
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Val Glu Gly Val Glu Asp
                325                 330                 335

Gln Asn Val Gln Pro Asn Lys Glu Ala Lys Glu Cys Thr Leu Leu Phe
            340                 345                 350

Ala Glu

<210> SEQ ID NO 63
<211> LENGTH: 1062
<212> TYPE: DNA
<213> ORGANISM: Platycerium bifurcatum

<400> SEQUENCE: 63

| | | | | | |
|---|---|---|---|---|---|
| atgtcgctgg | ttcagacacc | cgtgtatgtc | atcggagggc | aaggaggcaa | tgcgtttact | 60 |
| tacgatcaga | gcagaaacgg | gaggatcctg | cggaggattg | gggtgtgggc | gggcgagtgg | 120 |
| caactgcgcg | gaatccgcgt | gtggatgacg | ggcaccgaca | ccccggccac | tttcggcacg | 180 |
| gccacgggct | cttacagtga | atataccttc | gcggatggcg | agcgcatcac | ccgcttgtcc | 240 |
| ttgtggggca | acgggctgg | tacacgttca | ggaggcatca | gattctacac | cacaacagga | 300 |
| ggttcttttct | tccataaaat | gacatcttgg | ggcttacaaa | ccgagtatcc | aatcgacgtg | 360 |
| gcatctggtc | tttgtgtggg | gatcatggga | cgagctaatg | ttgatgtgga | ttcattgggt | 420 |
| gttttgttct | taaggaccat | agcatctgct | cgtatgatca | atgtaagcta | ccctaccttg | 480 |
| ggcttagagc | aagccggaat | catccctgtt | acacttgatt | ccttcaatga | ctccaacaat | 540 |
| gcaggtacta | tttccaaaaa | ttggactttc | tcgggtagcc | gaaccgtgac | aatatcatca | 600 |
| tcatggtctc | tcacttcagg | gatagagaca | catgcaagtg | tgagcgtgca | agcagggatc | 660 |
| cccatggtcg | cagaagtgag | tggagagtat | ggatggtctg | taagtgtatc | tgggacctat | 720 |
| gcaaccactc | aagaggaaag | tcgaacccta | gcatgggacc | aatctggaac | cctacagcct | 780 |
| gggcaatgga | tttcactcca | agctaccact | cgaagaggaa | ccatcacatt | accctttcaa | 840 |
| gcaaccatgg | aaatcacttt | gcagtctgga | acgatctttc | aatatgccat | ctcctcaatg | 900 |
| tactccggtg | tggattatac | tagtgtggat | ataactaaca | ctggaagtag | agcattagat | 960 |
| caggttgagg | tcaaaactac | tgagcaacaa | gttgaagggg | tcgaggatca | aaatgtacaa | 1020 |
| cctaataaag | aagctaaaga | gtgcacactc | ctctttgctg | aa | | 1062 |

<210> SEQ ID NO 64
<211> LENGTH: 354
<212> TYPE: PRT
<213> ORGANISM: Platycerium bifurcatum

<400> SEQUENCE: 64

Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
            165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
            195                 200                 205

Glu Thr His Ala Ser Val Ser Val Gln Ala Gly Ile Pro Met Val Ala
210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
            245                 250                 255

Thr Leu Gln Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Gln
            275                 280                 285

Ser Gly Thr Ile Phe Gln Tyr Ala Ile Ser Ser Met Tyr Ser Gly Val
            290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Val Glu Gly Val Glu Asp
            325                 330                 335

Gln Asn Val Gln Pro Asn Lys Glu Ala Lys Glu Cys Thr Leu Leu Phe
            340                 345                 350

Ala Glu

<210> SEQ ID NO 65
<211> LENGTH: 1062
<212> TYPE: DNA
<213> ORGANISM: Platycerium bifurcatum

<400> SEQUENCE: 65

```
atgtcgctgg ttcagacacc cgtctatgtc atcggagggc aaggaggcaa tgcgtttact     60
tacgatcaga gcagaaacgg gaggatcctg cggaggattg gggtgtgggc gggcgagtgg    120
caactgcgcg gaatccgcgt gtggatgacg ggcaccgaca ccccggccac tttcggcacg    180
gccacgggct cttacagtga atataccttc gcggatggcg agcgcatcac ccgcttgtcc    240
ttgtggggca acggggctgg tacacgttca ggaggcatca gattctacac cacaacagga    300
ggttctttct tccataaaat gacatcttgg ggcttacaaa ccgagtatcc aatcgacgtg    360
gcatctggtc tttgtgtggg gatcatggga cgagctaatg ttgatgtgga ttcattgggt    420
gttttgttct taaggaccat agcatctgct cgtatgatca atgtaagcta ccctaccttg    480
ggcttagagc aagccggaat catccctgtt acacttgatt ccttcaatga ctccaacaat    540
gcaggtacta tttccaaaaa ttggactttc tcgggtagcc gaaccgtgac aatatcatca    600
tcatggtctc tcacttcagg gatagagaca catgcaagtg tgagcgtgca agcagggatc    660
cccatggtcg cagaagtgag tggagagtat ggatggtctg taagtgtatc tgggacctat    720
gcaaccactc aagaggaaag tcgaacccta gcatgggacc aatctggaac cctacagcct    780
gggcaatgga tttcactcca agctaccact cgaagaggaa ccatcacatt accctttcaa    840
gcaaccatgg aaatcacttt gctgtctgga acgatctttc aatatgccat ctcctctatg    900
```

```
tactccggtg tggattatac tagtgtggat ataactaaca ctggaagtag agcattagat    960
caggttgagg tcaaaactac tgagcaacaa gttgaagggg tcgaggatca aaatgtacaa   1020
cctaataaag aagctaaaga gtgcacactc ctctttgctg aa                      1062
```

<210> SEQ ID NO 66
<211> LENGTH: 354
<212> TYPE: PRT
<213> ORGANISM: Platycerium bifurcatum

<400> SEQUENCE: 66

```
Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Leu
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Gln Val Glu Gly Val Glu Asp
                325                 330                 335

Gln Asn Val Gln Pro Asn Lys Glu Ala Lys Glu Cys Thr Leu Leu Phe
```

Ala Glu

<210> SEQ ID NO 67
<211> LENGTH: 1062
<212> TYPE: DNA
<213> ORGANISM: Platycerium bifurcatum

<400> SEQUENCE: 67

```
atgtcgctgg ttcagacacc cgtctatgtc atcggagggc aaggaggcaa tgcgttttct      60
tacgatcaga gcagaaacgg gaggatcctg cggaggatag gggtgtgggc gggcgagtgg     120
caactgcgcg gaatccgcgt gtggatgacg ggcaccgaca ccccggccac ctttggcacg     180
gccacgggct cttatagtga atataccttc acggatggcg agcgcatcac ccgcttgtcc     240
ttgtggggca acgggctgg tacacgttct ggaggcatta gattctacac cacaacagga     300
ggttcttttt tccataaaat gacatcttgg ggcttacaga ccgagtatcc aatcgatgtg     360
gcatctggtc tttgtgtggg gatcatggga cgagctaatg ttgatgtgga ttcattgggt     420
gttttgttct aagaaccat agcatctgct cgtatgatca atgtaagcta ccctaccttg     480
ggcttagagc aagccggaat catccctgtt acccttgatt cgtacaatga ctccaacaat     540
gcaggtacta tttccaaaaa ttggactttc tcgggtagcc gaaccgtgac aatatcatca     600
tcatggtctc tcacttcagg gatagagaca catgcaagtg tgagcgtgca agcagggatc     660
cccatggtcg cagaagtgag tggagagtat ggatggtctg taagtgtatc tgggacctat     720
gcaaccactc aagaggaaag tcgaacccta gcatgggacc aatctggaac cctacagcct     780
gggcaatgga tttcactcca agctaccact cgaagaggaa ccatcacatt accctttcaa     840
gcaaccatga aatcactttt gcagtctgga acgatctttc aatatgccat ctcctcaatg     900
tactccggtg tggattatac tagtgtggat ataactaaca ctggaagtag agcattagat     960
caggttgagg tcaaaactac tgagcaacaa gttgaagggg tcgaggatca aaatgtacaa    1020
cctaataaag aagctaaaga gtgcacactc ctctttgctg aa                       1062
```

<210> SEQ ID NO 68
<211> LENGTH: 354
<212> TYPE: PRT
<213> ORGANISM: Platycerium bifurcatum

<400> SEQUENCE: 68

```
Met Ser Leu Val Gln Thr Pro Val Tyr Val Ile Gly Gly Gln Gly Gly
1               5                   10                  15

Asn Ala Phe Ser Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Thr Asp Gly Glu Arg Ile Thr Arg Leu Ser
65                  70                  75                  80

Leu Trp Gly Asn Gly Ala Gly Thr Arg Ser Gly Ile Arg Phe Tyr
            85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125
```

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
                165                 170                 175

Asp Ser Asn Asn Ala Gly Thr Ile Ser Lys Asn Trp Thr Phe Ser Gly
                180                 185                 190

Ser Arg Thr Val Thr Ile Ser Ser Trp Ser Leu Thr Ser Gly Ile
                195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Arg Arg
                260                 265                 270

Gly Thr Ile Thr Leu Pro Phe Gln Ala Thr Met Glu Ile Thr Leu Gln
                275                 280                 285

Ser Gly Thr Ile Phe Gln Tyr Ala Ile Ser Ser Met Tyr Ser Gly Val
                290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Gln Val Glu Gly Val Glu Asp
                325                 330                 335

Gln Asn Val Gln Pro Asn Lys Glu Ala Lys Glu Cys Thr Leu Leu Phe
                340                 345                 350

Ala Glu

<210> SEQ ID NO 69
<211> LENGTH: 1062
<212> TYPE: DNA
<213> ORGANISM: Platycerium bifurcatum

<400> SEQUENCE: 69
atgtcgctgg ttcagacacc cgtctatgtc atcggagggc aaggaggcaa tgcgttttct      60
tacgatcaga gcagaaacgg gaggatcctg cggaggatag gggtgtgggc gggcgagtgg     120
caactgcgcg gaatccgcgt gtggatgacg ggcaccgaca ccccggccac ctttggcacg     180
gccacgggct cttatagtga atataccttc acggatggcg agcgcatcac ccgcttgtcc     240
ttgtggggca acgggctgg tacacgttct ggaggcatta gattctacac cacaacagga     300
ggttctttct tccataaaat gacatcttgg ggcttacaaa ccgagtatcc aatcgacgtg     360
gcatctggtc tttgtgtggg gatcatggga cgagctaatg ttgatgtgga ttcattgggt     420
gttttgttct taaggaccat agcatctgct cgtatgatca atgtaagcta ccctaccttg     480
ggcttagagc aagccggaat catccctgtt acacttgatt ccttcaatga ctccaacaat     540
gcaggtacta tttccaaaaa ttggactttc tcgggtagcc gaaccgtgac aatatcatca     600
tcatggtctc tcacttcagg gatagagaca catgcaagtg tgagcgtgca agcagggatc     660
cccatggtcg cagaagtgag tggagagtat ggatggtctg taagtgtatc tgggacctat     720
gcaaccactc aagaggaaag tcgaaccta gcatgggacc aatctggaac cctacagcct     780

```
gggcaatgga tttcactcca agctaccact cgaagaggaa ccatcacatt accctttcaa    840
gcaaccatgg aaatcacttt gcagtctgga acgatctttc aatatgccat ctcctcaatg    900
tactccggtg tggattatac tagtgtggat ataactaaca ctggaagtag agcattagat    960
caggttgagg tcaaaactac tgagcaacaa gttgaagggg tcgaggatca aaatgtacaa   1020
cctaataaag aagctaaaga gtgcacactc ctctttgctg aa                      1062
```

<210> SEQ ID NO 70
<211> LENGTH: 354
<212> TYPE: PRT
<213> ORGANISM: Platycerium bifurcatum

<400> SEQUENCE: 70

```
Met Ser Leu Val Gln Thr Pro Val Tyr Val Ile Gly Gly Gln Gly Gly
1               5                   10                  15

Asn Ala Phe Ser Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Thr Asp Gly Glu Arg Ile Thr Arg Leu Ser
65                  70                  75                  80

Leu Trp Gly Asn Gly Ala Gly Thr Arg Ser Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Gln
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Gln Val Glu Gly Val Glu Asp
```

Gln Asn Val Gln Pro Asn Lys Glu Ala Lys Glu Cys Thr Leu Leu Phe
        325                 330                 335
            340                 345                 350

Ala Glu

<210> SEQ ID NO 71
<211> LENGTH: 1062
<212> TYPE: DNA
<213> ORGANISM: Platycerium bifurcatum

<400> SEQUENCE: 71

| | | | | | |
|---|---|---|---|---|---|
| atgtcgctgg | ttcagacacc | cgtctatgtc | atcggagggc | aaggaggcaa | tgcgttttct | 60 |
| tacgatcaga | gcagaaacgg | gaggatcctg | cggaggatag | gggtgtgggc | gggcgagtgg | 120 |
| caactgcgcg | gaatccgcgt | gtggatgacg | ggcaccgaca | ccccggccac | ctttggcacg | 180 |
| gccacgggct | cttatagtga | atataccttc | acggatggcg | agcgcatcac | ccgcttgtcc | 240 |
| ttgtggggca | acgggctgg | tacacgttct | ggaggcatta | gattctacac | cacaacagga | 300 |
| ggttcttttt | tccataaaat | gacatcttgg | ggcttacaga | ccgagtatcc | aatcgatgtg | 360 |
| gcatctggtc | tttgtgtggg | gatcatggga | cgagctaatg | ttgatgtgga | ttcattgggt | 420 |
| gttttgttct | taagaaccat | agcatctgct | cgtatgatca | atgtaagcta | ccctaccttg | 480 |
| ggcttagagc | aagccggaat | catccctgtt | acccttgatt | cgtacaatga | ctccaacaat | 540 |
| gcaggtacta | tttccaaaaa | ttggactttc | tcgggtagcc | gaacagtgac | aatatcatca | 600 |
| tcatggtcgc | tcacttcagg | gatagagaca | catgcaagtg | tgagcgtgca | agcagggatc | 660 |
| cccatggttg | cagaagtgag | tggagagttt | ggatggtctg | ttagtgtatc | tgggacctat | 720 |
| gcaaccactc | aagaggaaag | tcgaacccta | acttggaacc | aatctggaac | cctagagcct | 780 |
| gggcaatgga | tctcactcca | agctaccact | cgaagaggaa | ccatcacatt | acccttcaa | 840 |
| gcaaccatgg | aaatcacttt | gctgtctgga | acgatctttc | aatatgccat | ctcctcaatg | 900 |
| tactccggtg | tggattatac | tagtgtggat | ataactaaca | ctggaagtag | agcattagat | 960 |
| caggttgagg | tcaaaactac | tgagcaacaa | gttgaagggg | tcgaggatca | aaatgtacaa | 1020 |
| cctaataaag | aagctaaaga | gtgcacactc | ctctttgctg | aa | | 1062 |

<210> SEQ ID NO 72
<211> LENGTH: 354
<212> TYPE: PRT
<213> ORGANISM: Platycerium bifurcatum

<400> SEQUENCE: 72

Met Ser Leu Val Gln Thr Pro Val Tyr Val Ile Gly Gly Gln Gly Gly
1               5                   10                  15

Asn Ala Phe Ser Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Thr Asp Gly Glu Arg Ile Thr Arg Leu Ser
65                  70                  75                  80

Leu Trp Gly Asn Gly Ala Gly Thr Arg Ser Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
            165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
            195                 200                 205

Glu Thr His Ala Ser Val Ser Val Gln Ala Gly Ile Pro Met Val Ala
    210                 215                 220

Glu Val Ser Gly Glu Phe Gly Trp Ser Val Ser Val Ser Gly Thr Tyr
225                 230                 235                 240

Ala Thr Thr Gln Glu Glu Ser Arg Thr Leu Thr Trp Asn Gln Ser Gly
            245                 250                 255

Thr Leu Glu Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Leu
            275                 280                 285

Ser Gly Thr Ile Phe Gln Tyr Ala Ile Ser Ser Met Tyr Ser Gly Val
            290                 295                 300

Asp Tyr Thr Ser Val Asp Ile Thr Asn Thr Gly Ser Arg Ala Leu Asp
305                 310                 315                 320

Gln Val Glu Val Lys Thr Thr Glu Gln Gln Val Glu Gly Val Glu Asp
            325                 330                 335

Gln Asn Val Gln Pro Asn Lys Glu Ala Lys Glu Cys Thr Leu Leu Phe
            340                 345                 350

Ala Glu

<210> SEQ ID NO 73
<211> LENGTH: 1062
<212> TYPE: DNA
<213> ORGANISM: Platycerium bifurcatum

<400> SEQUENCE: 73

| | | |
|---|---|---|
| atgtcgctgg ttcagacacc cgtgtatgtc atcggagggc aaggaggcaa tgcgtttact | 60 |
| tacgatcaga gcagaaacgg gaggatcctg cggaggattg gggtgtgggc gggcgagtgg | 120 |
| caactgcgcg gaatccgcgt gtggatgacg ggcaccgaca ccccggccac tttcggcacg | 180 |
| gccacgggct cttacagtga atataccttc gcggatggcg agcgcatcac ccgcttgtcc | 240 |
| ttgtggggca acggggctgg tacacgttca ggaggcatca gattctacac cacaacagga | 300 |
| ggttcttcct tccataaaat gacatcttgg ggcttacaaa ccgagtatcc aatcgacgtg | 360 |
| gcatctggtc tttgtgtggg gatcatggga cgagctaatg ttgatgtgga ttcattgggt | 420 |
| gttttgttct taaggaccat agcatctgct cgtatgatca atgtaagcta ccctaccttg | 480 |
| ggcttagagc aagccggaat catccctgtt acacttgatt ccttcaatga ctccaacaat | 540 |
| gcaggtacta tttccaaaaa ttggactttt cgggtagcc gaaccgtgac aatatcatca | 600 |
| tcatggtctc tcacttcagg gatagagaca catgcaagtg tgagcgtgca agcagggatc | 660 |
| cccatggtcg cagaagtgag tggagagtat ggatggtctg taagtgtatc tgggacctat | 720 |

```
gcaaccactc aagaggaaag tcgaacccta gcatgggacc aatctggaac cctacagcct    780
gggcaatgga tttcactcca agctaccact cgaagaggaa ccatcacatt acccttcaa    840 gcaaccatgg aaatcacttt gcagtctgga acgatctttc aatatgtcat ctcctcaatg    900
tactccggtg tggattatac tagtgtggat ataactaaca ctggaagtag agcattagat    960
caggttgagg tcaaaactac tgagcaacaa gttgaagggg tcgaggatca aaatgtacaa   1020
cctaataaag aagctaaaga gtgcacactc ctctttgctg aa                      1062
```

<210> SEQ ID NO 74
<211> LENGTH: 354
<212> TYPE: PRT
<213> ORGANISM: Platycerium bifurcatum

<400> SEQUENCE: 74

```
Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Tyr Gly Trp Ser Val Ser Val Ser Gly Thr Tyr
225                 230                 235                 240

Ala Thr Thr Gln Glu Glu Ser Arg Thr Leu Ala Trp Asp Gln Ser Gly
                245                 250                 255

Thr Leu Gln Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Gln
        275                 280                 285

Ser Gly Thr Ile Phe Gln Tyr Val Ile Ser Ser Met Tyr Ser Gly Val
    290                 295                 300

Asp Tyr Thr Ser Val Asp Ile Thr Asn Thr Gly Ser Arg Ala Leu Asp
```

```
                305                 310                 315                 320
Gln Val Glu Val Lys Thr Thr Glu Gln Val Glu Gly Val Glu Asp
                    325                 330                 335
Gln Asn Val Gln Pro Asn Lys Glu Ala Lys Glu Cys Thr Leu Leu Phe
                    340                 345                 350
Ala Glu

<210> SEQ ID NO 75
<211> LENGTH: 1248
<212> TYPE: DNA
<213> ORGANISM: Polystichium tsus-simense

<400> SEQUENCE: 75
atgtctatct accagacacc ggtttcagtg attggaggca cgggtggatc agcgttctct       60
tacaatgcag gcgcgagcgg gcgcatcttg aggaagatcg gagtgtgggc aggcgggtgg      120
tacctgggag gcatccgggt gtggtggaca ggccttgata ccctagtac  cttcggcacg      180
gccaatgtcg gctcctacaa ggaatacacc ttcgaggacg ggagcgcat  caccagtctc      240
tctctctggg caacggtgc  aggtacgcgt tctggtggca tcaggttccg caccaccaag      300
ggaagtgagt ttttccacta catgacatca tgggggttga agcaagagta cccaatggat      360
gtagcgtcgg gcctgtgcgt gggtgtgatc ggcaggcatg cgaacacat  cgattccctg      420
ggcttcatgt tcctgcgctc catagcctct gctcgcatga tcaatgtgag ctacccgacc      480
ttggccctcg agacggctgg tattgtgccc gtcacgctgg actccctgac cgacaacaac      540
aatgcgggta ccatcgccaa gaactgggca ttacgaggca gtcgagaggt gacaatgtcc      600
tccacctggt cggttacatc gggcatagag ctctatgcca gcgttaccgt gacggcgggg      660
gtccctacgg ttgccgaggt gcaagggag  ttcggatgga aagtgagcac cagcgcgacc      720
tactcgacca cttaccagga aactcggagc cttcagtggg agcagtcggg agtcttacag      780
cctggagaat ggatctctat acaagctctc acgaggagag gaaccataag cctgccctac      840
cagggcacca tgcaaattac cctccaatcg ggcactgtgt tcacctaccc aatcagtgct      900
ctgtacgctg gagtggatta ccagcgtt   gagatagtaa atctgggaac ttatgtatca      960
tccaataata tatcaggaga agctatcccc aggcaattac ccgtcagcag cttcagcttg     1020
ccggctacta atattgcaaa tggggcggcc tgggccggtg ctaatgcaaa tggggccttg     1080
gcggccggta ctcgagctct aatcaacggg gagcctatca aacctcatta cagtaatgtc     1140
cttccacaca ctctaaccac tccgcaggat caggatcatc agctgtctgt tatcaaacct     1200
cattacaaaa atatccttga acttgtccat cttctggatt ggccaact              1248

<210> SEQ ID NO 76
<211> LENGTH: 416
<212> TYPE: PRT
<213> ORGANISM: Polystichium tsus-simense

<400> SEQUENCE: 76

Met Ser Ile Tyr Gln Thr Pro Val Ser Val Ile Gly Gly Thr Gly Gly
1               5                   10                  15

Ser Ala Phe Ser Tyr Asn Ala Gly Ala Ser Gly Arg Ile Leu Arg Lys
                20                  25                  30

Ile Gly Val Trp Ala Gly Gly Trp Tyr Leu Gly Gly Ile Arg Val Trp
            35                  40                  45

Trp Thr Gly Leu Asp Thr Pro Ser Thr Phe Gly Thr Ala Asn Val Gly
        50                  55                  60
```

Ser Tyr Lys Glu Tyr Thr Phe Glu Asp Gly Glu Arg Ile Thr Ser Leu
65                  70                  75                  80

Ser Leu Trp Gly Asn Gly Ala Gly Thr Arg Ser Gly Gly Ile Arg Phe
            85                  90                  95

Arg Thr Thr Lys Gly Ser Glu Phe Phe His Tyr Met Thr Ser Trp Gly
                100                 105                 110

Leu Lys Gln Glu Tyr Pro Met Asp Val Ala Ser Gly Leu Cys Val Gly
                115                 120                 125

Val Ile Gly Arg His Gly Glu His Ile Asp Ser Leu Gly Phe Met Phe
130                 135                 140

Leu Arg Ser Ile Ala Ser Ala Arg Met Ile Asn Val Ser Tyr Pro Thr
145                 150                 155                 160

Leu Ala Leu Glu Thr Ala Gly Ile Val Pro Val Thr Leu Asp Ser Leu
                165                 170                 175

Thr Asp Asn Asn Asn Ala Gly Thr Ile Ala Lys Asn Trp Ala Leu Arg
                180                 185                 190

Gly Ser Arg Glu Val Thr Met Ser Ser Thr Trp Ser Val Thr Ser Gly
            195                 200                 205

Ile Glu Leu Tyr Ala Ser Val Thr Val Thr Ala Gly Val Pro Thr Val
210                 215                 220

Ala Glu Val Gln Gly Glu Phe Gly Trp Lys Val Ser Thr Ser Ala Thr
225                 230                 235                 240

Tyr Ser Thr Thr Tyr Gln Glu Thr Arg Ser Leu Gln Trp Glu Gln Ser
                245                 250                 255

Gly Val Leu Gln Pro Gly Glu Trp Ile Ser Ile Gln Ala Leu Thr Arg
            260                 265                 270

Arg Gly Thr Ile Ser Leu Pro Tyr Gln Gly Thr Met Gln Ile Thr Leu
            275                 280                 285

Gln Ser Gly Thr Val Phe Thr Tyr Pro Ile Ser Ala Leu Tyr Ala Gly
290                 295                 300

Val Asp Tyr Thr Ser Val Glu Ile Val Asn Leu Gly Thr Tyr Val Ser
305                 310                 315                 320

Ser Asn Asn Ile Ser Gly Glu Ala Ile Pro Arg Gln Leu Pro Val Ser
                325                 330                 335

Ser Phe Ser Leu Pro Ala Thr Asn Ile Ala Asn Gly Ala Ala Trp Ala
                340                 345                 350

Gly Ala Asn Ala Asn Gly Ala Leu Ala Ala Gly Thr Arg Ala Leu Ile
            355                 360                 365

Asn Gly Glu Pro Ile Lys Pro His Tyr Ser Asn Val Leu Pro His Thr
370                 375                 380

Leu Thr Thr Pro Gln Asp Gln Asp His Gln Leu Ser Val Ile Lys Pro
385                 390                 395                 400

His Tyr Lys Asn Ile Leu Glu Leu Val His Leu Leu Asp Trp Pro Thr
                405                 410                 415

<210> SEQ ID NO 77
<211> LENGTH: 1344
<212> TYPE: DNA
<213> ORGANISM: Polystichium tsus-simense

<400> SEQUENCE: 77
atgtctatct accagacacc ggtttcagtg attggaggca cgggtggatc agcgttctct     60
tacaatgcag gcgcgagcgg gcgcatcttg aggaagatcg agtgtgggc aggcgggtgg    120

```
tacctgggag gcatccgggt gtggtggaca ggccttgata cccctagtac cttcggcacg      180
gccaatgtcg gctcctacaa ggaatacacc ttcgaggacg gggagcgcat caccagtctc      240
tctctctggg gcaacggtgc aggtacgcgt tctggtggca tcaggttccg caccaccaag      300
ggaagtgagt ttttccacta catgacatca tgggggttga agcaagagta cccaatggat      360
gtagcgtcgg gcctgtgcgt gggtgtgatc ggcaggcatg gcgaacacat cgattccctg      420
ggcttcatgt tcctgcgctc catagcctct gctcgcatga tcaatgtgag ctacccgacc      480
ttggccctcg agacggctgg tattgtgccc gtcacgctgg actccctgac cgacaacaac      540
aatgcgggta ccatcgccaa gaactgggca ttacgaggca gtcgagaggt gacaatgtcc      600
tccacctggt cggttacatc gggcatagag ctctatgcca gcgttaccgt gacggcgggg      660
gtccctacgg ttgccgaggt gcaagggag ttcggatgga agtgagcac agcgcgacc        720 tactcgacca cttaccagga aactcggagc cttcagtggg agcagtcggg agtcttacag      780
cctggagaat ggatctctat acaagctctc acgaggagag gaaccataag cctgccctac      840
cagggcacca tgcaaattac cctccaatcg ggcactgtgt tcacctaccc aatcagtgct      900
ctgtacgctg gagtggatta caccagcgtt gagatagtaa atctgggaac ttatgtatca      960
tccaataata tatcaggaga agctatcccc aggcaattac ccgtcagcag cttcagcttg     1020
ccggctacta atattgcaaa tggggcggcc tgggccggtg ctaatgcaaa tggggccttg     1080
gcggccggta ctcgagctct aatcaacggg agcctatca aacctcatta cagtaatgtc      1140
cttccacaca ctctaaccac tccgcaggat caggatcatc agctgtctgt tatcaaacct     1200
cattacaaaa atatccttga tggggacaat actaattatc agccccagcc ccagccccag     1260
ggagtggtcg aagagcgtac acttgtgctt tagacttgtc catcttctgg attggccaac     1320
ttaattaatg tatgaaataa aagg                                            1344
```

<210> SEQ ID NO 78
<211> LENGTH: 430
<212> TYPE: PRT
<213> ORGANISM: Polystichium tsus-simense

<400> SEQUENCE: 78

```
Met Ser Ile Tyr Gln Thr Pro Val Ser Val Ile Gly Gly Thr Gly Gly
1               5                   10                  15

Ser Ala Phe Ser Tyr Asn Ala Gly Ala Ser Gly Arg Ile Leu Arg Lys
            20                  25                  30

Ile Gly Val Trp Ala Gly Gly Trp Tyr Leu Gly Gly Ile Arg Val Trp
        35                  40                  45

Trp Thr Gly Leu Asp Thr Pro Ser Thr Phe Gly Thr Ala Asn Val Gly
    50                  55                  60

Ser Tyr Lys Glu Tyr Thr Phe Glu Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Arg Thr Thr Lys Gly Ser Glu Phe Phe His Tyr Met Thr Ser Trp Gly
            100                 105                 110

Leu Lys Gln Glu Tyr Pro Met Asp Val Ala Ser Gly Leu Cys Val Gly
        115                 120                 125

Val Ile Gly Arg His Gly Glu His Ile Asp Ser Leu Gly Phe Met Phe
    130                 135                 140

Leu Arg Ser Ile Ala Ser Ala Arg Met Ile Asn Val Ser Tyr Pro Thr
145                 150                 155                 160
```

Leu Ala Leu Glu Thr Ala Gly Ile Val Pro Val Thr Leu Asp Ser Leu
              165                 170                 175

Thr Asp Asn Asn Asn Ala Gly Thr Ile Ala Lys Asn Trp Ala Leu Arg
            180                 185                 190

Gly Ser Arg Glu Val Thr Met Ser Ser Thr Trp Ser Val Thr Ser Gly
        195                 200                 205

Ile Glu Leu Tyr Ala Ser Val Thr Val Thr Ala Gly Val Pro Thr Val
    210                 215                 220

Ala Glu Val Gln Gly Glu Phe Gly Trp Lys Val Ser Thr Ser Ala Thr
225                 230                 235                 240

Tyr Ser Thr Thr Tyr Gln Glu Thr Arg Ser Leu Gln Trp Glu Gln Ser
                245                 250                 255

Gly Val Leu Gln Pro Gly Glu Trp Ile Ser Ile Gln Ala Leu Thr Arg
            260                 265                 270

Arg Gly Thr Ile Ser Leu Pro Tyr Gln Gly Thr Met Gln Ile Thr Leu
        275                 280                 285

Gln Ser Gly Thr Val Phe Thr Tyr Pro Ile Ser Ala Leu Tyr Ala Gly
    290                 295                 300

Val Asp Tyr Thr Ser Val Glu Ile Val Asn Leu Gly Tyr Val Ser
305                 310                 315                 320

Ser Asn Asn Ile Ser Gly Glu Ala Ile Pro Arg Gln Leu Pro Val Ser
                325                 330                 335

Ser Phe Ser Leu Pro Ala Thr Asn Ile Ala Asn Gly Ala Ala Trp Ala
            340                 345                 350

Gly Ala Asn Ala Asn Gly Ala Leu Ala Ala Gly Thr Arg Ala Leu Ile
        355                 360                 365

Asn Gly Glu Pro Ile Lys Pro His Tyr Ser Asn Val Leu Pro His Thr
    370                 375                 380

Leu Thr Thr Pro Gln Asp Gln Asp His Gln Leu Ser Val Ile Lys Pro
385                 390                 395                 400

His Tyr Lys Asn Ile Leu Asp Gly Asp Asn Thr Asn Tyr Gln Pro Gln
                405                 410                 415

Pro Gln Pro Gln Gly Val Val Glu Glu Arg Thr Leu Val Leu
            420                 425                 430

<210> SEQ ID NO 79
<211> LENGTH: 1242
<212> TYPE: DNA
<213> ORGANISM: Davallia fejeensis

<400> SEQUENCE: 79
atgtctatct atcagacacc catttcagtg atcggaggca cgggtggatc agccttctct     60
tacaatgcag gcgcgagcgg gcgcatcttg aggaagatcg gagtgtgggc gggcgggtgg    120
tacctgggag catccgggt gtggtggaca ggccttgata ccctagtac cttcggcacg      180 gccaatgtcg gctcctacaa ggaatacacc ttcgaggacg gggagcgcat caccagtctc    240
tctctctggg gcaacggtgc aggtacgcgt tctggtggca tcaggttccg caccaccaag    300
ggaagtgagt ttttccacta catgacatca tggggggttga aacaagagta cccaatcgat   360
gtagcggcgg gcctgtgcgt gggtgtgatc ggcaggcatg cgaacacat cgattccctg     420 ggcttcatgt tcctgcgctc catagcgtct gctcgcatga tcaatgtgag ctacccgacc    480
ttggccctcg agacggctgg tattgtgccc gtcacgctgg actccctgac cgacagcaac   540
aatgcaggta ccatctccaa gaactgggca ttgcgaggca gtcgagaggt gacgatgtcc   600

-continued

```
tccacctggt cggttacatc gggcatagag ctgtatgcca gcgtgaccgt gacggcgggg    660
gtccctacgg ttgccgaggt gcaagggag ttcggatgga gagtgagcac cagcgcgacc    720
tactcgacca ctcacacgga aactcgcacg cttcagtggg aacagtcggg agtgttacag    780
cctggagagt ggatctctct acaagctctg acgaggagag gaaacataag cctgccctac    840
cagggcacca tgcaaatcac cctgcaatcg ggcactgtgt ttacctaccc aatcagtgct    900
ctgtacgctg gagtggatta caccaacgtt gagatagtaa atctgggaac ttttgtagca    960
tccaataata tatcagccgg agaatttatc cccaggcaac ccatcagctt gccggcggct   1020
actactaata ctaatgcaaa tggggcctgg actaatgcag gggccttggc cggtactact   1080
cgagctgtaa tcaacgagga acccatcaaa cctcattaca ctagtaatca ggatcatcag   1140
ctgtctgtta tcaaacctca ttacaaaaat ataaatatcc aggatgggga caatactact   1200
tatcagcccc agggagtggt cgaagagcgc tcacttgtct tt                      1242
```

<210> SEQ ID NO 80
<211> LENGTH: 414
<212> TYPE: PRT
<213> ORGANISM: Davallia fejeensis

<400> SEQUENCE: 80

```
Met Ser Ile Tyr Gln Thr Pro Ile Ser Val Ile Gly Gly Thr Gly Gly
1               5                   10                  15

Ser Ala Phe Ser Tyr Asn Ala Gly Ala Ser Gly Arg Ile Leu Arg Lys
            20                  25                  30

Ile Gly Val Trp Ala Gly Gly Trp Tyr Leu Gly Gly Ile Arg Val Trp
        35                  40                  45

Trp Thr Gly Leu Asp Thr Pro Ser Thr Phe Gly Thr Ala Asn Val Gly
    50                  55                  60

Ser Tyr Lys Glu Tyr Thr Phe Glu Asp Gly Glu Arg Ile Thr Ser Leu
65                  70                  75                  80

Ser Leu Trp Gly Asn Gly Ala Gly Thr Arg Ser Gly Gly Ile Arg Phe
                85                  90                  95

Arg Thr Thr Lys Gly Ser Glu Phe Phe His Tyr Met Thr Ser Trp Gly
            100                 105                 110

Leu Lys Gln Glu Tyr Pro Ile Asp Val Ala Ala Gly Leu Cys Val Gly
        115                 120                 125

Val Ile Gly Arg His Gly Glu His Ile Asp Ser Leu Gly Phe Met Phe
    130                 135                 140

Leu Arg Ser Ile Ala Ser Ala Arg Met Ile Asn Val Ser Tyr Pro Thr
145                 150                 155                 160

Leu Ala Leu Glu Thr Ala Gly Ile Val Pro Val Thr Leu Asp Ser Leu
                165                 170                 175

Thr Asp Ser Asn Asn Ala Gly Thr Ile Ser Lys Asn Trp Ala Leu Arg
            180                 185                 190

Gly Ser Arg Glu Val Thr Met Ser Ser Thr Trp Ser Val Thr Ser Gly
        195                 200                 205

Ile Glu Leu Tyr Ala Ser Val Thr Val Thr Ala Gly Val Pro Thr Val
    210                 215                 220

Ala Glu Val Gln Gly Glu Phe Gly Trp Arg Val Ser Thr Ser Ala Thr
225                 230                 235                 240

Tyr Ser Thr Thr His Thr Glu Thr Arg Thr Leu Gln Trp Glu Gln Ser
                245                 250                 255
```

Gly Val Leu Gln Pro Gly Glu Trp Ile Ser Leu Gln Ala Leu Thr Arg
            260                 265                 270

Arg Gly Asn Ile Ser Leu Pro Tyr Gln Gly Thr Met Gln Ile Thr Leu
        275                 280                 285

Gln Ser Gly Thr Val Phe Thr Tyr Pro Ile Ser Ala Leu Tyr Ala Gly
    290                 295                 300

Val Asp Tyr Thr Asn Val Glu Ile Val Asn Leu Gly Thr Phe Val Ala
305                 310                 315                 320

Ser Asn Asn Ile Ser Ala Gly Glu Phe Ile Pro Arg Gln Pro Ile Ser
                325                 330                 335

Leu Pro Ala Ala Thr Thr Asn Thr Asn Ala Asn Gly Ala Trp Thr Asn
            340                 345                 350

Ala Gly Ala Leu Ala Gly Thr Thr Arg Ala Val Ile Asn Glu Glu Pro
        355                 360                 365

Ile Lys Pro His Tyr Thr Ser Asn Gln Asp His Gln Leu Ser Val Ile
    370                 375                 380

Lys Pro His Tyr Lys Asn Ile Asn Ile Gln Asp Gly Asp Asn Thr Thr
385                 390                 395                 400

Tyr Gln Pro Gln Gly Val Val Glu Glu Arg Ser Leu Val Phe
                405                 410

<210> SEQ ID NO 81
<211> LENGTH: 1059
<212> TYPE: DNA
<213> ORGANISM: Aglaomorpha meyeniana

<400> SEQUENCE: 81
atggcgctgt atcagacacc tgtgtctatt atcggagggc aaggtggcac atcgtttact      60
tatgatcaga gcccgaacgg gaagatcatg aggaagattg gggtttgggc tggcgagtgg     120
caactgcgtg gcatccgcat atgggtttct ggctccgacg acccaaccac ctttggcaca     180
gcctcgggct cttataatga gtatacattc gcggatggcg agaccatcac cagtttgtcc     240
ttgtggggca atggtgcagg tacacgctct ggagccatta gattctacac ctcaacagga     300
ggctcatttt tcccaaaaat gacgtcttgg ggcttaaaga cagagtatcc aattgatgtg     360
gcatcgggtc tttgtgtggg gatcatggga cgagctggtg atgacattga cgctttgggg     420
ttcttattcc taagaaccat aacatctgct cgtatgatca atgtaaccta cccaaccttg     480
ggcttagagg aagctgcaat tatccctgtc acacttgatt catacaatga cgctaataat     540
gcaggtacta tttccaagag ttggactttt tctggtagtc gaacagtgac agtatcagag     600
tcttggacgc tcactgcggg gatagaggta cacgctaccg tgagtgttca agcagggatc     660
cctcttgttg cagaggtgaa cggagagtat ggatggtcat tgagtacaac aggaagctat     720
gcaaccaccc aagaagagag ccgcacccta agttggaacc aatctggaac cttggagcca     780
gggcaatgga tttccatcca agctaccact cgaagaggaa ccataacatt accctaccaa     840
ggaaccatgg agatcaccct acagtctggc actaagtttc ataccccat atcctctaca     900
tacactggtg tggattacac tagtgttgac atagttagca ttggatctag agtattgaat     960
caagctaagg ttgaagctac taataaaaaa gctttagaag gagatccaaa tgtccagcct    1020
agtaaagaag ttcaagaatg caaactccta tatattgaa                            1059

<210> SEQ ID NO 82
<211> LENGTH: 353
<212> TYPE: PRT
<213> ORGANISM: Aglaomorpha meyeniana

<400> SEQUENCE: 82

```
Met Ala Leu Tyr Gln Thr Pro Val Ser Ile Ile Gly Gly Gln Gly Gly
1               5                   10                  15

Thr Ser Phe Thr Tyr Asp Gln Ser Pro Asn Gly Lys Ile Met Arg Lys
            20                  25                  30

Ile Gly Val Trp Ala Gly Glu Trp Gln Leu Arg Gly Ile Arg Ile Trp
        35                  40                  45

Val Ser Gly Ser Asp Asp Pro Thr Thr Phe Gly Thr Ala Ser Gly Ser
    50                  55                  60

Tyr Asn Glu Tyr Thr Phe Ala Asp Gly Glu Thr Ile Thr Ser Leu Ser
65                  70                  75                  80

Leu Trp Gly Asn Gly Ala Gly Thr Arg Ser Gly Ala Ile Arg Phe Tyr
                85                  90                  95

Thr Ser Thr Gly Gly Ser Phe Phe Pro Lys Met Thr Ser Trp Gly Leu
            100                 105                 110

Lys Thr Glu Tyr Pro Ile Asp Val Ala Ser Gly Leu Cys Val Gly Ile
        115                 120                 125

Met Gly Arg Ala Gly Asp Asp Ile Asp Ala Leu Gly Phe Leu Phe Leu
    130                 135                 140

Arg Thr Ile Thr Ser Ala Arg Met Ile Asn Val Thr Tyr Pro Thr Leu
145                 150                 155                 160

Gly Leu Glu Glu Ala Ala Ile Ile Pro Val Thr Leu Asp Ser Tyr Asn
                165                 170                 175

Asp Ala Asn Asn Ala Gly Thr Ile Ser Lys Ser Trp Thr Phe Ser Gly
            180                 185                 190

Ser Arg Thr Val Thr Val Ser Glu Ser Trp Thr Leu Thr Ala Gly Ile
        195                 200                 205

Glu Val His Ala Thr Val Ser Val Gln Ala Gly Ile Pro Leu Val Ala
    210                 215                 220

Glu Val Asn Gly Glu Tyr Gly Trp Ser Leu Ser Thr Thr Gly Ser Tyr
225                 230                 235                 240

Ala Thr Thr Gln Glu Glu Ser Arg Thr Leu Ser Trp Asn Gln Ser Gly
                245                 250                 255

Thr Leu Glu Pro Gly Gln Trp Ile Ser Ile Gln Ala Thr Thr Arg Arg
            260                 265                 270

Gly Thr Ile Thr Leu Pro Tyr Gln Gly Thr Met Glu Ile Thr Leu Gln
        275                 280                 285

Ser Gly Thr Lys Phe Gln Tyr Pro Ile Ser Ser Thr Tyr Thr Gly Val
    290                 295                 300

Asp Tyr Thr Ser Val Asp Ile Val Ser Ile Gly Ser Arg Val Leu Asn
305                 310                 315                 320

Gln Ala Lys Val Glu Ala Thr Asn Lys Lys Ala Leu Glu Gly Asp Pro
                325                 330                 335

Asn Val Gln Pro Ser Lys Glu Val Gln Glu Cys Lys Leu Leu Tyr Ile
            340                 345                 350

Glu
```

<210> SEQ ID NO 83
<211> LENGTH: 1059
<212> TYPE: DNA
<213> ORGANISM: Aglaomorpha meyeniana

<400> SEQUENCE: 83

```
atggcgctgt atcagacacc tgtgtctatt atcggagggc aaggtggcac atcgtttact      60
tatgatcaga gcccgaacgg gaagatcatg aggaagattg gggtttgggc tggcgagtgg     120
caactgcgtg gcatccgcat atgggtttct ggctccgacg acccaaccac ctttggcaca     180
gcctcgggct cttataatga gtatacattc gcggatggcg agaccatcac cagtttgtcc     240
ttgtggggca atggtgcagg tacacgctct ggagccatta gattctacac ctcaacagga     300
ggctcatttt tcccaaaaat gacgtcttgg gacttaaaga cagagtatcc aattgatgtg     360
gcatcgggtc tttgtgtggg gatcatggga cgagctggtg atgacattga cgctttgggg     420
ttcttattcc taagaaccat aacatctgct cgtatgatca atgtaaccta cccaaccttg     480
ggcttagagg aagctgcaat tatccctgtc acacttgatt catacaatga cgctaataat     540
gcaggtacta tttccaagag ttggactttt tctggtagtc gaacagtgac agtatcagag     600
tcttggacgc tcactgcggg gatagaggta cacgctaccg tgagtgttca agcagggatc     660
cctcttgttg cagaggtgaa cggagagtat ggatggtcat tgagtacaac aggaagctat     720
gcaaccaccc aagaagagag ccgcacccta agttggaacc aatctggaac cttggagcca     780
gggcaatgga tttccatcca agctaccact cgaagaggaa ccataacatt accctaccaa     840
ggaaccatgg agatcaccct acagtctggc actaagtttc aatacccat atcctctaca      900
tacactggtg tggattacac tagtgttgac atagttagca ttggatctag agtattgaat     960
caagctaagg ttgaagctac taataaaaaa gctttagaag gagatccaaa tgtccagcct    1020
agtaaagaag ttcaagaatg caaactccta tatattgaa                            1059
```

<210> SEQ ID NO 84
<211> LENGTH: 353
<212> TYPE: PRT
<213> ORGANISM: Aglaomorpha meyeniana

<400> SEQUENCE: 84

```
Met Ala Leu Tyr Gln Thr Pro Val Ser Ile Ile Gly Gly Gln Gly Gly
1               5                   10                  15

Thr Ser Phe Thr Tyr Asp Gln Ser Pro Asn Gly Lys Ile Met Arg Lys
                20                  25                  30

Ile Gly Val Trp Ala Gly Glu Trp Gln Leu Arg Gly Ile Arg Ile Trp
            35                  40                  45

Val Ser Gly Ser Asp Asp Pro Thr Thr Phe Gly Thr Ala Ser Gly Ser
        50                  55                  60

Tyr Asn Glu Tyr Thr Phe Ala Asp Gly Glu Thr Ile Thr Ser Leu Ser
65                  70                  75                  80

Leu Trp Gly Asn Gly Ala Gly Thr Arg Ser Gly Ala Ile Arg Phe Tyr
                85                  90                  95

Thr Ser Thr Gly Gly Ser Phe Phe Pro Lys Met Thr Ser Trp Asp Leu
            100                 105                 110

Lys Thr Glu Tyr Pro Ile Asp Val Ala Ser Gly Leu Cys Val Gly Ile
        115                 120                 125

Met Gly Arg Ala Gly Asp Asp Ile Asp Ala Leu Gly Phe Leu Phe Leu
    130                 135                 140

Arg Thr Ile Thr Ser Ala Arg Met Ile Asn Val Thr Tyr Pro Thr Leu
145                 150                 155                 160

Gly Leu Glu Glu Ala Ala Ile Ile Pro Val Thr Leu Asp Ser Tyr Asn
                165                 170                 175

Asp Ala Asn Asn Ala Gly Thr Ile Ser Lys Ser Trp Thr Phe Ser Gly
            180                 185                 190
```

```
Ser Arg Thr Val Thr Val Ser Glu Ser Trp Thr Leu Thr Ala Gly Ile
    195                 200                 205
Glu Val His Ala Thr Val Ser Val Gln Ala Gly Ile Pro Leu Val Ala
    210                 215                 220
Glu Val Asn Gly Glu Tyr Gly Trp Ser Leu Ser Thr Thr Gly Ser Tyr
225                 230                 235                 240
Ala Thr Thr Gln Glu Glu Ser Arg Thr Leu Ser Trp Asn Gln Ser Gly
                245                 250                 255
Thr Leu Glu Pro Gly Gln Trp Ile Ser Ile Gln Ala Thr Thr Arg Arg
            260                 265                 270
Gly Thr Ile Thr Leu Pro Tyr Gln Gly Thr Met Glu Ile Thr Leu Gln
            275                 280                 285
Ser Gly Thr Lys Phe Gln Tyr Pro Ile Ser Ser Thr Tyr Thr Gly Val
        290                 295                 300
Asp Tyr Thr Ser Val Asp Ile Val Ser Ile Gly Ser Arg Val Leu Asn
305                 310                 315                 320
Gln Ala Lys Val Glu Ala Thr Asn Lys Lys Ala Leu Glu Gly Asp Pro
                325                 330                 335
Asn Val Gln Pro Ser Lys Glu Val Gln Glu Cys Lys Leu Leu Tyr Ile
            340                 345                 350
Glu

<210> SEQ ID NO 85
<211> LENGTH: 1059
<212> TYPE: DNA
<213> ORGANISM: Aglaomorpha meyeniana

<400> SEQUENCE: 85
atggcgctgt atcagacacc tgtgtatgtc atcggagggc aaggtggcaa ctcgttcaca      60
tatgatcaga gcaggaacgg gaaggtcttg aggaagattg gtgtgtgggc tggtgagtgg     120
caactcgcgc gtatccgggt atggatgtct ggttccgata gcccagccac cttcggcaca     180
gcctcgggct cttataatga gtatacattt gcagatggtg agcgcatcac ccgtttgtcc     240
ttgtggggca atggtgctgg tacacgttct ggggcatta gattctacac cacgactgga     300
ggctcatttt tgctaaaat gacatcttgg ggcttacaaa ctgagtatcc aatcgatgtg     360
gcatctggtc tttgtgttgg gatactggga cgagctaatg ttgacattga ttcattgggt     420
ttcatgttcc ttcgaaccat agcatctgct cgtatgatca atgtaagtta cccaacattg     480
ggcttagagc aagctggaat tgtgcctgtc acgcttgatt cgtacaacga ttccaacaat     540
gcaggtacaa tttccaagaa ttggactttc tccggaagtc gaacagtgac aatatcatct     600
tcatggacgc tcacttcggg catagaggca catgctactg tgagtgttca agcggggatc     660
cccttggttg cagaagtgag cggagagttt ggatggtcat taagtgttac aggaagctac     720
acaaccaccc aagaggagag tcgaacactc acgtggaacc aatccggaac cttagagcca     780
gggcaatgga tttccctcca agcgaccact cgtaggta ccatcaccttacc ctatcaa     840 gggaccatgg agataactct acagtctgga actgtatttc aatacccat ctcttctatg     900 tatgccggtg tggattatac tagtgttgac attaccaaca ctggaactag cattgaat     960 cgggttgaga ctgaagctat tgatcaacaa gcccgtgaag agaccagaa tgtccaacct    1020 agtaaagacg tccaggaatg caaactcctc tttactgat                          1059

<210> SEQ ID NO 86
```

```
<211> LENGTH: 353
<212> TYPE: PRT
<213> ORGANISM: Aglaomorpha meyeniana

<400> SEQUENCE: 86

Met Ala Leu Tyr Gln Thr Pro Val Tyr Val Ile Gly Gly Gln Gly Gly
1               5                   10                  15

Asn Ser Phe Thr Tyr Asp Gln Ser Arg Asn Gly Lys Val Leu Arg Lys
            20                  25                  30

Ile Gly Val Trp Ala Gly Glu Trp Gln Leu Arg Gly Ile Arg Val Trp
        35                  40                  45

Met Ser Gly Ser Asp Ser Pro Ala Thr Phe Gly Thr Ala Ser Gly Ser
    50                  55                  60

Tyr Asn Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe Ala Lys Met Thr Ser Trp Gly Leu
            100                 105                 110

Gln Thr Glu Tyr Pro Ile Asp Val Ala Ser Gly Leu Cys Val Gly Ile
        115                 120                 125

Leu Gly Arg Ala Asn Val Asp Ile Asp Ser Leu Gly Phe Met Phe Leu
130                 135                 140

Arg Thr Ile Ala Ser Ala Arg Met Ile Asn Val Ser Tyr Pro Thr Leu
145                 150                 155                 160

Gly Leu Glu Gln Ala Gly Ile Val Pro Val Thr Leu Asp Ser Tyr Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Trp Thr Leu Thr Ser Gly Ile
        195                 200                 205

Glu Ala His Ala Thr Val Ser Val Gln Ala Gly Ile Pro Leu Val Ala
    210                 215                 220

Glu Val Ser Gly Glu Phe Gly Trp Ser Leu Ser Val Thr Gly Ser Tyr
225                 230                 235                 240

Thr Thr Thr Gln Glu Glu Ser Arg Thr Leu Thr Trp Asn Gln Ser Gly
                245                 250                 255

Thr Leu Glu Pro Gly Gln Trp Ile Ser Leu Gln Ala Thr Thr Arg Arg
            260                 265                 270

Gly Thr Ile Thr Leu Pro Tyr Gln Gly Thr Met Glu Ile Thr Leu Gln
        275                 280                 285

Ser Gly Thr Val Phe Gln Tyr Pro Ile Ser Ser Met Tyr Ala Gly Val
    290                 295                 300

Asp Tyr Thr Ser Val Asp Ile Thr Asn Thr Gly Thr Arg Ala Leu Asn
305                 310                 315                 320

Arg Val Glu Thr Glu Ala Ile Asp Gln Gln Ala Arg Glu Gly Asp Gln
                325                 330                 335

Asn Val Gln Pro Ser Lys Asp Val Gln Glu Cys Lys Leu Leu Phe Thr
            340                 345                 350

Asp

<210> SEQ ID NO 87
<211> LENGTH: 1098
<212> TYPE: DNA
<213> ORGANISM: Aglaomorpha meyeniana
```

<400> SEQUENCE: 87

```
atggcgctgt atcagacacc cgtgtatgtc atcggagggc aaggaggcaa tgcgtttact      60
tacgatcaga gcagaaacgg gaggatcctg cggaggattg gggtgtgggc gggcgagtgg     120
caactgcgcg gaatccgcgt gtggatgacg ggcaccgaca ccccggccac tttcggcacg     180
gccacgggct cttacagtga atataccttc gcggatggcg agcgcatcac ccgcttgtcc     240
ttgtggggca acgggctgg tacacgttca ggaggcatca gattctacac cacaacagga     300
ggttctttct tccataaaat gacatcttgg ggcttacaaa ccgagtatcc aatcgacgtg     360
gcatctggtc tttgtgtggg gatcatggga cgagctaatg ttgatgtgga ttcattgggt     420
gttttgttct taaggaccat agcatctgct cgtatgatca atgtaagcta ccctaccttg     480
ggcttagagc aagccggaat catccctgtt acacttgatt ccttcaatga ctccaacaat     540
gcaggtacta tttccaaaaa ttggactttc tcgggtagcc gaaccgtgac aatatcatca     600
tcatggtctc tcacttcagg gatagagaca catgcaagtg tgagcgtgca agcagggatc     660
cccatggtcg cagaagtgag tggagagtat ggatggtctg taagtgtatc tgggacctat     720
gcaaccactc aagaggaaag tcgaacccta gcatgggacc aatctggaac cctacagcct     780
gggcaatgga tttcactcca agctaccact cgaagaggaa ccatcacatt ccctttcaa     840
gcaaccatgg aaatcacttt gcagtctgga acgatctttc aatatgccat ctcctcaatg     900
tactccggtg tggattatac tagtgtggat ataactaaca ctggaagtag agcattagat     960
caggttgagg tcaaaactac tgagcaacaa gttgaagggg tcgaggatca aaatgtacaa    1020
cctaataaag aagctaaaga gtgcacactc ctctttgctg aaggcgcagc ttacccatac    1080
gatgtgccag attatgct                                                   1098
```

<210> SEQ ID NO 88
<211> LENGTH: 360
<212> TYPE: PRT
<213> ORGANISM: Aglaomorpha meyeniana

<400> SEQUENCE: 88

```
Met Ala Leu Tyr Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Ile Arg Phe Tyr
            85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160
```

| | | | | | | | | | | | |
|---|---|---|---|---|---|---|---|---|---|---|---|
|Gly|Leu|Glu|Gln|Ala|Gly|Ile|Ile|Pro|Val|Thr|Leu|Asp|Ser|Phe|Asn|
| | | | |165| | | |170| | | |175| | | |

Gly Leu Glu Gln Ala Gly Ile Ile Pro Val Thr Leu Asp Ser Phe Asn
                165                170                175

Asp Ser Asn Asn Ala Gly Thr Ile Ser Lys Asn Trp Thr Phe Ser Gly
        180                185                190

Ser Arg Thr Val Thr Ile Ser Ser Trp Ser Leu Thr Ser Gly Ile
       195                200              205

Glu Thr His Ala Ser Val Ser Val Gln Ala Gly Ile Pro Met Val Ala
        210                215              220

Glu Val Ser Gly Glu Tyr Gly Trp Ser Val Ser Val Ser Gly Thr Tyr
225                230              235              240

Ala Thr Gln Glu Glu Ser Arg Thr Leu Ala Trp Asp Gln Ser Gly
            245              250              255

Thr Leu Gln Pro Gly Gln Trp Ile Ser Leu Gln Ala Thr Thr Arg Arg
        260                265              270

Gly Thr Ile Thr Leu Pro Phe Gln Ala Thr Met Glu Ile Thr Leu Gln
       275                280              285

Ser Gly Thr Ile Phe Gln Tyr Ala Ile Ser Ser Met Tyr Ser Gly Val
        290                295              300

Asp Tyr Thr Ser Val Asp Ile Thr Asn Thr Gly Ser Arg Ala Leu Asp
305                310              315              320

Gln Val Glu Val Lys Thr Thr Glu Gln Val Glu Gly Val Glu Asp
            325              330              335

Gln Asn Val Gln Pro Asn Lys Glu Ala Lys Glu Cys Thr Leu Leu Phe
        340                345              350

Ala Glu Gly Ala Ala Tyr Pro Tyr
       355                360

<210> SEQ ID NO 89
<211> LENGTH: 1059
<212> TYPE: DNA
<213> ORGANISM: Aglaomorpha meyeniana

<400> SEQUENCE: 89

```
atggcgctgt atcagacacc tgtgtatgtc atcggagggc aaggtggcaa ctcgttcaca      60
tatgatcaga gcaggaacgg gaaggtcttg aggaagattg gtgtgtgggc tggtgagtgg     120
caactgcgcg gtatccgggt atggatgtct ggttccgata gcccagccac cttcggcaca     180
gcctcgggct cttataatga gtatacattt gcagatggtg agcgcatcac ccgtttgtcc     240
ttgtggggca atggtgctgg tacacgttct ggggcatta gattctacac cacgactgga     300
ggctcatttt ttgctaaaat gacatcttgg ggcttacaaa ctgagtatcc aatcgatgtg     360
gcatctggtc tttgtgttgg gatactggga cgagctaatg ttgacattga ttcattgggt     420
ttcatgttcc ttcgaaccat agcatctgct cgtatgatca atgtaagtta cccaacattg     480
ggcttagagc aagctggaat tgtgcctgtc acgcttgatt cgtacaacga ttccaacaat     540
gcaggtacaa tttccaagaa ttggactttc tccggaagtc gaacagtgac aatatcatct     600
tcatggacgc tcacttcggg catagaggca catgctactg tgagtgttca gcggggatc     660
cccttggttg cagaagtgag cggagagttt ggatggtcat aagtgttac aggaagctac     720
acaaccaccc aagaggagag tcgaacactc acgtggaacc aatccggaac cttagagcca     780
gggcaatgga tttccctcca agcgaccact cgtagaggta ccatcacctt accctatcaa     840
ggaccatgg agataactct acagtctgga actgtatttc aatacccat ctcttctatg     900
tatgccggtg tggattatac tagtgttgac attaccaaca ctggaactag agcattgaat     960
```

-continued

```
cgggttgaga ctgaagctat tgatcaacaa gcccgtgaag gagaccagaa tgtccaacct    1020
agtaaagacg tccaggaatg caaactcctc tttaatgat                            1059
```

<210> SEQ ID NO 90
<211> LENGTH: 353
<212> TYPE: PRT
<213> ORGANISM: Aglaomorpha meyeniana

<400> SEQUENCE: 90

```
Met Ala Leu Tyr Gln Thr Pro Val Tyr Val Ile Gly Gly Gln Gly Gly
1               5                   10                  15

Asn Ser Phe Thr Tyr Asp Gln Ser Arg Asn Gly Lys Val Leu Arg Lys
            20                  25                  30

Ile Gly Val Trp Ala Gly Glu Trp Gln Leu Arg Gly Ile Arg Val Trp
        35                  40                  45

Met Ser Gly Ser Asp Ser Pro Ala Thr Phe Gly Thr Ala Ser Gly Ser
    50                  55                  60

Tyr Asn Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe Ala Lys Met Thr Ser Trp Gly Leu
            100                 105                 110

Gln Thr Glu Tyr Pro Ile Asp Val Ala Ser Gly Leu Cys Val Gly Ile
        115                 120                 125

Leu Gly Arg Ala Asn Val Asp Ile Asp Ser Leu Gly Phe Met Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Val Pro Val Thr Leu Asp Ser Tyr Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Ser Trp Thr Leu Thr Ser Gly Ile
        195                 200                 205

Glu Ala His Ala Thr Val Ser Val Gln Ala Gly Ile Pro Leu Val Ala
    210                 215                 220

Glu Val Ser Gly Glu Phe Gly Trp Ser Leu Ser Val Thr Gly Ser Tyr
225                 230                 235                 240

Thr Thr Thr Gln Glu Glu Ser Arg Thr Leu Thr Trp Asn Gln Ser Gly
                245                 250                 255

Thr Leu Glu Pro Gly Gln Trp Ile Ser Leu Gln Ala Thr Thr Arg Arg
            260                 265                 270

Gly Thr Ile Thr Leu Pro Tyr Gln Gly Thr Met Glu Ile Thr Leu Gln
        275                 280                 285

Ser Gly Thr Val Phe Gln Tyr Pro Ile Ser Ser Met Tyr Ala Gly Val
    290                 295                 300

Asp Tyr Thr Ser Val Asp Ile Thr Asn Thr Gly Thr Arg Ala Leu Asn
305                 310                 315                 320

Arg Val Glu Thr Glu Ala Ile Asp Gln Gln Ala Arg Glu Gly Asp Gln
                325                 330                 335

Asn Val Gln Pro Ser Lys Asp Val Gln Glu Cys Lys Leu Leu Phe Asn
            340                 345                 350

Asp
```

<210> SEQ ID NO 91
<211> LENGTH: 1185
<212> TYPE: DNA
<213> ORGANISM: Selaginella victoriae

<400> SEQUENCE: 91

```
atgcaatatg gcctggccaa tatggaagca agcccctga tcgagaagtt ccaatctcta      60
atggaaggtg gcatagatga gagcatcctt gcgactaagc ttgttggtgc tgaaggagat    120
gcttctcatt tgccaccacc tggagagacg cctagtgagg atggtgccgg caaggatcca    180
cccaatgaat cgctggagac tgaagatgta gaggagcatg ctgatgatag caaagcccgt    240
tctgctagtg tcatggcccc tctgcgcttc ataggcggcc ccggtgggtc gcaacgttcc    300
gtccgaggat ggaccaacgg cagggtcatc accaggatgc gtgtctacag ggcccggggg    360
actatcaaag cgtaccagat ctggctcaca gactctgctc cccagactca tggtgttcct    420
gggaacagcg acttcgccga gtacacgttc cgcaccggag agcgtcttac aagattaaca    480
ctgtggggaa acggaatggg cactcgtgct ggatggatcg agtttgagac gagcttgggt    540
ggaaggtttt catatggcat gagccattgg tcgctgagaa ctccttaccc tgtcgacgtc    600
ggttctggca tccttgtggg ctacattttt aatgctggag aggacgtcga tgcacacggc    660
ttctggtttc tcaaccacat tgagcaggcc gagctcacca atgtgaggta tccgactctt    720
ggatttgaca cggcaggtat tgtacccacg gccctggata ccttccggtt cagaaacaac    780
tcatccacgc caagagactg ggacttcagc cggaacatga gcaggagcac tgagcggaca    840
tggtcgatca ccgtggatct tactgtccat gcgagcatca cggtgagtgc agggtttcca    900
ggcattgcaa acgtgagtgg tcagtatgga tgggagattg gggcgacggg gcatttcgaa    960
acaacagaga cgtccgagca cgacttgagc tggagcgtga gtgggagagt ccagcctggg   1020
gatgttgtcg atctcactgc gctcactcgg actggaactc ttaacattcc ttacgaaggt   1080
acgatggtgg tgaggatgag aaatggtgcc tccttcagct atgccgtgcg tggaacctac   1140
agaggcctta gctataccgg cacaaaaata aacgacaact caact                   1185
```

<210> SEQ ID NO 92
<211> LENGTH: 395
<212> TYPE: PRT
<213> ORGANISM: Selaginella victoriae

<400> SEQUENCE: 92

Met Gln Tyr Gly Leu Ala Asn Met Glu Ala Ser Pro Leu Ile Glu Lys
1               5                   10                  15

Phe Gln Ser Leu Met Glu Gly Gly Ile Asp Glu Ser Ile Leu Ala Thr
            20                  25                  30

Lys Leu Val Gly Ala Glu Gly Asp Ala Ser His Leu Pro Pro Pro Gly
        35                  40                  45

Glu Thr Pro Ser Glu Asp Gly Ala Gly Lys Asp Pro Pro Asn Glu Ser
    50                  55                  60

Leu Glu Thr Glu Asp Val Glu Glu His Ala Asp Asp Ser Lys Ala Arg
65                  70                  75                  80

Ser Ala Ser Val Met Ala Pro Leu Arg Phe Ile Gly Gly Pro Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp

```
                115                 120                 125
Leu Thr Asp Ser Ala Pro Gln Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Met Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270

Met Ser Arg Ser Thr Glu Arg Thr Trp Ser Ile Thr Val Asp Leu Thr
        275                 280                 285

Val His Ala Ser Ile Thr Val Ser Ala Gly Phe Pro Gly Ile Ala Asn
    290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Arg
                325                 330                 335

Val Gln Pro Gly Asp Val Val Asp Leu Thr Ala Leu Thr Arg Thr Gly
            340                 345                 350

Thr Leu Asn Ile Pro Tyr Glu Gly Thr Met Val Val Arg Met Arg Asn
        355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395
```

<210> SEQ ID NO 93
<211> LENGTH: 1185
<212> TYPE: DNA
<213> ORGANISM: Selaginella victoriae

<400> SEQUENCE: 93

```
atgcaatatg gcctggccaa tatggaagca agcccctga tcgagaagtt ccaatctcta      60
atggaaggtg catagatga gagcatcctt gcgactaagc ttgttggtgc tgaaggagat     120
gcttctcatt tgccaccacc tggagagacg cctagtgagg atggtgccgg caaggatcca     180
cccaatgaat cgctggagac tgaagatgta gaggagcatg ctgatgatag caaagcccgt     240
tctgctagtg tcacggcccc tctgcgcttc ataggcggca ccggtgggtc gcaacgttcc     300
gtccgaggat ggaccaacgg cagggtcatc accaggatgc gtgtctacag ggcccggggg     360
actatcaaag cgtacaggat ctggctcaca gactctggtc ccgagactca tggtgttcct     420
gggaacagcg acttcgccga gtacactttc gcaccggag agcgtcttac aagattaaca     480
ctgtggggaa acggaatcgg cactcgtgct ggatggatcg agtttgagac cagcttgggt     540
```

```
ggaaggtttt catatggcat gagccattgg tcgctgagaa ctccttaccc tgtcgacgtc    600
ggttctggca tccttgtggg ttacattttt aatgctggag aggacgtcga tgcacacggc    660
ttctggtttc tcaaccacat tcagcaggcc gagctcacca atgtgaggta tccgactctt    720
ggatttgaca cggcaggtat tgtacccacg gccctggata ccttccggtt cagaaacaac    780
tcatcaacgc caagagactg ggacttcagc cggaacatga gcaggagcac tgagcggaca    840
tggtcgatca ccgtggatct tactgtccat gcgagcatca cggtgagtgc agggtttcca    900
ggcattgcaa acgtgagtgg tcagtatgga tgggagattg gggcgacggg gcatttcgaa    960
acaacagaga cgtccgagca cgacttgagc tggagcgtga gtgggagagt ccagcctggg   1020
gaatttgtcg atctcactgc gctcactcgg actggaactc ttaacattcc ttacgaaggt   1080
acgatggtgg tgaggatgag aaatggtgcc tccttcagct atgccgtgcg tggaacctac   1140
agaggcctta gctataccgg cacaaaaata aacgacaact caact                   1185
```

<210> SEQ ID NO 94
<211> LENGTH: 395
<212> TYPE: PRT
<213> ORGANISM: Selaginella victoriae

<400> SEQUENCE: 94

```
Met Gln Tyr Gly Arg Ala Asn Met Glu Ala Ser Pro Leu Ile Glu Lys
1               5                   10                  15

Phe Gln Ser Leu Met Glu Gly Gly Ile Asp Glu Ser Ile Leu Ala Thr
            20                  25                  30

Lys Leu Val Gly Ala Glu Gly Asp Ala Ser His Leu Pro Pro Pro Gly
        35                  40                  45

Glu Thr Pro Ser Glu Asp Gly Ala Gly Lys Asp Pro Pro Asn Glu Ser
    50                  55                  60

Leu Glu Thr Glu Asp Val Glu His Ala Asp Asp Ser Lys Ala Arg
65                  70                  75                  80

Ser Ala Ser Val Thr Ala Pro Leu Arg Phe Ile Gly Gly Thr Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Arg Ile Trp
        115                 120                 125

Leu Thr Asp Ser Gly Pro Glu Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Ile Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Gln Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
```

```
                    260                 265                 270
Met Ser Arg Ser Thr Glu Arg Thr Trp Ser Ile Thr Val Asp Leu Thr
            275                 280                 285

Val His Ala Ser Ile Thr Val Ser Ala Gly Phe Pro Gly Ile Ala Asn
        290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Arg
                325                 330                 335

Val Gln Pro Gly Glu Phe Val Asp Leu Thr Ala Leu Thr Arg Thr Gly
            340                 345                 350

Thr Leu Asn Ile Pro Tyr Glu Gly Thr Met Val Val Arg Met Arg Asn
            355                 360                 365

Gly Ala Ser Phe Ser Tyr Ala Val Arg Gly Thr Tyr Arg Gly Leu Ser
            370                 375                 380

Tyr Thr Gly Thr Lys Ile Asn Asp Asn Ser Thr
385                 390                 395
```

<210> SEQ ID NO 95
<211> LENGTH: 1185
<212> TYPE: DNA
<213> ORGANISM: Selaginella victoriae

<400> SEQUENCE: 95

| | | | | | |
|---|---|---|---|---|---|
| atgcaatatg | gcctggccaa | tactgaagca | agcccctga | tcgagaagtt | ccaagctcta | 60 |
| atggaaggcg | gcatagatga | gagcatcctt | gcgactaagc | ttgttggtgc | tgaaggagat | 120 |
| gcatctcgtg | tgccaccacc | tggagagacg | cctagtgagg | atggtgccgg | caaggatcca | 180 |
| cccaatgaat | cgctggagac | tgaagatgta | gaggagcatg | ctgatgatag | caaagcccgt | 240 |
| tctgctagtg | tcacggcccc | tctgcgcttc | ataggcggca | ccggtgggtc | gcaacgttcc | 300 |
| gtccgaggat | ggaccaacgg | cagggtcatc | accaggatgc | gtgtctacag | ggccagggg | 360 |
| actatcaaag | cgtacaggat | ctggctcaca | gactctggtc | ccgagactca | tggtgttcct | 420 |
| gggaacagcg | acttcgccga | gtacactttc | cgcaccggag | agcgtcttac | aagattaaca | 480 |
| ctgtggggaa | acggaatcgg | cactcgtgct | ggatggatcg | agtttgagac | cagcttgggt | 540 |
| ggaaggtttt | catatggcat | gagccattgg | tcgctgagaa | ctcctacc | tgtcgacgtc | 600 |
| ggttctggca | tccttgtggg | ttacatttt | aatgctggag | aggacgtcga | tgcacacggc | 660 |
| ttctggtttc | tcaaccacat | tcagcaggcc | gagctcacca | atgtgaggta | tccgactctt | 720 |
| ggatttgaca | cggcaggtat | tgtacccacg | gccctggata | ccttccggtt | cagaaacaac | 780 |
| tcatcaacgc | caagagactg | ggacttcagc | cggaacatga | gcaggagcac | tgagcggaca | 840 |
| tggtcgatca | ccgtggatct | tactgtccat | gcgagcatca | cggtgagtgc | agggtttcca | 900 |
| ggcattgcaa | acgtgagtgg | tcagtatgga | tgggagattg | gggcgacggg | gcatttcgaa | 960 |
| acaacagaga | cgtccgagca | cgacttgagc | tggagcgtga | gtgggagagt | ccagcctggg | 1020 |
| gaatttgtcg | atctcactgc | gctcactcgg | actggaactc | ttaacattcc | ttacgaaggt | 1080 |
| acgatggtgg | tgaggatgag | aaatggtgcc | tccttcagct | atgccgtgcg | tggaacctac | 1140 |
| agaggcctta | gctataccgg | cacaaaaata | aacgacaact | caact | | 1185 |

<210> SEQ ID NO 96
<211> LENGTH: 395
<212> TYPE: PRT
<213> ORGANISM: Selaginella victoriae

<400> SEQUENCE: 96

```
Met Gln Tyr Gly Leu Ala Asn Thr Glu Ala Ser Pro Leu Ile Glu Lys
1               5                   10                  15

Phe Gln Ala Leu Met Glu Gly Gly Ile Asp Glu Ser Ile Leu Ala Thr
            20                  25                  30

Lys Leu Val Gly Ala Glu Gly Asp Ala Ser Arg Val Pro Pro Pro Gly
        35                  40                  45

Glu Thr Pro Ser Glu Asp Gly Ala Gly Lys Asp Pro Pro Asn Glu Ser
    50                  55                  60

Leu Glu Thr Glu Asp Val Glu His Ala Asp Asp Ser Lys Ala Arg
65                  70                  75                  80

Ser Ala Ser Val Thr Ala Pro Leu Arg Phe Ile Gly Thr Gly Gly
                85                  90                  95

Ser Gln Arg Ser Val Arg Gly Trp Thr Asn Gly Arg Val Ile Thr Arg
                100                 105                 110

Met Arg Val Tyr Arg Ala Arg Gly Thr Ile Lys Ala Tyr Arg Ile Trp
            115                 120                 125

Leu Thr Asp Ser Gly Pro Glu Thr His Gly Val Pro Gly Asn Ser Asp
130                 135                 140

Phe Ala Glu Tyr Thr Phe Arg Thr Gly Glu Arg Leu Thr Arg Leu Thr
145                 150                 155                 160

Leu Trp Gly Asn Gly Ile Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
210                 215                 220

Asn His Ile Gln Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270

Met Ser Arg Ser Thr Glu Arg Thr Trp Ser Ile Thr Val Asp Leu Thr
        275                 280                 285

Val His Ala Ser Ile Thr Val Ser Ala Gly Phe Pro Gly Ile Ala Asn
    290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Arg
                325                 330                 335

Val Gln Pro Gly Glu Phe Val Asp Leu Thr Ala Leu Thr Arg Thr Gly
            340                 345                 350

Thr Leu Asn Ile Pro Tyr Glu Gly Thr Met Val Val Arg Met Arg Asn
        355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395
```

<210> SEQ ID NO 97
<211> LENGTH: 1188
<212> TYPE: DNA
<213> ORGANISM: Selaginella victoriae

<400> SEQUENCE: 97

| | | | | | |
|---|---|---|---|---|---|
| atgcaatatg | gcctggccaa | tactgaagca | agcccctga | tcgagaagtt | ccaagctcta | 60 |
| atggaaggcg | gcatagatga | gagcatcctt | gcgactaagc | ttgttggtgc | tgaaggagat | 120 |
| gcttctcatt | tgccaccacc | tggagagacg | cctagtgagg | atggtgccgg | caaggatcca | 180 |
| cccaatgaat | cgctggagac | tgaagatgta | gaggagcatg | ctgatgatag | caaagcccgt | 240 |
| tctgctagta | gtgtcacggc | ccctctgcgc | ttcataggcg | gcaccggtgg | gtcgcaacgt | 300 |
| tccgtccgag | gatggaccaa | cggcagggtc | atcaccagga | tgcgtgtcta | cagggcccgg | 360 |
| gggactatca | aagcgtacag | gatctggctc | acagactctg | gtcccgagac | tcatggtgtt | 420 |
| cctgggaaca | gcgacttcgc | cgagtacact | ttccgcaccg | gagagcgtct | tacaagatta | 480 |
| acactgtggg | aaacggaat | cggcactcgt | gctggatgga | tcgagtttga | gacgagcttg | 540 |
| ggtggaaggt | tttcatatgg | catgagccat | ggtcgctga | aactcctta | ccctgtcgac | 600 |
| gtcggttctg | gcatccttgt | gggctacatt | tttaatgctg | agaggaggt | cgatgcacac | 660 |
| ggcttctggt | ttctcaacca | cattcagcag | gccgagctca | ccaatgtgag | gtatccgact | 720 |
| cttggatttg | acacggcagg | tattgtaccc | acggccctgg | ataccttccg | gttcagaaac | 780 |
| aactcatcaa | cgccaagaga | ctgggacttc | agccggaaca | tgagcaggag | cactgagcgg | 840 |
| acatggtcga | tcaccgtgga | tcttactgtc | catgcgagca | tcacggtgag | tgcagggttt | 900 |
| ccaggcattg | caaacgtgag | tggtcagtat | ggatgggaga | ttgggcgac | ggggcatttc | 960 |
| gaaacaacag | agacgtccga | gcacgacttg | agctggagcg | tgagtgggag | agtccagcct | 1020 |
| ggagatgttg | tcgatctcac | tgcgctcact | cggactggaa | ctcttaacat | tccttacgaa | 1080 |
| ggtacgatgg | tggtgaggat | gagaaatggt | gcctccttca | gctatgccgt | gcgtggaacc | 1140 |
| tacagaggcc | ttagctatac | cggcacaaaa | ataaacgaca | actcaact | | 1188 |

<210> SEQ ID NO 98
<211> LENGTH: 396
<212> TYPE: PRT
<213> ORGANISM: Selaginella victoriae

<400> SEQUENCE: 98

```
Met Gln Tyr Gly Leu Ala Asn Thr Glu Ala Ser Pro Leu Ile Glu Lys
1               5                   10                  15

Phe Gln Ala Leu Met Glu Gly Gly Ile Asp Glu Ser Ile Leu Ala Thr
            20                  25                  30

Lys Leu Val Gly Ala Glu Gly Asp Ala Ser His Leu Pro Pro Pro Gly
        35                  40                  45

Glu Thr Pro Ser Glu Asp Gly Ala Gly Lys Asp Pro Pro Asn Glu Ser
    50                  55                  60

Leu Glu Thr Glu Asp Val Glu Glu His Ala Asp Asp Ser Lys Ala Arg
65                  70                  75                  80

Ser Ala Ser Ser Val Thr Ala Pro Leu Arg Phe Ile Gly Gly Thr Gly
                85                  90                  95

Gly Ser Gln Arg Ser Val Arg Gly Trp Thr Asn Gly Arg Val Ile Thr
            100                 105                 110

Arg Met Arg Val Tyr Arg Ala Arg Gly Thr Ile Lys Ala Tyr Arg Ile
        115                 120                 125
```

Trp Leu Thr Asp Ser Gly Pro Glu Thr His Gly Val Pro Gly Asn Ser
130                 135                 140

Asp Phe Ala Glu Tyr Thr Phe Arg Thr Gly Glu Arg Leu Thr Arg Leu
145                 150                 155                 160

Thr Leu Trp Gly Asn Gly Ile Gly Thr Arg Ala Gly Trp Ile Glu Phe
            165                 170                 175

Glu Thr Ser Leu Gly Gly Arg Phe Ser Tyr Gly Met Ser His Trp Ser
            180                 185                 190

Leu Arg Thr Pro Tyr Pro Val Asp Val Gly Ser Gly Ile Leu Val Gly
            195                 200                 205

Tyr Ile Phe Asn Ala Gly Glu Glu Val Asp Ala His Gly Phe Trp Phe
210                 215                 220

Leu Asn His Ile Gln Gln Ala Glu Leu Thr Asn Val Arg Tyr Pro Thr
225                 230                 235                 240

Leu Gly Phe Asp Thr Ala Gly Ile Val Pro Thr Ala Leu Asp Thr Phe
                245                 250                 255

Arg Phe Arg Asn Asn Ser Ser Thr Pro Arg Asp Trp Asp Phe Ser Arg
                260                 265                 270

Asn Met Ser Arg Ser Thr Glu Arg Thr Trp Ser Ile Thr Val Asp Leu
                275                 280                 285

Thr Val His Ala Ser Ile Thr Val Ser Ala Gly Phe Pro Gly Ile Ala
290                 295                 300

Asn Val Ser Gly Gln Tyr Gly Trp Glu Ile Gly Ala Thr Gly His Phe
305                 310                 315                 320

Glu Thr Thr Glu Thr Ser Glu His Asp Leu Ser Trp Ser Val Ser Gly
                325                 330                 335

Arg Val Gln Pro Gly Asp Val Val Asp Leu Thr Ala Leu Thr Arg Thr
                340                 345                 350

Gly Thr Leu Asn Ile Pro Tyr Glu Gly Thr Met Val Val Arg Met Arg
            355                 360                 365

Asn Gly Ala Ser Phe Ser Tyr Ala Val Arg Gly Thr Tyr Arg Gly Leu
            370                 375                 380

Ser Tyr Thr Gly Thr Lys Ile Asn Asp Asn Ser Thr
385                 390                 395

<210> SEQ ID NO 99
<211> LENGTH: 1185
<212> TYPE: DNA
<213> ORGANISM: Selaginella victoriae

<400> SEQUENCE: 99
atgcaatatg gcctggccaa tactgaagca agcccctga tcgagaagtt ccaagctcta      60
atggaaggcg gcatagatga gagcatcctt gcgactaagc ttgttggtgc tgaaggagat    120
gcatctcgtg tgccaccacc tggagagacg cctggtgagg atggtgccgg caaggatcca    180
cccaatgaat cgctggagac tgaagatgta gaggagcatg ctgatgatag caaagcccgt    240
tctgctagtg tcacggcccc tctgcgcttc ataggcggcc ccggtgggtc gcaacgttcc    300
gtccgaggat ggaccaacgg cagggtcatc accaggatgc gtgtctacag ggcccggggg    360
actatcaaag cgtaccagat ctggctcaca gactctggtc ccgagactca tggtgttcct    420
gggaacagcg acttcgccga gtacactttc gcaccggag agcgtcttac aagattaaca    480
ctgtggggaa acggaatcgg cactcgtgct ggatggatcg agtttgagac gagcttgggt    540
ggaaggtttt catatggcat gagccattgg tcgctgagaa ctccttaccc tgtcgacgtt    600

```
ggttctggca tccttgtggg ctacattttc aatgctggag aggacgtcga tgcacacggc    660
ttctggtttc tcaaccacat tgagcaggcc gagctcacca atgtgaggta tccgactctt    720
ggatttgaca cggcaggtat tgtacccacg gccctggata ccttccggtt cagaaacaac    780
tcgtcaacgc caagagactg ggacttcagc cggaacatga gcaggagcac tgagcggaca    840
tggtcgatca ccgtggatct tactgtccat gcgagcatca cggtgagtgc agggtttcca    900
ggcattgcaa acgtgagtgg tcagtatgga tgggagattg gggcgacggg gcatttcgaa    960
acaacagaga cgtccgagca cgacttgagc tggagcgtga gtgggatagt ccagcctggg   1020
gatgttgtcg atctcactgc gctcactcgg actggaactc ttaacattcc ttacgaaggt   1080
acgatggtgg tgaggatgag aaatggtgcc tccttcagct atgccgtgcg tggaacctac   1140
agaggcctta gctataccgg cacaaaaata aacgacaact caact                   1185
```

<210> SEQ ID NO 100
<211> LENGTH: 395
<212> TYPE: PRT
<213> ORGANISM: Selaginella victoriae

<400> SEQUENCE: 100

```
Met Gln Tyr Gly Leu Ala Asn Thr Glu Ala Ser Pro Leu Ile Glu Lys
1               5                   10                  15

Phe Gln Ala Leu Met Glu Gly Gly Ile Asp Glu Ser Ile Leu Ala Thr
            20                  25                  30

Lys Leu Val Gly Ala Glu Gly Asp Ala Ser Arg Val Pro Pro Gly
        35                  40                  45

Glu Thr Pro Gly Glu Asp Gly Ala Gly Lys Asp Pro Pro Asn Glu Ser
    50                  55                  60

Leu Glu Thr Glu Asp Val Glu Glu His Ala Asp Asp Ser Lys Ala Arg
65                  70                  75                  80

Ser Ala Ser Val Thr Ala Pro Leu Arg Phe Ile Gly Pro Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp
        115                 120                 125

Leu Thr Asp Ser Gly Pro Glu Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Ile Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270
```

Met Ser Arg Ser Thr Glu Arg Thr Trp Ser Ile Thr Val Asp Leu Thr
                275                 280                 285

Val His Ala Ser Ile Thr Val Ser Ala Gly Phe Pro Gly Ile Ala Asn
    290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Ile
                325                 330                 335

Val Gln Pro Gly Asp Val Val Asp Leu Thr Ala Leu Thr Arg Thr Gly
                340                 345                 350

Thr Leu Asn Ile Pro Tyr Glu Gly Thr Met Val Val Arg Met Arg Asn
            355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395

<210> SEQ ID NO 101
<211> LENGTH: 1185
<212> TYPE: DNA
<213> ORGANISM: Selaginella

<400> SEQUENCE: 101

| | | | | | |
|---|---|---|---|---|---|
| atgcaatatg | gcctggccaa | tactgaagca | agcccctga | tcgagaagtt | ccaagctcta | 60 |
| atggaaggcg | gcatagatga | gagcatcctt | gcgactaagc | ttgttggtgc | tgaaggagat | 120 |
| gcatctcgtg | tgccaccacc | tggagagacg | cctggtgagg | atggtgccgg | caaggatcca | 180 |
| cccaatgaat | cgctggagac | tgaagatgta | gaggagcatg | ctgatgatag | caaagcccgt | 240 |
| tctgctagtc | tcacggcccc | tctgcgcttc | ataggcggcc | ccgtgggtc | gcaacgttcc | 300 |
| gtccgaggat | ggaccaacgg | cagggtcatc | accaggatgc | gtgtctacag | ggcccggggg | 360 |
| actatcaaag | cgtaccagat | ctggctcaca | gactctggtc | ccgagactca | tggtgttcct | 420 |
| gggaacagcg | acttcgccga | gtacactttc | cgcaccggag | agcgtcttac | aagattaaca | 480 |
| ctgtggggaa | acggaatcgg | cactcgtgct | ggatggatcg | agtttgagac | gagcttgggt | 540 |
| ggaaggtttt | catatggcat | gagccattgg | tcgctgagaa | cttcttaccc | tgtcgacgtt | 600 |
| ggttctggca | tccttgtggg | ctacattttc | aatgctggag | aggacgtcga | tgcacacggc | 660 |
| ttctggtttc | tcaaccacat | tgagcaggcc | gagctcacca | atgtgaggta | tccgactctt | 720 |
| ggatttgaca | cggcaggtat | tgtacccacg | gccctggata | ccttccggtt | cagaaacaac | 780 |
| tcgtcaacgc | caagagactg | ggacttcagc | cggaacatga | gcaggagcac | tgagcggaca | 840 |
| tggtcgatca | ccgtggatct | tactgtccat | gcgagcatca | cggtgagtgc | agggtttcca | 900 |
| ggcattgcaa | acgtgagtgg | tcagtatgga | tgggagattg | gggcgacggg | gcatttcgaa | 960 |
| acaacagaga | cgtccgagca | cgacttgagc | tggagcgtga | gtgggatagt | ccagcctggg | 1020 |
| gatgttgtcg | atctcactgc | gctcactcgg | actggaactc | ttaacattcc | ttacgaaggt | 1080 |
| acgatggtgg | tgaggatgag | aaatggtgcc | tccttcagct | atgccgtgcg | tggaacctac | 1140 |
| agaggcctta | gctataccgg | cacaaaaata | aacgacaact | caact | | 1185 |

<210> SEQ ID NO 102
<211> LENGTH: 395
<212> TYPE: PRT
<213> ORGANISM: Selaginella victoriae

<400> SEQUENCE: 102

```
Met Gln Tyr Gly Leu Ala Asn Thr Glu Ala Ser Pro Leu Ile Glu Lys
1               5                   10                  15

Phe Gln Ala Leu Met Glu Gly Gly Ile Asp Glu Ser Ile Leu Ala Thr
            20                  25                  30

Lys Leu Val Gly Ala Glu Gly Asp Ala Ser Arg Val Pro Pro Gly
            35                  40                  45

Glu Thr Pro Gly Glu Asp Gly Ala Gly Lys Asp Pro Pro Asn Glu Ser
        50                  55                  60

Leu Glu Thr Glu Asp Val Glu His Ala Asp Asp Ser Lys Ala Arg
65              70                  75                  80

Ser Ala Ser Val Thr Ala Pro Leu Arg Phe Ile Gly Pro Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp
        115                 120                 125

Leu Thr Asp Ser Gly Pro Glu Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Ile Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Ser Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270

Met Ser Arg Ser Thr Glu Arg Thr Trp Ser Ile Thr Val Asp Leu Thr
        275                 280                 285

Val His Ala Ser Ile Thr Val Ser Ala Gly Phe Pro Gly Ile Ala Asn
    290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Ile
                325                 330                 335

Val Gln Pro Gly Asp Val Val Asp Leu Thr Ala Leu Thr Arg Thr Gly
            340                 345                 350

Thr Leu Asn Ile Pro Tyr Glu Gly Thr Met Val Val Arg Met Arg Asn
        355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395

<210> SEQ ID NO 103
<211> LENGTH: 1185
```

<212> TYPE: DNA
<213> ORGANISM: Selaginella victoriae

<400> SEQUENCE: 103

```
atgcaatatg gcctggccaa tatggaagca agcccctga tcgagaagtt ccaatctcta     60
atggaaggtg gcatagatga gagcatcctt gcgactaagc ttgttggtgc tgaaggagat   120
gcttctcatt tgccaccacc tggagagacg cctagtgagg atggtgccgg caaggatcca   180
cccaatgaat cgctggagac tgaagatgta gaggagcatg ctgatgatag caaagcccgt   240
tctgctagtg tcacggcccc tctgcgcttc ataggcggcc ccgtgggtc gcaacgttcc    300
gtccgaggat ggaccaacgg cagggtcatc accaggatgc gtgtctacag ggcccggggg   360
actatcaaag cgtaccagat ctggctcaca gactctgctc cccagactca tggtgttcct   420
gggaacagcg acttcgccga gtacacgttc cgcaccggag agcgtcttac aagattaaca   480
ctgtggggaa acggaatggg cactcgtgct ggatggatcg agtttgagac gagcttgggt   540
ggaaggtttt catatggcat gagccattgg tcgctgagaa ctccttaccc tgtcgacgtc   600
ggttctggca tccttgtggg ctacattttt aatgctggag aggacgtcga tgcacacggc   660
ttctggtttc tcaaccacat tgagcaggcc gagctcacca atgtgaggta tccgactctt   720
ggatttgaca cggcaggtat tgtacccacg gccctggata ccttccggtt cagaaacaac   780
tcatccacgc caagagactg ggacttcagc cggaacatga gcaggagcac tgagcggaca   840
tggtcgatca ccgtggatct tactgtccat gcgatcatca cggtgagtgc agggtttcca   900
ggcattgcaa acgtgagtgg tcagtatgga tgggagattg gggcgacggg gcatttcgaa   960
acaacagaga cgtccgagca cgacttgagc tggagcgtga gtgggagagt ccagcctggg  1020
gatgttgtcg atctcactgc gctcactcgg actggaactc ttaacattcc ttacgaaggt  1080
acgatggtgg tgaggatgag aaatggtgcc tccttcagct atgccgtgcg tggaacctac  1140
agaggcctta gctataccgg cacaaaaata aacgacaact caact              1185
```

<210> SEQ ID NO 104
<211> LENGTH: 395
<212> TYPE: PRT
<213> ORGANISM: Selaginella victoriae

<400> SEQUENCE: 104

```
Met Gln Tyr Gly Leu Ala Asn Met Glu Ala Ser Pro Leu Ile Glu Lys
 1               5                  10                  15

Phe Gln Ser Leu Met Glu Gly Gly Ile Asp Glu Ser Ile Leu Ala Thr
             20                  25                  30

Lys Leu Val Gly Ala Glu Gly Asp Ala Ser His Leu Pro Pro Pro Gly
         35                  40                  45

Glu Thr Pro Ser Glu Asp Gly Ala Gly Lys Asp Pro Pro Asn Glu Ser
     50                  55                  60

Leu Glu Thr Glu Asp Val Glu Glu His Ala Asp Asp Ser Lys Ala Arg
 65                  70                  75                  80

Ser Ala Ser Val Thr Ala Pro Leu Arg Phe Ile Gly Gly Pro Gly Gly
                 85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp
        115                 120                 125

Leu Thr Asp Ser Ala Pro Gln Thr His Gly Val Pro Gly Asn Ser Asp
    130                 135                 140
```

Phe Ala Glu Tyr Thr Phe Arg Thr Gly Glu Arg Leu Thr Arg Leu Thr
145                 150                 155                 160

Leu Trp Gly Asn Gly Met Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270

Met Ser Arg Ser Thr Glu Arg Thr Trp Ser Ile Thr Val Asp Leu Thr
        275                 280                 285

Val His Ala Ile Ile Thr Val Ser Ala Gly Phe Pro Gly Ile Ala Asn
    290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Arg
                325                 330                 335

Val Gln Pro Gly Asp Val Val Asp Leu Thr Ala Leu Thr Arg Thr Gly
            340                 345                 350

Thr Leu Asn Ile Pro Tyr Glu Gly Thr Met Val Val Arg Met Arg Asn
        355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395

<210> SEQ ID NO 105
<211> LENGTH: 1185
<212> TYPE: DNA
<213> ORGANISM: Selaginella victoriae

<400> SEQUENCE: 105
atgcaatatg gcctggccaa tatggaagca agcccctga tcgagaagtt ccaatctcta      60
atggaaggtg catagatga gagcatcctt gcgactaagc ttgttggtgc tgaaggagat     120
gcttctcatt tgccaccacc tggagagacg cctagtgagg atggtgccgg caaggatcca     180
cccaatgaat cgctggagac tgaagatgta gaggagcatg ctgatgatag caaagcccgt     240
tctgctagtg tcacggcccc tctgcgcttc ataggcggcc ccgtgggtc gcaacgttcc      300 gtccgaggat ggaccaacgg cagggtcatc accaggatgc gtgtctacag ggcccggggg     360
actatcaaag cgtaccagat ctggctcaca gactctggtc ccgagactca tggtgttcct     420
gggaacagcg acttcgccga gtacactttc cgcaccggag agcgtcttac aagattaaca     480
ctgtggggaa acggaatcgg cactcgtgct ggatggatcg agtttgagac gagcttgggt     540
ggaaggtttt catatggcat gagccattgg tcgctgagaa ctccttaccc tgtcgacgtt     600
ggttctggca tccttgtggg ctacattttc aatgctggag aggacgtcga tgcacacggc     660

-continued

```
ttctggtttc tcaaccacat tgagcaggcc gagctcacca atgtgaggta tccgactttt    720
ggatttgaca cggcaggtat tgtacccacg gccctggata ccttccggtt cagaaacaac    780
tcgtcaacgc caagagactg ggacttcagc cggaacatga gcaggagcac tgagcggaca    840
tggtcgatca ccgtggatct tactgtccat gcgagcatca cggtgagtgc agggtttcca    900
ggcattgcaa acgtgagtgg tcagtatgga tgggagattg gggcgacggg gcatttcgaa    960
acaacagaga cgtccgagca cgacttgagc tggagcgtga gtgggatagt ccagcctggg   1020
gatgttgtcg atctcactgc gctcactcgg actggaactc ttaacattcc ttacgaaggt   1080
acgatggtgg tgaggatgag aaatggtgcc tccttcagct atgccgtgcg tggaacctac   1140
agaggcctta gctataccgg cacaaaaata aacgacaact caact                    1185
```

<210> SEQ ID NO 106
<211> LENGTH: 395
<212> TYPE: PRT
<213> ORGANISM: Selaginella victoriae

<400> SEQUENCE: 106

```
Met Gln Tyr Gly Leu Ala Asn Met Glu Ala Ser Pro Leu Ile Glu Lys
1               5                   10                  15

Phe Gln Ser Leu Met Glu Gly Gly Ile Asp Glu Ser Ile Leu Ala Thr
            20                  25                  30

Lys Leu Val Gly Ala Glu Gly Asp Ala Ser His Leu Pro Pro Pro Gly
        35                  40                  45

Glu Thr Pro Ser Glu Asp Gly Ala Gly Lys Asp Pro Pro Asn Glu Ser
    50                  55                  60

Leu Glu Thr Glu Asp Val Glu His Ala Asp Asp Ser Lys Ala Arg
65                  70                  75                  80

Ser Ala Ser Val Thr Ala Pro Leu Arg Phe Ile Gly Pro Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp
        115                 120                 125

Leu Thr Asp Ser Gly Pro Glu Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Ile Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Phe
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270

Met Ser Arg Ser Thr Glu Arg Thr Trp Ser Ile Thr Val Asp Leu Thr
        275                 280                 285
```

Val His Ala Ser Ile Thr Val Ser Ala Gly Phe Pro Gly Ile Ala Asn
            290                 295                 300

Val Ser Gly Gln Tyr Gly Trp Glu Ile Gly Ala Thr Gly His Phe Glu
305                 310                 315                 320

Thr Thr Glu Thr Ser Glu His Asp Leu Ser Trp Ser Val Ser Gly Ile
                325                 330                 335

Val Gln Pro Gly Asp Val Val Asp Leu Thr Ala Leu Thr Arg Thr Gly
            340                 345                 350

Thr Leu Asn Ile Pro Tyr Glu Gly Thr Met Val Val Arg Met Arg Asn
            355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395

<210> SEQ ID NO 107
<211> LENGTH: 1188
<212> TYPE: DNA
<213> ORGANISM: Selaginella victoriae

<400> SEQUENCE: 107
atgcaatatg gcctggccaa tactgaagca agcccctga tcgagaagtt ccaagctcta      60
atggaaggcg gcatagatga gagcatcctt gcgactaagc ttgttggtgc tgaaggagat    120
gcttctcatt tgccaccacc tggagagacg cctagtgagg atggtgccgg caaggatcca    180
cccaatgaat cgctggagac tgaagatgta gaggagcatg ctgatgatag caaagcccgt    240
tctgctagta gtgtcacggc ccctctgcgc ttcataggcg gcaccggtgg gtcgcaacgt    300
tccgtccgag gatggaccaa cggcagggtc atcaccagga tgcgtgtcta cagggcccgg    360
gggactatca aagcgtacag gatctggctc acagactctg gtcccgagac tcatggtgtt    420
cctgggaaca gcgacttcgc cgagtacact ttccgcaccg gagagcgtct acaagatta    480
acactgtggg gaaacggaat cggcactcgt gctggatgga tcgagtttga gacgagcttg    540
ggtggaaggt tttcatatgg catgagccat tggtcgctga gaactcctta ccctgtcgac    600
gtcggttctg gcatccttgt gggctacatt tttaatgctg gagaggaggt cgatgcacac    660
ggcttctggt ttctcaacca cattcagcag gccgagctca ccaatgtgag gtatccgact    720
cttggatttg acacggcagg tattgtaccc acggccctgg ataccttccg gttcagaaac    780
aactcatcaa cgccaagaga ctgggacttc agccggaaca tgagcaggag cactgagcgg    840
acatggtcga tcaccgtgga tcttactgtc atgcgagca tcacggtgag tgcagggttt    900
ccaggcattg caaacgtgag tggtcagtat ggatgggaga ttggggcgac ggggcatttc    960
gaaacaacag agacgtccga gcacgacttg agctggagcg tgagtgggag agtccagcct   1020
ggagatgttg tcgatctcac tgcgctcact cggactggaa ctcttaacat tccttacgaa   1080
ggtacgatgg tggtgaggat gagaaatggt gcctccttca gctatgccgt gcgtggaacc   1140
tacagaggcc ttagctatac cgacacaaaa ataaacgaca actcaact                1188

<210> SEQ ID NO 108
<211> LENGTH: 396
<212> TYPE: PRT
<213> ORGANISM: Selaginella victoriae

<400> SEQUENCE: 108

Met Gln Tyr Gly Leu Ala Asn Thr Glu Ala Ser Pro Leu Ile Glu Lys
1               5                   10                  15

```
Phe Gln Ala Leu Met Glu Gly Gly Ile Asp Glu Ser Ile Leu Ala Thr
             20                  25                  30

Lys Leu Val Gly Ala Glu Gly Asp Ala Ser His Leu Pro Pro Pro Gly
         35                  40                  45

Glu Thr Pro Ser Glu Asp Gly Ala Gly Lys Asp Pro Pro Asn Glu Ser
     50                  55                  60

Leu Glu Thr Glu Asp Val Glu His Ala Asp Asp Ser Lys Ala Arg
65                  70                  75                  80

Ser Ala Ser Ser Val Thr Ala Pro Leu Arg Phe Ile Gly Gly Thr Gly
                 85                  90                  95

Gly Ser Gln Arg Ser Val Arg Gly Trp Thr Asn Gly Arg Val Ile Thr
             100                 105                 110

Arg Met Arg Val Tyr Arg Ala Arg Gly Thr Ile Lys Ala Tyr Arg Ile
         115                 120                 125

Trp Leu Thr Asp Ser Gly Pro Glu Thr His Gly Val Pro Gly Asn Ser
     130                 135                 140

Asp Phe Ala Glu Tyr Thr Phe Arg Thr Gly Glu Arg Leu Thr Arg Leu
145                 150                 155                 160

Thr Leu Trp Gly Asn Gly Ile Gly Thr Arg Ala Gly Trp Ile Glu Phe
                 165                 170                 175

Glu Thr Ser Leu Gly Gly Arg Phe Ser Tyr Gly Met Ser His Trp Ser
             180                 185                 190

Leu Arg Thr Pro Tyr Pro Val Asp Val Gly Ser Gly Ile Leu Val Gly
         195                 200                 205

Tyr Ile Phe Asn Ala Gly Glu Glu Val Asp Ala His Gly Phe Trp Phe
     210                 215                 220

Leu Asn His Ile Gln Gln Ala Glu Leu Thr Asn Val Arg Tyr Pro Thr
225                 230                 235                 240

Leu Gly Phe Asp Thr Ala Gly Ile Val Pro Thr Ala Leu Asp Thr Phe
                 245                 250                 255

Arg Phe Arg Asn Asn Ser Ser Thr Pro Arg Asp Trp Asp Phe Ser Arg
             260                 265                 270

Asn Met Ser Arg Ser Thr Glu Arg Thr Trp Ser Ile Thr Val Asp Leu
         275                 280                 285

Thr Val His Ala Ser Ile Thr Val Ser Ala Gly Phe Pro Gly Ile Ala
     290                 295                 300

Asn Val Ser Gly Gln Tyr Gly Trp Glu Ile Gly Ala Thr Gly His Phe
305                 310                 315                 320

Glu Thr Thr Glu Thr Ser Glu His Asp Leu Ser Trp Ser Val Ser Gly
                 325                 330                 335

Arg Val Gln Pro Gly Asp Val Val Asp Leu Thr Ala Leu Thr Arg Thr
             340                 345                 350

Gly Thr Leu Asn Ile Pro Tyr Glu Gly Thr Met Val Val Arg Met Arg
         355                 360                 365

Asn Gly Ala Ser Phe Ser Tyr Ala Val Arg Gly Thr Tyr Arg Gly Leu
     370                 375                 380

Ser Tyr Thr Asp Thr Lys Ile Asn Asp Asn Ser Thr
385                 390                 395

<210> SEQ ID NO 109
<211> LENGTH: 1065
<212> TYPE: DNA
<213> ORGANISM: Platycerium bifurcatum
```

```
<400> SEQUENCE: 109
atgtcgctgg ttcagacacc cgtctatgtc atcggagggc aaggaggcaa tgcgtttact        60
tacgatcaga gcagaaacgg gaggatcctg cggaggattg gggtgtgggc gggcgagtgg       120
caactgcgcg gaatccgcgt gtggatgacg ggcaccgaca ccccggccac tttcggcacg       180
gccacgggct cttacagtga atataccttc gcggatggcg agcgcatcac ccgcttgtcc       240
ttgtggggca acggggctgg tacacgttca ggaggcatca gattctacac cacaacagga       300
ggttctttct tccataaaat gacatcttgg ggcttacaaa ccgagtatcc aatcgacgtg       360
gcatctggtc tttgtgtggg gatcatggga cgagctaatg ttgatgtgga ttcattgggt       420
gttttgttct taaggaccat agcatctgct cgtatgatca atgtaagcta ccctaccttg       480
ggcttagagc aagccggaat catccctgtt acacttgatt ccttcaatga ctccaacaat       540
gcaggtacta tttccaaaaa ttggactttc tcgggtagcc gaaccgtgac aatatcatca       600
tcatggtcgc tcacttcagg gatagagaca catgcaagtg tgagcgtgca agcagggatc       660
cccatggttg cagaagtgag tggagagttt ggatggtctg ttagtgtatc tgggacctat       720
gcaaccactc aagaggaaag tcgaacccta acttggaacc aatctggaac cctagagcct       780
gggcaatgga tctcactcca agctaccact cgaagaggaa ccatcacatt acccttttcaa       840 gcaaccatgg aaatcacttt gctgtctgga acgatctttc aatatgccat ctcctctatg       900
tactccggtg tggattatac tagtgtggat ataactaaca ctggaactag agcatcagat       960
catgttgagg tcgaagctac tgagcaacaa gtccaagggg tcaaagatca aagtgtacaa      1020
cctaataaag aagctaaaga gtgcacactc ctctttgctg aataa                      1065
```